(12) United States Patent
Narayan et al.

(10) Patent No.: US 9,144,596 B2
(45) Date of Patent: Sep. 29, 2015

(54) COMPOSITIONS AND METHODS OF TREATING NEOPLASIA

(75) Inventors: Satya Narayan, Gainesville, FL (US);
Aruna S. Jaiswal, Gainesville, FL (US);
David A. Ostrov, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1060 days.

(21) Appl. No.: 12/527,164

(22) PCT Filed: Feb. 14, 2008

(86) PCT No.: PCT/US2008/001991
§ 371 (c)(1),
(2), (4) Date: Mar. 1, 2010

(87) PCT Pub. No.: WO2008/100584
PCT Pub. Date: Aug. 21, 2008

(65) Prior Publication Data
US 2010/0190702 A1    Jul. 29, 2010

Related U.S. Application Data

(60) Provisional application No. 60/901,613, filed on Feb. 14, 2007, provisional application No. 60/904,214, filed on Feb. 28, 2007.

(51) Int. Cl.
| | |
|---|---|
| *A61K 31/70* | (2006.01) |
| *A61K 38/17* | (2006.01) |
| *A61K 45/06* | (2006.01) |
| *A61K 31/122* | (2006.01) |
| *A61K 31/194* | (2006.01) |
| *A61K 31/4196* | (2006.01) |
| *A61K 31/7068* | (2006.01) |

(52) U.S. Cl.
CPC ........... *A61K 38/1709* (2013.01); *A61K 31/122* (2013.01); *A61K 31/194* (2013.01); *A61K 31/4196* (2013.01); *A61K 31/7068* (2013.01); *A61K 45/06* (2013.01)

(58) Field of Classification Search
CPC . A61K 38/1709; A61K 45/06; A61K 31/122; A61K 31/194; A61K 31/4196; A61K 31/7068
USPC .......................................... 424/130.1; 514/48
See application file for complete search history.

(56) References Cited

PUBLICATIONS

Cowled et al. (Cancer Res. Feb. 15, 1987; 47: 971-974).*
Suggitt et al. (Clin. Cancer Res. Feb. 1, 2005; 11: 971-981).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Gopalakrishnan et al. (J. Chem. Inf. Model. Jul.-Aug. 2005; 45 (4): 1101-8).*
Boothman et al. (Cancer Res. May 1, 1987; 47 (9): 2354-62).*
Trivedi et al. (Cancer Res. Jul. 15, 2005; 65 (14): 6394-400).*
Liu et al. (Clin. Cancer Res. Oct. 1999; 5 (10): 2908-17).*
Barvaux et al. (Mol. Cancer Ther. Oct. 2004; 3 (10): 1215-20).*
Miknyoczki et al. (Mol. Cancer Ther. Aug. 2007; 6 (8): 2290-302).*
Jaiswal et al. (Mol. Cancer Res. Dec. 2009; 7 (12): 1973-83).*
Balusu et al. "Structure/function analysis of the interaction of adenomatous polyposis coli with DNA polymerase beta and its complications for base excision repair." Biochemistry. 2007; 46: 13961-74.
Written Opinion of the International Searching Authority for International Application No. PCT/US08/01991 dated Sep. 10, 2008.
Jaiswal et al. "Mechanism of adenomatous polyposis coli (APC)-mediated blockage of long-patch excision repair." Biochemistry. 2006; 45:15903-14.
Narayan et al. "Tumor suppressor APC blocks DNA polymerase beta-dependent strand displacement synthesis during long patch but not short patch base excision repair and increases sensitivity to methylmenthane sulfonate." The Journal of Biological Chemistry. 2005; 280(8): 6942-9.
Newlands et al. "Phase I study of temozolamide (TMZ) combined with procarbazine (PCB) in patients with gliomas." British Journal of Cancer. 2003; 89: 248-51.

\* cited by examiner

*Primary Examiner* — Stephen Rawlings
(74) *Attorney, Agent, or Firm* — Locke Lord LLP; Jeffrey D. Hsi; Stephen W. Rafferty

(57) ABSTRACT

The invention features compositions and methods that are useful for the treatment of neoplasia by reducing base excision repair (BER). Such compositions are useful, for example, for enhancing the efficacy of known chemotherapeutics, such as DNA alkylating agents. In particular, the invention features agents that mimic the interaction of APC with pol-β. Such agents reduce the activity of long patch- and single nucleotide-base extension repair pathways.

8 Claims, 85 Drawing Sheets

Figure 5
A. Deletion constructs of pol-β
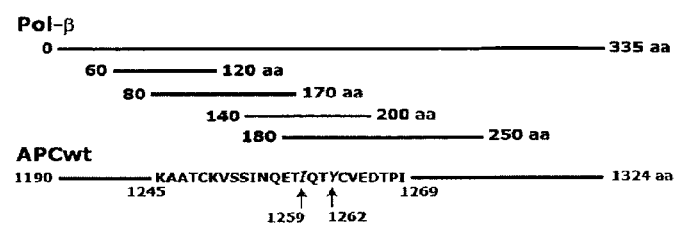
B. Yeast two-hybrid analysis
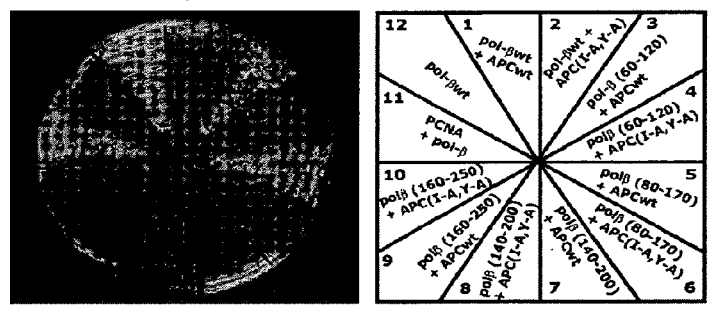

Figure 6
A. Structure of peptides
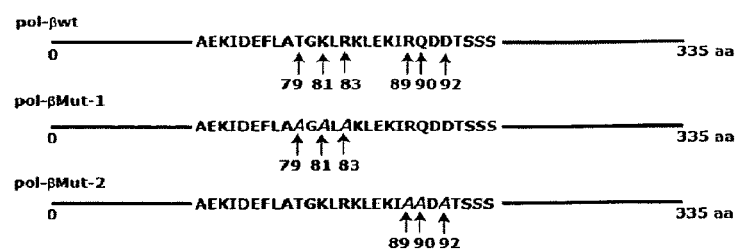
B. Yeast two-hybrid analysis
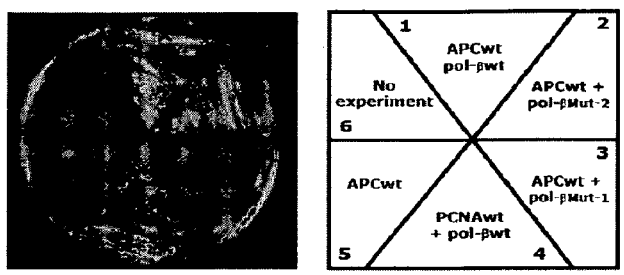

Figure 7

A. Protocol

32P-F-DNA   Pol-β
APE         APC

↓ 5 min dNTPs
DNA ligase I

↓ 30 min

Stop

B. Strand-displacement synthesis

63-mer →

Strand-
displacement
product 1-nt incorporation →
23-mer product →

```
            1  2  3  4  5  6  7  8  9
Pol-β       -  -  +  +  +  +  +  +  +
APCwt       -  -  -  ◁────▷  -  -  -
APC(I-A,Y-A) -  -  -  -  -  -  ◁────▷
```

Figure 9

```
LOCUS       P06746                   335 aa            linear   PRI 15-JAN-2008
DEFINITION  DNA polymerase beta.
ACCESSION   P06746
VERSION     P06746.3
    1 mskrkapqet lnggitdmlt elanfeknvs qaihkynayr kaasviakyp hkiksgaeak
   61 klpgvgtkia ekideflatg klrklekirq ddtsssinfl trvsgigpsa arkfvdegik
  121 tledlrkned klnhhqrigl kyfgdfekri preemlqmqd ivlnevkkvd seyiatvcgs
  181 frrgaessgd mdvllthpsf tsestkqpkl lhqvveqlqk vhfitdtlsk getkfmgvcq
  241 lpskndekey phrridirli pkdqyycgvl yftgsdifnk nmrahalekg ftineytirp
  301 lgvtgvagep lpvdsekdif dyiqwkyrep kdrse
```

Figure 15
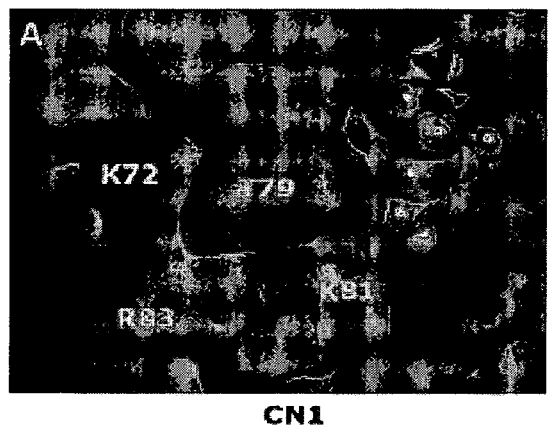
CN1
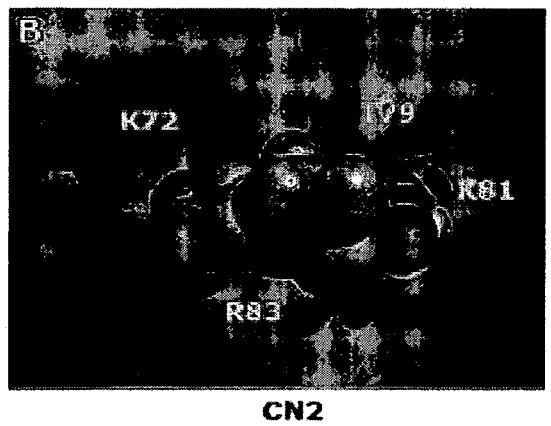
CN2

Figure 16
A. substrate
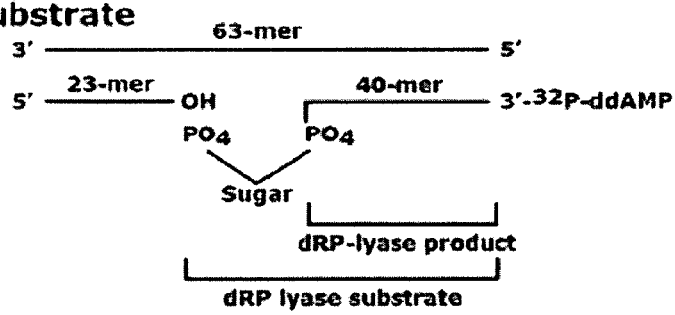
B. dRP-lyase activity
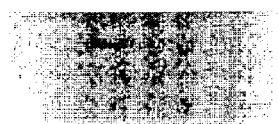
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|
| Pol-βwt | − | − | + | + | + | + | + | + | + | + | + | + | + | + | + | + | + | + | + | + | + | + | + |
| CN3 (μM) | − | − | − | 25 | 50 | 100 | 150 | 200 | − | − | − | − | − | − | − | − | − | − | − | − | − | − | − |
| CN4 (μM) | − | − | − | − | − | − | − | − | 25 | 50 | 100 | 150 | 200 | − | − | − | − | − | − | − | − | − | − |
| CN1 (μM) | − | − | − | − | − | − | − | − | − | − | − | − | − | 5 | 10 | 25 | 50 | 100 | − | − | − | − | − |
| CN2 (μM) | − | − | − | − | − | − | − | − | − | − | − | − | − | − | − | − | − | − | 5 | 10 | 25 | 50 | 100 |

Figure 21
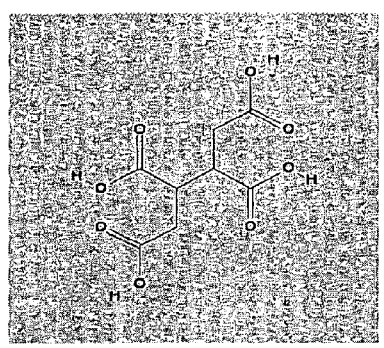
NSC21371
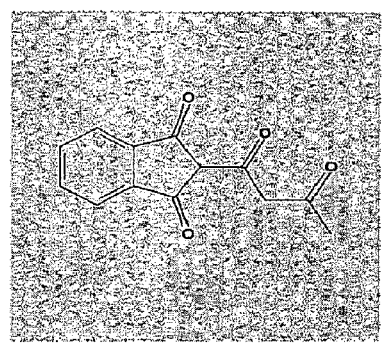
NSC91855
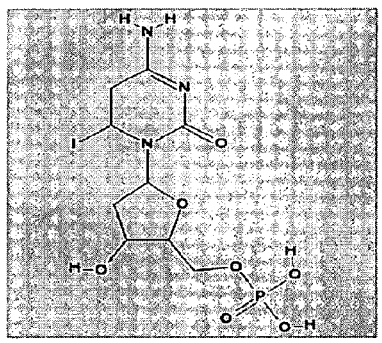
NSC12485
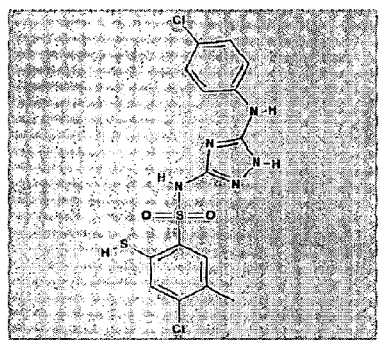
NSC666715

Figure 22A

```
HEADER    TRANSFERASE/DNA                           14-APR-97   1BPZ
TITLE     HUMAN DNA POLYMERASE BETA COMPLEXED WITH NICKED DNA
COMPND    MOL_ID: 1;
COMPND   2 MOLECULE: DNA POLYMERASE BETA;
COMPND   3 CHAIN: A;
COMPND   4 SYNONYM: POL BETA, BETA-POL;
COMPND   5 EC: 2.7.7.7;
COMPND   6 ENGINEERED: YES;
COMPND   7 MOL_ID: 2;
COMPND   8 MOLECULE: DNA (5'-
COMPND   9 D(*CP*CP*GP*AP*CP*CP*AP*CP*GP*CP*AP*TP*CP*AP*GP*C)-3');
COMPND  10 CHAIN: T;
COMPND  11 ENGINEERED: YES;
COMPND  12 MOL_ID: 3;
COMPND  13 MOLECULE: DNA (5'-D(*GP*CP*TP*GP*AP*TP*GP*CP*GP*TP*G)-3');
COMPND  14 CHAIN: P;
COMPND  15 ENGINEERED: YES;
COMPND  16 MOL_ID: 4;
COMPND  17 MOLECULE: DNA (5'-D(*GP*TP*CP*GP*G)-3');
COMPND  18 CHAIN: D;
COMPND  19 ENGINEERED: YES
SOURCE    MOL_ID: 1;
SOURCE   2 ORGANISM_SCIENTIFIC: HOMO SAPIENS;
SOURCE   3 ORGANISM_COMMON: HUMAN;
SOURCE   4 GENUS: HOMO;
SOURCE   5 SPECIES: SAPIENS;
SOURCE   6 CELLULAR_LOCATION: NUCLEUS;
SOURCE   7 EXPRESSION_SYSTEM: ESCHERICHIA COLI;
SOURCE   8 EXPRESSION_SYSTEM_COMMON: BACTERIA;
SOURCE   9 EXPRESSION_SYSTEM_GENUS: ESCHERICHIA;
SOURCE  10 EXPRESSION_SYSTEM_SPECIES: COLI;
SOURCE  11 MOL_ID: 2;
SOURCE  12 SYNTHETIC: YES;
SOURCE  13 MOL_ID: 3;
SOURCE  14 SYNTHETIC: YES;
SOURCE  15 MOL_ID: 4;
SOURCE  16 SYNTHETIC: YES
KEYWDS    NUCLEOTIDYLTRANSFERASE, DNA REPAIR, BASE EXCISION REPAIR
KEYWDS   2 PATHWAY
EXPDTA    X-RAY DIFFRACTION
AUTHOR    M.R.SAWAYA,R.PRASAD,S.H.WILSON,J.KRAUT,H.PELLETIER
REVDAT   2   03-FEB-04 1BPZ    1          JRNL    LINK
REVDAT   1   16-JUN-97 1BPZ    0
JRNL        AUTH   M.R.SAWAYA,R.PRASAD,S.H.WILSON,J.KRAUT,H.PELLETIER
JRNL        TITL   CRYSTAL STRUCTURES OF HUMAN DNA POLYMERASE BETA
JRNL        TITL 2 COMPLEXED WITH GAPPED AND NICKED DNA: EVIDENCE FOR
JRNL        TITL 3 AN INDUCED FIT MECHANISM.
JRNL        REF    BIOCHEMISTRY                  V.  36 11205 1997
JRNL        REFN   ASTM BICHAW  US ISSN 0006-2960
REMARK   1
REMARK   1 REFERENCE 1
REMARK   1  AUTH   H.PELLETIER,M.R.SAWAYA
REMARK   1  TITL   CHARACTERIZATION OF THE METAL ION BINDING
REMARK   1  TITL 2 HELIX-HAIRPIN-HELIX MOTIFS IN HUMAN DNA POLYMERASE
REMARK   1  TITL 3 BETA BY X-RAY STRUCTURAL ANALYSIS
REMARK   1  REF    BIOCHEMISTRY                  V.  35 12778 1996
REMARK   1  REFN   ASTM BICHAW  US ISSN 0006-2960
REMARK   1 REFERENCE 2
REMARK   1  AUTH   H.PELLETIER,M.R.SAWAYA,W.WOLFLE,S.H.WILSON,J.KRAUT
REMARK   1  TITL   A STRUCTURAL BASIS FOR METAL ION MUTAGENICITY AND
REMARK   1  TITL 2 NUCLEOTIDE SELECTIVITY IN HUMAN DNA POLYMERASE BETA
REMARK   1  REF    BIOCHEMISTRY                  V.  35 12762 1996
REMARK   1  REFN   ASTM BICHAW  US ISSN 0006-2960
```

Figure 22B

```
REMARK    1 REFERENCE 3
REMARK    1  AUTH    H.PELLETIER,M.R.SAWAYA,W.WOLFLE,S.H.WILSON,J.KRAUT
REMARK    1  TITL    CRYSTAL STRUCTURES OF HUMAN DNA POLYMERASE BETA
REMARK    1  TITL 2 COMPLEXED WITH DNA: IMPLICATIONS FOR CATALYTIC
REMARK    1  TITL 3 MECHANISM, PROCESSIVITY, AND FIDELITY
REMARK    1  REF     BIOCHEMISTRY                  V.  35 12742 1996
REMARK    1  REFN    ASTM BICHAW   US ISSN 0006-2960
REMARK    1 REFERENCE 4
REMARK    1  AUTH    M.R.SAWAYA,H.PELLETIER,A.KUMAR,S.H.WILSON,J.KRAUT
REMARK    1  TITL    CRYSTAL STRUCTURE OF RAT DNA POLYMERASE BETA:
REMARK    1  TITL 2 EVIDENCE FOR A COMMON POLYMERASE MECHANISM
REMARK    1  REF     SCIENCE                       V. 264  1930 1994
REMARK    1  REFN    ASTM SCIEAS   US ISSN 0036-8075
REMARK    1 REFERENCE 5
REMARK    1  AUTH    H.PELLETIER,M.R.SAWAYA,A.KUMAR,S.H.WILSON,J.KRAUT
REMARK    1  TITL    STRUCTURES OF TERNARY COMPLEXES OF RAT DNA
REMARK    1  TITL 2 POLYMERASE BETA, A DNA TEMPLATE- PRIMER, AND DDCTP
REMARK    1  REF     SCIENCE                       V. 264  1891 1994
REMARK    1  REFN    ASTM SCIEAS   US ISSN 0036-8075
REMARK    2
REMARK    2 RESOLUTION. 2.60 ANGSTROMS.
REMARK    3
REMARK    3 REFINEMENT.
REMARK    3   PROGRAM     : TNT 5D
REMARK    3   AUTHORS     : TRONRUD,TEN EYCK,MATTHEWS
REMARK    3
REMARK    3  DATA USED IN REFINEMENT.
REMARK    3   RESOLUTION RANGE HIGH (ANGSTROMS) : 2.60
REMARK    3   RESOLUTION RANGE LOW  (ANGSTROMS) : 20.00
REMARK    3   DATA CUTOFF            (SIGMA(F)) : 0.000
REMARK    3   COMPLETENESS FOR RANGE        (%) : 94.0
REMARK    3   NUMBER OF REFLECTIONS             : 14702
REMARK    3
REMARK    3  USING DATA ABOVE SIGMA CUTOFF.
REMARK    3   CROSS-VALIDATION METHOD          :NULL
REMARK    3   FREE R VALUE TEST SET SELECTION  :NULL
REMARK    3   R VALUE     (WORKING + TEST SET) :0.243
REMARK    3   R VALUE            (WORKING SET) :NULL
REMARK    3   FREE R VALUE                     :NULL
REMARK    3   FREE R VALUE TEST SET SIZE   (%) :NULL
REMARK    3   FREE R VALUE TEST SET COUNT      :NULL
REMARK    3
REMARK    3  USING ALL DATA, NO SIGMA CUTOFF.
REMARK    3   R VALUE   (WORKING + TEST SET, NO CUTOFF) : NULL
REMARK    3   R VALUE            (WORKING SET, NO CUTOFF) : 0.2430
REMARK    3   FREE R VALUE                  (NO CUTOFF) : NULL
REMARK    3   FREE R VALUE TEST SET SIZE (%, NO CUTOFF) : NULL
REMARK    3   FREE R VALUE TEST SET COUNT   (NO CUTOFF) : NULL
REMARK    3   TOTAL NUMBER OF REFLECTIONS   (NO CUTOFF) : 14702
REMARK    3
REMARK    3  NUMBER OF NON-HYDROGEN ATOMS USED IN REFINEMENT.
REMARK    3   PROTEIN ATOMS            : 2653
REMARK    3   NUCLEIC ACID ATOMS       : 651
REMARK    3   HETEROGEN ATOMS          : 2
REMARK    3   SOLVENT ATOMS            : 27
REMARK    3
REMARK    3  WILSON B VALUE (FROM FCALC, A**2) : NULL
REMARK    3
REMARK    3  RMS DEVIATIONS FROM IDEAL VALUES.     RMS    WEIGHT  COUNT
REMARK    3   BOND LENGTHS                 (A) : 0.020 ; 0.550 ; 3474
REMARK    3   BOND ANGLES            (DEGREES) : 3.000 ; 1.000 ; 4754
REMARK    3   TORSION ANGLES         (DEGREES) : 22.200; 1.000 ; 2027
REMARK    3   PSEUDOROTATION ANGLES  (DEGREES) : NULL  ; NULL  ; NULL
```

Figure 22C

```
REMARK   3    TRIGONAL CARBON PLANES       (A)  : 0.013 ; 1.000 ; 74
REMARK   3    GENERAL PLANES               (A)  : 0.007 ; 10.000; 432
REMARK   3    ISOTROPIC THERMAL FACTORS (A**2) : 7.000 ; 0.025 ; 3474
REMARK   3    NON-BONDED CONTACTS          (A)  : 0.022 ; 10.000; 270
REMARK   3
REMARK   3  INCORRECT CHIRAL-CENTERS (COUNT) : 0.000
REMARK   3
REMARK   3  BULK SOLVENT MODELING.
REMARK   3   METHOD USED : MOEWS
REMARK   3   KSOL        : 0.71
REMARK   3   BSOL        : 88.70
REMARK   3
REMARK   3  RESTRAINT LIBRARIES.
REMARK   3   STEREOCHEMISTRY : TNT PROTGEO
REMARK   3   ISOTROPIC THERMAL FACTOR RESTRAINTS : NULL
REMARK   3
REMARK   3  OTHER REFINEMENT REMARKS: NULL
REMARK   4
REMARK   4  1BPZ COMPLIES WITH FORMAT V. 2.3, 09-JULY-1998
REMARK   6
REMARK   6 THIS CRYSTAL STRUCTURE REPRESENTS ONE OF THREE
REMARK   6 INTERMEDIATES IN THE 1 NUCLEOTIDE GAP FILLING REACTION OF
REMARK   6 DNA POLYMERASE BETA. CRYSTAL STRUCTURES REPRESENTING ALL
REMARK   6 THREE INTERMEDIATES HAVE BEEN SUBMITTED TO THE PDB. THE
REMARK   6 STRUCTURES HAVE BEEN ASSEMBLED INTO A MOVIE DEPICTING ONE
REMARK   6 CATALYTIC CYCLE. SEE:
REMARK   6 HTTP://WWW-CHEM.UCSD.EDU/FACULTY/KRAUT/BPOL.HTML
REMARK   7
REMARK   7 THE 5'-TERMINUS OF G D 1 IS PHOSPHORYLATED.
REMARK   8
REMARK   8 THE ENTIRE THUMB SUBDOMAIN (RESIDUES 261 - 335) IS MODELED
REMARK   8 WITH ONLY 0.5 OCCUPANCY DUE TO WEAK ELECTRON DENSITY.
REMARK   8 THERE IS NO OTHER PATTERN OF DENSITY WARRANTING A SECOND
REMARK   8 POSITION FOR THE THUMB SUBDOMAIN.
REMARK 100
REMARK 100 THIS ENTRY HAS BEEN PROCESSED BY THE NUCLEIC ACID DATABASE
REMARK 100 ON 26-JAN-2004.
REMARK 100 THE NDB ID CODE IS PDE0124.
REMARK 105
REMARK 105 THE PROTEIN DATA BANK HAS ADOPTED THE SACCHARIDE CHEMISTS
REMARK 105 NOMENCLATURE FOR ATOMS OF THE DEOXYRIBOSE/RIBOSE MOIETY
REMARK 105 RATHER THAN THAT OF THE NUCLEOSIDE CHEMISTS. THE RING
REMARK 105 OXYGEN ATOM IS LABELLED O4* INSTEAD OF O1*.
REMARK 200
REMARK 200 EXPERIMENTAL DETAILS
REMARK 200  EXPERIMENT TYPE              : X-RAY DIFFRACTION
REMARK 200  DATE OF DATA COLLECTION      : 15-NOV-1996
REMARK 200  TEMPERATURE      (KELVIN)    : 100.0
REMARK 200  PH                           : 7.00
REMARK 200  NUMBER OF CRYSTALS USED      : 1
REMARK 200
REMARK 200  SYNCHROTRON         (Y/N)    : Y
REMARK 200  RADIATION SOURCE             : SSRL
REMARK 200  BEAMLINE                     : 7-1
REMARK 200  X-RAY GENERATOR MODEL        : NULL
REMARK 200  MONOCHROMATIC OR LAUE (M/L)  : M
REMARK 200  WAVELENGTH OR RANGE   (A)    : 1.0800
REMARK 200  MONOCHROMATOR                : SI(111) CRYSTAL
REMARK 200  OPTICS                       : MIRRORS
REMARK 200
REMARK 200  DETECTOR TYPE                : IMAGE PLATE
REMARK 200  DETECTOR MANUFACTURER        : MARRESEARCH
REMARK 200  INTENSITY-INTEGRATION SOFTWARE : DENZO
```

Figure 22D

```
REMARK 200  DATA SCALING SOFTWARE              : SCALEPACK
REMARK 200
REMARK 200  NUMBER OF UNIQUE REFLECTIONS       : 14702
REMARK 200  RESOLUTION RANGE HIGH        (A)   : 2.600
REMARK 200  RESOLUTION RANGE LOW         (A)   : 20.000
REMARK 200  REJECTION CRITERIA  (SIGMA(I))     : 0.000
REMARK 200
REMARK 200 OVERALL.
REMARK 200   COMPLETENESS FOR RANGE     (%)    : 94.0
REMARK 200   DATA REDUNDANCY                   : 2.900
REMARK 200   R MERGE                     (I)   : NULL
REMARK 200   R SYM                       (I)   : 0.07300
REMARK 200   <I/SIGMA(I)> FOR THE DATA SET     : NULL
REMARK 200
REMARK 200 IN THE HIGHEST RESOLUTION SHELL.
REMARK 200   HIGHEST RESOLUTION SHELL, RANGE HIGH (A) : 2.60
REMARK 200   HIGHEST RESOLUTION SHELL, RANGE LOW  (A) : 2.69
REMARK 200   COMPLETENESS FOR SHELL     (%)    : 95.6
REMARK 200   DATA REDUNDANCY IN SHELL          : NULL
REMARK 200   R MERGE FOR SHELL           (I)   : NULL
REMARK 200   R SYM FOR SHELL             (I)   : 0.34400
REMARK 200   <I/SIGMA(I)> FOR SHELL            : NULL
REMARK 200
REMARK 200 DIFFRACTION PROTOCOL: SINGLE WAVELENGTH
REMARK 200 METHOD USED TO DETERMINE THE STRUCTURE: MOLECULAR REPLACEMENT
REMARK 200 SOFTWARE USED: MERLOT
REMARK 200 STARTING MODEL: PDB ENTRY 9ICJ
REMARK 200
REMARK 200 REMARK: NULL
REMARK 280
REMARK 280 CRYSTAL
REMARK 280 SOLVENT CONTENT, VS   (%): 41.40
REMARK 280 MATTHEWS COEFFICIENT, VM (ANGSTROMS**3/DA): 2.10
REMARK 280
REMARK 280 CRYSTALLIZATION CONDITIONS: PH 7.00, VAPOR DIFFUSION
REMARK 290
REMARK 290 CRYSTALLOGRAPHIC SYMMETRY
REMARK 290 SYMMETRY OPERATORS FOR SPACE GROUP: P 1 21 1
REMARK 290
REMARK 290      SYMOP    SYMMETRY
REMARK 290      NNNMMM   OPERATOR
REMARK 290       1555    X,Y,Z
REMARK 290       2555    -X,1/2+Y,-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290    SMTRY1   1  1.000000  0.000000  0.000000        0.00000
REMARK 290    SMTRY2   1  0.000000  1.000000  0.000000        0.00000
REMARK 290    SMTRY3   1  0.000000  0.000000  1.000000        0.00000
REMARK 290    SMTRY1   2 -1.000000  0.000000  0.000000        0.00000
REMARK 290    SMTRY2   2  0.000000  1.000000  0.000000       39.32800
REMARK 290    SMTRY3   2  0.000000  0.000000 -1.000000        0.00000
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 4 CHAIN(S). SEE REMARK 350 FOR
```

Figure 22E

```
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: T, P, D, A
REMARK 350    BIOMT1   1  1.000000  0.000000  0.000000        0.00000
REMARK 350    BIOMT2   1  0.000000  1.000000  0.000000        0.00000
REMARK 350    BIOMT3   1  0.000000  0.000000  1.000000        0.00000
REMARK 465
REMARK 465 MISSING RESIDUES
REMARK 465 THE FOLLOWING RESIDUES WERE NOT LOCATED IN THE
REMARK 465 EXPERIMENT. (M=MODEL NUMBER; RES=RESIDUE NAME; C=CHAIN
REMARK 465 IDENTIFIER; SSSEQ=SEQUENCE NUMBER; I=INSERTION CODE.)
REMARK 465
REMARK 465   M RES C SSSEQI
REMARK 465     MET A    1
REMARK 465     SER A    2
REMARK 465     LYS A    3
REMARK 465     ARG A    4
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500  M RES CSSEQI ATM1   ATM2   ATM3
REMARK 500    GLN A    8   N  -  CA  -  C    ANGL. DEV. = 23.7 DEGREES
REMARK 650
REMARK 650 HELIX
REMARK 650 DETERMINATION METHOD: AUTHOR-DETERMINED
REMARK 650 HELICES C AND D FORM A HELIX-HAIRPIN-HELIX MOTIF.
REMARK 650 HELICES F AND G FORM A HELIX-HAIRPIN-HELIX MOTIF.
REMARK 700
REMARK 700 SHEET
REMARK 700 DETERMINATION METHOD: AUTHOR-DETERMINED
REMARK 800
REMARK 800 SITE
REMARK 800 SITE_IDENTIFIER: ACT
REMARK 800 SITE_DESCRIPTION: ACTIVE SITE OF NUCLEOTIDYL TRANSFER.
REMARK 900
REMARK 900 RELATED ENTRIES
REMARK 900 THIS ENTRY IS RELATED TO PDB ENTRIES 1BPX AND 1BPY.
REMARK 999
REMARK 999 SEQUENCE
REMARK 999 1BPZ   A    SWS      P06746       1 -     3 NOT IN ATOMS LIST
REMARK 999
REMARK 999 THE N-TERMINAL METHIONINE IS INCLUDED IN THE GENE SEQUENCE
REMARK 999 EVEN THOUGH IT IS REMOVED AFTER TRANSLATION IN THE CELL;
REMARK 999 SEE MATSUKAGE ET AL., J. BIOL. CHEM. 262, 8960, (1987).
```

Figure 22F

```
REMARK 999
REMARK 999 FOR THE COMPLETE SEQUENCES OF RAT AND HUMAN POLYMERASE
REMARK 999 BETA, SEE J.ITO AND J.K.BRAITHWAITE, NUC. ACIDS RES. 19,
REMARK 999 4045, (1991).
DBREF  1BPZ A    2   335  SWS    P06746   DPOB_HUMAN     1    334
SEQRES   1 A  335  MET SER LYS ARG LYS ALA PRO GLN GLU THR LEU ASN GLY
SEQRES   2 A  335  GLY ILE THR ASP MET LEU THR GLU LEU ALA ASN PHE GLU
SEQRES   3 A  335  LYS ASN VAL SER GLN ALA ILE HIS LYS TYR ASN ALA TYR
SEQRES   4 A  335  ARG LYS ALA ALA SER VAL ILE ALA LYS TYR PRO HIS LYS
SEQRES   5 A  335  ILE LYS SER GLY ALA GLU ALA LYS LYS LEU PRO GLY VAL
SEQRES   6 A  335  GLY THR LYS ILE ALA GLU LYS ILE ASP GLU PHE LEU ALA
SEQRES   7 A  335  THR GLY LYS LEU ARG LYS LEU GLU LYS ILE ARG GLN ASP
SEQRES   8 A  335  ASP THR SER SER SER ILE ASN PHE LEU THR ARG VAL SER
SEQRES   9 A  335  GLY ILE GLY PRO SER ALA ALA ARG LYS PHE VAL ASP GLU
SEQRES  10 A  335  GLY ILE LYS THR LEU GLU ASP LEU ARG LYS ASN GLU ASP
SEQRES  11 A  335  LYS LEU ASN HIS HIS GLN ARG ILE GLY LEU LYS TYR PHE
SEQRES  12 A  335  GLY ASP PHE GLU LYS ARG ILE PRO ARG GLU GLU MET LEU
SEQRES  13 A  335  GLN MET GLN ASP ILE VAL LEU ASN GLU VAL LYS LYS VAL
SEQRES  14 A  335  ASP SER GLU TYR ILE ALA THR VAL CYS GLY SER PHE ARG
SEQRES  15 A  335  ARG GLY ALA GLU SER GLY MET ASP VAL LEU LEU
SEQRES  16 A  335  THR HIS PRO SER PHE THR SER GLU SER THR LYS GLN PRO
SEQRES  17 A  335  LYS LEU LEU HIS GLN VAL VAL GLU GLN LEU GLN LYS VAL
SEQRES  18 A  335  HIS PHE ILE THR ASP THR LEU SER LYS GLY GLU THR LYS
SEQRES  19 A  335  PHE MET GLY VAL CYS GLN LEU PRO SER LYS ASN ASP GLU
SEQRES  20 A  335  LYS GLU TYR PRO HIS ARG ARG ILE ASP ILE ARG LEU ILE
SEQRES  21 A  335  PRO LYS ASP GLN TYR TYR CYS GLY VAL LEU TYR PHE THR
SEQRES  22 A  335  GLY SER ASP ILE PHE ASN LYS ASN MET ARG ALA HIS ALA
SEQRES  23 A  335  LEU GLU LYS GLY PHE THR ILE ASN GLU TYR THR ILE ARG
SEQRES  24 A  335  PRO LEU GLY VAL THR GLY VAL ALA GLY GLU PRO LEU PRO
SEQRES  25 A  335  VAL ASP SER GLU LYS ASP ILE PHE ASP TYR ILE GLN TRP
SEQRES  26 A  335  LYS TYR ARG GLU PRO LYS ASP ARG SER GLU
SEQRES   1 T   16    C   C   G     A   C     C     A   C     G     C     A     T     C
SEQRES   2 T   16    A   G   C
SEQRES   1 P   11    G   C   T     G   A     T     G   C     G     T     G
SEQRES   1 D    5    G   T   C     G   G
MODRES         G D    1          PHOSPHORYLATED 5'-TERMINUS
HET    NA     341    1
HET    NA     342    1
HETNAM     NA SODIUM ION
FORMUL  5   NA    2(NA1 1+)
FORMUL  7  HOH   *27(H2 O1)
HELIX    1   A GLY A   13  SER A   30  1                                  18
HELIX    2   B ILE A   33  LYS A   48  1                                  16
HELIX    3   C GLY A   56  LYS A   61  1                                   6
HELIX    4   D THR A   67  THR A   79  1SEE REMARK 650                    13
HELIX    5   E ARG A   83  GLN A   90  1                                   8
HELIX    6   F ASP A   92  ARG A  102  1                                  11
HELIX    7   G PRO A  108  ASP A  116  1SEE REMARK 650                     9
HELIX    8   H LEU A  122  LYS A  127  1                                   6
HELIX    9   I HIS A  134  GLU A  147  1                                  14
HELIX   10   J ARG A  152  VAL A  169  1                                  18
HELIX   11   K SER A  180  ARG A  183  1                                   4
HELIX   12   L PRO A  208  LYS A  220  1                                  13
HELIX   13   M LYS A  262  THR A  273  1                                  12
HELIX   14   N ASP A  276  GLU A  288  1                                  13
HELIX   15   O GLU A  316  ILE A  323  1                                   8
HELIX   16   P PRO A  330  ASP A  332  5                                   3
SHEET    1  S1 2 ILE A 150  PRO A 151  0
SHEET    2  S1 2 SER A 187  SER A 188 -1  N  SER A 188   O  ILE A 150
SHEET    1  S2 5 ILE A 174  CYS A 178  0
SHEET    2  S2 5 MET A 191  THR A 196 -1  N  THR A 196   O  ILE A 174
SHEET    3  S2 5 ARG A 253  ARG A 258  1  N  ASP A 256   O  MET A 191
SHEET    4  S2 5 LYS A 234  CYS A 239 -1  N  CYS A 239   O  ARG A 253
```

Figure 22G

```
SHEET    5  S2 5 SER A 229  GLY A 231 -1  O  SER A 229   N  MET A 236
SHEET    1  S3 2 PHE A 291  ASN A 294  0
SHEET    2  S3 2 THR A 297  PRO A 300 -1  N  ARG A 299   O  THR A 292
CISPEP   1 GLY A  274    SER A  275          0          0.48
SITE     1 ACT  3 ASP A 190  ASP A 192  ASP A 256
CRYST1   53.535   78.656   54.618  90.00 107.54  90.00 P 1 21 1      2
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.018679  0.000000  0.005904        0.00000
SCALE2      0.000000  0.012714  0.000000        0.00000
SCALE3      0.000000  0.000000  0.019202        0.00000
ATOM      1  N   LYS A   5      12.782 -12.603   0.239  1.00100.00           N
ATOM      2  CA  LYS A   5      13.243 -13.795   0.974  1.00100.00           C
ATOM      3  C   LYS A   5      14.480 -13.501   1.889  1.00100.00           C
ATOM      4  O   LYS A   5      15.497 -12.986   1.394  1.00100.00           O
ATOM      5  CB  LYS A   5      13.483 -14.979   0.017  1.00100.00           C
ATOM      6  CG  LYS A   5      13.900 -16.272   0.717  1.00100.00           C
ATOM      7  CD  LYS A   5      14.332 -17.354  -0.265  1.00100.00           C
ATOM      8  CE  LYS A   5      14.524 -18.745   0.360  1.00100.00           C
ATOM      9  NZ  LYS A   5      15.840 -18.988   0.996  1.00100.00           N
ATOM     10  N   ALA A   6      14.390 -13.836   3.227  1.00100.00           N
ATOM     11  CA  ALA A   6      15.478 -13.626   4.224  1.00100.00           C
ATOM     12  C   ALA A   6      15.547 -14.717   5.353  1.00100.00           C
ATOM     13  O   ALA A   6      14.595 -14.884   6.160  1.00 99.48           O
ATOM     14  CB  ALA A   6      15.499 -12.171   4.733  1.00 97.95           C
ATOM     15  N   PRO A   7      16.706 -15.454   5.369  1.00 99.81           N
ATOM     16  CA  PRO A   7      17.094 -16.584   6.273  1.00100.00           C
ATOM     17  C   PRO A   7      17.705 -16.104   7.573  1.00100.00           C
ATOM     18  O   PRO A   7      17.069 -16.017   8.625  1.00100.00           O
ATOM     19  CB  PRO A   7      18.258 -17.255   5.512  1.00 97.85           C
ATOM     20  CG  PRO A   7      18.612 -16.394   4.281  1.00 95.58           C
ATOM     21  CD  PRO A   7      17.761 -15.143   4.349  1.00 96.76           C
ATOM     22  N   GLN A   8      19.004 -15.842   7.377  1.00100.00           N
ATOM     23  CA  GLN A   8      20.124 -15.320   8.190  1.00100.00           C
ATOM     24  C   GLN A   8      20.678 -15.618   9.589  1.00 95.36           C
ATOM     25  O   GLN A   8      21.764 -15.031   9.833  1.00 98.07           O
ATOM     26  CB  GLN A   8      19.881 -13.818   8.177  1.00100.00           C
ATOM     27  CG  GLN A   8      18.576 -13.519   8.907  1.00100.00           C
ATOM     28  CD  GLN A   8      18.030 -12.230   8.486  1.00100.00           C
ATOM     29  OE1 GLN A   8      17.248 -11.618   9.242  1.00100.00           O
ATOM     30  NE2 GLN A   8      18.351 -11.693   7.323  1.00100.00           N
ATOM     31  N   GLU A   9      20.109 -16.506  10.585  1.00 93.14           N
ATOM     32  CA  GLU A   9      20.825 -16.400  11.891  1.00 99.05           C
ATOM     33  C   GLU A   9      22.211 -17.017  12.039  1.00100.00           C
ATOM     34  O   GLU A   9      23.236 -16.328  12.022  1.00 99.53           O
ATOM     35  CB  GLU A   9      20.033 -16.196  13.180  1.00100.00           C
ATOM     36  CG  GLU A   9      19.776 -14.576  13.333  1.00100.00           C
ATOM     37  CD  GLU A   9      19.508 -14.057  14.749  1.00100.00           C
ATOM     38  OE1 GLU A   9      19.566 -14.861  15.702  1.00100.00           O
ATOM     39  OE2 GLU A   9      19.234 -12.809  14.888  1.00100.00           O
ATOM     40  N   THR A  10      22.252 -18.356  12.176  1.00100.00           N
ATOM     41  CA  THR A  10      23.512 -19.099  12.306  1.00100.00           C
ATOM     42  C   THR A  10      24.433 -18.934  11.079  1.00 97.06           C
ATOM     43  O   THR A  10      25.562 -19.457  10.992  1.00 99.36           O
ATOM     44  CB  THR A  10      23.212 -20.565  12.606  1.00100.00           C
ATOM     45  OG1 THR A  10      24.330 -21.368  12.238  1.00100.00           O
ATOM     46  CG2 THR A  10      21.943 -20.940  11.854  1.00 97.16           C
ATOM     47  N   LEU A  11      23.881 -18.172  10.122  1.00 89.47           N
ATOM     48  CA  LEU A  11      24.441 -17.793   8.861  1.00 70.78           C
ATOM     49  C   LEU A  11      25.455 -16.669   8.996  1.00 63.20           C
ATOM     50  O   LEU A  11      26.639 -16.959   9.135  1.00 64.96           O
ATOM     51  CB  LEU A  11      23.339 -17.300   7.901  1.00 66.21           C
```

Figure 22H

```
ATOM     52  CG  LEU A  11      23.036 -18.275   6.774  1.00 68.10           C
ATOM     53  CD1 LEU A  11      22.086 -17.606   5.757  1.00 64.59           C
ATOM     54  CD2 LEU A  11      24.367 -18.737   6.153  1.00 70.53           C
ATOM     55  N   ASN A  12      24.985 -15.444   8.963  1.00 66.00           N
ATOM     56  CA  ASN A  12      25.907 -14.327   9.070  1.00 62.33           C
ATOM     57  C   ASN A  12      25.883 -13.428  10.284  1.00 52.67           C
ATOM     58  O   ASN A  12      26.745 -12.571  10.402  1.00 41.22           O
ATOM     59  CB  ASN A  12      25.798 -13.489   7.779  1.00 57.64           C
ATOM     60  CG  ASN A  12      26.146 -14.322   6.568  1.00 37.99           C
ATOM     61  OD1 ASN A  12      25.254 -14.519   5.714  1.00 30.35           O
ATOM     62  ND2 ASN A  12      27.411 -14.782   6.526  1.00 22.53           N
ATOM     63  N   GLY A  13      24.912 -13.649  11.174  1.00 49.53           N
ATOM     64  CA  GLY A  13      24.732 -12.886  12.392  1.00 33.45           C
ATOM     65  C   GLY A  13      25.971 -12.354  13.083  1.00 32.97           C
ATOM     66  O   GLY A  13      25.946 -11.189  13.503  1.00 32.06           O
ATOM     67  N   GLY A  14      27.032 -13.166  13.216  1.00 32.28           N
ATOM     68  CA  GLY A  14      28.247 -12.674  13.890  1.00 34.11           C
ATOM     69  C   GLY A  14      28.725 -11.364  13.287  1.00 43.48           C
ATOM     70  O   GLY A  14      28.921 -10.356  13.980  1.00 46.82           O
ATOM     71  N   ILE A  15      28.888 -11.450  11.959  1.00 37.89           N
ATOM     72  CA  ILE A  15      29.316 -10.395  11.093  1.00 28.10           C
ATOM     73  C   ILE A  15      28.362  -9.239  11.206  1.00 25.02           C
ATOM     74  O   ILE A  15      28.760  -8.133  11.483  1.00 29.15           O
ATOM     75  CB  ILE A  15      29.381 -10.896   9.629  1.00 26.04           C
ATOM     76  CG1 ILE A  15      30.578 -11.822   9.409  1.00 28.39           C
ATOM     77  CG2 ILE A  15      29.533  -9.747   8.658  1.00 19.63           C
ATOM     78  CD1 ILE A  15      30.504 -12.534   8.054  1.00 21.40           C
ATOM     79  N   THR A  16      27.109  -9.522  10.986  1.00 20.23           N
ATOM     80  CA  THR A  16      26.048  -8.549  11.038  1.00 27.24           C
ATOM     81  C   THR A  16      25.916  -7.833  12.369  1.00 41.12           C
ATOM     82  O   THR A  16      25.304  -6.785  12.503  1.00 45.15           O
ATOM     83  CB  THR A  16      24.790  -9.335  10.865  1.00 37.69           C
ATOM     84  OG1 THR A  16      25.189 -10.525  10.220  1.00 53.42           O
ATOM     85  CG2 THR A  16      23.844  -8.573   9.961  1.00 39.57           C
ATOM     86  N   ASP A  17      26.440  -8.430  13.394  1.00 41.20           N
ATOM     87  CA  ASP A  17      26.331  -7.806  14.645  1.00 32.95           C
ATOM     88  C   ASP A  17      27.532  -6.943  14.953  1.00 29.16           C
ATOM     89  O   ASP A  17      27.378  -5.842  15.451  1.00 40.77           O
ATOM     90  CB  ASP A  17      25.844  -8.733  15.743  1.00 45.39           C
ATOM     91  CG  ASP A  17      24.501  -9.314  15.452  1.00 54.72           C
ATOM     92  OD1 ASP A  17      23.707  -8.862  14.647  1.00 65.14           O
ATOM     93  OD2 ASP A  17      24.307 -10.387  16.160  1.00 56.84           O
ATOM     94  N   MET A  18      28.713  -7.444  14.676  1.00 18.69           N
ATOM     95  CA  MET A  18      29.917  -6.663  14.900  1.00 31.20           C
ATOM     96  C   MET A  18      29.762  -5.358  14.110  1.00 33.26           C
ATOM     97  O   MET A  18      30.269  -4.309  14.456  1.00 39.25           O
ATOM     98  CB  MET A  18      31.170  -7.332  14.265  1.00 39.44           C
ATOM     99  CG  MET A  18      31.248  -7.157  12.723  1.00 34.17           C
ATOM    100  SD  MET A  18      32.850  -7.661  11.999  1.00 40.09           S
ATOM    101  CE  MET A  18      33.993  -6.942  13.191  1.00 32.32           C
ATOM    102  N   LEU A  19      29.040  -5.475  13.004  1.00 30.65           N
ATOM    103  CA  LEU A  19      28.774  -4.390  12.114  1.00 31.00           C
ATOM    104  C   LEU A  19      27.928  -3.338  12.757  1.00 41.95           C
ATOM    105  O   LEU A  19      28.298  -2.168  12.799  1.00 50.55           O
ATOM    106  CB  LEU A  19      28.034  -4.821  10.860  1.00 30.40           C
ATOM    107  CG  LEU A  19      28.879  -5.408   9.746  1.00 28.38           C
ATOM    108  CD1 LEU A  19      28.113  -4.986   8.495  1.00 26.72           C
ATOM    109  CD2 LEU A  19      30.321  -4.855   9.761  1.00 19.71           C
ATOM    110  N   THR A  20      26.771  -3.757  13.244  1.00 41.66           N
ATOM    111  CA  THR A  20      25.852  -2.858  13.913  1.00 33.06           C
ATOM    112  C   THR A  20      26.492  -2.291  15.133  1.00 27.66           C
ATOM    113  O   THR A  20      26.102  -1.263  15.591  1.00 25.98           O
ATOM    114  CB  THR A  20      24.561  -3.524  14.251  1.00 31.61           C
```

Figure 22I

| ATOM | 115 | OG1 | THR | A | 20 | 23.918 | -3.781 | 13.021 | 1.00 | 38.00 | O |
| ATOM | 116 | CG2 | THR | A | 20 | 23.718 | -2.638 | 15.155 | 1.00 | 29.16 | C |
| ATOM | 117 | N | GLU | A | 21 | 27.474 | -2.975 | 15.650 | 1.00 | 29.48 | N |
| ATOM | 118 | CA | GLU | A | 21 | 28.113 | -2.463 | 16.809 | 1.00 | 32.53 | C |
| ATOM | 119 | C | GLU | A | 21 | 28.771 | -1.210 | 16.353 | 1.00 | 41.06 | C |
| ATOM | 120 | O | GLU | A | 21 | 28.618 | -0.099 | 16.926 | 1.00 | 48.74 | O |
| ATOM | 121 | CB | GLU | A | 21 | 29.162 | -3.407 | 17.353 | 1.00 | 36.83 | C |
| ATOM | 122 | CG | GLU | A | 21 | 29.625 | -2.927 | 18.726 | 1.00 | 54.91 | C |
| ATOM | 123 | CD | GLU | A | 21 | 29.838 | -4.037 | 19.709 | 1.00 | 63.00 | C |
| ATOM | 124 | OE1 | GLU | A | 21 | 29.137 | -5.117 | 19.423 | 1.00 | 65.31 | O |
| ATOM | 125 | OE2 | GLU | A | 21 | 30.568 | -3.911 | 20.683 | 1.00 | 65.18 | O |
| ATOM | 126 | N | LEU | A | 22 | 29.499 | -1.481 | 15.270 | 1.00 | 39.63 | N |
| ATOM | 127 | CA | LEU | A | 22 | 30.295 | -0.530 | 14.508 | 1.00 | 37.39 | C |
| ATOM | 128 | C | LEU | A | 22 | 29.521 | 0.770 | 14.128 | 1.00 | 32.91 | C |
| ATOM | 129 | O | LEU | A | 22 | 29.995 | 1.846 | 14.292 | 1.00 | 33.40 | O |
| ATOM | 130 | CB | LEU | A | 22 | 30.907 | -1.333 | 13.335 | 1.00 | 37.37 | C |
| ATOM | 131 | CG | LEU | A | 22 | 32.400 | -1.626 | 13.574 | 1.00 | 40.35 | C |
| ATOM | 132 | CD1 | LEU | A | 22 | 32.785 | -1.707 | 15.053 | 1.00 | 31.96 | C |
| ATOM | 133 | CD2 | LEU | A | 22 | 32.930 | -2.815 | 12.770 | 1.00 | 39.87 | C |
| ATOM | 134 | N | ALA | A | 23 | 28.315 | 0.630 | 13.652 | 1.00 | 26.90 | N |
| ATOM | 135 | CA | ALA | A | 23 | 27.426 | 1.651 | 13.252 | 1.00 | 26.62 | C |
| ATOM | 136 | C | ALA | A | 23 | 27.040 | 2.601 | 14.369 | 1.00 | 43.57 | C |
| ATOM | 137 | O | ALA | A | 23 | 27.175 | 3.852 | 14.260 | 1.00 | 46.29 | O |
| ATOM | 138 | CB | ALA | A | 23 | 26.131 | 0.936 | 12.817 | 1.00 | 18.54 | C |
| ATOM | 139 | N | ASN | A | 24 | 26.520 | 1.960 | 15.441 | 1.00 | 45.10 | N |
| ATOM | 140 | CA | ASN | A | 24 | 26.060 | 2.662 | 16.608 | 1.00 | 36.27 | C |
| ATOM | 141 | C | ASN | A | 24 | 27.173 | 3.485 | 17.086 | 1.00 | 25.36 | C |
| ATOM | 142 | O | ASN | A | 24 | 27.032 | 4.683 | 17.323 | 1.00 | 26.84 | O |
| ATOM | 143 | CB | ASN | A | 24 | 25.560 | 1.748 | 17.734 | 1.00 | 45.12 | C |
| ATOM | 144 | CG | ASN | A | 24 | 24.200 | 1.149 | 17.407 | 1.00 | 58.87 | C |
| ATOM | 145 | OD1 | ASN | A | 24 | 23.316 | 1.806 | 16.805 | 1.00 | 59.38 | O |
| ATOM | 146 | ND2 | ASN | A | 24 | 24.036 | -0.124 | 17.783 | 1.00 | 63.94 | N |
| ATOM | 147 | N | PHE | A | 25 | 28.315 | 2.843 | 17.196 | 1.00 | 8.80 | N |
| ATOM | 148 | CA | PHE | A | 25 | 29.477 | 3.586 | 17.682 | 1.00 | 12.87 | C |
| ATOM | 149 | C | PHE | A | 25 | 29.824 | 4.854 | 16.988 | 1.00 | 34.05 | C |
| ATOM | 150 | O | PHE | A | 25 | 30.196 | 5.797 | 17.656 | 1.00 | 43.30 | O |
| ATOM | 151 | CB | PHE | A | 25 | 30.654 | 2.703 | 17.437 | 1.00 | 11.15 | C |
| ATOM | 152 | CG | PHE | A | 25 | 31.998 | 3.254 | 17.746 | 1.00 | 30.53 | C |
| ATOM | 153 | CD1 | PHE | A | 25 | 32.690 | 4.084 | 16.873 | 1.00 | 43.19 | C |
| ATOM | 154 | CD2 | PHE | A | 25 | 32.617 | 2.876 | 18.935 | 1.00 | 48.99 | C |
| ATOM | 155 | CE1 | PHE | A | 25 | 33.971 | 4.546 | 17.185 | 1.00 | 52.57 | C |
| ATOM | 156 | CE2 | PHE | A | 25 | 33.885 | 3.331 | 19.272 | 1.00 | 53.37 | C |
| ATOM | 157 | CZ | PHE | A | 25 | 34.561 | 4.174 | 18.386 | 1.00 | 53.89 | C |
| ATOM | 158 | N | GLU | A | 26 | 29.746 | 4.806 | 15.640 | 1.00 | 42.14 | N |
| ATOM | 159 | CA | GLU | A | 26 | 30.038 | 5.894 | 14.692 | 1.00 | 43.75 | C |
| ATOM | 160 | C | GLU | A | 26 | 29.018 | 6.999 | 14.891 | 1.00 | 36.61 | C |
| ATOM | 161 | O | GLU | A | 26 | 29.345 | 8.173 | 14.970 | 1.00 | 33.53 | O |
| ATOM | 162 | CB | GLU | A | 26 | 30.079 | 5.411 | 13.197 | 1.00 | 42.10 | C |
| ATOM | 163 | CG | GLU | A | 26 | 31.229 | 4.426 | 12.835 | 1.00 | 36.94 | C |
| ATOM | 164 | CD | GLU | A | 26 | 32.544 | 5.108 | 12.623 | 1.00 | 45.16 | C |
| ATOM | 165 | OE1 | GLU | A | 26 | 32.420 | 6.112 | 11.810 | 1.00 | 50.82 | O |
| ATOM | 166 | OE2 | GLU | A | 26 | 33.598 | 4.796 | 13.169 | 1.00 | 51.53 | O |
| ATOM | 167 | N | LYS | A | 27 | 27.776 | 6.575 | 14.976 | 1.00 | 27.80 | N |
| ATOM | 168 | CA | LYS | A | 27 | 26.689 | 7.509 | 15.189 | 1.00 | 30.66 | C |
| ATOM | 169 | C | LYS | A | 27 | 26.980 | 8.314 | 16.464 | 1.00 | 44.45 | C |
| ATOM | 170 | O | LYS | A | 27 | 27.486 | 9.451 | 16.428 | 1.00 | 47.48 | O |
| ATOM | 171 | CB | LYS | A | 27 | 25.466 | 6.670 | 15.450 | 1.00 | 17.06 | C |
| ATOM | 172 | CG | LYS | A | 27 | 24.217 | 7.472 | 15.475 | 1.00 | 22.30 | C |
| ATOM | 173 | CD | LYS | A | 27 | 22.919 | 6.630 | 15.424 | 1.00 | 33.95 | C |
| ATOM | 174 | CE | LYS | A | 27 | 22.603 | 5.826 | 16.691 | 1.00 | 46.35 | C |
| ATOM | 175 | NZ | LYS | A | 27 | 21.155 | 5.662 | 16.947 | 1.00 | 50.69 | N |
| ATOM | 176 | N | ASN | A | 28 | 26.638 | 7.620 | 17.574 | 1.00 | 43.67 | N |
| ATOM | 177 | CA | ASN | A | 28 | 26.709 | 7.959 | 18.995 | 1.00 | 28.18 | C |

Figure 22J

```
ATOM    178  C   ASN A  28      27.994   8.577  19.467  1.00 36.04           C
ATOM    179  O   ASN A  28      27.977   9.646  20.063  1.00 51.88           O
ATOM    180  CB  ASN A  28      26.487   6.720  19.858  1.00  9.15           C
ATOM    181  CG  ASN A  28      25.245   5.943  19.475  1.00 23.52           C
ATOM    182  OD1 ASN A  28      25.173   4.700  19.694  1.00 32.13           O
ATOM    183  ND2 ASN A  28      24.252   6.679  18.933  1.00 20.32           N
ATOM    184  N   VAL A  29      29.094   7.931  19.227  1.00 18.45           N
ATOM    185  CA  VAL A  29      30.334   8.485  19.686  1.00 20.26           C
ATOM    186  C   VAL A  29      31.268   9.105  18.662  1.00 43.71           C
ATOM    187  O   VAL A  29      32.278   9.739  18.978  1.00 45.45           O
ATOM    188  CB  VAL A  29      30.983   7.280  20.173  1.00 16.41           C
ATOM    189  CG1 VAL A  29      32.329   7.575  20.788  1.00 14.37           C
ATOM    190  CG2 VAL A  29      29.972   6.704  21.145  1.00 22.29           C
ATOM    191  N   SER A  30      30.982   8.922  17.399  1.00 59.51           N
ATOM    192  CA  SER A  30      31.884   9.520  16.427  1.00 56.06           C
ATOM    193  C   SER A  30      31.271  10.721  15.759  1.00 47.41           C
ATOM    194  O   SER A  30      31.953  11.684  15.458  1.00 42.38           O
ATOM    195  CB  SER A  30      32.473   8.506  15.469  1.00 57.52           C
ATOM    196  OG  SER A  30      33.573   7.902  16.137  1.00 62.32           O
ATOM    197  N   GLN A  31      29.958  10.590  15.582  1.00 46.88           N
ATOM    198  CA  GLN A  31      29.067  11.536  14.979  1.00 50.04           C
ATOM    199  C   GLN A  31      29.087  11.522  13.469  1.00 53.03           C
ATOM    200  O   GLN A  31      28.948  12.563  12.809  1.00 57.59           O
ATOM    201  CB  GLN A  31      29.010  12.918  15.610  1.00 57.25           C
ATOM    202  CG  GLN A  31      28.934  12.805  17.145  1.00 62.24           C
ATOM    203  CD  GLN A  31      28.597  14.106  17.838  1.00 58.72           C
ATOM    204  OE1 GLN A  31      27.499  14.680  17.640  1.00 61.40           O
ATOM    205  NE2 GLN A  31      29.576  14.588  18.601  1.00 50.67           N
ATOM    206  N   ALA A  32      29.259  10.295  12.957  1.00 40.80           N
ATOM    207  CA  ALA A  32      29.289   9.996  11.557  1.00 27.70           C
ATOM    208  C   ALA A  32      28.001   9.359  11.127  1.00 22.71           C
ATOM    209  O   ALA A  32      27.926   8.176  10.985  1.00 32.99           O
ATOM    210  CB  ALA A  32      30.451   9.081  11.225  1.00 29.99           C
ATOM    211  N   ILE A  33      26.978  10.114  10.916  1.00 20.25           N
ATOM    212  CA  ILE A  33      25.778   9.505  10.508  1.00 27.61           C
ATOM    213  C   ILE A  33      25.910   8.806   9.174  1.00 40.45           C
ATOM    214  O   ILE A  33      25.228   7.871   8.821  1.00 53.09           O
ATOM    215  CB  ILE A  33      24.795  10.606  10.338  1.00 35.14           C
ATOM    216  CG1 ILE A  33      24.666  11.302  11.678  1.00 61.68           C
ATOM    217  CG2 ILE A  33      23.448  10.000   9.981  1.00 29.75           C
ATOM    218  CD1 ILE A  33      25.704  12.391  11.976  1.00 74.90           C
ATOM    219  N   HIS A  34      26.789   9.285   8.362  1.00 41.50           N
ATOM    220  CA  HIS A  34      26.940   8.679   7.061  1.00 26.94           C
ATOM    221  C   HIS A  34      27.666   7.421   7.210  1.00 22.33           C
ATOM    222  O   HIS A  34      27.258   6.402   6.720  1.00 39.64           O
ATOM    223  CB  HIS A  34      27.652   9.641   6.111  1.00 30.17           C
ATOM    224  CG  HIS A  34      26.788  10.834   5.893  1.00 29.35           C
ATOM    225  ND1 HIS A  34      25.460  10.655   5.487  1.00 26.45           N
ATOM    226  CD2 HIS A  34      27.056  12.163   6.059  1.00 22.68           C
ATOM    227  CE1 HIS A  34      24.925  11.876   5.390  1.00 25.56           C
ATOM    228  NE2 HIS A  34      25.862  12.797   5.726  1.00 30.76           N
ATOM    229  N   LYS A  35      28.767   7.499   7.895  1.00 11.36           N
ATOM    230  CA  LYS A  35      29.539   6.310   8.132  1.00 12.14           C
ATOM    231  C   LYS A  35      28.662   5.271   8.917  1.00 31.10           C
ATOM    232  O   LYS A  35      28.741   4.047   8.842  1.00 47.23           O
ATOM    233  CB  LYS A  35      30.701   6.611   9.007  1.00  6.31           C
ATOM    234  CG  LYS A  35      31.942   7.170   8.379  1.00  4.47           C
ATOM    235  CD  LYS A  35      33.131   6.631   9.172  1.00  2.23           C
ATOM    236  CE  LYS A  35      34.446   7.271   8.828  1.00 16.97           C
ATOM    237  NZ  LYS A  35      35.611   6.703   9.578  1.00 32.12           N
ATOM    238  N   TYR A  36      27.811   5.777   9.732  1.00 31.37           N
ATOM    239  CA  TYR A  36      26.969   4.954  10.490  1.00 27.87           C
ATOM    240  C   TYR A  36      26.045   4.250   9.540  1.00 23.55           C
```

Figure 22K

| | | | | | | | | | | |
|---|---|---|---|---|---|---|---|---|---|---|
| ATOM | 241 | O | TYR | A | 36 | 25.894 | 3.054 | 9.593 | 1.00 30.51 | O |
| ATOM | 242 | CB | TYR | A | 36 | 26.176 | 5.819 | 11.550 | 1.00 24.83 | C |
| ATOM | 243 | CG | TYR | A | 36 | 24.858 | 5.194 | 11.982 | 1.00 10.61 | C |
| ATOM | 244 | CD1 | TYR | A | 36 | 24.748 | 4.181 | 12.930 | 1.00 17.39 | C |
| ATOM | 245 | CD2 | TYR | A | 36 | 23.707 | 5.657 | 11.395 | 1.00 3.19 | C |
| ATOM | 246 | CE1 | TYR | A | 36 | 23.494 | 3.651 | 13.259 | 1.00 17.64 | C |
| ATOM | 247 | CE2 | TYR | A | 36 | 22.433 | 5.146 | 11.683 | 1.00 1.52 | C |
| ATOM | 248 | CZ | TYR | A | 36 | 22.353 | 4.129 | 12.640 | 1.00 17.32 | C |
| ATOM | 249 | OH | TYR | A | 36 | 21.113 | 3.677 | 12.909 | 1.00 35.60 | O |
| ATOM | 250 | N | ASN | A | 37 | 25.412 | 5.015 | 8.681 | 1.00 25.55 | N |
| ATOM | 251 | CA | ASN | A | 37 | 24.457 | 4.492 | 7.707 | 1.00 37.77 | C |
| ATOM | 252 | C | ASN | A | 37 | 25.068 | 3.480 | 6.735 | 1.00 46.46 | C |
| ATOM | 253 | O | ASN | A | 37 | 24.388 | 2.610 | 6.184 | 1.00 51.83 | O |
| ATOM | 254 | CB | ASN | A | 37 | 23.815 | 5.584 | 6.888 | 1.00 45.42 | C |
| ATOM | 255 | CG | ASN | A | 37 | 22.814 | 6.478 | 7.591 | 1.00 53.92 | C |
| ATOM | 256 | OD1 | ASN | A | 37 | 23.139 | 7.647 | 7.896 | 1.00 63.46 | O |
| ATOM | 257 | ND2 | ASN | A | 37 | 21.537 | 6.104 | 7.499 | 1.00 49.28 | N |
| ATOM | 258 | N | ALA | A | 38 | 26.364 | 3.620 | 6.495 | 1.00 38.35 | N |
| ATOM | 259 | CA | ALA | A | 38 | 27.030 | 2.734 | 5.613 | 1.00 34.98 | C |
| ATOM | 260 | C | ALA | A | 38 | 26.887 | 1.332 | 6.227 | 1.00 39.74 | C |
| ATOM | 261 | O | ALA | A | 38 | 26.130 | 0.465 | 5.737 | 1.00 43.97 | O |
| ATOM | 262 | CB | ALA | A | 38 | 28.495 | 3.167 | 5.610 | 1.00 34.84 | C |
| ATOM | 263 | N | TYR | A | 39 | 27.630 | 1.169 | 7.336 | 1.00 36.80 | N |
| ATOM | 264 | CA | TYR | A | 39 | 27.706 | -0.025 | 8.169 | 1.00 26.45 | C |
| ATOM | 265 | C | TYR | A | 39 | 26.329 | -0.581 | 8.290 | 1.00 28.98 | C |
| ATOM | 266 | O | TYR | A | 39 | 26.086 | -1.770 | 8.270 | 1.00 33.22 | O |
| ATOM | 267 | CB | TYR | A | 39 | 28.148 | 0.434 | 9.481 | 1.00 11.00 | C |
| ATOM | 268 | CG | TYR | A | 39 | 29.646 | 0.499 | 9.597 | 1.00 12.55 | C |
| ATOM | 269 | CD1 | TYR | A | 39 | 30.327 | -0.677 | 9.369 | 1.00 12.22 | C |
| ATOM | 270 | CD2 | TYR | A | 39 | 30.401 | 1.617 | 9.972 | 1.00 11.12 | C |
| ATOM | 271 | CE1 | TYR | A | 39 | 31.712 | -0.766 | 9.500 | 1.00 16.18 | C |
| ATOM | 272 | CE2 | TYR | A | 39 | 31.791 | 1.551 | 10.118 | 1.00 14.24 | C |
| ATOM | 273 | CZ | TYR | A | 39 | 32.452 | 0.339 | 9.881 | 1.00 18.48 | C |
| ATOM | 274 | OH | TYR | A | 39 | 33.812 | 0.165 | 9.973 | 1.00 26.06 | O |
| ATOM | 275 | N | ARG | A | 40 | 25.394 | 0.309 | 8.383 | 1.00 32.89 | N |
| ATOM | 276 | CA | ARG | A | 40 | 24.075 | -0.218 | 8.450 | 1.00 42.38 | C |
| ATOM | 277 | C | ARG | A | 40 | 23.727 | -0.931 | 7.185 | 1.00 42.83 | C |
| ATOM | 278 | O | ARG | A | 40 | 23.411 | -2.100 | 7.339 | 1.00 37.48 | O |
| ATOM | 279 | CB | ARG | A | 40 | 22.940 | 0.535 | 9.125 | 1.00 54.45 | C |
| ATOM | 280 | CG | ARG | A | 40 | 23.194 | 2.003 | 9.463 | 1.00 73.04 | C |
| ATOM | 281 | CD | ARG | A | 40 | 21.906 | 2.688 | 9.953 | 1.00 84.65 | C |
| ATOM | 282 | NE | ARG | A | 40 | 21.063 | 1.803 | 10.776 | 1.00 93.31 | N |
| ATOM | 283 | CZ | ARG | A | 40 | 19.744 | 1.947 | 11.015 | 1.00 94.05 | C |
| ATOM | 284 | NH1 | ARG | A | 40 | 19.024 | 2.953 | 10.500 | 1.00 94.80 | N |
| ATOM | 285 | NH2 | ARG | A | 40 | 19.126 | 1.037 | 11.785 | 1.00 87.80 | N |
| ATOM | 286 | N | LYS | A | 41 | 23.844 | -0.271 | 5.979 | 1.00 51.87 | N |
| ATOM | 287 | CA | LYS | A | 41 | 23.524 | -0.915 | 4.649 | 1.00 42.23 | C |
| ATOM | 288 | C | LYS | A | 41 | 24.262 | -2.255 | 4.430 | 1.00 23.55 | C |
| ATOM | 289 | O | LYS | A | 41 | 23.678 | -3.274 | 4.032 | 1.00 17.88 | O |
| ATOM | 290 | CB | LYS | A | 41 | 23.328 | -0.013 | 3.408 | 1.00 37.54 | C |
| ATOM | 291 | CG | LYS | A | 41 | 24.316 | -0.203 | 2.242 | 1.00 40.61 | C |
| ATOM | 292 | CD | LYS | A | 41 | 25.568 | 0.720 | 2.200 | 1.00 48.18 | C |
| ATOM | 293 | CE | LYS | A | 41 | 26.811 | 0.301 | 3.007 | 1.00 42.96 | C |
| ATOM | 294 | NZ | LYS | A | 41 | 28.063 | 0.939 | 2.550 | 1.00 41.99 | N |
| ATOM | 295 | N | ALA | A | 42 | 25.543 | -2.181 | 4.764 | 1.00 8.40 | N |
| ATOM | 296 | CA | ALA | A | 42 | 26.438 | -3.283 | 4.701 | 1.00 10.81 | C |
| ATOM | 297 | C | ALA | A | 42 | 25.742 | -4.418 | 5.444 | 1.00 37.29 | C |
| ATOM | 298 | O | ALA | A | 42 | 25.133 | -5.250 | 4.786 | 1.00 50.08 | O |
| ATOM | 299 | CB | ALA | A | 42 | 27.776 | -2.803 | 5.311 | 1.00 3.99 | C |
| ATOM | 300 | N | ALA | A | 43 | 25.771 | -4.400 | 6.785 | 1.00 44.74 | N |
| ATOM | 301 | CA | ALA | A | 43 | 25.160 | -5.378 | 7.679 | 1.00 25.86 | C |
| ATOM | 302 | C | ALA | A | 43 | 23.805 | -5.810 | 7.144 | 1.00 27.05 | C |
| ATOM | 303 | O | ALA | A | 43 | 23.432 | -6.973 | 7.130 | 1.00 32.29 | O |

Figure 22L

```
ATOM    304  CB  ALA A  43      24.923  -4.584   8.923  1.00 22.67           C
ATOM    305  N   SER A  44      23.036  -4.874   6.670  1.00 21.84           N
ATOM    306  CA  SER A  44      21.761  -5.294   6.164  1.00 37.84           C
ATOM    307  C   SER A  44      21.892  -6.191   4.938  1.00 39.61           C
ATOM    308  O   SER A  44      21.256  -7.252   4.841  1.00 37.15           O
ATOM    309  CB  SER A  44      20.885  -4.119   5.795  1.00 52.38           C
ATOM    310  OG  SER A  44      21.448  -3.559   4.609  1.00 67.57           O
ATOM    311  N   VAL A  45      22.706  -5.748   3.979  1.00 38.35           N
ATOM    312  CA  VAL A  45      22.879  -6.550   2.748  1.00 33.57           C
ATOM    313  C   VAL A  45      23.343  -7.934   3.111  1.00 39.62           C
ATOM    314  O   VAL A  45      22.729  -8.907   2.642  1.00 42.20           O
ATOM    315  CB  VAL A  45      23.706  -5.897   1.659  1.00 18.85           C
ATOM    316  CG1 VAL A  45      23.210  -4.464   1.543  1.00 32.05           C
ATOM    317  CG2 VAL A  45      25.170  -5.833   2.033  1.00  9.36           C
ATOM    318  N   ILE A  46      24.398  -7.990   3.967  1.00 33.56           N
ATOM    319  CA  ILE A  46      24.863  -9.274   4.383  1.00 32.11           C
ATOM    320  C   ILE A  46      23.752 -10.029   5.128  1.00 38.31           C
ATOM    321  O   ILE A  46      23.681 -11.247   5.104  1.00 52.23           O
ATOM    322  CB  ILE A  46      26.179  -9.369   5.114  1.00 27.04           C
ATOM    323  CG1 ILE A  46      25.846  -9.616   6.567  1.00 38.00           C
ATOM    324  CG2 ILE A  46      27.055  -8.134   4.922  1.00 16.89           C
ATOM    325  CD1 ILE A  46      26.951 -10.376   7.307  1.00 43.76           C
ATOM    326  N   ALA A  47      22.850  -9.332   5.787  1.00 35.96           N
ATOM    327  CA  ALA A  47      21.797 -10.041   6.481  1.00 41.74           C
ATOM    328  C   ALA A  47      20.953 -10.842   5.532  1.00 51.48           C
ATOM    329  O   ALA A  47      20.397 -11.900   5.806  1.00 57.22           O
ATOM    330  CB  ALA A  47      20.918  -9.060   7.197  1.00 46.88           C
ATOM    331  N   LYS A  48      20.832 -10.314   4.356  1.00 59.20           N
ATOM    332  CA  LYS A  48      20.041 -10.987   3.376  1.00 56.10           C
ATOM    333  C   LYS A  48      20.678 -12.105   2.619  1.00 52.02           C
ATOM    334  O   LYS A  48      20.018 -13.067   2.285  1.00 65.50           O
ATOM    335  CB  LYS A  48      19.374 -10.010   2.431  1.00 59.34           C
ATOM    336  CG  LYS A  48      18.197  -9.313   3.102  1.00 60.09           C
ATOM    337  CD  LYS A  48      17.002  -9.167   2.171  1.00 59.20           C
ATOM    338  CE  LYS A  48      15.663  -9.134   2.899  1.00 64.92           C
ATOM    339  NZ  LYS A  48      14.526  -9.720   2.154  1.00 68.16           N
ATOM    340  N   TYR A  49      21.947 -11.982   2.329  1.00 47.63           N
ATOM    341  CA  TYR A  49      22.746 -12.965   1.549  1.00 48.07           C
ATOM    342  C   TYR A  49      22.752 -14.434   1.989  1.00 48.45           C
ATOM    343  O   TYR A  49      23.410 -14.792   2.956  1.00 57.76           O
ATOM    344  CB  TYR A  49      24.147 -12.385   1.487  1.00 42.66           C
ATOM    345  CG  TYR A  49      25.218 -13.165   0.820  1.00 40.69           C
ATOM    346  CD1 TYR A  49      25.347 -13.165  -0.568  1.00 36.47           C
ATOM    347  CD2 TYR A  49      26.144 -13.856   1.602  1.00 40.18           C
ATOM    348  CE1 TYR A  49      26.385 -13.885  -1.171  1.00 39.83           C
ATOM    349  CE2 TYR A  49      27.183 -14.572   1.011  1.00 40.70           C
ATOM    350  CZ  TYR A  49      27.297 -14.589  -0.383  1.00 44.13           C
ATOM    351  OH  TYR A  49      28.324 -15.308  -0.970  1.00 42.92           O
ATOM    352  N   PRO A  50      22.031 -15.274   1.243  1.00 34.74           N
ATOM    353  CA  PRO A  50      21.910 -16.700   1.506  1.00 22.69           C
ATOM    354  C   PRO A  50      23.112 -17.600   1.554  1.00 23.26           C
ATOM    355  O   PRO A  50      23.014 -18.647   0.962  1.00 36.35           O
ATOM    356  CB  PRO A  50      20.948 -17.284   0.476  1.00 21.47           C
ATOM    357  CG  PRO A  50      20.253 -16.094  -0.192  1.00 30.84           C
ATOM    358  CD  PRO A  50      21.017 -14.838   0.249  1.00 33.51           C
ATOM    359  N   HIS A  51      24.193 -17.270   2.237  1.00 20.22           N
ATOM    360  CA  HIS A  51      25.321 -18.164   2.269  1.00 34.63           C
ATOM    361  C   HIS A  51      26.132 -17.838   3.433  1.00 38.51           C
ATOM    362  O   HIS A  51      25.875 -16.920   4.135  1.00 44.58           O
ATOM    363  CB  HIS A  51      26.284 -18.036   1.067  1.00 45.23           C
ATOM    364  CG  HIS A  51      25.530 -18.374  -0.133  1.00 40.82           C
ATOM    365  ND1 HIS A  51      25.079 -19.655  -0.315  1.00 43.69           N
ATOM    366  CD2 HIS A  51      25.105 -17.620  -1.140  1.00 41.84           C
```

Figure 22M

```
ATOM    367  CE1 HIS A  51      24.404 -19.680  -1.437  1.00 41.33           C
ATOM    368  NE2 HIS A  51      24.407 -18.465  -1.959  1.00 45.34           N
ATOM    369  N   LYS A  52      27.124 -18.584   3.641  1.00 41.48           N
ATOM    370  CA  LYS A  52      27.883 -18.264   4.763  1.00 48.49           C
ATOM    371  C   LYS A  52      29.109 -17.601   4.204  1.00 48.69           C
ATOM    372  O   LYS A  52      29.839 -18.170   3.398  1.00 56.59           O
ATOM    373  CB  LYS A  52      28.097 -19.560   5.523  1.00 63.57           C
ATOM    374  CG  LYS A  52      28.811 -19.387   6.842  1.00 75.95           C
ATOM    375  CD  LYS A  52      29.510 -20.641   7.324  1.00 84.37           C
ATOM    376  CE  LYS A  52      30.427 -20.334   8.504  1.00 93.02           C
ATOM    377  NZ  LYS A  52      31.143 -21.514   9.030  1.00100.00           N
ATOM    378  N   ILE A  53      29.353 -16.384   4.600  1.00 46.54           N
ATOM    379  CA  ILE A  53      30.516 -15.729   4.056  1.00 45.07           C
ATOM    380  C   ILE A  53      31.767 -16.422   4.487  1.00 49.56           C
ATOM    381  O   ILE A  53      31.906 -16.680   5.676  1.00 46.64           O
ATOM    382  CB  ILE A  53      30.420 -14.221   4.238  1.00 35.12           C
ATOM    383  CG1 ILE A  53      29.099 -13.931   3.486  1.00 25.61           C
ATOM    384  CG2 ILE A  53      31.636 -13.623   3.551  1.00 32.58           C
ATOM    385  CD1 ILE A  53      28.256 -12.720   3.899  1.00 20.29           C
ATOM    386  N   LYS A  54      32.646 -16.737   3.509  1.00 58.46           N
ATOM    387  CA  LYS A  54      33.928 -17.432   3.767  1.00 55.18           C
ATOM    388  C   LYS A  54      35.114 -16.499   3.710  1.00 49.98           C
ATOM    389  O   LYS A  54      36.182 -16.845   4.235  1.00 48.91           O
ATOM    390  CB  LYS A  54      34.191 -18.546   2.777  1.00 58.89           C
ATOM    391  CG  LYS A  54      33.256 -19.734   2.891  1.00 67.45           C
ATOM    392  CD  LYS A  54      33.757 -20.798   3.872  1.00 77.74           C
ATOM    393  CE  LYS A  54      35.148 -21.363   3.516  1.00 74.76           C
ATOM    394  NZ  LYS A  54      35.687 -22.408   4.417  1.00 57.69           N
ATOM    395  N   SER A  55      34.908 -15.335   3.057  1.00 42.57           N
ATOM    396  CA  SER A  55      35.981 -14.355   2.939  1.00 42.59           C
ATOM    397  C   SER A  55      35.463 -12.901   2.870  1.00 40.91           C
ATOM    398  O   SER A  55      34.281 -12.652   2.574  1.00 35.51           O
ATOM    399  CB  SER A  55      36.784 -14.616   1.669  1.00 39.34           C
ATOM    400  OG  SER A  55      35.983 -14.207   0.543  1.00 33.96           O
ATOM    401  N   GLY A  56      36.377 -11.940   3.132  1.00 41.07           N
ATOM    402  CA  GLY A  56      36.068 -10.525   3.087  1.00 43.88           C
ATOM    403  C   GLY A  56      35.677 -10.226   1.655  1.00 56.71           C
ATOM    404  O   GLY A  56      34.628  -9.606   1.352  1.00 59.03           O
ATOM    405  N   ALA A  57      36.565 -10.715   0.763  1.00 58.93           N
ATOM    406  CA  ALA A  57      36.416 -10.567  -0.676  1.00 51.95           C
ATOM    407  C   ALA A  57      35.086 -11.107  -1.093  1.00 46.96           C
ATOM    408  O   ALA A  57      34.408 -10.645  -2.018  1.00 49.43           O
ATOM    409  CB  ALA A  57      37.500 -11.341  -1.402  1.00 51.33           C
ATOM    410  N   GLU A  58      34.690 -12.139  -0.389  1.00 44.27           N
ATOM    411  CA  GLU A  58      33.421 -12.711  -0.750  1.00 34.56           C
ATOM    412  C   GLU A  58      32.276 -11.792  -0.582  1.00 36.28           C
ATOM    413  O   GLU A  58      31.393 -11.748  -1.438  1.00 37.58           O
ATOM    414  CB  GLU A  58      33.161 -14.068  -0.134  1.00 28.69           C
ATOM    415  CG  GLU A  58      31.732 -14.475  -0.494  1.00 18.16           C
ATOM    416  CD  GLU A  58      31.416 -15.625   0.413  1.00 28.18           C
ATOM    417  OE1 GLU A  58      32.458 -15.964   1.225  1.00 24.75           O
ATOM    418  OE2 GLU A  58      30.303 -16.124   0.406  1.00 26.57           O
ATOM    419  N   ALA A  59      32.315 -11.088   0.557  1.00 43.74           N
ATOM    420  CA  ALA A  59      31.285 -10.125   0.921  1.00 42.86           C
ATOM    421  C   ALA A  59      31.401  -8.838   0.048  1.00 37.45           C
ATOM    422  O   ALA A  59      30.392  -8.256  -0.418  1.00 26.41           O
ATOM    423  CB  ALA A  59      31.373  -9.933   2.413  1.00 35.11           C
ATOM    424  N   LYS A  60      32.691  -8.459  -0.171  1.00 35.86           N
ATOM    425  CA  LYS A  60      33.086  -7.324  -0.973  1.00 28.11           C
ATOM    426  C   LYS A  60      32.254  -7.250  -2.219  1.00 30.92           C
ATOM    427  O   LYS A  60      31.783  -6.211  -2.654  1.00 43.19           O
ATOM    428  CB  LYS A  60      34.544  -7.302  -1.249  1.00 22.91           C
ATOM    429  CG  LYS A  60      34.884  -6.004  -1.922  1.00 36.98           C
```

Figure 22N

| ATOM | 430 | CD | LYS | A | 60 | 36.320 | -5.590 | -1.625 | 1.00 | 46.89 | C |
|------|-----|-----|-----|---|----|--------|--------|--------|------|-------|---|
| ATOM | 431 | CE | LYS | A | 60 | 36.653 | -4.142 | -2.018 | 1.00 | 61.20 | C |
| ATOM | 432 | NZ | LYS | A | 60 | 36.235 | -3.709 | -3.385 | 1.00 | 69.41 | N |
| ATOM | 433 | N | LYS | A | 61 | 32.013 | -8.418 | -2.761 | 1.00 | 34.57 | N |
| ATOM | 434 | CA | LYS | A | 61 | 31.204 | -8.658 | -3.948 | 1.00 | 35.67 | C |
| ATOM | 435 | C | LYS | A | 61 | 29.845 | -8.001 | -3.748 | 1.00 | 34.85 | C |
| ATOM | 436 | O | LYS | A | 61 | 29.039 | -7.803 | -4.691 | 1.00 | 34.68 | O |
| ATOM | 437 | CB | LYS | A | 61 | 30.986 | -10.191 | -4.073 | 1.00 | 41.35 | C |
| ATOM | 438 | CG | LYS | A | 61 | 29.523 | -10.504 | -4.417 | 1.00 | 42.32 | C |
| ATOM | 439 | CD | LYS | A | 61 | 28.777 | -11.769 | -3.990 | 1.00 | 40.23 | C |
| ATOM | 440 | CE | LYS | A | 61 | 27.337 | -11.570 | -4.526 | 1.00 | 39.68 | C |
| ATOM | 441 | NZ | LYS | A | 61 | 26.569 | -12.733 | -4.983 | 1.00 | 31.57 | N |
| ATOM | 442 | N | LEU | A | 62 | 29.554 | -7.672 | -2.473 | 1.00 | 34.90 | N |
| ATOM | 443 | CA | LEU | A | 62 | 28.301 | -7.061 | -2.156 | 1.00 | 29.25 | C |
| ATOM | 444 | C | LEU | A | 62 | 28.293 | -5.502 | -2.290 | 1.00 | 23.65 | C |
| ATOM | 445 | O | LEU | A | 62 | 29.288 | -4.755 | -2.179 | 1.00 | 19.01 | O |
| ATOM | 446 | CB | LEU | A | 62 | 27.718 | -7.632 | -0.866 | 1.00 | 42.18 | C |
| ATOM | 447 | CG | LEU | A | 62 | 27.270 | -9.100 | -0.812 | 1.00 | 46.86 | C |
| ATOM | 448 | CD1 | LEU | A | 62 | 26.112 | -9.376 | -1.776 | 1.00 | 47.30 | C |
| ATOM | 449 | CD2 | LEU | A | 62 | 28.404 | -10.089 | -1.025 | 1.00 | 51.75 | C |
| ATOM | 450 | N | PRO | A | 63 | 27.102 | -5.051 | -2.564 | 1.00 | 13.68 | N |
| ATOM | 451 | CA | PRO | A | 63 | 26.748 | -3.690 | -2.748 | 1.00 | 22.12 | C |
| ATOM | 452 | C | PRO | A | 63 | 26.565 | -2.938 | -1.418 | 1.00 | 28.44 | C |
| ATOM | 453 | O | PRO | A | 63 | 25.445 | -2.772 | -0.961 | 1.00 | 26.10 | O |
| ATOM | 454 | CB | PRO | A | 63 | 25.374 | -3.715 | -3.440 | 1.00 | 14.87 | C |
| ATOM | 455 | CG | PRO | A | 63 | 24.810 | -5.091 | -3.293 | 1.00 | 14.21 | C |
| ATOM | 456 | CD | PRO | A | 63 | 25.988 | -5.976 | -2.820 | 1.00 | 19.34 | C |
| ATOM | 457 | N | GLY | A | 64 | 27.676 | -2.504 | -0.872 | 1.00 | 23.32 | N |
| ATOM | 458 | CA | GLY | A | 64 | 27.856 | -1.779 | 0.341 | 1.00 | 16.98 | C |
| ATOM | 459 | C | GLY | A | 64 | 29.179 | -2.310 | 0.907 | 1.00 | 32.12 | C |
| ATOM | 460 | O | GLY | A | 64 | 29.844 | -1.709 | 1.762 | 1.00 | 47.44 | O |
| ATOM | 461 | N | VAL | A | 65 | 29.623 | -3.477 | 0.452 | 1.00 | 22.69 | N |
| ATOM | 462 | CA | VAL | A | 65 | 30.864 | -3.895 | 1.036 | 1.00 | 22.79 | C |
| ATOM | 463 | C | VAL | A | 65 | 31.963 | -3.312 | 0.271 | 1.00 | 27.13 | C |
| ATOM | 464 | O | VAL | A | 65 | 31.803 | -3.040 | -0.922 | 1.00 | 39.82 | O |
| ATOM | 465 | CB | VAL | A | 65 | 31.091 | -5.375 | 1.232 | 1.00 | 24.87 | C |
| ATOM | 466 | CG1 | VAL | A | 65 | 32.369 | -5.607 | 2.049 | 1.00 | 26.06 | C |
| ATOM | 467 | CG2 | VAL | A | 65 | 29.871 | -5.880 | 1.918 | 1.00 | 22.17 | C |
| ATOM | 468 | N | GLY | A | 66 | 33.046 | -3.137 | 0.970 | 1.00 | 10.83 | N |
| ATOM | 469 | CA | GLY | A | 66 | 34.178 | -2.545 | 0.381 | 1.00 | 1.00 | C |
| ATOM | 470 | C | GLY | A | 66 | 35.366 | -2.987 | 1.166 | 1.00 | 26.83 | C |
| ATOM | 471 | O | GLY | A | 66 | 35.288 | -3.769 | 2.129 | 1.00 | 42.20 | O |
| ATOM | 472 | N | THR | A | 67 | 36.479 | -2.488 | 0.743 | 1.00 | 27.64 | N |
| ATOM | 473 | CA | THR | A | 67 | 37.725 | -2.826 | 1.368 | 1.00 | 34.51 | C |
| ATOM | 474 | C | THR | A | 67 | 37.774 | -2.747 | 2.877 | 1.00 | 37.51 | C |
| ATOM | 475 | O | THR | A | 67 | 37.945 | -3.772 | 3.500 | 1.00 | 44.94 | O |
| ATOM | 476 | CB | THR | A | 67 | 38.832 | -2.169 | 0.565 | 1.00 | 38.73 | C |
| ATOM | 477 | OG1 | THR | A | 67 | 40.007 | -1.886 | 1.313 | 1.00 | 50.68 | O |
| ATOM | 478 | CG2 | THR | A | 67 | 38.161 | -0.922 | 0.005 | 1.00 | 39.25 | C |
| ATOM | 479 | N | LYS | A | 68 | 37.613 | -1.584 | 3.478 | 1.00 | 40.27 | N |
| ATOM | 480 | CA | LYS | A | 68 | 37.652 | -1.496 | 4.930 | 1.00 | 43.90 | C |
| ATOM | 481 | C | LYS | A | 68 | 36.770 | -2.520 | 5.692 | 1.00 | 35.69 | C |
| ATOM | 482 | O | LYS | A | 68 | 37.212 | -3.174 | 6.605 | 1.00 | 32.49 | O |
| ATOM | 483 | CB | LYS | A | 68 | 37.431 | -0.073 | 5.357 | 1.00 | 49.25 | C |
| ATOM | 484 | CG | LYS | A | 68 | 38.181 | 0.926 | 4.500 | 1.00 | 48.81 | C |
| ATOM | 485 | CD | LYS | A | 68 | 38.240 | 2.319 | 5.117 | 1.00 | 60.36 | C |
| ATOM | 486 | CE | LYS | A | 68 | 39.279 | 2.441 | 6.249 | 1.00 | 72.39 | C |
| ATOM | 487 | NZ | LYS | A | 68 | 39.575 | 3.823 | 6.727 | 1.00 | 72.13 | N |
| ATOM | 488 | N | ILE | A | 69 | 35.514 | -2.698 | 5.330 | 1.00 | 36.99 | N |
| ATOM | 489 | CA | ILE | A | 69 | 34.657 | -3.664 | 6.025 | 1.00 | 31.07 | C |
| ATOM | 490 | C | ILE | A | 69 | 35.010 | -5.104 | 5.635 | 1.00 | 39.98 | C |
| ATOM | 491 | O | ILE | A | 69 | 34.828 | -6.090 | 6.370 | 1.00 | 40.19 | O |
| ATOM | 492 | CB | ILE | A | 69 | 33.255 | -3.475 | 5.533 | 1.00 | 23.63 | C |

Figure 22O

```
ATOM    430  CD  LYS A  60      36.320  -5.590  -1.625  1.00 46.89           C
ATOM    431  CE  LYS A  60      36.653  -4.142  -2.018  1.00 61.20           C
ATOM    432  NZ  LYS A  60      36.235  -3.709  -3.385  1.00 69.41           N
ATOM    433  N   LYS A  61      32.013  -8.418  -2.761  1.00 34.57           N
ATOM    434  CA  LYS A  61      31.204  -8.658  -3.948  1.00 35.67           C
ATOM    435  C   LYS A  61      29.845  -8.001  -3.748  1.00 34.85           C
ATOM    436  O   LYS A  61      29.039  -7.803  -4.691  1.00 34.68           O
ATOM    437  CB  LYS A  61      30.986 -10.191  -4.073  1.00 41.35           C
ATOM    438  CG  LYS A  61      29.523 -10.504  -4.417  1.00 42.32           C
ATOM    439  CD  LYS A  61      28.777 -11.769  -3.990  1.00 40.23           C
ATOM    440  CE  LYS A  61      27.337 -11.570  -4.526  1.00 39.68           C
ATOM    441  NZ  LYS A  61      26.569 -12.733  -4.983  1.00 31.57           N
ATOM    442  N   LEU A  62      29.554  -7.672  -2.473  1.00 34.90           N
ATOM    443  CA  LEU A  62      28.301  -7.061  -2.156  1.00 29.25           C
ATOM    444  C   LEU A  62      28.293  -5.502  -2.290  1.00 23.65           C
ATOM    445  O   LEU A  62      29.288  -4.755  -2.179  1.00 19.01           O
ATOM    446  CB  LEU A  62      27.718  -7.632  -0.866  1.00 46.18           C
ATOM    447  CG  LEU A  62      27.270  -9.100  -0.812  1.00 46.86           C
ATOM    448  CD1 LEU A  62      26.112  -9.376  -1.776  1.00 47.30           C
ATOM    449  CD2 LEU A  62      28.404 -10.089  -1.025  1.00 51.75           C
ATOM    450  N   PRO A  63      27.102  -5.051  -2.564  1.00 13.68           N
ATOM    451  CA  PRO A  63      26.748  -3.690  -2.748  1.00 22.12           C
ATOM    452  C   PRO A  63      26.565  -2.938  -1.418  1.00 28.44           C
ATOM    453  O   PRO A  63      25.445  -2.772  -0.961  1.00 26.10           O
ATOM    454  CB  PRO A  63      25.374  -3.715  -3.440  1.00 14.87           C
ATOM    455  CG  PRO A  63      24.810  -5.091  -3.293  1.00 14.21           C
ATOM    456  CD  PRO A  63      25.988  -5.976  -2.820  1.00 19.34           C
ATOM    457  N   GLY A  64      27.676  -2.504  -0.872  1.00 23.32           N
ATOM    458  CA  GLY A  64      27.856  -1.779   0.341  1.00 16.98           C
ATOM    459  C   GLY A  64      29.179  -2.310   0.907  1.00 32.12           C
ATOM    460  O   GLY A  64      29.844  -1.709   1.762  1.00 47.44           O
ATOM    461  N   VAL A  65      29.623  -3.477   0.452  1.00 22.69           N
ATOM    462  CA  VAL A  65      30.864  -3.895   1.036  1.00 22.79           C
ATOM    463  C   VAL A  65      31.963  -3.312   0.271  1.00 27.13           C
ATOM    464  O   VAL A  65      31.803  -3.040  -0.922  1.00 39.82           O
ATOM    465  CB  VAL A  65      31.091  -5.375   1.232  1.00 24.87           C
ATOM    466  CG1 VAL A  65      32.369  -5.607   2.049  1.00 26.06           C
ATOM    467  CG2 VAL A  65      29.871  -5.880   1.918  1.00 22.17           C
ATOM    468  N   GLY A  66      33.046  -3.137   0.970  1.00 10.83           N
ATOM    469  CA  GLY A  66      34.178  -2.545   0.381  1.00  1.00           C
ATOM    470  C   GLY A  66      35.366  -2.987   1.166  1.00 26.83           C
ATOM    471  O   GLY A  66      35.288  -3.769   2.129  1.00 42.20           O
ATOM    472  N   THR A  67      36.479  -2.488   0.743  1.00 27.64           N
ATOM    473  CA  THR A  67      37.725  -2.826   1.368  1.00 34.51           C
ATOM    474  C   THR A  67      37.774  -2.747   2.877  1.00 37.51           C
ATOM    475  O   THR A  67      37.945  -3.772   3.500  1.00 44.94           O
ATOM    476  CB  THR A  67      38.832  -2.169   0.565  1.00 38.73           C
ATOM    477  OG1 THR A  67      40.007  -1.886   1.313  1.00 50.68           O
ATOM    478  CG2 THR A  67      38.161  -0.922   0.005  1.00 39.25           C
ATOM    479  N   LYS A  68      37.613  -1.584   3.478  1.00 40.27           N
ATOM    480  CA  LYS A  68      37.652  -1.496   4.930  1.00 43.90           C
ATOM    481  C   LYS A  68      36.770  -2.520   5.692  1.00 35.69           C
ATOM    482  O   LYS A  68      37.212  -3.174   6.605  1.00 32.49           O
ATOM    483  CB  LYS A  68      37.431  -0.073   5.357  1.00 49.25           C
ATOM    484  CG  LYS A  68      38.181   0.926   4.500  1.00 48.81           C
ATOM    485  CD  LYS A  68      38.240   2.319   5.117  1.00 60.36           C
ATOM    486  CE  LYS A  68      39.279   2.441   6.249  1.00 72.39           C
ATOM    487  NZ  LYS A  68      39.575   3.823   6.727  1.00 72.13           N
ATOM    488  N   ILE A  69      35.514  -2.698   5.330  1.00 36.99           N
ATOM    489  CA  ILE A  69      34.657  -3.664   6.025  1.00 31.07           C
ATOM    490  C   ILE A  69      35.010  -5.104   5.635  1.00 39.98           C
ATOM    491  O   ILE A  69      34.828  -6.090   6.370  1.00 40.19           O
ATOM    492  CB  ILE A  69      33.255  -3.475   5.533  1.00 23.63           C
```

Figure 22P

```
ATOM    493  CG1 ILE A  69      32.530  -2.239   6.066  1.00 22.91           C
ATOM    494  CG2 ILE A  69      32.485  -4.807   5.551  1.00 19.70           C
ATOM    495  CD1 ILE A  69      31.169  -1.996   5.353  1.00 29.02           C
ATOM    496  N   ALA A  70      35.484  -5.201   4.421  1.00 41.74           N
ATOM    497  CA  ALA A  70      35.868  -6.472   3.939  1.00 46.75           C
ATOM    498  C   ALA A  70      36.987  -6.907   4.860  1.00 42.24           C
ATOM    499  O   ALA A  70      36.963  -8.003   5.390  1.00 44.12           O
ATOM    500  CB  ALA A  70      36.316  -6.403   2.486  1.00 48.86           C
ATOM    501  N   GLU A  71      37.949  -6.018   5.073  1.00 39.80           N
ATOM    502  CA  GLU A  71      39.066  -6.340   5.945  1.00 46.51           C
ATOM    503  C   GLU A  71      38.578  -6.706   7.325  1.00 55.62           C
ATOM    504  O   GLU A  71      39.165  -7.534   8.018  1.00 61.29           O
ATOM    505  CB  GLU A  71      40.072  -5.192   6.088  1.00 54.74           C
ATOM    506  CG  GLU A  71      40.356  -4.464   4.757  1.00 70.72           C
ATOM    507  CD  GLU A  71      41.409  -3.363   4.811  1.00 82.48           C
ATOM    508  OE1 GLU A  71      42.469  -3.443   5.445  1.00 79.63           O
ATOM    509  OE2 GLU A  71      41.061  -2.303   4.088  1.00 89.86           O
ATOM    510  N   LYS A  72      37.493  -6.057   7.740  1.00 54.36           N
ATOM    511  CA  LYS A  72      36.974  -6.336   9.059  1.00 52.50           C
ATOM    512  C   LYS A  72      36.614  -7.813   9.158  1.00 42.80           C
ATOM    513  O   LYS A  72      37.137  -8.567   9.995  1.00 26.51           O
ATOM    514  CB  LYS A  72      36.013  -5.256   9.571  1.00 51.29           C
ATOM    515  CG  LYS A  72      36.674  -3.852   9.618  1.00 51.30           C
ATOM    516  CD  LYS A  72      36.247  -2.944  10.786  1.00 49.85           C
ATOM    517  CE  LYS A  72      37.111  -1.703  11.041  1.00 48.06           C
ATOM    518  NZ  LYS A  72      36.610  -0.468  10.392  1.00 44.79           N
ATOM    519  N   ILE A  73      35.751  -8.197   8.226  1.00 44.03           N
ATOM    520  CA  ILE A  73      35.284  -9.566   8.085  1.00 41.56           C
ATOM    521  C   ILE A  73      36.423 -10.581   8.129  1.00 52.38           C
ATOM    522  O   ILE A  73      36.233 -11.667   8.633  1.00 56.97           O
ATOM    523  CB  ILE A  73      34.451  -9.747   6.843  1.00 28.42           C
ATOM    524  CG1 ILE A  73      33.515  -8.526   6.717  1.00 22.10           C
ATOM    525  CG2 ILE A  73      33.679 -11.043   7.017  1.00 14.67           C
ATOM    526  CD1 ILE A  73      32.183  -8.825   6.048  1.00 22.35           C
ATOM    527  N   ASP A  74      37.614 -10.258   7.612  1.00 57.25           N
ATOM    528  CA  ASP A  74      38.739 -11.201   7.663  1.00 54.53           C
ATOM    529  C   ASP A  74      39.255 -11.360   9.063  1.00 57.63           C
ATOM    530  O   ASP A  74      39.548 -12.475   9.480  1.00 65.19           O
ATOM    531  CB  ASP A  74      39.913 -10.870   6.759  1.00 56.80           C
ATOM    532  CG  ASP A  74      39.563 -11.041   5.305  1.00 67.89           C
ATOM    533  OD1 ASP A  74      38.454 -11.401   4.883  1.00 65.09           O
ATOM    534  OD2 ASP A  74      40.601 -10.782   4.544  1.00 73.28           O
ATOM    535  N   GLU A  75      39.376 -10.228   9.777  1.00 55.86           N
ATOM    536  CA  GLU A  75      39.842 -10.231  11.166  1.00 52.40           C
ATOM    537  C   GLU A  75      38.800 -10.979  12.007  1.00 48.56           C
ATOM    538  O   GLU A  75      39.097 -11.722  12.889  1.00 51.56           O
ATOM    539  CB  GLU A  75      40.034  -8.829  11.724  1.00 54.63           C
ATOM    540  CG  GLU A  75      40.965  -8.792  12.954  1.00 59.41           C
ATOM    541  CD  GLU A  75      40.782  -7.539  13.784  1.00 64.05           C
ATOM    542  OE1 GLU A  75      39.743  -6.820  13.426  1.00 63.99           O
ATOM    543  OE2 GLU A  75      41.509  -7.235  14.709  1.00 62.76           O
ATOM    544  N   PHE A  76      37.545 -10.793  11.723  1.00 44.48           N
ATOM    545  CA  PHE A  76      36.516 -11.471  12.447  1.00 42.81           C
ATOM    546  C   PHE A  76      36.538 -12.974  12.224  1.00 52.18           C
ATOM    547  O   PHE A  76      36.669 -13.769  13.159  1.00 57.94           O
ATOM    548  CB  PHE A  76      35.177 -11.001  11.916  1.00 41.00           C
ATOM    549  CG  PHE A  76      33.987 -11.482  12.701  1.00 50.26           C
ATOM    550  CD1 PHE A  76      33.993 -11.440  14.095  1.00 50.89           C
ATOM    551  CD2 PHE A  76      32.844 -11.942  12.054  1.00 52.09           C
ATOM    552  CE1 PHE A  76      32.885 -11.853  14.827  1.00 48.83           C
ATOM    553  CE2 PHE A  76      31.722 -12.359  12.769  1.00 49.60           C
ATOM    554  CZ  PHE A  76      31.754 -12.317  14.159  1.00 48.86           C
ATOM    555  N   LEU A  77      36.385 -13.371  10.952  1.00 52.17           N
```

Figure 22Q

```
ATOM    556  CA  LEU A  77      36.356 -14.782  10.538  1.00 44.35           C
ATOM    557  C   LEU A  77      37.478 -15.570  11.174  1.00 48.60           C
ATOM    558  O   LEU A  77      37.266 -16.570  11.896  1.00 53.84           O
ATOM    559  CB  LEU A  77      36.457 -14.881   9.015  1.00 36.69           C
ATOM    560  CG  LEU A  77      35.164 -15.315   8.287  1.00 27.32           C
ATOM    561  CD1 LEU A  77      33.944 -15.052   9.140  1.00 19.01           C
ATOM    562  CD2 LEU A  77      35.018 -14.743   6.833  1.00 18.49           C
ATOM    563  N   ALA A  78      38.674 -15.070  10.883  1.00 42.09           N
ATOM    564  CA  ALA A  78      39.908 -15.636  11.368  1.00 44.17           C
ATOM    565  C   ALA A  78      40.001 -15.669  12.895  1.00 62.92           C
ATOM    566  O   ALA A  78      39.996 -16.763  13.456  1.00 75.16           O
ATOM    567  CB  ALA A  78      41.094 -14.924  10.737  1.00 36.19           C
ATOM    568  N   THR A  79      40.081 -14.476  13.547  1.00 67.68           N
ATOM    569  CA  THR A  79      40.187 -14.285  15.006  1.00 61.74           C
ATOM    570  C   THR A  79      38.914 -14.614  15.784  1.00 70.09           C
ATOM    571  O   THR A  79      38.963 -15.179  16.879  1.00 79.38           O
ATOM    572  CB  THR A  79      40.485 -12.841  15.447  1.00 53.77           C
ATOM    573  OG1 THR A  79      39.423 -11.944  15.138  1.00 50.09           O
ATOM    574  CG2 THR A  79      41.900 -12.304  15.255  1.00 53.81           C
ATOM    575  N   GLY A  80      37.751 -14.249  15.258  1.00 68.91           N
ATOM    576  CA  GLY A  80      36.513 -14.535  15.985  1.00 62.89           C
ATOM    577  C   GLY A  80      35.995 -13.318  16.735  1.00 64.78           C
ATOM    578  O   GLY A  80      35.056 -13.432  17.506  1.00 66.60           O
ATOM    579  N   LYS A  81      36.640 -12.165  16.485  1.00 74.29           N
ATOM    580  CA  LYS A  81      36.364 -10.839  17.052  1.00 78.12           C
ATOM    581  C   LYS A  81      36.959  -9.753  16.187  1.00 73.67           C
ATOM    582  O   LYS A  81      37.295  -9.983  15.020  1.00 76.71           O
ATOM    583  CB  LYS A  81      36.886 -10.631  18.477  1.00 88.13           C
ATOM    584  CG  LYS A  81      35.791 -10.677  19.555  1.00 97.89           C
ATOM    585  CD  LYS A  81      36.307 -10.601  21.001  1.00100.00           C
ATOM    586  CE  LYS A  81      35.464 -11.388  22.019  1.00100.00           C
ATOM    587  NZ  LYS A  81      36.156 -11.695  23.293  1.00 99.51           N
ATOM    588  N   LEU A  82      37.091  -8.573  16.799  1.00 69.31           N
ATOM    589  CA  LEU A  82      37.647  -7.369  16.167  1.00 62.56           C
ATOM    590  C   LEU A  82      38.377  -6.536  17.207  1.00 51.89           C
ATOM    591  O   LEU A  82      37.700  -5.951  18.048  1.00 53.87           O
ATOM    592  CB  LEU A  82      36.482  -6.509  15.666  1.00 56.70           C
ATOM    593  CG  LEU A  82      36.828  -5.714  14.452  1.00 48.82           C
ATOM    594  CD1 LEU A  82      36.957  -6.675  13.293  1.00 40.82           C
ATOM    595  CD2 LEU A  82      35.706  -4.716  14.196  1.00 54.23           C
ATOM    596  N   ARG A  83      39.716  -6.497  17.141  1.00 42.16           N
ATOM    597  CA  ARG A  83      40.531  -5.746  18.089  1.00 45.08           C
ATOM    598  C   ARG A  83      39.961  -4.392  18.385  1.00 50.38           C
ATOM    599  O   ARG A  83      39.781  -4.037  19.548  1.00 53.02           O
ATOM    600  CB  ARG A  83      42.015  -5.642  17.796  1.00 48.41           C
ATOM    601  CG  ARG A  83      42.796  -5.887  19.081  1.00 55.79           C
ATOM    602  CD  ARG A  83      44.276  -5.603  18.993  1.00 63.05           C
ATOM    603  NE  ARG A  83      44.434  -4.317  18.378  1.00 77.23           N
ATOM    604  CZ  ARG A  83      44.440  -3.137  18.980  1.00 87.54           C
ATOM    605  NH1 ARG A  83      44.319  -2.961  20.297  1.00 85.66           N
ATOM    606  NH2 ARG A  83      44.600  -2.077  18.193  1.00 96.16           N
ATOM    607  N   LYS A  84      39.659  -3.679  17.318  1.00 52.61           N
ATOM    608  CA  LYS A  84      39.077  -2.358  17.398  1.00 57.79           C
ATOM    609  C   LYS A  84      37.901  -2.391  18.343  1.00 57.42           C
ATOM    610  O   LYS A  84      37.843  -1.627  19.295  1.00 63.28           O
ATOM    611  CB  LYS A  84      38.529  -1.974  16.018  1.00 65.84           C
ATOM    612  CG  LYS A  84      37.667  -0.708  15.926  1.00 69.94           C
ATOM    613  CD  LYS A  84      37.055  -0.530  14.536  1.00 73.23           C
ATOM    614  CE  LYS A  84      36.359   0.804  14.241  1.00 78.19           C
ATOM    615  NZ  LYS A  84      37.259   1.964  14.092  1.00 82.82           N
ATOM    616  N   LEU A  85      36.970  -3.298  18.059  1.00 51.29           N
ATOM    617  CA  LEU A  85      35.762  -3.460  18.853  1.00 39.91           C
ATOM    618  C   LEU A  85      36.046  -3.820  20.311  1.00 56.19           C
```

Figure 22R

```
ATOM    619  O    LEU A   85      35.297  -3.525  21.262  1.00 59.43           O
ATOM    620  CB   LEU A   85      34.716  -4.332  18.170  1.00 21.38           C
ATOM    621  CG   LEU A   85      33.372  -3.697  18.362  1.00 30.71           C
ATOM    622  CD1  LEU A   85      33.411  -2.231  17.955  1.00 37.99           C
ATOM    623  CD2  LEU A   85      32.289  -4.431  17.601  1.00 29.91           C
ATOM    624  N    GLU A   86      37.156  -4.487  20.524  1.00 63.10           N
ATOM    625  CA   GLU A   86      37.371  -4.775  21.890  1.00 69.87           C
ATOM    626  C    GLU A   86      37.769  -3.564  22.722  1.00 69.16           C
ATOM    627  O    GLU A   86      37.284  -3.378  23.830  1.00 70.65           O
ATOM    628  CB   GLU A   86      37.753  -6.187  22.316  1.00 78.05           C
ATOM    629  CG   GLU A   86      39.257  -6.422  22.292  1.00 89.90           C
ATOM    630  CD   GLU A   86      39.521  -7.799  22.791  1.00 98.99           C
ATOM    631  OE1  GLU A   86      38.395  -8.369  23.171  1.00100.00           O
ATOM    632  OE2  GLU A   86      40.628  -8.331  22.797  1.00100.00           O
ATOM    633  N    LYS A   87      38.653  -2.724  22.183  1.00 71.73           N
ATOM    634  CA   LYS A   87      39.053  -1.537  22.931  1.00 77.67           C
ATOM    635  C    LYS A   87      37.821  -0.703  23.225  1.00 69.24           C
ATOM    636  O    LYS A   87      37.543  -0.355  24.366  1.00 72.33           O
ATOM    637  CB   LYS A   87      40.053  -0.609  22.243  1.00 82.12           C
ATOM    638  CG   LYS A   87      40.012   0.797  22.855  1.00 83.02           C
ATOM    639  CD   LYS A   87      40.492   1.941  21.956  1.00 84.27           C
ATOM    640  CE   LYS A   87      39.652   3.221  22.109  1.00 81.84           C
ATOM    641  NZ   LYS A   87      40.337   4.454  21.691  1.00 78.49           N
ATOM    642  N    ILE A   88      37.102  -0.391  22.169  1.00 57.78           N
ATOM    643  CA   ILE A   88      35.903   0.387  22.282  1.00 59.63           C
ATOM    644  C    ILE A   88      34.977  -0.162  23.334  1.00 63.91           C
ATOM    645  O    ILE A   88      34.543   0.568  24.202  1.00 62.92           O
ATOM    646  CB   ILE A   88      35.210   0.491  20.936  1.00 58.47           C
ATOM    647  CG1  ILE A   88      36.056   1.408  20.033  1.00 53.73           C
ATOM    648  CG2  ILE A   88      33.740   0.945  21.092  1.00 49.61           C
ATOM    649  CD1  ILE A   88      35.839   1.154  18.546  1.00 53.12           C
ATOM    650  N    ARG A   89      34.698  -1.455  23.277  1.00 76.34           N
ATOM    651  CA   ARG A   89      33.824  -2.034  24.285  1.00 81.80           C
ATOM    652  C    ARG A   89      34.423  -1.848  25.659  1.00 82.99           C
ATOM    653  O    ARG A   89      33.687  -1.737  26.631  1.00 85.69           O
ATOM    654  CB   ARG A   89      33.582  -3.507  24.080  1.00 78.27           C
ATOM    655  CG   ARG A   89      32.705  -3.819  22.893  1.00 73.24           C
ATOM    656  CD   ARG A   89      32.929  -5.264  22.519  1.00 75.90           C
ATOM    657  NE   ARG A   89      31.978  -5.801  21.569  1.00 82.43           N
ATOM    658  CZ   ARG A   89      32.099  -7.030  21.041  1.00 94.45           C
ATOM    659  NH1  ARG A   89      33.115  -7.833  21.370  1.00100.00           N
ATOM    660  NH2  ARG A   89      31.190  -7.481  20.154  1.00 95.37           N
ATOM    661  N    GLN A   90      35.761  -1.825  25.724  1.00 80.50           N
ATOM    662  CA   GLN A   90      36.444  -1.637  26.983  1.00 82.39           C
ATOM    663  C    GLN A   90      36.451  -0.157  27.391  1.00 87.85           C
ATOM    664  O    GLN A   90      36.438   0.166  28.573  1.00100.00           O
ATOM    665  CB   GLN A   90      37.813  -2.347  27.116  1.00 85.14           C
ATOM    666  CG   GLN A   90      38.992  -1.734  26.321  1.00 92.50           C
ATOM    667  CD   GLN A   90      39.353  -0.294  26.700  1.00 97.08           C
ATOM    668  OE1  GLN A   90      40.208  -0.045  27.564  1.00100.00           O
ATOM    669  NE2  GLN A   90      38.741   0.679  26.030  1.00 96.40           N
ATOM    670  N    ASP A   91      36.455   0.746  26.396  1.00 79.99           N
ATOM    671  CA   ASP A   91      36.463   2.206  26.568  1.00 70.13           C
ATOM    672  C    ASP A   91      35.319   2.786  27.431  1.00 64.64           C
ATOM    673  O    ASP A   91      34.127   2.670  27.107  1.00 64.79           O
ATOM    674  CB   ASP A   91      36.529   2.875  25.184  1.00 68.65           C
ATOM    675  CG   ASP A   91      36.481   4.363  25.288  1.00 70.75           C
ATOM    676  OD1  ASP A   91      37.652   4.884  25.633  1.00 66.62           O
ATOM    677  OD2  ASP A   91      35.437   4.986  25.222  1.00 73.47           O
ATOM    678  N    ASP A   92      35.694   3.437  28.541  1.00 59.45           N
ATOM    679  CA   ASP A   92      34.730   4.034  29.470  1.00 68.13           C
ATOM    680  C    ASP A   92      33.722   4.947  28.834  1.00 62.58           C
ATOM    681  O    ASP A   92      32.478   4.711  28.827  1.00 57.08           O
```

Figure 22S

| ATOM | 682 | CB | ASP | A | 92 | 35.446 | 4.908 | 30.507 | 1.00 | 85.97 | C |
|---|---|---|---|---|---|---|---|---|---|---|---|
| ATOM | 683 | CG | ASP | A | 92 | 36.642 | 4.226 | 31.121 | 1.00 | 99.71 | C |
| ATOM | 684 | OD1 | ASP | A | 92 | 37.746 | 4.429 | 30.412 | 1.00 | 100.00 | O |
| ATOM | 685 | OD2 | ASP | A | 92 | 36.576 | 3.514 | 32.133 | 1.00 | 100.00 | O |
| ATOM | 686 | N | THR | A | 93 | 34.361 | 6.009 | 28.319 | 1.00 | 55.46 | N |
| ATOM | 687 | CA | THR | A | 93 | 33.704 | 7.106 | 27.641 | 1.00 | 51.56 | C |
| ATOM | 688 | C | THR | A | 93 | 32.737 | 6.645 | 26.576 | 1.00 | 44.05 | C |
| ATOM | 689 | O | THR | A | 93 | 31.507 | 6.856 | 26.754 | 1.00 | 34.09 | O |
| ATOM | 690 | CB | THR | A | 93 | 34.739 | 8.118 | 27.163 | 1.00 | 55.13 | C |
| ATOM | 691 | OG1 | THR | A | 93 | 35.881 | 7.381 | 26.795 | 1.00 | 72.86 | O |
| ATOM | 692 | CG2 | THR | A | 93 | 35.157 | 9.064 | 28.276 | 1.00 | 40.78 | C |
| ATOM | 693 | N | SER | A | 94 | 33.324 | 6.000 | 25.541 | 1.00 | 37.94 | N |
| ATOM | 694 | CA | SER | A | 94 | 32.550 | 5.499 | 24.458 | 1.00 | 38.55 | C |
| ATOM | 695 | C | SER | A | 94 | 31.382 | 4.736 | 24.979 | 1.00 | 28.91 | C |
| ATOM | 696 | O | SER | A | 94 | 30.234 | 4.832 | 24.492 | 1.00 | 19.02 | O |
| ATOM | 697 | CB | SER | A | 94 | 33.285 | 4.601 | 23.524 | 1.00 | 55.93 | C |
| ATOM | 698 | OG | SER | A | 94 | 32.365 | 3.564 | 23.235 | 1.00 | 67.77 | O |
| ATOM | 699 | N | SER | A | 95 | 31.665 | 3.988 | 26.008 | 1.00 | 32.01 | N |
| ATOM | 700 | CA | SER | A | 95 | 30.537 | 3.248 | 26.541 | 1.00 | 37.30 | C |
| ATOM | 701 | C | SER | A | 95 | 29.425 | 4.068 | 27.138 | 1.00 | 31.20 | C |
| ATOM | 702 | O | SER | A | 95 | 28.232 | 3.933 | 26.715 | 1.00 | 25.37 | O |
| ATOM | 703 | CB | SER | A | 95 | 30.994 | 2.263 | 27.548 | 1.00 | 42.51 | C |
| ATOM | 704 | OG | SER | A | 95 | 32.087 | 1.612 | 26.947 | 1.00 | 53.30 | O |
| ATOM | 705 | N | SER | A | 96 | 29.822 | 4.884 | 28.137 | 1.00 | 23.28 | N |
| ATOM | 706 | CA | SER | A | 96 | 28.788 | 5.697 | 28.807 | 1.00 | 23.98 | C |
| ATOM | 707 | C | SER | A | 96 | 28.115 | 6.496 | 27.726 | 1.00 | 34.99 | C |
| ATOM | 708 | O | SER | A | 96 | 26.880 | 6.722 | 27.766 | 1.00 | 33.72 | O |
| ATOM | 709 | CB | SER | A | 96 | 29.273 | 6.673 | 29.879 | 1.00 | 12.67 | C |
| ATOM | 710 | OG | SER | A | 96 | 30.661 | 6.412 | 30.160 | 1.00 | 21.68 | O |
| ATOM | 711 | N | ILE | A | 97 | 28.994 | 6.898 | 26.769 | 1.00 | 28.82 | N |
| ATOM | 712 | CA | ILE | A | 97 | 28.476 | 7.662 | 25.697 | 1.00 | 29.16 | C |
| ATOM | 713 | C | ILE | A | 97 | 27.531 | 6.812 | 24.870 | 1.00 | 39.51 | C |
| ATOM | 714 | O | ILE | A | 97 | 26.446 | 7.293 | 24.435 | 1.00 | 43.29 | O |
| ATOM | 715 | CB | ILE | A | 97 | 29.502 | 8.284 | 24.801 | 1.00 | 25.22 | C |
| ATOM | 716 | CG1 | ILE | A | 97 | 30.534 | 9.103 | 25.508 | 1.00 | 19.59 | C |
| ATOM | 717 | CG2 | ILE | A | 97 | 28.763 | 9.277 | 23.947 | 1.00 | 10.98 | C |
| ATOM | 718 | CD1 | ILE | A | 97 | 31.051 | 10.029 | 24.434 | 1.00 | 13.47 | C |
| ATOM | 719 | N | ASN | A | 98 | 27.952 | 5.545 | 24.651 | 1.00 | 38.03 | N |
| ATOM | 720 | CA | ASN | A | 98 | 27.078 | 4.701 | 23.873 | 1.00 | 46.89 | C |
| ATOM | 721 | C | ASN | A | 98 | 25.713 | 4.612 | 24.551 | 1.00 | 47.49 | C |
| ATOM | 722 | O | ASN | A | 98 | 24.730 | 5.114 | 23.978 | 1.00 | 47.67 | O |
| ATOM | 723 | CB | ASN | A | 98 | 27.685 | 3.330 | 23.383 | 1.00 | 58.77 | C |
| ATOM | 724 | CG | ASN | A | 98 | 27.891 | 3.148 | 21.844 | 1.00 | 53.26 | C |
| ATOM | 725 | OD1 | ASN | A | 98 | 28.939 | 2.585 | 21.365 | 1.00 | 41.42 | O |
| ATOM | 726 | ND2 | ASN | A | 98 | 26.848 | 3.544 | 21.068 | 1.00 | 45.05 | N |
| ATOM | 727 | N | PHE | A | 99 | 25.693 | 4.023 | 25.780 | 1.00 | 43.12 | N |
| ATOM | 728 | CA | PHE | A | 99 | 24.501 | 3.811 | 26.618 | 1.00 | 38.76 | C |
| ATOM | 729 | C | PHE | A | 99 | 23.508 | 4.979 | 26.725 | 1.00 | 31.68 | C |
| ATOM | 730 | O | PHE | A | 99 | 22.302 | 4.886 | 26.354 | 1.00 | 21.42 | O |
| ATOM | 731 | CB | PHE | A | 99 | 25.009 | 3.484 | 28.013 | 1.00 | 48.15 | C |
| ATOM | 732 | CG | PHE | A | 99 | 23.870 | 3.381 | 28.954 | 1.00 | 55.54 | C |
| ATOM | 733 | CD1 | PHE | A | 99 | 22.799 | 2.537 | 28.640 | 1.00 | 62.31 | C |
| ATOM | 734 | CD2 | PHE | A | 99 | 23.857 | 4.117 | 30.135 | 1.00 | 55.35 | C |
| ATOM | 735 | CE1 | PHE | A | 99 | 21.710 | 2.417 | 29.497 | 1.00 | 62.42 | C |
| ATOM | 736 | CE2 | PHE | A | 99 | 22.771 | 4.006 | 31.009 | 1.00 | 56.89 | C |
| ATOM | 737 | CZ | PHE | A | 99 | 21.711 | 3.158 | 30.682 | 1.00 | 61.44 | C |
| ATOM | 738 | N | LEU | A | 100 | 24.072 | 6.103 | 27.209 | 1.00 | 23.65 | N |
| ATOM | 739 | CA | LEU | A | 100 | 23.339 | 7.349 | 27.384 | 1.00 | 24.09 | C |
| ATOM | 740 | C | LEU | A | 100 | 22.394 | 7.703 | 26.253 | 1.00 | 28.75 | C |
| ATOM | 741 | O | LEU | A | 100 | 21.381 | 8.311 | 26.533 | 1.00 | 24.99 | O |
| ATOM | 742 | CB | LEU | A | 100 | 24.336 | 8.510 | 27.596 | 1.00 | 25.19 | C |
| ATOM | 743 | CG | LEU | A | 100 | 24.146 | 9.387 | 28.856 | 1.00 | 38.73 | C |
| ATOM | 744 | CD1 | LEU | A | 100 | 23.904 | 8.596 | 30.182 | 1.00 | 34.49 | C |

Figure 22T

| ATOM | 745 | CD2 | LEU | A | 100 | 25.319 | 10.369 | 29.012 | 1.00 | 40.35 | C |
|---|---|---|---|---|---|---|---|---|---|---|---|
| ATOM | 746 | N | THR | A | 101 | 22.701 | 7.368 | 24.967 | 1.00 | 34.16 | N |
| ATOM | 747 | CA | THR | A | 101 | 21.772 | 7.741 | 23.876 | 1.00 | 30.33 | C |
| ATOM | 748 | C | THR | A | 101 | 20.630 | 6.793 | 23.786 | 1.00 | 29.63 | C |
| ATOM | 749 | O | THR | A | 101 | 19.638 | 7.033 | 23.027 | 1.00 | 23.09 | O |
| ATOM | 750 | CB | THR | A | 101 | 22.495 | 7.716 | 22.582 | 1.00 | 27.32 | C |
| ATOM | 751 | OG1 | THR | A | 101 | 22.502 | 6.327 | 22.448 | 1.00 | 36.96 | O |
| ATOM | 752 | CG2 | THR | A | 101 | 23.958 | 8.144 | 22.838 | 1.00 | 20.55 | C |
| ATOM | 753 | N | ARG | A | 102 | 20.776 | 5.695 | 24.586 | 1.00 | 18.52 | N |
| ATOM | 754 | CA | ARG | A | 102 | 19.655 | 4.793 | 24.552 | 1.00 | 13.74 | C |
| ATOM | 755 | C | ARG | A | 102 | 18.467 | 5.533 | 25.096 | 1.00 | 20.73 | C |
| ATOM | 756 | O | ARG | A | 102 | 17.340 | 5.168 | 24.849 | 1.00 | 33.03 | O |
| ATOM | 757 | CB | ARG | A | 102 | 19.957 | 3.609 | 25.346 | 1.00 | 20.90 | C |
| ATOM | 758 | CG | ARG | A | 102 | 21.153 | 2.939 | 24.753 | 1.00 | 21.42 | C |
| ATOM | 759 | CD | ARG | A | 102 | 21.597 | 1.741 | 25.506 | 1.00 | 27.92 | C |
| ATOM | 760 | NE | ARG | A | 102 | 20.448 | 0.909 | 25.870 | 1.00 | 32.41 | N |
| ATOM | 761 | CZ | ARG | A | 102 | 20.622 | -0.127 | 26.700 | 1.00 | 23.88 | C |
| ATOM | 762 | NH1 | ARG | A | 102 | 21.862 | -0.427 | 27.216 | 1.00 | 6.24 | N |
| ATOM | 763 | NH2 | ARG | A | 102 | 19.523 | -0.836 | 26.995 | 1.00 | 11.43 | N |
| ATOM | 764 | N | VAL | A | 103 | 18.714 | 6.610 | 25.839 | 1.00 | 26.46 | N |
| ATOM | 765 | CA | VAL | A | 103 | 17.632 | 7.419 | 26.394 | 1.00 | 33.35 | C |
| ATOM | 766 | C | VAL | A | 103 | 16.998 | 8.335 | 25.318 | 1.00 | 42.47 | C |
| ATOM | 767 | O | VAL | A | 103 | 17.730 | 8.989 | 24.590 | 1.00 | 47.78 | O |
| ATOM | 768 | CB | VAL | A | 103 | 18.119 | 8.276 | 27.543 | 1.00 | 33.17 | C |
| ATOM | 769 | CG1 | VAL | A | 103 | 17.008 | 9.231 | 27.920 | 1.00 | 40.46 | C |
| ATOM | 770 | CG2 | VAL | A | 103 | 18.486 | 7.457 | 28.783 | 1.00 | 24.40 | C |
| ATOM | 771 | N | SER | A | 104 | 15.649 | 8.392 | 25.214 | 1.00 | 35.23 | N |
| ATOM | 772 | CA | SER | A | 104 | 14.973 | 9.226 | 24.211 | 1.00 | 26.45 | C |
| ATOM | 773 | C | SER | A | 104 | 15.072 | 10.683 | 24.515 | 1.00 | 37.46 | C |
| ATOM | 774 | O | SER | A | 104 | 14.650 | 11.128 | 25.562 | 1.00 | 44.65 | O |
| ATOM | 775 | CB | SER | A | 104 | 13.512 | 8.873 | 23.963 | 1.00 | 25.86 | C |
| ATOM | 776 | OG | SER | A | 104 | 12.951 | 9.499 | 22.799 | 1.00 | 30.74 | O |
| ATOM | 777 | N | GLY | A | 105 | 15.620 | 11.401 | 23.547 | 1.00 | 39.54 | N |
| ATOM | 778 | CA | GLY | A | 105 | 15.852 | 12.828 | 23.580 | 1.00 | 27.45 | C |
| ATOM | 779 | C | GLY | A | 105 | 17.335 | 13.046 | 23.751 | 1.00 | 29.70 | C |
| ATOM | 780 | O | GLY | A | 105 | 17.812 | 14.156 | 23.690 | 1.00 | 33.42 | O |
| ATOM | 781 | N | ILE | A | 106 | 18.089 | 11.976 | 23.987 | 1.00 | 34.85 | N |
| ATOM | 782 | CA | ILE | A | 106 | 19.516 | 12.196 | 24.123 | 1.00 | 37.39 | C |
| ATOM | 783 | C | ILE | A | 106 | 20.102 | 11.714 | 22.862 | 1.00 | 46.43 | C |
| ATOM | 784 | O | ILE | A | 106 | 19.727 | 10.677 | 22.313 | 1.00 | 53.00 | O |
| ATOM | 785 | CB | ILE | A | 106 | 20.286 | 11.557 | 25.276 | 1.00 | 32.98 | C |
| ATOM | 786 | CG1 | ILE | A | 106 | 19.769 | 12.038 | 26.622 | 1.00 | 31.54 | C |
| ATOM | 787 | CG2 | ILE | A | 106 | 21.832 | 11.657 | 25.132 | 1.00 | 23.51 | C |
| ATOM | 788 | CD1 | ILE | A | 106 | 20.679 | 11.607 | 27.756 | 1.00 | 36.96 | C |
| ATOM | 789 | N | GLY | A | 107 | 21.016 | 12.508 | 22.426 | 1.00 | 42.30 | N |
| ATOM | 790 | CA | GLY | A | 107 | 21.706 | 12.232 | 21.241 | 1.00 | 31.53 | C |
| ATOM | 791 | C | GLY | A | 107 | 23.097 | 12.281 | 21.711 | 1.00 | 37.00 | C |
| ATOM | 792 | O | GLY | A | 107 | 23.359 | 12.288 | 22.914 | 1.00 | 38.85 | O |
| ATOM | 793 | N | PRO | A | 108 | 23.945 | 12.319 | 20.721 | 1.00 | 42.05 | N |
| ATOM | 794 | CA | PRO | A | 108 | 25.369 | 12.344 | 20.892 | 1.00 | 36.01 | C |
| ATOM | 795 | C | PRO | A | 108 | 25.905 | 13.663 | 21.344 | 1.00 | 25.75 | C |
| ATOM | 796 | O | PRO | A | 108 | 27.008 | 13.717 | 21.916 | 1.00 | 25.33 | O |
| ATOM | 797 | CB | PRO | A | 108 | 25.991 | 11.733 | 19.621 | 1.00 | 35.53 | C |
| ATOM | 798 | CG | PRO | A | 108 | 24.815 | 11.370 | 18.702 | 1.00 | 31.83 | C |
| ATOM | 799 | CD | PRO | A | 108 | 23.519 | 11.831 | 19.362 | 1.00 | 37.85 | C |
| ATOM | 800 | N | SER | A | 109 | 25.169 | 14.741 | 21.085 | 1.00 | 26.53 | N |
| ATOM | 801 | CA | SER | A | 109 | 25.807 | 15.959 | 21.598 | 1.00 | 32.57 | C |
| ATOM | 802 | C | SER | A | 109 | 25.649 | 15.897 | 23.102 | 1.00 | 30.71 | C |
| ATOM | 803 | O | SER | A | 109 | 26.649 | 15.852 | 23.827 | 1.00 | 31.47 | O |
| ATOM | 804 | CB | SER | A | 109 | 25.665 | 17.317 | 20.895 | 1.00 | 31.80 | C |
| ATOM | 805 | OG | SER | A | 109 | 24.413 | 17.435 | 20.200 | 1.00 | 33.96 | O |
| ATOM | 806 | N | ALA | A | 110 | 24.371 | 15.827 | 23.511 | 1.00 | 21.33 | N |
| ATOM | 807 | CA | ALA | A | 110 | 23.979 | 15.709 | 24.896 | 1.00 | 13.82 | C |

Figure 22U

| ATOM | 808 | C | ALA | A | 110 | 24.842 | 14.646 | 25.543 | 1.00 | 18.46 | C |
| ATOM | 809 | O | ALA | A | 110 | 25.643 | 14.889 | 26.425 | 1.00 | 20.57 | O |
| ATOM | 810 | CB | ALA | A | 110 | 22.594 | 15.181 | 24.763 | 1.00 | 6.25 | C |
| ATOM | 811 | N | ALA | A | 111 | 24.720 | 13.438 | 25.048 | 1.00 | 32.39 | N |
| ATOM | 812 | CA | ALA | A | 111 | 25.495 | 12.311 | 25.546 | 1.00 | 28.72 | C |
| ATOM | 813 | C | ALA | A | 111 | 26.962 | 12.627 | 25.674 | 1.00 | 34.19 | C |
| ATOM | 814 | O | ALA | A | 111 | 27.643 | 12.279 | 26.625 | 1.00 | 42.13 | O |
| ATOM | 815 | CB | ALA | A | 111 | 25.278 | 11.077 | 24.737 | 1.00 | 15.22 | C |
| ATOM | 816 | N | ARG | A | 112 | 27.504 | 13.315 | 24.735 | 1.00 | 35.48 | N |
| ATOM | 817 | CA | ARG | A | 112 | 28.903 | 13.568 | 24.935 | 1.00 | 35.96 | C |
| ATOM | 818 | C | ARG | A | 112 | 29.042 | 14.671 | 25.928 | 1.00 | 40.80 | C |
| ATOM | 819 | O | ARG | A | 112 | 30.049 | 14.853 | 26.624 | 1.00 | 33.75 | O |
| ATOM | 820 | CB | ARG | A | 112 | 29.537 | 13.999 | 23.684 | 1.00 | 40.06 | C |
| ATOM | 821 | CG | ARG | A | 112 | 31.000 | 14.264 | 23.935 | 1.00 | 59.96 | C |
| ATOM | 822 | CD | ARG | A | 112 | 31.663 | 14.847 | 22.685 | 1.00 | 78.33 | C |
| ATOM | 823 | NE | ARG | A | 112 | 31.635 | 13.972 | 21.503 | 1.00 | 91.50 | N |
| ATOM | 824 | CZ | ARG | A | 112 | 32.725 | 13.430 | 20.938 | 1.00 | 99.79 | C |
| ATOM | 825 | NH1 | ARG | A | 112 | 33.956 | 13.637 | 21.424 | 1.00 | 100.00 | N |
| ATOM | 826 | NH2 | ARG | A | 112 | 32.578 | 12.652 | 19.859 | 1.00 | 100.00 | N |
| ATOM | 827 | N | LYS | A | 113 | 27.973 | 15.443 | 25.949 | 1.00 | 45.33 | N |
| ATOM | 828 | CA | LYS | A | 113 | 27.974 | 16.573 | 26.839 | 1.00 | 48.97 | C |
| ATOM | 829 | C | LYS | A | 113 | 28.085 | 16.112 | 28.246 | 1.00 | 46.15 | C |
| ATOM | 830 | O | LYS | A | 113 | 29.145 | 16.315 | 28.867 | 1.00 | 43.22 | O |
| ATOM | 831 | CB | LYS | A | 113 | 26.751 | 17.461 | 26.605 | 1.00 | 54.47 | C |
| ATOM | 832 | CG | LYS | A | 113 | 26.386 | 18.434 | 27.722 | 1.00 | 50.41 | C |
| ATOM | 833 | CD | LYS | A | 113 | 25.094 | 19.208 | 27.446 | 1.00 | 44.19 | C |
| ATOM | 834 | CE | LYS | A | 113 | 23.931 | 18.356 | 26.944 | 1.00 | 40.42 | C |
| ATOM | 835 | NZ | LYS | A | 113 | 22.573 | 18.911 | 27.180 | 1.00 | 34.18 | N |
| ATOM | 836 | N | PHE | A | 114 | 26.969 | 15.466 | 28.660 | 1.00 | 42.64 | N |
| ATOM | 837 | CA | PHE | A | 114 | 26.782 | 14.911 | 29.994 | 1.00 | 35.46 | C |
| ATOM | 838 | C | PHE | A | 114 | 28.018 | 14.261 | 30.440 | 1.00 | 37.25 | C |
| ATOM | 839 | O | PHE | A | 114 | 28.652 | 14.691 | 31.382 | 1.00 | 51.33 | O |
| ATOM | 840 | CB | PHE | A | 114 | 25.713 | 13.844 | 30.023 | 1.00 | 21.03 | C |
| ATOM | 841 | CG | PHE | A | 114 | 24.359 | 14.419 | 29.877 | 1.00 | 6.62 | C |
| ATOM | 842 | CD1 | PHE | A | 114 | 24.038 | 15.630 | 30.478 | 1.00 | 13.62 | C |
| ATOM | 843 | CD2 | PHE | A | 114 | 23.381 | 13.776 | 29.131 | 1.00 | 17.04 | C |
| ATOM | 844 | CE1 | PHE | A | 114 | 22.762 | 16.169 | 30.354 | 1.00 | 22.95 | C |
| ATOM | 845 | CE2 | PHE | A | 114 | 22.112 | 14.323 | 28.995 | 1.00 | 20.62 | C |
| ATOM | 846 | CZ | PHE | A | 114 | 21.774 | 15.532 | 29.601 | 1.00 | 13.53 | C |
| ATOM | 847 | N | VAL | A | 115 | 28.341 | 13.246 | 29.718 | 1.00 | 29.14 | N |
| ATOM | 848 | CA | VAL | A | 115 | 29.531 | 12.479 | 29.988 | 1.00 | 41.79 | C |
| ATOM | 849 | C | VAL | A | 115 | 30.804 | 13.273 | 30.347 | 1.00 | 49.52 | C |
| ATOM | 850 | O | VAL | A | 115 | 31.623 | 12.832 | 31.136 | 1.00 | 47.07 | O |
| ATOM | 851 | CB | VAL | A | 115 | 29.741 | 11.578 | 28.791 | 1.00 | 36.82 | C |
| ATOM | 852 | CG1 | VAL | A | 115 | 31.043 | 10.807 | 29.029 | 1.00 | 23.17 | C |
| ATOM | 853 | CG2 | VAL | A | 115 | 28.492 | 10.689 | 28.730 | 1.00 | 27.38 | C |
| ATOM | 854 | N | ASP | A | 116 | 30.973 | 14.442 | 29.751 | 1.00 | 59.77 | N |
| ATOM | 855 | CA | ASP | A | 116 | 32.126 | 15.260 | 30.035 | 1.00 | 61.07 | C |
| ATOM | 856 | C | ASP | A | 116 | 32.016 | 15.777 | 31.473 | 1.00 | 52.67 | C |
| ATOM | 857 | O | ASP | A | 116 | 32.903 | 15.655 | 32.350 | 1.00 | 49.78 | O |
| ATOM | 858 | CB | ASP | A | 116 | 32.195 | 16.409 | 29.023 | 1.00 | 67.23 | C |
| ATOM | 859 | CG | ASP | A | 116 | 32.440 | 15.859 | 27.661 | 1.00 | 80.72 | C |
| ATOM | 860 | OD1 | ASP | A | 116 | 32.215 | 14.691 | 27.391 | 1.00 | 89.00 | O |
| ATOM | 861 | OD2 | ASP | A | 116 | 32.989 | 16.718 | 26.831 | 1.00 | 82.79 | O |
| ATOM | 862 | N | GLU | A | 117 | 30.862 | 16.360 | 31.752 | 1.00 | 41.02 | N |
| ATOM | 863 | CA | GLU | A | 117 | 30.649 | 16.876 | 33.082 | 1.00 | 33.66 | C |
| ATOM | 864 | C | GLU | A | 117 | 30.559 | 15.724 | 34.092 | 1.00 | 45.88 | C |
| ATOM | 865 | O | GLU | A | 117 | 29.995 | 15.877 | 35.154 | 1.00 | 60.57 | O |
| ATOM | 866 | CB | GLU | A | 117 | 29.466 | 17.894 | 33.136 | 1.00 | 12.62 | C |
| ATOM | 867 | CG | GLU | A | 117 | 28.196 | 17.415 | 32.391 | 1.00 | 11.85 | C |
| ATOM | 868 | CD | GLU | A | 117 | 27.119 | 18.480 | 32.350 | 1.00 | 29.71 | C |
| ATOM | 869 | OE1 | GLU | A | 117 | 27.615 | 19.632 | 32.686 | 1.00 | 35.39 | O |
| ATOM | 870 | OE2 | GLU | A | 117 | 25.933 | 18.332 | 32.005 | 1.00 | 38.63 | O |

Figure 22V

| ATOM | 871 | N | GLY | A | 118 | 31.100 | 14.543 | 33.769 | 1.00 | 42.41 | N |
| ATOM | 872 | CA | GLY | A | 118 | 31.082 | 13.383 | 34.643 | 1.00 | 36.11 | C |
| ATOM | 873 | C | GLY | A | 118 | 29.729 | 12.702 | 34.773 | 1.00 | 36.97 | C |
| ATOM | 874 | O | GLY | A | 118 | 29.587 | 11.744 | 35.513 | 1.00 | 41.39 | O |
| ATOM | 875 | N | ILE | A | 119 | 28.717 | 13.167 | 34.082 | 1.00 | 30.23 | N |
| ATOM | 876 | CA | ILE | A | 119 | 27.449 | 12.489 | 34.201 | 1.00 | 33.35 | C |
| ATOM | 877 | C | ILE | A | 119 | 27.523 | 11.256 | 33.348 | 1.00 | 46.80 | C |
| ATOM | 878 | O | ILE | A | 119 | 28.014 | 11.340 | 32.237 | 1.00 | 54.26 | O |
| ATOM | 879 | CB | ILE | A | 119 | 26.412 | 13.349 | 33.558 | 1.00 | 39.16 | C |
| ATOM | 880 | CG1 | ILE | A | 119 | 26.273 | 14.636 | 34.377 | 1.00 | 38.67 | C |
| ATOM | 881 | CG2 | ILE | A | 119 | 25.117 | 12.558 | 33.329 | 1.00 | 39.08 | C |
| ATOM | 882 | CD1 | ILE | A | 119 | 24.956 | 15.366 | 34.119 | 1.00 | 35.60 | C |
| ATOM | 883 | N | LYS | A | 120 | 27.073 | 10.106 | 33.788 | 1.00 | 55.28 | N |
| ATOM | 884 | CA | LYS | A | 120 | 27.238 | 9.023 | 32.849 | 1.00 | 57.80 | C |
| ATOM | 885 | C | LYS | A | 120 | 26.410 | 7.809 | 33.143 | 1.00 | 51.98 | C |
| ATOM | 886 | O | LYS | A | 120 | 26.616 | 6.742 | 32.554 | 1.00 | 46.68 | O |
| ATOM | 887 | CB | LYS | A | 120 | 28.705 | 8.670 | 32.591 | 1.00 | 61.44 | C |
| ATOM | 888 | CG | LYS | A | 120 | 29.409 | 7.819 | 33.631 | 1.00 | 66.53 | C |
| ATOM | 889 | CD | LYS | A | 120 | 30.931 | 7.755 | 33.450 | 1.00 | 67.89 | C |
| ATOM | 890 | CE | LYS | A | 120 | 31.595 | 9.133 | 33.484 | 1.00 | 69.84 | C |
| ATOM | 891 | NZ | LYS | A | 120 | 33.030 | 9.126 | 33.148 | 1.00 | 71.41 | N |
| ATOM | 892 | N | THR | A | 121 | 25.471 | 7.967 | 34.051 | 1.00 | 48.85 | N |
| ATOM | 893 | CA | THR | A | 121 | 24.668 | 6.816 | 34.334 | 1.00 | 51.62 | C |
| ATOM | 894 | C | THR | A | 121 | 23.276 | 7.209 | 34.390 | 1.00 | 45.76 | C |
| ATOM | 895 | O | THR | A | 121 | 22.918 | 8.325 | 34.062 | 1.00 | 45.44 | O |
| ATOM | 896 | CB | THR | A | 121 | 24.975 | 6.165 | 35.677 | 1.00 | 63.56 | C |
| ATOM | 897 | OG1 | THR | A | 121 | 24.914 | 7.172 | 36.669 | 1.00 | 70.43 | O |
| ATOM | 898 | CG2 | THR | A | 121 | 26.337 | 5.476 | 35.630 | 1.00 | 63.87 | C |
| ATOM | 899 | N | LEU | A | 122 | 22.501 | 6.269 | 34.817 | 1.00 | 41.79 | N |
| ATOM | 900 | CA | LEU | A | 122 | 21.134 | 6.570 | 34.897 | 1.00 | 38.98 | C |
| ATOM | 901 | C | LEU | A | 122 | 20.914 | 7.374 | 36.131 | 1.00 | 47.48 | C |
| ATOM | 902 | O | LEU | A | 122 | 20.119 | 8.311 | 36.208 | 1.00 | 51.73 | O |
| ATOM | 903 | CB | LEU | A | 122 | 20.307 | 5.318 | 34.672 | 1.00 | 45.90 | C |
| ATOM | 904 | CG | LEU | A | 122 | 19.056 | 5.641 | 33.864 | 1.00 | 60.09 | C |
| ATOM | 905 | CD1 | LEU | A | 122 | 18.388 | 4.419 | 33.232 | 1.00 | 53.60 | C |
| ATOM | 906 | CD2 | LEU | A | 122 | 18.098 | 6.267 | 34.842 | 1.00 | 67.67 | C |
| ATOM | 907 | N | GLU | A | 123 | 21.673 | 7.011 | 37.125 | 1.00 | 54.39 | N |
| ATOM | 908 | CA | GLU | A | 123 | 21.549 | 7.720 | 38.359 | 1.00 | 58.11 | C |
| ATOM | 909 | C | GLU | A | 123 | 21.932 | 9.160 | 38.226 | 1.00 | 50.19 | C |
| ATOM | 910 | O | GLU | A | 123 | 21.213 | 10.013 | 38.706 | 1.00 | 52.35 | O |
| ATOM | 911 | CB | GLU | A | 123 | 22.301 | 7.066 | 39.510 | 1.00 | 73.72 | C |
| ATOM | 912 | CG | GLU | A | 123 | 21.861 | 5.612 | 39.687 | 1.00 | 87.81 | C |
| ATOM | 913 | CD | GLU | A | 123 | 22.351 | 4.719 | 38.584 | 1.00 | 97.55 | C |
| ATOM | 914 | OE1 | GLU | A | 123 | 23.507 | 4.714 | 38.185 | 1.00 | 100.00 | O |
| ATOM | 915 | OE2 | GLU | A | 123 | 21.396 | 3.969 | 38.083 | 1.00 | 100.00 | O |
| ATOM | 916 | N | ASP | A | 124 | 23.056 | 9.424 | 37.595 | 1.00 | 43.74 | N |
| ATOM | 917 | CA | ASP | A | 124 | 23.462 | 10.800 | 37.442 | 1.00 | 39.68 | C |
| ATOM | 918 | C | ASP | A | 124 | 22.347 | 11.522 | 36.711 | 1.00 | 44.97 | C |
| ATOM | 919 | O | ASP | A | 124 | 22.037 | 12.686 | 36.927 | 1.00 | 48.39 | O |
| ATOM | 920 | CB | ASP | A | 124 | 24.803 | 10.868 | 36.760 | 1.00 | 37.53 | C |
| ATOM | 921 | CG | ASP | A | 124 | 25.753 | 9.778 | 37.194 | 1.00 | 48.88 | C |
| ATOM | 922 | OD1 | ASP | A | 124 | 25.582 | 9.348 | 38.424 | 1.00 | 54.39 | O |
| ATOM | 923 | OD2 | ASP | A | 124 | 26.601 | 9.313 | 36.449 | 1.00 | 52.43 | O |
| ATOM | 924 | N | LEU | A | 125 | 21.695 | 10.784 | 35.839 | 1.00 | 44.35 | N |
| ATOM | 925 | CA | LEU | A | 125 | 20.603 | 11.376 | 35.119 | 1.00 | 44.22 | C |
| ATOM | 926 | C | LEU | A | 125 | 19.551 | 11.692 | 36.126 | 1.00 | 47.01 | C |
| ATOM | 927 | O | LEU | A | 125 | 19.022 | 12.793 | 36.140 | 1.00 | 46.59 | O |
| ATOM | 928 | CB | LEU | A | 125 | 20.071 | 10.442 | 34.046 | 1.00 | 46.09 | C |
| ATOM | 929 | CG | LEU | A | 125 | 21.182 | 10.256 | 33.038 | 1.00 | 46.45 | C |
| ATOM | 930 | CD1 | LEU | A | 125 | 20.938 | 9.012 | 32.204 | 1.00 | 50.46 | C |
| ATOM | 931 | CD2 | LEU | A | 125 | 21.212 | 11.485 | 32.167 | 1.00 | 38.80 | C |
| ATOM | 932 | N | ARG | A | 126 | 19.296 | 10.686 | 36.972 | 1.00 | 51.03 | N |
| ATOM | 933 | CA | ARG | A | 126 | 18.333 | 10.723 | 38.059 | 1.00 | 45.15 | C |

Figure 22W

| ATOM | 934 | C | ARG | A | 126 | 18.603 | 11.943 | 38.959 | 1.00 | 45.61 | C |
|---|---|---|---|---|---|---|---|---|---|---|---|
| ATOM | 935 | O | ARG | A | 126 | 17.728 | 12.754 | 39.261 | 1.00 | 39.16 | O |
| ATOM | 936 | CB | ARG | A | 126 | 18.523 | 9.420 | 38.819 | 1.00 | 48.20 | C |
| ATOM | 937 | CG | ARG | A | 126 | 18.051 | 8.173 | 38.075 | 1.00 | 48.83 | C |
| ATOM | 938 | CD | ARG | A | 126 | 16.577 | 7.896 | 38.387 | 1.00 | 45.47 | C |
| ATOM | 939 | NE | ARG | A | 126 | 15.879 | 7.110 | 37.363 | 1.00 | 49.10 | N |
| ATOM | 940 | CZ | ARG | A | 126 | 16.112 | 5.824 | 37.011 | 1.00 | 37.46 | C |
| ATOM | 941 | NH1 | ARG | A | 126 | 17.077 | 5.038 | 37.562 | 1.00 | 26.22 | N |
| ATOM | 942 | NH2 | ARG | A | 126 | 15.335 | 5.341 | 36.040 | 1.00 | 39.14 | N |
| ATOM | 943 | N | LYS | A | 127 | 19.859 | 12.076 | 39.402 | 1.00 | 42.67 | N |
| ATOM | 944 | CA | LYS | A | 127 | 20.309 | 13.183 | 40.250 | 1.00 | 37.45 | C |
| ATOM | 945 | C | LYS | A | 127 | 20.782 | 14.512 | 39.574 | 1.00 | 56.14 | C |
| ATOM | 946 | O | LYS | A | 127 | 21.686 | 15.210 | 40.103 | 1.00 | 56.54 | O |
| ATOM | 947 | CB | LYS | A | 127 | 21.389 | 12.729 | 41.201 | 1.00 | 30.78 | C |
| ATOM | 948 | CG | LYS | A | 127 | 22.095 | 11.408 | 40.922 | 1.00 | 22.85 | C |
| ATOM | 949 | CD | LYS | A | 127 | 23.365 | 11.539 | 41.704 | 1.00 | 28.75 | C |
| ATOM | 950 | CE | LYS | A | 127 | 24.433 | 10.597 | 41.296 | 1.00 | 39.70 | C |
| ATOM | 951 | NZ | LYS | A | 127 | 25.737 | 11.181 | 41.649 | 1.00 | 52.16 | N |
| ATOM | 952 | N | ASN | A | 128 | 20.190 | 14.878 | 38.422 | 1.00 | 58.71 | N |
| ATOM | 953 | CA | ASN | A | 128 | 20.549 | 16.077 | 37.715 | 1.00 | 43.01 | C |
| ATOM | 954 | C | ASN | A | 128 | 19.483 | 16.489 | 36.761 | 1.00 | 50.91 | C |
| ATOM | 955 | O | ASN | A | 128 | 19.751 | 17.332 | 35.911 | 1.00 | 63.68 | O |
| ATOM | 956 | CB | ASN | A | 128 | 21.756 | 15.793 | 36.865 | 1.00 | 35.77 | C |
| ATOM | 957 | CG | ASN | A | 128 | 22.995 | 15.642 | 37.689 | 1.00 | 42.31 | C |
| ATOM | 958 | OD1 | ASN | A | 128 | 23.542 | 16.626 | 38.181 | 1.00 | 57.69 | O |
| ATOM | 959 | ND2 | ASN | A | 128 | 23.381 | 14.410 | 37.945 | 1.00 | 34.75 | N |
| ATOM | 960 | N | GLU | A | 129 | 18.287 | 15.910 | 36.875 | 1.00 | 49.26 | N |
| ATOM | 961 | CA | GLU | A | 129 | 17.185 | 16.261 | 35.950 | 1.00 | 59.96 | C |
| ATOM | 962 | C | GLU | A | 129 | 17.009 | 17.714 | 35.542 | 1.00 | 48.15 | C |
| ATOM | 963 | O | GLU | A | 129 | 16.340 | 18.019 | 34.572 | 1.00 | 41.88 | O |
| ATOM | 964 | CB | GLU | A | 129 | 15.829 | 15.528 | 36.110 | 1.00 | 77.04 | C |
| ATOM | 965 | CG | GLU | A | 129 | 15.209 | 15.646 | 37.510 | 1.00 | 88.12 | C |
| ATOM | 966 | CD | GLU | A | 129 | 15.871 | 14.672 | 38.422 | 1.00 | 99.28 | C |
| ATOM | 967 | OE1 | GLU | A | 129 | 15.875 | 13.483 | 38.152 | 1.00 | 100.00 | O |
| ATOM | 968 | OE2 | GLU | A | 129 | 16.539 | 15.232 | 39.429 | 1.00 | 100.00 | O |
| ATOM | 969 | N | ASP | A | 130 | 17.591 | 18.590 | 36.323 | 1.00 | 52.03 | N |
| ATOM | 970 | CA | ASP | A | 130 | 17.509 | 20.002 | 36.076 | 1.00 | 59.80 | C |
| ATOM | 971 | C | ASP | A | 130 | 18.221 | 20.342 | 34.755 | 1.00 | 63.69 | C |
| ATOM | 972 | O | ASP | A | 130 | 17.902 | 21.311 | 34.007 | 1.00 | 68.71 | O |
| ATOM | 973 | CB | ASP | A | 130 | 17.933 | 20.794 | 37.318 | 1.00 | 57.96 | C |
| ATOM | 974 | CG | ASP | A | 130 | 19.387 | 20.740 | 37.680 | 1.00 | 67.19 | C |
| ATOM | 975 | OD1 | ASP | A | 130 | 20.217 | 20.090 | 37.073 | 1.00 | 68.37 | O |
| ATOM | 976 | OD2 | ASP | A | 130 | 19.662 | 21.521 | 38.708 | 1.00 | 71.75 | O |
| ATOM | 977 | N | LYS | A | 131 | 19.222 | 19.502 | 34.509 | 1.00 | 51.26 | N |
| ATOM | 978 | CA | LYS | A | 131 | 20.007 | 19.596 | 33.328 | 1.00 | 44.67 | C |
| ATOM | 979 | C | LYS | A | 131 | 19.455 | 18.735 | 32.184 | 1.00 | 49.94 | C |
| ATOM | 980 | O | LYS | A | 131 | 20.250 | 18.243 | 31.415 | 1.00 | 68.48 | O |
| ATOM | 981 | CB | LYS | A | 131 | 21.493 | 19.502 | 33.563 | 1.00 | 34.62 | C |
| ATOM | 982 | CG | LYS | A | 131 | 21.882 | 18.727 | 34.794 | 1.00 | 39.05 | C |
| ATOM | 983 | CD | LYS | A | 131 | 23.293 | 19.055 | 35.308 | 1.00 | 55.38 | C |
| ATOM | 984 | CE | LYS | A | 131 | 23.328 | 20.082 | 36.460 | 1.00 | 73.88 | C |
| ATOM | 985 | NZ | LYS | A | 131 | 22.594 | 19.687 | 37.701 | 1.00 | 76.95 | N |
| ATOM | 986 | N | LEU | A | 132 | 18.119 | 18.555 | 32.062 | 1.00 | 27.08 | N |
| ATOM | 987 | CA | LEU | A | 132 | 17.533 | 17.759 | 31.021 | 1.00 | 14.28 | C |
| ATOM | 988 | C | LEU | A | 132 | 16.253 | 18.365 | 30.540 | 1.00 | 20.18 | C |
| ATOM | 989 | O | LEU | A | 132 | 15.394 | 18.691 | 31.324 | 1.00 | 32.43 | O |
| ATOM | 990 | CB | LEU | A | 132 | 16.933 | 16.486 | 31.597 | 1.00 | 20.82 | C |
| ATOM | 991 | CG | LEU | A | 132 | 17.754 | 15.257 | 31.947 | 1.00 | 29.05 | C |
| ATOM | 992 | CD1 | LEU | A | 132 | 17.097 | 14.141 | 31.132 | 1.00 | 28.76 | C |
| ATOM | 993 | CD2 | LEU | A | 132 | 19.285 | 15.339 | 31.782 | 1.00 | 24.78 | C |
| ATOM | 994 | N | ASN | A | 133 | 16.045 | 18.514 | 29.273 | 1.00 | 17.51 | N |
| ATOM | 995 | CA | ASN | A | 133 | 14.785 | 19.110 | 28.944 | 1.00 | 7.60 | C |
| ATOM | 996 | C | ASN | A | 133 | 13.694 | 18.135 | 29.187 | 1.00 | 9.42 | C |

Figure 22X

```
ATOM    997  O   ASN A 133      13.943  17.042  29.636  1.00 15.17           O
ATOM    998  CB  ASN A 133      14.812  19.433  27.466  1.00 22.64           C
ATOM    999  CG  ASN A 133      15.118  18.218  26.595  1.00 32.62           C
ATOM   1000  OD1 ASN A 133      16.015  18.299  25.754  1.00 34.49           O
ATOM   1001  ND2 ASN A 133      14.293  17.149  26.660  1.00 33.00           N
ATOM   1002  N   HIS A 134      12.495  18.533  28.824  1.00  6.41           N
ATOM   1003  CA  HIS A 134      11.369  17.681  28.989  1.00 16.17           C
ATOM   1004  C   HIS A 134      11.542  16.373  28.306  1.00 33.45           C
ATOM   1005  O   HIS A 134      11.519  15.380  29.038  1.00 41.67           O
ATOM   1006  CB  HIS A 134      10.171  18.271  28.301  1.00 27.72           C
ATOM   1007  CG  HIS A 134       8.856  17.645  28.653  1.00 35.58           C
ATOM   1008  ND1 HIS A 134       8.519  17.314  29.958  1.00 38.38           N
ATOM   1009  CD2 HIS A 134       7.795  17.351  27.854  1.00 38.69           C
ATOM   1010  CE1 HIS A 134       7.275  16.831  29.914  1.00 37.84           C
ATOM   1011  NE2 HIS A 134       6.822  16.827  28.663  1.00 38.97           N
ATOM   1012  N   HIS A 135      11.689  16.428  26.938  1.00 32.62           N
ATOM   1013  CA  HIS A 135      11.860  15.229  26.143  1.00 28.93           C
ATOM   1014  C   HIS A 135      12.840  14.373  26.857  1.00 25.93           C
ATOM   1015  O   HIS A 135      12.450  13.264  27.205  1.00 28.85           O
ATOM   1016  CB  HIS A 135      12.479  15.436  24.752  1.00 34.28           C
ATOM   1017  CG  HIS A 135      12.155  14.316  23.765  1.00 33.46           C
ATOM   1018  ND1 HIS A 135      12.965  13.182  23.594  1.00 29.02           N
ATOM   1019  CD2 HIS A 135      11.081  14.210  22.916  1.00 29.59           C
ATOM   1020  CE1 HIS A 135      12.370  12.439  22.678  1.00 34.75           C
ATOM   1021  NE2 HIS A 135      11.240  13.022  22.252  1.00 33.57           N
ATOM   1022  N   GLN A 136      14.055  14.901  27.102  1.00 12.20           N
ATOM   1023  CA  GLN A 136      14.977  14.071  27.802  1.00 23.68           C
ATOM   1024  C   GLN A 136      14.459  13.559  29.116  1.00 43.60           C
ATOM   1025  O   GLN A 136      14.905  12.498  29.534  1.00 48.90           O
ATOM   1026  CB  GLN A 136      16.247  14.737  28.133  1.00 24.22           C
ATOM   1027  CG  GLN A 136      16.590  15.653  27.030  1.00 27.02           C
ATOM   1028  CD  GLN A 136      18.027  15.959  27.207  1.00 44.11           C
ATOM   1029  OE1 GLN A 136      18.859  15.593  26.342  1.00 49.99           O
ATOM   1030  NE2 GLN A 136      18.341  16.472  28.406  1.00 49.16           N
ATOM   1031  N   ARG A 137      13.564  14.295  29.784  1.00 47.96           N
ATOM   1032  CA  ARG A 137      13.036  13.825  31.074  1.00 43.32           C
ATOM   1033  C   ARG A 137      12.112  12.641  30.919  1.00 32.00           C
ATOM   1034  O   ARG A 137      12.369  11.582  31.479  1.00 33.58           O
ATOM   1035  CB  ARG A 137      12.457  14.925  31.965  1.00 52.67           C
ATOM   1036  CG  ARG A 137      13.563  15.680  32.721  1.00 53.01           C
ATOM   1037  CD  ARG A 137      13.087  16.730  33.698  1.00 57.74           C
ATOM   1038  NE  ARG A 137      12.833  18.016  33.078  1.00 74.98           N
ATOM   1039  CZ  ARG A 137      11.659  18.365  32.562  1.00 91.41           C
ATOM   1040  NH1 ARG A 137      10.617  17.535  32.566  1.00 93.75           N
ATOM   1041  NH2 ARG A 137      11.521  19.579  32.019  1.00 98.00           N
ATOM   1042  N   ILE A 138      11.050  12.828  30.139  1.00 18.65           N
ATOM   1043  CA  ILE A 138      10.074  11.767  29.877  1.00 26.11           C
ATOM   1044  C   ILE A 138      10.706  10.422  29.528  1.00 42.83           C
ATOM   1045  O   ILE A 138      10.249   9.364  29.895  1.00 58.32           O
ATOM   1046  CB  ILE A 138       9.022  12.089  28.837  1.00 17.82           C
ATOM   1047  CG1 ILE A 138       8.099  13.094  29.401  1.00 32.63           C
ATOM   1048  CG2 ILE A 138       8.222  10.883  28.434  1.00 26.20           C
ATOM   1049  CD1 ILE A 138       8.884  14.395  29.398  1.00 54.58           C
ATOM   1050  N   GLY A 139      11.757  10.434  28.779  1.00 39.98           N
ATOM   1051  CA  GLY A 139      12.394   9.211  28.445  1.00 23.81           C
ATOM   1052  C   GLY A 139      13.342   8.801  29.567  1.00 22.22           C
ATOM   1053  O   GLY A 139      13.825   7.724  29.558  1.00 27.88           O
ATOM   1054  N   LEU A 140      13.709   9.630  30.537  1.00 35.92           N
ATOM   1055  CA  LEU A 140      14.609   9.139  31.613  1.00 39.56           C
ATOM   1056  C   LEU A 140      13.659   8.270  32.419  1.00 45.06           C
ATOM   1057  O   LEU A 140      13.929   7.250  33.078  1.00 48.89           O
ATOM   1058  CB  LEU A 140      15.136  10.226  32.596  1.00 26.78           C
ATOM   1059  CG  LEU A 140      15.997   9.676  33.736  1.00 21.43           C
```

Figure 22Y

| ATOM | 1060 | CD1 | LEU | A | 140 | 16.641 | 8.378 | 33.350 | 1.00 | 18.52 | C |
|------|------|-----|-----|---|-----|--------|-------|--------|------|-------|---|
| ATOM | 1061 | CD2 | LEU | A | 140 | 17.093 | 10.620 | 34.132 | 1.00 | 23.07 | C |
| ATOM | 1062 | N | LYS | A | 141 | 12.469 | 8.775 | 32.310 | 1.00 | 43.71 | N |
| ATOM | 1063 | CA | LYS | A | 141 | 11.372 | 8.185 | 32.943 | 1.00 | 49.31 | C |
| ATOM | 1064 | C | LYS | A | 141 | 11.276 | 6.794 | 32.419 | 1.00 | 61.60 | C |
| ATOM | 1065 | O | LYS | A | 141 | 11.931 | 5.863 | 32.939 | 1.00 | 73.13 | O |
| ATOM | 1066 | CB | LYS | A | 141 | 10.099 | 8.970 | 32.633 | 1.00 | 44.69 | C |
| ATOM | 1067 | CG | LYS | A | 141 | 8.895 | 8.684 | 33.485 | 1.00 | 45.41 | C |
| ATOM | 1068 | CD | LYS | A | 141 | 7.788 | 9.676 | 33.171 | 1.00 | 48.74 | C |
| ATOM | 1069 | CE | LYS | A | 141 | 6.627 | 9.647 | 34.159 | 1.00 | 50.19 | C |
| ATOM | 1070 | NZ | LYS | A | 141 | 5.500 | 10.526 | 33.772 | 1.00 | 51.88 | N |
| ATOM | 1071 | N | TYR | A | 142 | 10.438 | 6.735 | 31.373 | 1.00 | 55.19 | N |
| ATOM | 1072 | CA | TYR | A | 142 | 10.093 | 5.554 | 30.624 | 1.00 | 32.14 | C |
| ATOM | 1073 | C | TYR | A | 142 | 11.220 | 4.854 | 29.935 | 1.00 | 27.60 | C |
| ATOM | 1074 | O | TYR | A | 142 | 10.931 | 4.256 | 28.870 | 1.00 | 32.18 | O |
| ATOM | 1075 | CB | TYR | A | 142 | 9.074 | 5.833 | 29.562 | 1.00 | 29.66 | C |
| ATOM | 1076 | CG | TYR | A | 142 | 7.904 | 6.583 | 30.083 | 1.00 | 45.68 | C |
| ATOM | 1077 | CD1 | TYR | A | 142 | 7.084 | 6.021 | 31.059 | 1.00 | 48.83 | C |
| ATOM | 1078 | CD2 | TYR | A | 142 | 7.603 | 7.848 | 29.588 | 1.00 | 56.12 | C |
| ATOM | 1079 | CE1 | TYR | A | 142 | 5.975 | 6.702 | 31.548 | 1.00 | 54.14 | C |
| ATOM | 1080 | CE2 | TYR | A | 142 | 6.493 | 8.541 | 30.065 | 1.00 | 65.41 | C |
| ATOM | 1081 | CZ | TYR | A | 142 | 5.677 | 7.969 | 31.043 | 1.00 | 63.36 | C |
| ATOM | 1082 | OH | TYR | A | 142 | 4.566 | 8.650 | 31.517 | 1.00 | 63.47 | O |
| ATOM | 1083 | N | PHE | A | 143 | 12.435 | 4.909 | 30.519 | 1.00 | 20.00 | N |
| ATOM | 1084 | CA | PHE | A | 143 | 13.575 | 4.236 | 29.903 | 1.00 | 31.90 | C |
| ATOM | 1085 | C | PHE | A | 143 | 13.180 | 2.838 | 29.464 | 1.00 | 43.18 | C |
| ATOM | 1086 | O | PHE | A | 143 | 12.933 | 2.618 | 28.302 | 1.00 | 44.30 | O |
| ATOM | 1087 | CB | PHE | A | 143 | 14.797 | 4.143 | 30.835 | 1.00 | 36.34 | C |
| ATOM | 1088 | CG | PHE | A | 143 | 16.062 | 3.698 | 30.107 | 1.00 | 47.51 | C |
| ATOM | 1089 | CD1 | PHE | A | 143 | 16.841 | 4.617 | 29.397 | 1.00 | 45.21 | C |
| ATOM | 1090 | CD2 | PHE | A | 143 | 16.485 | 2.364 | 30.114 | 1.00 | 54.52 | C |
| ATOM | 1091 | CE1 | PHE | A | 143 | 17.999 | 4.227 | 28.717 | 1.00 | 47.22 | C |
| ATOM | 1092 | CE2 | PHE | A | 143 | 17.647 | 1.951 | 29.450 | 1.00 | 49.30 | C |
| ATOM | 1093 | CZ | PHE | A | 143 | 18.407 | 2.890 | 28.750 | 1.00 | 46.40 | C |
| ATOM | 1094 | N | GLY | A | 144 | 13.046 | 1.954 | 30.422 | 1.00 | 52.71 | N |
| ATOM | 1095 | CA | GLY | A | 144 | 12.672 | 0.590 | 30.195 | 1.00 | 45.05 | C |
| ATOM | 1096 | C | GLY | A | 144 | 11.521 | 0.411 | 29.247 | 1.00 | 39.40 | C |
| ATOM | 1097 | O | GLY | A | 144 | 11.637 | -0.440 | 28.389 | 1.00 | 53.96 | O |
| ATOM | 1098 | N | ASP | A | 145 | 10.441 | 1.172 | 29.383 | 1.00 | 35.36 | N |
| ATOM | 1099 | CA | ASP | A | 145 | 9.260 | 1.033 | 28.495 | 1.00 | 48.77 | C |
| ATOM | 1100 | C | ASP | A | 145 | 9.529 | 1.151 | 27.035 | 1.00 | 52.64 | C |
| ATOM | 1101 | O | ASP | A | 145 | 8.894 | 0.457 | 26.186 | 1.00 | 36.80 | O |
| ATOM | 1102 | CB | ASP | A | 145 | 7.957 | 1.757 | 28.876 | 1.00 | 60.52 | C |
| ATOM | 1103 | CG | ASP | A | 145 | 7.438 | 1.198 | 30.180 | 1.00 | 69.83 | C |
| ATOM | 1104 | OD1 | ASP | A | 145 | 8.021 | 0.273 | 30.738 | 1.00 | 72.67 | O |
| ATOM | 1105 | OD2 | ASP | A | 145 | 6.384 | 1.837 | 30.685 | 1.00 | 68.37 | O |
| ATOM | 1106 | N | PHE | A | 146 | 10.479 | 2.082 | 26.834 | 1.00 | 57.88 | N |
| ATOM | 1107 | CA | PHE | A | 146 | 11.021 | 2.491 | 25.546 | 1.00 | 51.55 | C |
| ATOM | 1108 | C | PHE | A | 146 | 11.753 | 1.443 | 24.689 | 1.00 | 47.24 | C |
| ATOM | 1109 | O | PHE | A | 146 | 11.618 | 1.523 | 23.471 | 1.00 | 50.36 | O |
| ATOM | 1110 | CB | PHE | A | 146 | 11.594 | 3.910 | 25.507 | 1.00 | 42.82 | C |
| ATOM | 1111 | CG | PHE | A | 146 | 10.493 | 4.932 | 25.677 | 1.00 | 41.46 | C |
| ATOM | 1112 | CD1 | PHE | A | 146 | 9.173 | 4.615 | 25.346 | 1.00 | 46.24 | C |
| ATOM | 1113 | CD2 | PHE | A | 146 | 10.772 | 6.210 | 26.156 | 1.00 | 36.36 | C |
| ATOM | 1114 | CE1 | PHE | A | 146 | 8.143 | 5.547 | 25.488 | 1.00 | 51.09 | C |
| ATOM | 1115 | CE2 | PHE | A | 146 | 9.755 | 7.153 | 26.310 | 1.00 | 44.80 | C |
| ATOM | 1116 | CZ | PHE | A | 146 | 8.442 | 6.819 | 25.974 | 1.00 | 49.32 | C |
| ATOM | 1117 | N | GLU | A | 147 | 12.495 | 0.504 | 25.323 | 1.00 | 33.31 | N |
| ATOM | 1118 | CA | GLU | A | 147 | 13.229 | -0.567 | 24.673 | 1.00 | 27.53 | C |
| ATOM | 1119 | C | GLU | A | 147 | 12.312 | -1.819 | 24.567 | 1.00 | 37.42 | C |
| ATOM | 1120 | O | GLU | A | 147 | 12.776 | -2.919 | 24.405 | 1.00 | 46.83 | O |
| ATOM | 1121 | CB | GLU | A | 147 | 14.609 | -0.867 | 25.342 | 1.00 | 13.10 | C |
| ATOM | 1122 | CG | GLU | A | 147 | 15.562 | 0.351 | 25.313 | 1.00 | 14.09 | C |

Figure 22Z

```
ATOM   1123  CD  GLU A 147      16.980   0.108  25.804  1.00 26.46           C
ATOM   1124  OE1 GLU A 147      17.277  -0.796  26.574  1.00 29.83           O
ATOM   1125  OE2 GLU A 147      17.875   0.965  25.319  1.00 28.46           O
ATOM   1126  N   LYS A 148      10.987  -1.686  24.664  1.00 41.58           N
ATOM   1127  CA  LYS A 148      10.106  -2.861  24.580  1.00 43.83           C
ATOM   1128  C   LYS A 148       9.397  -2.960  23.328  1.00 60.20           C
ATOM   1129  O   LYS A 148       8.946  -1.937  22.824  1.00 73.99           O
ATOM   1130  CB  LYS A 148       8.912  -2.824  25.491  1.00 45.96           C
ATOM   1131  CG  LYS A 148       9.402  -2.693  26.897  1.00 51.10           C
ATOM   1132  CD  LYS A 148       8.592  -3.459  27.897  1.00 41.63           C
ATOM   1133  CE  LYS A 148       9.499  -3.791  29.044  1.00 40.58           C
ATOM   1134  NZ  LYS A 148       8.742  -3.751  30.282  1.00 50.72           N
ATOM   1135  N   ARG A 149       9.258  -4.186  22.854  1.00 63.38           N
ATOM   1136  CA  ARG A 149       8.543  -4.325  21.615  1.00 65.24           C
ATOM   1137  C   ARG A 149       7.065  -4.310  21.861  1.00 63.43           C
ATOM   1138  O   ARG A 149       6.592  -4.760  22.915  1.00 69.96           O
ATOM   1139  CB  ARG A 149       9.006  -5.515  20.816  1.00 69.15           C
ATOM   1140  CG  ARG A 149      10.454  -5.279  20.478  1.00 73.94           C
ATOM   1141  CD  ARG A 149      10.798  -5.755  19.089  1.00 74.00           C
ATOM   1142  NE  ARG A 149       9.836  -5.349  18.073  1.00 71.82           N
ATOM   1143  CZ  ARG A 149       9.972  -4.255  17.334  1.00 76.44           C
ATOM   1144  NH1 ARG A 149      11.016  -3.426  17.496  1.00 80.19           N
ATOM   1145  NH2 ARG A 149       9.032  -3.992  16.417  1.00 74.64           N
ATOM   1146  N   ILE A 150       6.340  -3.782  20.904  1.00 47.09           N
ATOM   1147  CA  ILE A 150       4.924  -3.760  21.119  1.00 49.79           C
ATOM   1148  C   ILE A 150       4.225  -4.876  20.404  1.00 51.15           C
ATOM   1149  O   ILE A 150       4.366  -5.046  19.231  1.00 51.98           O
ATOM   1150  CB  ILE A 150       4.291  -2.423  20.797  1.00 52.31           C
ATOM   1151  CG1 ILE A 150       4.939  -1.368  21.685  1.00 52.53           C
ATOM   1152  CG2 ILE A 150       2.789  -2.510  21.025  1.00 51.78           C
ATOM   1153  CD1 ILE A 150       4.347   0.008  21.469  1.00 53.30           C
ATOM   1154  N   PRO A 151       3.467  -5.640  21.128  1.00 51.39           N
ATOM   1155  CA  PRO A 151       2.731  -6.735  20.573  1.00 47.22           C
ATOM   1156  C   PRO A 151       1.490  -6.316  19.861  1.00 58.47           C
ATOM   1157  O   PRO A 151       0.547  -5.972  20.566  1.00 68.58           O
ATOM   1158  CB  PRO A 151       2.293  -7.489  21.819  1.00 38.45           C
ATOM   1159  CG  PRO A 151       3.505  -7.400  22.737  1.00 43.83           C
ATOM   1160  CD  PRO A 151       4.250  -6.135  22.294  1.00 47.61           C
ATOM   1161  N   ARG A 152       1.513  -6.372  18.513  1.00 59.79           N
ATOM   1162  CA  ARG A 152       0.392  -6.009  17.648  1.00 71.46           C
ATOM   1163  C   ARG A 152      -0.989  -6.250  18.275  1.00 81.32           C
ATOM   1164  O   ARG A 152      -1.961  -5.564  17.952  1.00 82.98           O
ATOM   1165  CB  ARG A 152       0.486  -6.691  16.308  1.00 77.37           C
ATOM   1166  CG  ARG A 152      -0.902  -7.073  15.820  1.00 81.32           C
ATOM   1167  CD  ARG A 152      -0.830  -8.004  14.627  1.00 83.57           C
ATOM   1168  NE  ARG A 152      -0.170  -7.314  13.546  1.00 87.20           N
ATOM   1169  CZ  ARG A 152      -0.862  -6.637  12.650  1.00 95.14           C
ATOM   1170  NH1 ARG A 152      -2.192  -6.575  12.704  1.00100.00           N
ATOM   1171  NH2 ARG A 152      -0.224  -6.005  11.676  1.00 95.89           N
ATOM   1172  N   GLU A 153      -1.055  -7.247  19.181  1.00 82.34           N
ATOM   1173  CA  GLU A 153      -2.288  -7.567  19.868  1.00 78.18           C
ATOM   1174  C   GLU A 153      -2.669  -6.401  20.754  1.00 74.37           C
ATOM   1175  O   GLU A 153      -3.805  -5.918  20.704  1.00 77.51           O
ATOM   1176  CB  GLU A 153      -2.257  -8.898  20.617  1.00 81.10           C
ATOM   1177  CG  GLU A 153      -3.294  -9.880  20.040  1.00 91.51           C
ATOM   1178  CD  GLU A 153      -4.715  -9.407  20.262  1.00 99.09           C
ATOM   1179  OE1 GLU A 153      -5.003  -8.254  20.581  1.00100.00           O
ATOM   1180  OE2 GLU A 153      -5.600 -10.376  20.121  1.00100.00           O
ATOM   1181  N   GLU A 154      -1.684  -5.974  21.556  1.00 68.55           N
ATOM   1182  CA  GLU A 154      -1.864  -4.855  22.443  1.00 65.00           C
ATOM   1183  C   GLU A 154      -2.160  -3.746  21.460  1.00 69.50           C
ATOM   1184  O   GLU A 154      -3.078  -2.933  21.650  1.00 76.23           O
ATOM   1185  CB  GLU A 154      -0.590  -4.436  23.198  1.00 61.89           C
```

Figure 22AA

```
ATOM   1186  CG   GLU A 154      -0.143  -5.325  24.363  1.00 72.61           C
ATOM   1187  CD   GLU A 154       1.001  -4.673  25.112  1.00 89.64           C
ATOM   1188  OE1  GLU A 154       1.400  -3.556  24.824  1.00 96.71           O
ATOM   1189  OE2  GLU A 154       1.542  -5.414  26.071  1.00 93.80           O
ATOM   1190  N    MET A 155      -1.335  -3.777  20.400  1.00 58.58           N
ATOM   1191  CA   MET A 155      -1.416  -2.829  19.337  1.00 56.48           C
ATOM   1192  C    MET A 155      -2.849  -2.754  18.894  1.00 63.55           C
ATOM   1193  O    MET A 155      -3.434  -1.678  18.884  1.00 70.65           O
ATOM   1194  CB   MET A 155      -0.341  -2.993  18.221  1.00 54.22           C
ATOM   1195  CG   MET A 155       1.055  -2.425  18.598  1.00 48.54           C
ATOM   1196  SD   MET A 155       1.519  -0.852  17.753  1.00 50.88           S
ATOM   1197  CE   MET A 155       3.242  -0.577  18.282  1.00 48.03           C
ATOM   1198  N    LEU A 156      -3.412  -3.914  18.598  1.00 67.75           N
ATOM   1199  CA   LEU A 156      -4.796  -4.035  18.172  1.00 67.04           C
ATOM   1200  C    LEU A 156      -5.669  -3.306  19.119  1.00 60.47           C
ATOM   1201  O    LEU A 156      -6.419  -2.465  18.683  1.00 51.21           O
ATOM   1202  CB   LEU A 156      -5.222  -5.485  18.249  1.00 71.57           C
ATOM   1203  CG   LEU A 156      -4.546  -6.253  17.152  1.00 76.48           C
ATOM   1204  CD1  LEU A 156      -5.209  -7.620  17.106  1.00 81.90           C
ATOM   1205  CD2  LEU A 156      -4.692  -5.477  15.824  1.00 72.02           C
ATOM   1206  N    GLN A 157      -5.501  -3.668  20.391  1.00 69.98           N
ATOM   1207  CA   GLN A 157      -6.232  -3.079  21.481  1.00 78.80           C
ATOM   1208  C    GLN A 157      -6.034  -1.580  21.270  1.00 77.69           C
ATOM   1209  O    GLN A 157      -7.008  -0.825  21.160  1.00 79.97           O
ATOM   1210  CB   GLN A 157      -5.701  -3.581  22.883  1.00 83.42           C
ATOM   1211  CG   GLN A 157      -6.791  -3.871  23.997  1.00 90.89           C
ATOM   1212  CD   GLN A 157      -6.337  -4.349  25.414  1.00 89.82           C
ATOM   1213  OE1  GLN A 157      -5.632  -5.359  25.595  1.00 84.94           O
ATOM   1214  NE2  GLN A 157      -6.759  -3.627  26.460  1.00 89.85           N
ATOM   1215  N    MET A 158      -4.755  -1.178  21.150  1.00 68.25           N
ATOM   1216  CA   MET A 158      -4.422   0.227  20.942  1.00 54.61           C
ATOM   1217  C    MET A 158      -5.223   0.860  19.827  1.00 56.07           C
ATOM   1218  O    MET A 158      -5.769   1.958  19.921  1.00 51.35           O
ATOM   1219  CB   MET A 158      -2.929   0.421  20.670  1.00 36.82           C
ATOM   1220  CG   MET A 158      -2.106  -0.330  21.680  1.00 38.55           C
ATOM   1221  SD   MET A 158      -0.391   0.240  21.710  1.00 54.52           S
ATOM   1222  CE   MET A 158       0.285  -0.536  23.204  1.00 53.42           C
ATOM   1223  N    GLN A 159      -5.269   0.123  18.768  1.00 59.37           N
ATOM   1224  CA   GLN A 159      -5.953   0.584  17.632  1.00 62.17           C
ATOM   1225  C    GLN A 159      -7.374   0.948  17.904  1.00 60.59           C
ATOM   1226  O    GLN A 159      -7.947   1.805  17.269  1.00 60.23           O
ATOM   1227  CB   GLN A 159      -5.821  -0.369  16.444  1.00 66.76           C
ATOM   1228  CG   GLN A 159      -7.093  -1.191  16.306  1.00 73.96           C
ATOM   1229  CD   GLN A 159      -7.100  -2.012  15.056  1.00 81.33           C
ATOM   1230  OE1  GLN A 159      -6.969  -1.468  13.944  1.00 87.96           O
ATOM   1231  NE2  GLN A 159      -7.279  -3.314  15.230  1.00 77.24           N
ATOM   1232  N    ASP A 160      -7.959   0.301  18.845  1.00 65.13           N
ATOM   1233  CA   ASP A 160      -9.316   0.676  19.035  1.00 77.67           C
ATOM   1234  C    ASP A 160      -9.599   2.069  19.492  1.00 79.10           C
ATOM   1235  O    ASP A 160     -10.283   2.822  18.799  1.00 81.03           O
ATOM   1236  CB   ASP A 160     -10.096  -0.253  19.942  1.00 91.42           C
ATOM   1237  CG   ASP A 160     -11.533  -0.154  19.532  1.00100.00           C
ATOM   1238  OD1  ASP A 160     -11.996   0.787  18.878  1.00100.00           O
ATOM   1239  OD2  ASP A 160     -12.199  -1.239  19.851  1.00100.00           O
ATOM   1240  N    ILE A 161      -9.084   2.364  20.662  1.00 77.32           N
ATOM   1241  CA   ILE A 161      -9.287   3.641  21.268  1.00 74.41           C
ATOM   1242  C    ILE A 161      -9.090   4.801  20.344  1.00 71.82           C
ATOM   1243  O    ILE A 161     -10.017   5.594  20.122  1.00 76.92           O
ATOM   1244  CB   ILE A 161      -8.361   3.756  22.446  1.00 76.47           C
ATOM   1245  CG1  ILE A 161      -8.666   2.605  23.408  1.00 80.12           C
ATOM   1246  CG2  ILE A 161      -8.598   5.112  23.092  1.00 75.71           C
ATOM   1247  CD1  ILE A 161      -7.442   1.989  24.091  1.00 79.73           C
ATOM   1248  N    VAL A 162      -7.883   4.872  19.809  1.00 64.30           N
```

Figure 22AB

```
ATOM   1249  CA  VAL A 162      -7.555   5.956  18.922  1.00 63.35           C
ATOM   1250  C   VAL A 162      -8.551   6.103  17.812  1.00 65.14           C
ATOM   1251  O   VAL A 162      -8.897   7.195  17.386  1.00 66.00           O
ATOM   1252  CB  VAL A 162      -6.099   6.017  18.514  1.00 55.78           C
ATOM   1253  CG1 VAL A 162      -5.285   4.972  19.278  1.00 50.26           C
ATOM   1254  CG2 VAL A 162      -5.931   5.973  17.012  1.00 54.64           C
ATOM   1255  N   LEU A 163      -9.004   4.964  17.368  1.00 69.90           N
ATOM   1256  CA  LEU A 163      -9.977   4.921  16.314  1.00 71.81           C
ATOM   1257  C   LEU A 163     -11.259   5.461  16.852  1.00 67.62           C
ATOM   1258  O   LEU A 163     -11.943   6.265  16.217  1.00 63.23           O
ATOM   1259  CB  LEU A 163     -10.194   3.486  15.829  1.00 75.42           C
ATOM   1260  CG  LEU A 163      -9.175   3.132  14.773  1.00 73.23           C
ATOM   1261  CD1 LEU A 163      -9.582   3.774  13.449  1.00 75.03           C
ATOM   1262  CD2 LEU A 163      -7.819   3.669  15.192  1.00 69.06           C
ATOM   1263  N   ASN A 164     -11.570   4.974  18.041  1.00 68.34           N
ATOM   1264  CA  ASN A 164     -12.774   5.435  18.635  1.00 74.90           C
ATOM   1265  C   ASN A 164     -12.763   6.878  19.076  1.00 75.54           C
ATOM   1266  O   ASN A 164     -13.667   7.657  18.709  1.00 79.24           O
ATOM   1267  CB  ASN A 164     -13.915   4.469  19.008  1.00 80.76           C
ATOM   1268  CG  ASN A 164     -14.122   3.344  17.992  1.00 86.85           C
ATOM   1269  OD1 ASN A 164     -15.256   3.093  17.531  1.00 88.05           O
ATOM   1270  ND2 ASN A 164     -13.043   2.609  17.680  1.00 86.80           N
ATOM   1271  N   GLU A 165     -11.697   7.188  19.839  1.00 65.07           N
ATOM   1272  CA  GLU A 165     -11.470   8.505  20.374  1.00 59.82           C
ATOM   1273  C   GLU A 165     -11.754   9.556  19.322  1.00 66.60           C
ATOM   1274  O   GLU A 165     -12.584  10.428  19.561  1.00 71.97           O
ATOM   1275  CB  GLU A 165     -10.084   8.617  21.026  1.00 54.32           C
ATOM   1276  CG  GLU A 165      -9.968   7.622  22.197  1.00 53.00           C
ATOM   1277  CD  GLU A 165     -11.285   7.273  22.851  1.00 60.69           C
ATOM   1278  OE1 GLU A 165     -11.831   7.947  23.715  1.00 49.75           O
ATOM   1279  OE2 GLU A 165     -11.792   6.147  22.387  1.00 73.89           O
ATOM   1280  N   VAL A 166     -11.087   9.420  18.161  1.00 63.93           N
ATOM   1281  CA  VAL A 166     -11.214  10.306  16.999  1.00 59.94           C
ATOM   1282  C   VAL A 166     -12.611  10.249  16.392  1.00 62.16           C
ATOM   1283  O   VAL A 166     -13.123  11.220  15.818  1.00 63.53           O
ATOM   1284  CB  VAL A 166     -10.148  10.076  15.885  1.00 60.47           C
ATOM   1285  CG1 VAL A 166      -8.752   9.821  16.434  1.00 59.68           C
ATOM   1286  CG2 VAL A 166     -10.512   8.955  14.918  1.00 55.64           C
ATOM   1287  N   LYS A 167     -13.215   9.078  16.503  1.00 63.37           N
ATOM   1288  CA  LYS A 167     -14.531   8.869  15.969  1.00 67.29           C
ATOM   1289  C   LYS A 167     -15.488   9.863  16.585  1.00 74.43           C
ATOM   1290  O   LYS A 167     -16.369  10.409  15.911  1.00 72.35           O
ATOM   1291  CB  LYS A 167     -14.984   7.457  16.228  1.00 73.32           C
ATOM   1292  CG  LYS A 167     -16.328   7.168  15.598  1.00 81.12           C
ATOM   1293  CD  LYS A 167     -16.273   7.128  14.077  1.00 86.92           C
ATOM   1294  CE  LYS A 167     -17.425   6.333  13.436  1.00 89.56           C
ATOM   1295  NZ  LYS A 167     -18.749   6.994  13.482  1.00 85.91           N
ATOM   1296  N   LYS A 168     -15.307  10.085  17.900  1.00 81.00           N
ATOM   1297  CA  LYS A 168     -16.149  11.027  18.651  1.00 76.62           C
ATOM   1298  C   LYS A 168     -15.906  12.500  18.266  1.00 69.91           C
ATOM   1299  O   LYS A 168     -16.837  13.222  17.897  1.00 73.03           O
ATOM   1300  CB  LYS A 168     -15.990  10.892  20.159  1.00 67.02           C
ATOM   1301  CG  LYS A 168     -16.329   9.551  20.727  1.00 66.76           C
ATOM   1302  CD  LYS A 168     -15.446   9.237  21.933  1.00 76.53           C
ATOM   1303  CE  LYS A 168     -15.352   7.737  22.222  1.00 85.19           C
ATOM   1304  NZ  LYS A 168     -14.089   7.338  22.874  1.00 85.91           N
ATOM   1305  N   VAL A 169     -14.639  12.934  18.362  1.00 56.37           N
ATOM   1306  CA  VAL A 169     -14.282  14.292  18.044  1.00 50.99           C
ATOM   1307  C   VAL A 169     -14.823  14.767  16.724  1.00 68.32           C
ATOM   1308  O   VAL A 169     -15.384  15.861  16.648  1.00 73.60           O
ATOM   1309  CB  VAL A 169     -12.837  14.700  18.315  1.00 36.16           C
ATOM   1310  CG1 VAL A 169     -11.965  13.487  18.273  1.00 29.20           C
ATOM   1311  CG2 VAL A 169     -12.342  15.705  17.277  1.00 39.17           C
```

Figure 22AC

```
ATOM   1312  N    ASP A 170     -14.660  13.935  15.693  1.00 74.26           N
ATOM   1313  CA   ASP A 170     -15.136  14.253  14.360  1.00 75.03           C
ATOM   1314  C    ASP A 170     -15.276  12.952  13.594  1.00 84.75           C
ATOM   1315  O    ASP A 170     -14.425  12.063  13.698  1.00 83.07           O
ATOM   1316  CB   ASP A 170     -14.216  15.276  13.635  1.00 71.17           C
ATOM   1317  CG   ASP A 170     -14.852  16.261  12.654  1.00 66.74           C
ATOM   1318  OD1  ASP A 170     -15.925  16.091  12.051  1.00 62.46           O
ATOM   1319  OD2  ASP A 170     -14.092  17.340  12.511  1.00 59.72           O
ATOM   1320  N    SER A 171     -16.391  12.880  12.849  1.00 94.28           N
ATOM   1321  CA   SER A 171     -16.839  11.766  12.001  1.00 95.83           C
ATOM   1322  C    SER A 171     -16.136  11.712  10.658  1.00 90.92           C
ATOM   1323  O    SER A 171     -15.966  10.639  10.082  1.00 83.42           O
ATOM   1324  CB   SER A 171     -18.349  11.868  11.764  1.00 97.72           C
ATOM   1325  OG   SER A 171     -18.731  11.111  10.630  1.00 96.48           O
ATOM   1326  N    GLU A 172     -15.763  12.904  10.197  1.00 94.53           N
ATOM   1327  CA   GLU A 172     -15.082  13.136   8.942  1.00 99.03           C
ATOM   1328  C    GLU A 172     -13.560  13.013   9.068  1.00 99.47           C
ATOM   1329  O    GLU A 172     -12.867  12.959   8.048  1.00100.00           O
ATOM   1330  CB   GLU A 172     -15.483  14.478   8.257  1.00100.00           C
ATOM   1331  CG   GLU A 172     -16.987  14.638   7.921  1.00 98.63           C
ATOM   1332  CD   GLU A 172     -17.318  15.909   7.153  1.00100.00           C
ATOM   1333  OE1  GLU A 172     -16.564  16.874   7.069  1.00100.00           O
ATOM   1334  OE2  GLU A 172     -18.503  15.874   6.566  1.00100.00           O
ATOM   1335  N    TYR A 173     -13.029  12.977  10.299  1.00 94.96           N
ATOM   1336  CA   TYR A 173     -11.583  12.855  10.482  1.00 96.35           C
ATOM   1337  C    TYR A 173     -11.110  11.570   9.821  1.00 96.45           C
ATOM   1338  O    TYR A 173     -11.914  10.670   9.555  1.00100.00           O
ATOM   1339  CB   TYR A 173     -11.200  12.725  11.963  1.00100.00           C
ATOM   1340  CG   TYR A 173     -10.741  13.956  12.699  1.00 98.60           C
ATOM   1341  CD1  TYR A 173      -9.647  14.691  12.243  1.00 98.91           C
ATOM   1342  CD2  TYR A 173     -11.387  14.346  13.874  1.00 94.99           C
ATOM   1343  CE1  TYR A 173      -9.216  15.821  12.940  1.00100.00           C
ATOM   1344  CE2  TYR A 173     -10.970  15.474  14.582  1.00 97.91           C
ATOM   1345  CZ   TYR A 173      -9.880  16.207  14.109  1.00100.00           C
ATOM   1346  OH   TYR A 173      -9.455  17.322  14.793  1.00100.00           O
ATOM   1347  N    ILE A 174      -9.808  11.456   9.571  1.00 88.54           N
ATOM   1348  CA   ILE A 174      -9.333  10.249   8.943  1.00 81.01           C
ATOM   1349  C    ILE A 174      -8.089   9.704   9.581  1.00 70.39           C
ATOM   1350  O    ILE A 174      -6.970  10.174   9.433  1.00 62.40           O
ATOM   1351  CB   ILE A 174      -9.193  10.428   7.437  1.00 90.73           C
ATOM   1352  CG1  ILE A 174     -10.564  10.676   6.805  1.00 91.34           C
ATOM   1353  CG2  ILE A 174      -8.537   9.200   6.817  1.00 97.27           C
ATOM   1354  CD1  ILE A 174     -10.482  11.203   5.376  1.00 93.62           C
ATOM   1355  N    ALA A 175      -8.314   8.676  10.337  1.00 72.88           N
ATOM   1356  CA   ALA A 175      -7.212   8.075  11.001  1.00 75.70           C
ATOM   1357  C    ALA A 175      -7.043   6.731  10.420  1.00 76.67           C
ATOM   1358  O    ALA A 175      -8.031   6.090   9.999  1.00 81.68           O
ATOM   1359  CB   ALA A 175      -7.495   7.939  12.479  1.00 80.07           C
ATOM   1360  N    THR A 176      -5.780   6.350  10.431  1.00 67.92           N
ATOM   1361  CA   THR A 176      -5.323   5.085   9.922  1.00 63.26           C
ATOM   1362  C    THR A 176      -3.942   4.839  10.460  1.00 63.61           C
ATOM   1363  O    THR A 176      -3.034   5.625  10.215  1.00 66.77           O
ATOM   1364  CB   THR A 176      -5.326   4.964   8.363  1.00 60.44           C
ATOM   1365  OG1  THR A 176      -4.239   4.151   7.992  1.00 57.19           O
ATOM   1366  CG2  THR A 176      -5.250   6.296   7.607  1.00 58.87           C
ATOM   1367  N    VAL A 177      -3.765   3.761  11.209  1.00 60.80           N
ATOM   1368  CA   VAL A 177      -2.444   3.516  11.733  1.00 60.87           C
ATOM   1369  C    VAL A 177      -1.553   3.260  10.553  1.00 66.90           C
ATOM   1370  O    VAL A 177      -2.054   3.065   9.451  1.00 75.48           O
ATOM   1371  CB   VAL A 177      -2.403   2.300  12.622  1.00 60.51           C
ATOM   1372  CG1  VAL A 177      -1.050   2.223  13.331  1.00 57.70           C
ATOM   1373  CG2  VAL A 177      -3.556   2.386  13.613  1.00 64.23           C
ATOM   1374  N    CYS A 178      -0.256   3.247  10.796  1.00 58.58           N
```

Figure 22AD

```
ATOM   1375  CA  CYS A 178       0.706   3.011   9.755  1.00 48.48           C
ATOM   1376  C   CYS A 178       1.988   2.473  10.322  1.00 56.14           C
ATOM   1377  O   CYS A 178       2.006   2.040  11.484  1.00 62.09           O
ATOM   1378  CB  CYS A 178       0.977   4.205   8.860  1.00 45.05           C
ATOM   1379  SG  CYS A 178      -0.419   4.546   7.780  1.00 59.24           S
ATOM   1380  N   GLY A 179       3.033   2.512   9.481  1.00 58.79           N
ATOM   1381  CA  GLY A 179       4.370   2.030   9.808  1.00 72.64           C
ATOM   1382  C   GLY A 179       4.449   0.497   9.677  1.00 86.24           C
ATOM   1383  O   GLY A 179       3.988  -0.098   8.688  1.00 83.01           O
ATOM   1384  N   SER A 180       5.038  -0.140  10.705  1.00 96.93           N
ATOM   1385  CA  SER A 180       5.193  -1.594  10.749  1.00 97.55           C
ATOM   1386  C   SER A 180       3.874  -2.343  10.897  1.00 92.14           C
ATOM   1387  O   SER A 180       3.542  -3.169  10.068  1.00 90.57           O
ATOM   1388  CB  SER A 180       6.270  -2.086  11.733  1.00 98.48           C
ATOM   1389  OG  SER A 180       6.375  -1.212  12.847  1.00 99.78           O
ATOM   1390  N   PHE A 181       3.111  -2.043  11.950  1.00 88.02           N
ATOM   1391  CA  PHE A 181       1.825  -2.687  12.201  1.00 78.18           C
ATOM   1392  C   PHE A 181       0.922  -2.780  10.957  1.00 72.26           C
ATOM   1393  O   PHE A 181       0.101  -3.686  10.840  1.00 73.01           O
ATOM   1394  CB  PHE A 181       1.129  -2.153  13.474  1.00 76.52           C
ATOM   1395  CG  PHE A 181      -0.341  -2.461  13.543  1.00 78.63           C
ATOM   1396  CD1 PHE A 181      -1.247  -1.775  12.732  1.00 80.15           C
ATOM   1397  CD2 PHE A 181      -0.834  -3.428  14.415  1.00 80.20           C
ATOM   1398  CE1 PHE A 181      -2.613  -2.043  12.763  1.00 80.40           C
ATOM   1399  CE2 PHE A 181      -2.200  -3.706  14.466  1.00 83.04           C
ATOM   1400  CZ  PHE A 181      -3.088  -3.014  13.642  1.00 81.19           C
ATOM   1401  N   ARG A 182       1.053  -1.831  10.033  1.00 71.07           N
ATOM   1402  CA  ARG A 182       0.239  -1.873   8.837  1.00 72.99           C
ATOM   1403  C   ARG A 182       0.759  -3.029   8.038  1.00 90.77           C
ATOM   1404  O   ARG A 182       0.047  -3.696   7.274  1.00 93.16           O
ATOM   1405  CB  ARG A 182       0.278  -0.637   7.979  1.00 63.62           C
ATOM   1406  CG  ARG A 182      -1.020  -0.525   7.204  1.00 62.20           C
ATOM   1407  CD  ARG A 182      -1.226   0.795   6.462  1.00 65.02           C
ATOM   1408  NE  ARG A 182      -0.674   0.896   5.086  1.00 67.99           N
ATOM   1409  CZ  ARG A 182      -1.412   1.095   3.973  1.00 63.50           C
ATOM   1410  NH1 ARG A 182      -2.750   1.223   4.003  1.00 54.44           N
ATOM   1411  NH2 ARG A 182      -0.783   1.172   2.799  1.00 63.83           N
ATOM   1412  N   ARG A 183       2.066  -3.219   8.242  1.00 99.51           N
ATOM   1413  CA  ARG A 183       2.813  -4.282   7.609  1.00 99.86           C
ATOM   1414  C   ARG A 183       2.585  -5.585   8.371  1.00 96.96           C
ATOM   1415  O   ARG A 183       3.548  -6.286   8.644  1.00100.00           O
ATOM   1416  CB  ARG A 183       4.326  -4.037   7.549  1.00100.00           C
ATOM   1417  CG  ARG A 183       4.802  -2.621   7.257  1.00 99.94           C
ATOM   1418  CD  ARG A 183       6.284  -2.605   6.875  1.00 97.33           C
ATOM   1419  NE  ARG A 183       7.173  -3.155   7.909  1.00 95.27           N
ATOM   1420  CZ  ARG A 183       7.927  -2.436   8.756  1.00 96.01           C
ATOM   1421  NH1 ARG A 183       7.942  -1.108   8.746  1.00100.00           N
ATOM   1422  NH2 ARG A 183       8.697  -3.057   9.649  1.00 93.65           N
ATOM   1423  N   GLY A 184       1.342  -5.905   8.738  1.00 91.12           N
ATOM   1424  CA  GLY A 184       1.021  -7.134   9.469  1.00 87.03           C
ATOM   1425  C   GLY A 184       1.995  -7.627  10.576  1.00 85.09           C
ATOM   1426  O   GLY A 184       1.813  -8.760  11.070  1.00 90.60           O
ATOM   1427  N   ALA A 185       3.018  -6.821  10.979  1.00 71.40           N
ATOM   1428  CA  ALA A 185       3.975  -7.247  12.011  1.00 63.01           C
ATOM   1429  C   ALA A 185       3.357  -7.878  13.233  1.00 69.24           C
ATOM   1430  O   ALA A 185       2.190  -7.650  13.551  1.00 73.41           O
ATOM   1431  CB  ALA A 185       4.947  -6.173  12.433  1.00 61.78           C
ATOM   1432  N   GLU A 186       4.163  -8.677  13.920  1.00 75.93           N
ATOM   1433  CA  GLU A 186       3.726  -9.368  15.125  1.00 90.63           C
ATOM   1434  C   GLU A 186       4.232  -8.715  16.432  1.00 97.37           C
ATOM   1435  O   GLU A 186       4.019  -9.229  17.557  1.00 97.50           O
ATOM   1436  CB  GLU A 186       4.001 -10.885  15.054  1.00 94.45           C
ATOM   1437  CG  GLU A 186       5.449 -11.226  15.443  1.00 97.79           C
```

Figure 22AE

```
ATOM   1438  CD   GLU A 186       6.471 -10.324  14.799  1.00100.00           C
ATOM   1439  OE1  GLU A 186       6.096  -9.868  13.621  1.00100.00           O
ATOM   1440  OE2  GLU A 186       7.552 -10.074  15.311  1.00100.00           O
ATOM   1441  N    SER A 187       4.917  -7.570  16.259  1.00 94.85           N
ATOM   1442  CA   SER A 187       5.466  -6.789  17.355  1.00 91.50           C
ATOM   1443  C    SER A 187       6.220  -5.526  16.906  1.00 90.90           C
ATOM   1444  O    SER A 187       7.369  -5.615  16.433  1.00 93.80           O
ATOM   1445  CB   SER A 187       6.054  -7.545  18.548  1.00 88.45           C
ATOM   1446  OG   SER A 187       7.458  -7.428  18.616  1.00 88.90           O
ATOM   1447  N    SER A 188       5.516  -4.356  17.068  1.00 76.76           N
ATOM   1448  CA   SER A 188       5.954  -2.999  16.731  1.00 53.47           C
ATOM   1449  C    SER A 188       6.783  -2.287  17.765  1.00 50.80           C
ATOM   1450  O    SER A 188       6.867  -2.684  18.929  1.00 49.46           O
ATOM   1451  CB   SER A 188       4.857  -2.094  16.235  1.00 44.39           C
ATOM   1452  OG   SER A 188       4.215  -2.707  15.127  1.00 47.09           O
ATOM   1453  N    GLY A 189       7.398  -1.220  17.259  1.00 55.65           N
ATOM   1454  CA   GLY A 189       8.276  -0.325  17.992  1.00 58.74           C
ATOM   1455  C    GLY A 189       7.515   0.811  18.680  1.00 52.72           C
ATOM   1456  O    GLY A 189       7.937   1.279  19.742  1.00 45.03           O
ATOM   1457  N    ASP A 190       6.410   1.221  18.072  1.00 44.99           N
ATOM   1458  CA   ASP A 190       5.627   2.254  18.617  1.00 45.83           C
ATOM   1459  C    ASP A 190       4.455   2.405  17.731  1.00 51.69           C
ATOM   1460  O    ASP A 190       4.460   1.908  16.616  1.00 51.21           O
ATOM   1461  CB   ASP A 190       6.412   3.521  18.518  1.00 52.26           C
ATOM   1462  CG   ASP A 190       6.861   3.624  17.115  1.00 59.36           C
ATOM   1463  OD1  ASP A 190       6.823   2.674  16.345  1.00 64.67           O
ATOM   1464  OD2  ASP A 190       7.384   4.796  16.837  1.00 58.81           O
ATOM   1465  N    MET A 191       3.464   3.098  18.198  1.00 54.77           N
ATOM   1466  CA   MET A 191       2.338   3.232  17.339  1.00 47.47           C
ATOM   1467  C    MET A 191       2.414   4.411  16.484  1.00 51.82           C
ATOM   1468  O    MET A 191       2.572   5.520  16.947  1.00 58.25           O
ATOM   1469  CB   MET A 191       1.065   3.385  18.113  1.00 41.59           C
ATOM   1470  CG   MET A 191       0.077   4.024  17.201  1.00 53.81           C
ATOM   1471  SD   MET A 191      -1.584   3.548  17.661  1.00 69.48           S
ATOM   1472  CE   MET A 191      -1.606   1.962  16.767  1.00 78.08           C
ATOM   1473  N    ASP A 192       2.290   4.193  15.218  1.00 58.38           N
ATOM   1474  CA   ASP A 192       2.342   5.345  14.365  1.00 59.69           C
ATOM   1475  C    ASP A 192       0.944   5.695  13.922  1.00 62.70           C
ATOM   1476  O    ASP A 192       0.229   4.816  13.466  1.00 68.47           O
ATOM   1477  CB   ASP A 192       3.271   5.034  13.228  1.00 67.79           C
ATOM   1478  CG   ASP A 192       4.439   4.249  13.762  1.00 80.64           C
ATOM   1479  OD1  ASP A 192       4.718   4.209  14.954  1.00 86.06           O
ATOM   1480  OD2  ASP A 192       5.107   3.587  12.828  1.00 82.90           O
ATOM   1481  N    VAL A 193       0.537   6.960  14.062  1.00 64.10           N
ATOM   1482  CA   VAL A 193      -0.806   7.317  13.656  1.00 57.91           C
ATOM   1483  C    VAL A 193      -0.931   8.458  12.724  1.00 63.27           C
ATOM   1484  O    VAL A 193      -0.618   9.617  13.024  1.00 66.34           O
ATOM   1485  CB   VAL A 193      -1.790   7.647  14.730  1.00 46.84           C
ATOM   1486  CG1  VAL A 193      -3.082   7.994  13.986  1.00 41.21           C
ATOM   1487  CG2  VAL A 193      -1.978   6.474  15.684  1.00 47.53           C
ATOM   1488  N    LEU A 194      -1.446   8.053  11.595  1.00 63.30           N
ATOM   1489  CA   LEU A 194      -1.680   8.937  10.525  1.00 64.81           C
ATOM   1490  C    LEU A 194      -3.110   9.319  10.455  1.00 64.41           C
ATOM   1491  O    LEU A 194      -4.050   8.512  10.559  1.00 63.81           O
ATOM   1492  CB   LEU A 194      -1.262   8.329   9.206  1.00 67.24           C
ATOM   1493  CG   LEU A 194      -0.534   9.350   8.350  1.00 70.55           C
ATOM   1494  CD1  LEU A 194      -1.243  10.708   8.334  1.00 68.79           C
ATOM   1495  CD2  LEU A 194       0.889   9.495   8.864  1.00 73.43           C
ATOM   1496  N    LEU A 195      -3.227  10.597  10.257  1.00 63.76           N
ATOM   1497  CA   LEU A 195      -4.496  11.160  10.172  1.00 62.06           C
ATOM   1498  C    LEU A 195      -4.567  12.486   9.423  1.00 66.40           C
ATOM   1499  O    LEU A 195      -3.569  13.203   9.247  1.00 65.59           O
ATOM   1500  CB   LEU A 195      -4.854  11.392  11.637  1.00 53.92           C
```

Figure 22AF

```
ATOM   1501  CG   LEU A 195      -6.069  12.247  11.718  1.00 49.11           C
ATOM   1502  CD1  LEU A 195      -7.308  11.404  11.921  1.00 49.61           C
ATOM   1503  CD2  LEU A 195      -5.887  13.356  12.723  1.00 44.42           C
ATOM   1504  N    THR A 196      -5.797  12.783   9.001  1.00 67.94           N
ATOM   1505  CA   THR A 196      -6.160  13.988   8.297  1.00 77.29           C
ATOM   1506  C    THR A 196      -7.612  14.365   8.547  1.00 84.09           C
ATOM   1507  O    THR A 196      -8.285  13.851   9.443  1.00 87.38           O
ATOM   1508  CB   THR A 196      -5.880  13.972   6.807  1.00 84.90           C
ATOM   1509  OG1  THR A 196      -6.849  13.272   6.063  1.00 88.59           O
ATOM   1510  CG2  THR A 196      -4.476  13.454   6.586  1.00 89.31           C
ATOM   1511  N    HIS A 197      -8.107  15.287   7.747  1.00 84.22           N
ATOM   1512  CA   HIS A 197      -9.475  15.710   7.897  1.00 82.22           C
ATOM   1513  C    HIS A 197      -9.865  16.507   6.687  1.00 80.99           C
ATOM   1514  O    HIS A 197      -8.991  17.183   6.133  1.00 73.90           O
ATOM   1515  CB   HIS A 197      -9.715  16.531   9.176  1.00 85.25           C
ATOM   1516  CG   HIS A 197     -11.149  16.943   9.289  1.00 89.60           C
ATOM   1517  ND1  HIS A 197     -11.734  17.821   8.382  1.00 89.94           N
ATOM   1518  CD2  HIS A 197     -12.094  16.597  10.200  1.00 93.14           C
ATOM   1519  CE1  HIS A 197     -12.998  17.980   8.749  1.00 90.69           C
ATOM   1520  NE2  HIS A 197     -13.250  17.260   9.839  1.00 93.62           N
ATOM   1521  N    PRO A 198     -11.166  16.408   6.303  1.00 86.21           N
ATOM   1522  CA   PRO A 198     -11.703  17.111   5.136  1.00 82.58           C
ATOM   1523  C    PRO A 198     -11.300  18.566   5.059  1.00 74.96           C
ATOM   1524  O    PRO A 198     -10.738  19.030   4.075  1.00 66.72           O
ATOM   1525  CB   PRO A 198     -13.229  16.915   5.140  1.00 85.39           C
ATOM   1526  CG   PRO A 198     -13.531  15.808   6.153  1.00 85.53           C
ATOM   1527  CD   PRO A 198     -12.223  15.511   6.888  1.00 87.46           C
ATOM   1528  N    SER A 199     -11.585  19.290   6.119  1.00 84.93           N
ATOM   1529  CA   SER A 199     -11.245  20.695   6.161  1.00 86.80           C
ATOM   1530  C    SER A 199      -9.742  20.873   6.043  1.00 93.31           C
ATOM   1531  O    SER A 199      -9.260  21.998   5.922  1.00 98.46           O
ATOM   1532  CB   SER A 199     -11.732  21.358   7.439  1.00 78.88           C
ATOM   1533  OG   SER A 199     -10.833  21.080   8.516  1.00 75.01           O
ATOM   1534  N    PHE A 200      -8.998  19.760   6.085  1.00 94.27           N
ATOM   1535  CA   PHE A 200      -7.546  19.842   5.987  1.00 98.00           C
ATOM   1536  C    PHE A 200      -6.936  19.467   4.653  1.00100.00           C
ATOM   1537  O    PHE A 200      -6.891  18.290   4.285  1.00100.00           O
ATOM   1538  CB   PHE A 200      -6.799  19.124   7.121  1.00 97.33           C
ATOM   1539  CG   PHE A 200      -5.318  19.424   7.077  1.00 97.74           C
ATOM   1540  CD1  PHE A 200      -4.832  20.580   6.460  1.00 97.63           C
ATOM   1541  CD2  PHE A 200      -4.399  18.570   7.682  1.00100.00           C
ATOM   1542  CE1  PHE A 200      -3.470  20.871   6.419  1.00 99.02           C
ATOM   1543  CE2  PHE A 200      -3.031  18.840   7.660  1.00100.00           C
ATOM   1544  CZ   PHE A 200      -2.572  19.994   7.026  1.00100.00           C
ATOM   1545  N    THR A 201      -6.433  20.489   3.953  1.00100.00           N
ATOM   1546  CA   THR A 201      -5.806  20.286   2.655  1.00100.00           C
ATOM   1547  C    THR A 201      -4.660  21.283   2.401  1.00100.00           C
ATOM   1548  O    THR A 201      -4.588  22.352   3.021  1.00100.00           O
ATOM   1549  CB   THR A 201      -6.864  20.308   1.536  1.00100.00           C
ATOM   1550  OG1  THR A 201      -6.546  19.366   0.526  1.00100.00           O
ATOM   1551  CG2  THR A 201      -6.927  21.717   0.966  1.00 99.81           C
ATOM   1552  N    SER A 202      -3.763  20.914   1.478  1.00100.00           N
ATOM   1553  CA   SER A 202      -2.598  21.723   1.111  1.00100.00           C
ATOM   1554  C    SER A 202      -2.815  23.257   1.053  1.00 99.50           C
ATOM   1555  O    SER A 202      -2.530  23.980   2.022  1.00 99.60           O
ATOM   1556  CB   SER A 202      -1.830  21.169  -0.107  1.00 99.56           C
ATOM   1557  OG   SER A 202      -1.493  19.789   0.040  1.00 96.17           O
ATOM   1558  N    GLU A 203      -3.319  23.742  -0.085  1.00 94.35           N
ATOM   1559  CA   GLU A 203      -3.576  25.152  -0.316  1.00 94.33           C
ATOM   1560  C    GLU A 203      -4.648  25.798   0.570  1.00 93.21           C
ATOM   1561  O    GLU A 203      -4.956  26.995   0.458  1.00 84.73           O
ATOM   1562  CB   GLU A 203      -3.805  25.402  -1.807  1.00 97.42           C
ATOM   1563  CG   GLU A 203      -4.679  24.298  -2.416  1.00 99.84           C
```

Figure 22AG

```
ATOM   1564  CD   GLU A 203      -5.987  24.147  -1.693  1.00100.00           C
ATOM   1565  OE1  GLU A 203      -6.591  25.297  -1.443  1.00100.00           O
ATOM   1566  OE2  GLU A 203      -6.452  23.059  -1.423  1.00100.00           O
ATOM   1567  N    SER A 204      -5.220  24.987   1.459  1.00100.00           N
ATOM   1568  CA   SER A 204      -6.258  25.439   2.385  1.00100.00           C
ATOM   1569  C    SER A 204      -5.670  26.169   3.611  1.00100.00           C
ATOM   1570  O    SER A 204      -4.439  26.358   3.693  1.00100.00           O
ATOM   1571  CB   SER A 204      -7.264  24.326   2.747  1.00100.00           C
ATOM   1572  OG   SER A 204      -6.679  23.252   3.465  1.00 97.90           O
ATOM   1573  N    THR A 205      -6.561  26.582   4.553  1.00100.00           N
ATOM   1574  CA   THR A 205      -6.185  27.283   5.801  1.00100.00           C
ATOM   1575  C    THR A 205      -6.185  26.310   6.999  1.00 99.70           C
ATOM   1576  O    THR A 205      -7.226  26.051   7.631  1.00 97.25           O
ATOM   1577  CB   THR A 205      -6.965  28.602   6.061  1.00100.00           C
ATOM   1578  OG1  THR A 205      -6.848  29.478   4.946  1.00100.00           O
ATOM   1579  CG2  THR A 205      -6.394  29.297   7.295  1.00100.00           C
ATOM   1580  N    LYS A 206      -4.972  25.782   7.278  1.00100.00           N
ATOM   1581  CA   LYS A 206      -4.678  24.811   8.343  1.00100.00           C
ATOM   1582  C    LYS A 206      -5.261  25.085   9.709  1.00100.00           C
ATOM   1583  O    LYS A 206      -4.908  26.060  10.395  1.00100.00           O
ATOM   1584  CB   LYS A 206      -3.277  24.195   8.372  1.00 97.73           C
ATOM   1585  CG   LYS A 206      -2.211  25.045   9.038  1.00 96.45           C
ATOM   1586  CD   LYS A 206      -2.192  26.460   8.514  1.00 97.34           C
ATOM   1587  CE   LYS A 206      -0.825  27.091   8.655  1.00 98.96           C
ATOM   1588  NZ   LYS A 206      -0.354  27.069  10.041  1.00100.00           N
ATOM   1589  N    GLN A 207      -6.168  24.176  10.084  1.00100.00           N
ATOM   1590  CA   GLN A 207      -6.829  24.279  11.362  1.00100.00           C
ATOM   1591  C    GLN A 207      -6.229  23.435  12.462  1.00100.00           C
ATOM   1592  O    GLN A 207      -6.527  22.249  12.653  1.00100.00           O
ATOM   1593  CB   GLN A 207      -8.359  24.461  11.336  1.00100.00           C
ATOM   1594  CG   GLN A 207      -9.202  23.184  11.249  1.00100.00           C
ATOM   1595  CD   GLN A 207     -10.654  23.539  11.513  1.00100.00           C
ATOM   1596  OE1  GLN A 207     -10.975  24.669  11.939  1.00100.00           O
ATOM   1597  NE2  GLN A 207     -11.531  22.568  11.287  1.00100.00           N
ATOM   1598  N    PRO A 208      -5.350  24.125  13.170  1.00100.00           N
ATOM   1599  CA   PRO A 208      -4.596  23.596  14.287  1.00100.00           C
ATOM   1600  C    PRO A 208      -5.449  22.706  15.192  1.00100.00           C
ATOM   1601  O    PRO A 208      -4.995  21.643  15.676  1.00100.00           O
ATOM   1602  CB   PRO A 208      -4.057  24.839  15.033  1.00100.00           C
ATOM   1603  CG   PRO A 208      -4.696  26.083  14.408  1.00100.00           C
ATOM   1604  CD   PRO A 208      -5.571  25.601  13.256  1.00100.00           C
ATOM   1605  N    LYS A 209      -6.684  23.202  15.369  1.00 98.05           N
ATOM   1606  CA   LYS A 209      -7.721  22.601  16.171  1.00 97.34           C
ATOM   1607  C    LYS A 209      -7.716  21.117  15.946  1.00 91.75           C
ATOM   1608  O    LYS A 209      -7.736  20.358  16.917  1.00 94.20           O
ATOM   1609  CB   LYS A 209      -9.116  23.096  15.772  1.00100.00           C
ATOM   1610  CG   LYS A 209      -9.279  24.601  15.555  1.00 97.46           C
ATOM   1611  CD   LYS A 209      -8.733  25.086  14.225  1.00 91.32           C
ATOM   1612  CE   LYS A 209      -9.511  26.273  13.673  1.00 85.47           C
ATOM   1613  NZ   LYS A 209      -8.836  26.929  12.554  1.00 81.60           N
ATOM   1614  N    LEU A 210      -7.675  20.757  14.649  1.00 81.66           N
ATOM   1615  CA   LEU A 210      -7.674  19.383  14.199  1.00 72.08           C
ATOM   1616  C    LEU A 210      -6.725  18.513  14.957  1.00 70.43           C
ATOM   1617  O    LEU A 210      -7.178  17.639  15.688  1.00 68.36           O
ATOM   1618  CB   LEU A 210      -7.539  19.258  12.699  1.00 65.41           C
ATOM   1619  CG   LEU A 210      -8.809  19.830  12.121  1.00 62.78           C
ATOM   1620  CD1  LEU A 210      -8.653  20.174  10.642  1.00 66.58           C
ATOM   1621  CD2  LEU A 210      -9.947  18.852  12.382  1.00 56.49           C
ATOM   1622  N    LEU A 211      -5.436  18.750  14.817  1.00 69.68           N
ATOM   1623  CA   LEU A 211      -4.562  17.908  15.576  1.00 78.13           C
ATOM   1624  C    LEU A 211      -4.821  18.161  17.061  1.00 77.09           C
ATOM   1625  O    LEU A 211      -4.955 -17.220  17.863  1.00 73.28           O
ATOM   1626  CB   LEU A 211      -3.049  18.030  15.196  1.00 86.10           C
```

Figure 22AH

```
ATOM   1627  CG   LEU A 211      -2.089  17.120  16.016  1.00 88.76           C
ATOM   1628  CD1  LEU A 211      -2.270  15.623  15.743  1.00 83.26           C
ATOM   1629  CD2  LEU A 211      -0.626  17.507  15.829  1.00 91.07           C
ATOM   1630  N    HIS A 212      -4.905  19.457  17.374  1.00 75.56           N
ATOM   1631  CA   HIS A 212      -5.127  19.902  18.718  1.00 70.86           C
ATOM   1632  C    HIS A 212      -6.185  19.127  19.443  1.00 52.29           C
ATOM   1633  O    HIS A 212      -5.928  18.347  20.362  1.00 40.39           O
ATOM   1634  CB   HIS A 212      -5.525  21.381  18.806  1.00 80.77           C
ATOM   1635  CG   HIS A 212      -5.564  21.663  20.260  1.00 95.06           C
ATOM   1636  ND1  HIS A 212      -4.398  21.886  20.978  1.00 99.85           N
ATOM   1637  CD2  HIS A 212      -6.611  21.720  21.116  1.00 99.90           C
ATOM   1638  CE1  HIS A 212      -4.755  22.089  22.234  1.00 99.54           C
ATOM   1639  NE2  HIS A 212      -6.076  21.997  22.350  1.00100.00           N
ATOM   1640  N    GLN A 213      -7.347  19.371  18.943  1.00 47.04           N
ATOM   1641  CA   GLN A 213      -8.515  18.802  19.435  1.00 52.64           C
ATOM   1642  C    GLN A 213      -8.403  17.292  19.693  1.00 59.85           C
ATOM   1643  O    GLN A 213      -8.797  16.829  20.781  1.00 67.32           O
ATOM   1644  CB   GLN A 213      -9.718  19.338  18.624  1.00 62.79           C
ATOM   1645  CG   GLN A 213     -10.512  18.312  17.771  1.00 74.96           C
ATOM   1646  CD   GLN A 213     -11.462  19.021  16.802  1.00 81.50           C
ATOM   1647  OE1  GLN A 213     -11.448  20.272  16.693  1.00 79.99           O
ATOM   1648  NE2  GLN A 213     -12.274  18.235  16.086  1.00 82.16           N
ATOM   1649  N    VAL A 214      -7.851  16.511  18.734  1.00 60.10           N
ATOM   1650  CA   VAL A 214      -7.700  15.030  18.875  1.00 56.54           C
ATOM   1651  C    VAL A 214      -6.744  14.455  19.897  1.00 44.95           C
ATOM   1652  O    VAL A 214      -7.014  13.428  20.507  1.00 42.51           O
ATOM   1653  CB   VAL A 214      -7.745  14.235  17.590  1.00 64.44           C
ATOM   1654  CG1  VAL A 214      -9.190  14.140  17.091  1.00 68.10           C
ATOM   1655  CG2  VAL A 214      -6.928  15.012  16.580  1.00 68.25           C
ATOM   1656  N    VAL A 215      -5.619  15.110  20.061  1.00 41.90           N
ATOM   1657  CA   VAL A 215      -4.655  14.680  21.017  1.00 40.58           C
ATOM   1658  C    VAL A 215      -5.393  14.721  22.362  1.00 56.45           C
ATOM   1659  O    VAL A 215      -5.298  13.801  23.178  1.00 64.81           O
ATOM   1660  CB   VAL A 215      -3.546  15.681  20.945  1.00 37.64           C
ATOM   1661  CG1  VAL A 215      -2.380  15.243  21.802  1.00 35.90           C
ATOM   1662  CG2  VAL A 215      -3.162  15.812  19.494  1.00 38.28           C
ATOM   1663  N    GLU A 216      -6.166  15.812  22.546  1.00 60.46           N
ATOM   1664  CA   GLU A 216      -6.983  16.081  23.723  1.00 58.09           C
ATOM   1665  C    GLU A 216      -7.993  15.021  24.010  1.00 55.30           C
ATOM   1666  O    GLU A 216      -8.187  14.699  25.177  1.00 59.21           O
ATOM   1667  CB   GLU A 216      -7.729  17.383  23.636  1.00 60.07           C
ATOM   1668  CG   GLU A 216      -6.769  18.537  23.816  1.00 60.86           C
ATOM   1669  CD   GLU A 216      -7.579  19.763  23.962  1.00 69.41           C
ATOM   1670  OE1  GLU A 216      -8.787  19.795  23.755  1.00 66.82           O
ATOM   1671  OE2  GLU A 216      -6.852  20.764  24.371  1.00 78.71           O
ATOM   1672  N    GLN A 217      -8.626  14.511  22.939  1.00 50.73           N
ATOM   1673  CA   GLN A 217      -9.617  13.442  23.043  1.00 45.28           C
ATOM   1674  C    GLN A 217      -8.911  12.299  23.743  1.00 44.42           C
ATOM   1675  O    GLN A 217      -9.275  11.848  24.805  1.00 45.47           O
ATOM   1676  CB   GLN A 217      -9.966  12.947  21.647  1.00 53.10           C
ATOM   1677  CG   GLN A 217     -11.194  12.046  21.637  1.00 64.49           C
ATOM   1678  CD   GLN A 217     -12.300  12.781  22.340  1.00 80.24           C
ATOM   1679  OE1  GLN A 217     -12.851  12.287  23.338  1.00 79.97           O
ATOM   1680  NE2  GLN A 217     -12.564  14.006  21.867  1.00 88.81           N
ATOM   1681  N    LEU A 218      -7.840  11.848  23.130  1.00 49.84           N
ATOM   1682  CA   LEU A 218      -7.017  10.780  23.641  1.00 51.24           C
ATOM   1683  C    LEU A 218      -6.385  11.086  24.992  1.00 50.13           C
ATOM   1684  O    LEU A 218      -5.863  10.217  25.705  1.00 49.55           O
ATOM   1685  CB   LEU A 218      -6.167  10.093  22.550  1.00 57.50           C
ATOM   1686  CG   LEU A 218      -7.106   9.266  21.629  1.00 58.72           C
ATOM   1687  CD1  LEU A 218      -6.965   9.595  20.149  1.00 54.75           C
ATOM   1688  CD2  LEU A 218      -7.017   7.760  21.891  1.00 52.71           C
ATOM   1689  N    GLN A 219      -6.422  12.372  25.318  1.00 52.41           N
```

Figure 22AI

```
ATOM   1690  CA   GLN A 219      -5.904  12.924  26.576  1.00 54.77           C
ATOM   1691  C    GLN A 219      -6.956  12.876  27.695  1.00 57.10           C
ATOM   1692  O    GLN A 219      -6.724  12.489  28.869  1.00 48.45           O
ATOM   1693  CB   GLN A 219      -5.440  14.350  26.401  1.00 49.97           C
ATOM   1694  CG   GLN A 219      -4.026  14.381  25.848  1.00 59.36           C
ATOM   1695  CD   GLN A 219      -3.633  15.787  25.473  1.00 70.57           C
ATOM   1696  OE1  GLN A 219      -4.465  16.544  24.936  1.00 79.99           O
ATOM   1697  NE2  GLN A 219      -2.391  16.160  25.804  1.00 70.81           N
ATOM   1698  N    LYS A 220      -8.128  13.307  27.263  1.00 63.58           N
ATOM   1699  CA   LYS A 220      -9.292  13.376  28.076  1.00 73.36           C
ATOM   1700  C    LYS A 220      -9.478  12.041  28.763  1.00 84.36           C
ATOM   1701  O    LYS A 220      -9.460  11.934  29.997  1.00 92.37           O
ATOM   1702  CB   LYS A 220     -10.481  13.704  27.192  1.00 78.60           C
ATOM   1703  CG   LYS A 220     -11.757  14.013  27.973  1.00 88.71           C
ATOM   1704  CD   LYS A 220     -12.994  14.308  27.113  1.00 92.41           C
ATOM   1705  CE   LYS A 220     -14.237  14.642  27.948  1.00 91.70           C
ATOM   1706  NZ   LYS A 220     -15.497  14.610  27.177  1.00 91.39           N
ATOM   1707  N    VAL A 221      -9.645  11.032  27.906  1.00 83.82           N
ATOM   1708  CA   VAL A 221      -9.855   9.624  28.246  1.00 76.19           C
ATOM   1709  C    VAL A 221      -8.563   8.849  28.588  1.00 73.94           C
ATOM   1710  O    VAL A 221      -8.383   7.694  28.218  1.00 72.19           O
ATOM   1711  CB   VAL A 221     -10.654   8.965  27.133  1.00 74.62           C
ATOM   1712  CG1  VAL A 221      -9.804   8.855  25.884  1.00 76.94           C
ATOM   1713  CG2  VAL A 221     -11.098   7.588  27.570  1.00 81.97           C
ATOM   1714  N    HIS A 222      -7.649   9.504  29.296  1.00 75.48           N
ATOM   1715  CA   HIS A 222      -6.356   8.961  29.746  1.00 74.90           C
ATOM   1716  C    HIS A 222      -5.472   8.076  28.829  1.00 72.43           C
ATOM   1717  O    HIS A 222      -4.618   7.305  29.312  1.00 69.90           O
ATOM   1718  CB   HIS A 222      -6.409   8.598  31.220  1.00 77.62           C
ATOM   1719  CG   HIS A 222      -6.885   9.812  31.973  1.00 89.38           C
ATOM   1720  ND1  HIS A 222      -8.172  10.320  31.798  1.00 93.99           N
ATOM   1721  CD2  HIS A 222      -6.241  10.610  32.870  1.00 95.74           C
ATOM   1722  CE1  HIS A 222      -8.285  11.395  32.580  1.00 97.17           C
ATOM   1723  NE2  HIS A 222      -7.142  11.595  33.235  1.00 99.56           N
ATOM   1724  N    PHE A 223      -5.654   8.193  27.509  1.00 69.11           N
ATOM   1725  CA   PHE A 223      -4.865   7.394  26.583  1.00 62.96           C
ATOM   1726  C    PHE A 223      -3.400   7.767  26.406  1.00 53.22           C
ATOM   1727  O    PHE A 223      -2.504   6.919  26.239  1.00 42.84           O
ATOM   1728  CB   PHE A 223      -5.598   7.245  25.255  1.00 66.19           C
ATOM   1729  CG   PHE A 223      -4.801   6.333  24.408  1.00 70.38           C
ATOM   1730  CD1  PHE A 223      -4.303   5.167  24.982  1.00 69.04           C
ATOM   1731  CD2  PHE A 223      -4.524   6.602  23.074  1.00 75.37           C
ATOM   1732  CE1  PHE A 223      -3.548   4.269  24.239  1.00 71.97           C
ATOM   1733  CE2  PHE A 223      -3.761   5.717  22.311  1.00 75.61           C
ATOM   1734  CZ   PHE A 223      -3.275   4.552  22.901  1.00 72.83           C
ATOM   1735  N    ILE A 224      -3.190   9.075  26.442  1.00 53.18           N
ATOM   1736  CA   ILE A 224      -1.883   9.653  26.303  1.00 53.46           C
ATOM   1737  C    ILE A 224      -1.384  10.138  27.651  1.00 53.43           C
ATOM   1738  O    ILE A 224      -1.990  10.988  28.226  1.00 55.88           O
ATOM   1739  CB   ILE A 224      -1.992  10.846  25.397  1.00 51.75           C
ATOM   1740  CG1  ILE A 224      -2.202  10.370  23.953  1.00 49.66           C
ATOM   1741  CG2  ILE A 224      -0.654  11.544  25.562  1.00 51.22           C
ATOM   1742  CD1  ILE A 224      -3.096  11.259  23.078  1.00 42.10           C
ATOM   1743  N    THR A 225      -0.295   9.621  28.173  1.00 48.38           N
ATOM   1744  CA   THR A 225       0.157  10.087  29.440  1.00 40.26           C
ATOM   1745  C    THR A 225       0.969  11.335  29.267  1.00 47.63           C
ATOM   1746  O    THR A 225       0.466  12.429  29.423  1.00 57.25           O
ATOM   1747  CB   THR A 225       0.826   8.962  30.239  1.00 41.28           C
ATOM   1748  OG1  THR A 225       2.243   8.827  30.029  1.00 39.40           O
ATOM   1749  CG2  THR A 225       0.075   7.683  29.866  1.00 33.90           C
ATOM   1750  N    ASP A 226       2.224  11.184  28.921  1.00 43.34           N
ATOM   1751  CA   ASP A 226       3.071  12.333  28.711  1.00 42.51           C
ATOM   1752  C    ASP A 226       2.954  12.949  27.281  1.00 42.70           C
```

Figure 22AJ

```
ATOM   1753  O    ASP A 226       2.000  12.572  26.568  1.00 38.68           O
ATOM   1754  CB   ASP A 226       4.441  12.186  29.377  1.00 48.52           C
ATOM   1755  CG   ASP A 226       4.269  11.425  30.673  1.00 44.91           C
ATOM   1756  OD1  ASP A 226       3.326  10.662  30.852  1.00 42.91           O
ATOM   1757  OD2  ASP A 226       5.156  11.754  31.612  1.00 38.26           O
ATOM   1758  N    THR A 227       3.875  13.894  26.891  1.00 38.58           N
ATOM   1759  CA   THR A 227       3.945  14.636  25.600  1.00 34.10           C
ATOM   1760  C    THR A 227       5.413  15.034  25.328  1.00 39.99           C
ATOM   1761  O    THR A 227       5.925  15.778  26.171  1.00 35.26           O
ATOM   1762  CB   THR A 227       3.193  16.011  25.570  1.00 35.83           C
ATOM   1763  OG1  THR A 227       1.765  16.002  25.707  1.00 37.18           O
ATOM   1764  CG2  THR A 227       3.578  16.728  24.267  1.00 34.93           C
ATOM   1765  N    LEU A 228       6.056  14.548  24.183  1.00 43.39           N
ATOM   1766  CA   LEU A 228       7.445  14.832  23.760  1.00 38.91           C
ATOM   1767  C    LEU A 228       7.564  16.149  22.976  1.00 37.48           C
ATOM   1768  O    LEU A 228       8.538  16.921  23.041  1.00 37.74           O
ATOM   1769  CB   LEU A 228       8.082  13.689  22.982  1.00 39.96           C
ATOM   1770  CG   LEU A 228       8.118  12.376  23.750  1.00 43.02           C
ATOM   1771  CD1  LEU A 228       8.745  12.589  25.117  1.00 39.54           C
ATOM   1772  CD2  LEU A 228       6.709  11.801  23.845  1.00 46.18           C
ATOM   1773  N    SER A 229       6.525  16.410  22.229  1.00 27.01           N
ATOM   1774  CA   SER A 229       6.470  17.600  21.467  1.00 28.00           C
ATOM   1775  C    SER A 229       5.178  17.599  20.711  1.00 31.48           C
ATOM   1776  O    SER A 229       4.598  16.547  20.482  1.00 36.67           O
ATOM   1777  CB   SER A 229       7.609  17.680  20.505  1.00 41.74           C
ATOM   1778  OG   SER A 229       7.429  16.618  19.566  1.00 51.51           O
ATOM   1779  N    LYS A 230       4.757  18.799  20.334  1.00 35.72           N
ATOM   1780  CA   LYS A 230       3.547  19.030  19.591  1.00 40.31           C
ATOM   1781  C    LYS A 230       3.548  20.370  18.771  1.00 53.97           C
ATOM   1782  O    LYS A 230       4.232  21.357  19.118  1.00 54.25           O
ATOM   1783  CB   LYS A 230       2.300  18.564  20.313  1.00 38.67           C
ATOM   1784  CG   LYS A 230       1.047  19.305  19.859  1.00 46.35           C
ATOM   1785  CD   LYS A 230      -0.105  19.256  20.848  1.00 40.31           C
ATOM   1786  CE   LYS A 230       0.374  19.043  22.273  1.00 52.92           C
ATOM   1787  NZ   LYS A 230       1.543  19.866  22.656  1.00 62.69           N
ATOM   1788  N    GLY A 231       2.782  20.377  17.648  1.00 55.07           N
ATOM   1789  CA   GLY A 231       2.623  21.492  16.709  1.00 54.84           C
ATOM   1790  C    GLY A 231       1.427  21.248  15.776  1.00 56.68           C
ATOM   1791  O    GLY A 231       0.835  20.177  15.764  1.00 52.75           O
ATOM   1792  N    GLU A 232       1.055  22.243  14.988  1.00 64.23           N
ATOM   1793  CA   GLU A 232      -0.083  22.106  14.089  1.00 69.58           C
ATOM   1794  C    GLU A 232      -0.108  20.853  13.239  1.00 60.64           C
ATOM   1795  O    GLU A 232      -1.175  20.351  12.908  1.00 60.71           O
ATOM   1796  CB   GLU A 232      -0.406  23.401  13.290  1.00 81.63           C
ATOM   1797  CG   GLU A 232      -0.714  23.146  11.790  1.00 95.64           C
ATOM   1798  CD   GLU A 232      -2.169  22.935  11.419  1.00100.00           C
ATOM   1799  OE1  GLU A 232      -3.090  23.537  11.950  1.00 97.34           O
ATOM   1800  OE2  GLU A 232      -2.327  22.092  10.406  1.00100.00           O
ATOM   1801  N    THR A 233       1.059  20.348  12.889  1.00 53.78           N
ATOM   1802  CA   THR A 233       1.067  19.167  12.050  1.00 54.58           C
ATOM   1803  C    THR A 233       1.235  17.787  12.718  1.00 53.80           C
ATOM   1804  O    THR A 233       0.477  16.820  12.458  1.00 51.07           O
ATOM   1805  CB   THR A 233       1.817  19.404  10.736  1.00 59.81           C
ATOM   1806  OG1  THR A 233       3.109  19.899  11.021  1.00 70.04           O
ATOM   1807  CG2  THR A 233       1.062  20.437   9.911  1.00 53.35           C
ATOM   1808  N    LYS A 234       2.213  17.646  13.594  1.00 45.90           N
ATOM   1809  CA   LYS A 234       2.269  16.330  14.149  1.00 44.28           C
ATOM   1810  C    LYS A 234       2.614  16.330  15.628  1.00 44.19           C
ATOM   1811  O    LYS A 234       3.414  17.139  16.074  1.00 44.76           O
ATOM   1812  CB   LYS A 234       3.251  15.443  13.419  1.00 42.07           C
ATOM   1813  CG   LYS A 234       4.618  15.524  14.097  1.00 35.50           C
ATOM   1814  CD   LYS A 234       5.637  14.516  13.597  1.00 36.41           C
ATOM   1815  CE   LYS A 234       7.015  14.640  14.245  1.00 44.86           C
```

Figure 22AK

| | | | | | | | | | | |
|---|---|---|---|---|---|---|---|---|---|---|
| ATOM | 1816 | NZ | LYS | A | 234 | 7.642 | 15.980 | 14.147 | 1.00 49.39 | N |
| ATOM | 1817 | N | PHE | A | 235 | 1.996 | 15.373 | 16.344 | 1.00 50.48 | N |
| ATOM | 1818 | CA | PHE | A | 235 | 2.169 | 15.118 | 17.772 | 1.00 53.00 | C |
| ATOM | 1819 | C | PHE | A | 235 | 3.068 | 13.910 | 18.043 | 1.00 48.17 | C |
| ATOM | 1820 | O | PHE | A | 235 | 2.848 | 12.836 | 17.463 | 1.00 47.10 | O |
| ATOM | 1821 | CB | PHE | A | 235 | 0.794 | 14.905 | 18.470 | 1.00 58.38 | C |
| ATOM | 1822 | CG | PHE | A | 235 | 0.860 | 14.338 | 19.885 | 1.00 61.06 | C |
| ATOM | 1823 | CD1 | PHE | A | 235 | 1.093 | 12.978 | 20.104 | 1.00 57.89 | C |
| ATOM | 1824 | CD2 | PHE | A | 235 | 0.678 | 15.155 | 21.003 | 1.00 62.71 | C |
| ATOM | 1825 | CE1 | PHE | A | 235 | 1.158 | 12.437 | 21.392 | 1.00 56.38 | C |
| ATOM | 1826 | CE2 | PHE | A | 235 | 0.727 | 14.641 | 22.304 | 1.00 60.11 | C |
| ATOM | 1827 | CZ | PHE | A | 235 | 0.969 | 13.278 | 22.492 | 1.00 57.66 | C |
| ATOM | 1828 | N | MET | A | 236 | 4.061 | 14.128 | 18.922 | 1.00 44.32 | N |
| ATOM | 1829 | CA | MET | A | 236 | 5.031 | 13.155 | 19.383 | 1.00 46.60 | C |
| ATOM | 1830 | C | MET | A | 236 | 4.900 | 12.923 | 20.906 | 1.00 51.86 | C |
| ATOM | 1831 | O | MET | A | 236 | 5.611 | 13.569 | 21.685 | 1.00 56.68 | O |
| ATOM | 1832 | CB | MET | A | 236 | 6.471 | 13.602 | 19.140 | 1.00 59.58 | C |
| ATOM | 1833 | CG | MET | A | 236 | 7.101 | 13.203 | 17.814 | 1.00 71.48 | C |
| ATOM | 1834 | SD | MET | A | 236 | 8.842 | 12.672 | 18.048 | 1.00 85.44 | S |
| ATOM | 1835 | CE | MET | A | 236 | 8.825 | 12.020 | 19.756 | 1.00 82.96 | C |
| ATOM | 1836 | N | GLY | A | 237 | 4.032 | 12.007 | 21.356 | 1.00 45.52 | N |
| ATOM | 1837 | CA | GLY | A | 237 | 3.908 | 11.789 | 22.773 | 1.00 46.01 | C |
| ATOM | 1838 | C | GLY | A | 237 | 3.955 | 10.338 | 23.197 | 1.00 55.08 | C |
| ATOM | 1839 | O | GLY | A | 237 | 4.442 | 9.507 | 22.444 | 1.00 52.97 | O |
| ATOM | 1840 | N | VAL | A | 238 | 3.449 | 10.082 | 24.439 | 1.00 60.90 | N |
| ATOM | 1841 | CA | VAL | A | 238 | 3.341 | 8.776 | 25.129 | 1.00 53.24 | C |
| ATOM | 1842 | C | VAL | A | 238 | 1.867 | 8.343 | 25.284 | 1.00 60.33 | C |
| ATOM | 1843 | O | VAL | A | 238 | 0.949 | 9.192 | 25.293 | 1.00 64.64 | O |
| ATOM | 1844 | CB | VAL | A | 238 | 4.025 | 8.709 | 26.493 | 1.00 41.14 | C |
| ATOM | 1845 | CG1 | VAL | A | 238 | 3.872 | 7.300 | 27.006 | 1.00 38.31 | C |
| ATOM | 1846 | CG2 | VAL | A | 238 | 5.527 | 9.003 | 26.418 | 1.00 46.07 | C |
| ATOM | 1847 | N | CYS | A | 239 | 1.611 | 7.019 | 25.396 | 1.00 53.86 | N |
| ATOM | 1848 | CA | CYS | A | 239 | 0.248 | 6.539 | 25.539 | 1.00 51.02 | C |
| ATOM | 1849 | C | CYS | A | 239 | 0.217 | 5.304 | 26.389 | 1.00 62.95 | C |
| ATOM | 1850 | O | CYS | A | 239 | 1.244 | 4.647 | 26.595 | 1.00 69.28 | O |
| ATOM | 1851 | CB | CYS | A | 239 | -0.409 | 6.158 | 24.212 | 1.00 46.24 | C |
| ATOM | 1852 | SG | CYS | A | 239 | 0.379 | 4.761 | 23.369 | 1.00 42.20 | S |
| ATOM | 1853 | N | GLN | A | 240 | -0.980 | 4.986 | 26.877 | 1.00 62.56 | N |
| ATOM | 1854 | CA | GLN | A | 240 | -1.124 | 3.803 | 27.680 | 1.00 64.79 | C |
| ATOM | 1855 | C | GLN | A | 240 | -2.481 | 3.137 | 27.586 | 1.00 80.13 | C |
| ATOM | 1856 | O | GLN | A | 240 | -3.502 | 3.705 | 27.191 | 1.00 84.32 | O |
| ATOM | 1857 | CB | GLN | A | 240 | -0.587 | 3.877 | 29.104 | 1.00 57.94 | C |
| ATOM | 1858 | CG | GLN | A | 240 | -0.516 | 2.496 | 29.794 | 1.00 54.15 | C |
| ATOM | 1859 | CD | GLN | A | 240 | 0.152 | 2.585 | 31.148 | 1.00 54.41 | C |
| ATOM | 1860 | OE1 | GLN | A | 240 | -0.267 | 3.407 | 31.989 | 1.00 57.06 | O |
| ATOM | 1861 | NE2 | GLN | A | 240 | 1.266 | 1.846 | 31.323 | 1.00 47.77 | N |
| ATOM | 1862 | N | LEU | A | 241 | -2.470 | 1.874 | 27.945 | 1.00 84.67 | N |
| ATOM | 1863 | CA | LEU | A | 241 | -3.656 | 1.083 | 27.923 | 1.00 83.33 | C |
| ATOM | 1864 | C | LEU | A | 241 | -4.363 | 0.993 | 29.273 | 1.00 79.90 | C |
| ATOM | 1865 | O | LEU | A | 241 | -3.719 | 0.802 | 30.324 | 1.00 75.36 | O |
| ATOM | 1866 | CB | LEU | A | 241 | -3.362 | -0.305 | 27.353 | 1.00 76.91 | C |
| ATOM | 1867 | CG | LEU | A | 241 | -3.662 | -0.380 | 25.880 | 1.00 68.24 | C |
| ATOM | 1868 | CD1 | LEU | A | 241 | -3.687 | -1.848 | 25.499 | 1.00 61.77 | C |
| ATOM | 1869 | CD2 | LEU | A | 241 | -5.001 | 0.315 | 25.583 | 1.00 66.67 | C |
| ATOM | 1870 | N | PRO | A | 242 | -5.705 | 1.125 | 29.193 | 1.00 75.64 | N |
| ATOM | 1871 | CA | PRO | A | 242 | -6.529 | 1.046 | 30.357 | 1.00 77.64 | C |
| ATOM | 1872 | C | PRO | A | 242 | -6.202 | -0.237 | 31.093 | 1.00 93.37 | C |
| ATOM | 1873 | O | PRO | A | 242 | -6.618 | -1.315 | 30.673 | 1.00 99.99 | O |
| ATOM | 1874 | CB | PRO | A | 242 | -7.962 | 0.972 | 29.820 | 1.00 69.01 | C |
| ATOM | 1875 | CG | PRO | A | 242 | -7.939 | 1.422 | 28.376 | 1.00 65.54 | C |
| ATOM | 1876 | CD | PRO | A | 242 | -6.485 | 1.539 | 27.988 | 1.00 70.39 | C |
| ATOM | 1877 | N | SER | A | 243 | -5.452 | -0.145 | 32.189 | 1.00 98.55 | N |
| ATOM | 1878 | CA | SER | A | 243 | -5.155 | -1.394 | 32.850 | 1.00 99.13 | C |

Figure 22AL

```
ATOM   1879  C    SER A 243      -6.390   -2.093   33.378  1.00  97.05           C
ATOM   1880  O    SER A 243      -7.206   -1.582   34.124  1.00  96.30           O
ATOM   1881  CB   SER A 243      -3.986   -1.441   33.801  1.00 100.00           C
ATOM   1882  OG   SER A 243      -3.831   -2.771   34.275  1.00 100.00           O
ATOM   1883  N    LYS A 244      -6.456   -3.304   32.919  1.00  98.11           N
ATOM   1884  CA   LYS A 244      -7.478   -4.262   33.212  1.00 100.00           C
ATOM   1885  C    LYS A 244      -7.383   -4.596   34.677  1.00 100.00           C
ATOM   1886  O    LYS A 244      -6.282   -4.948   35.162  1.00  98.52           O
ATOM   1887  CB   LYS A 244      -7.344   -5.521   32.406  1.00 100.00           C
ATOM   1888  CG   LYS A 244      -8.682   -6.247   32.344  1.00 100.00           C
ATOM   1889  CD   LYS A 244      -8.769   -7.244   31.186  1.00 100.00           C
ATOM   1890  CE   LYS A 244      -9.787   -8.369   31.399  1.00 100.00           C
ATOM   1891  NZ   LYS A 244      -9.957   -9.283   30.251  1.00 100.00           N
ATOM   1892  N    ASN A 245      -8.546   -4.471   35.351  1.00 100.00           N
ATOM   1893  CA   ASN A 245      -8.675   -4.724   36.772  1.00 100.00           C
ATOM   1894  C    ASN A 245      -7.912   -5.934   37.236  1.00 100.00           C
ATOM   1895  O    ASN A 245      -8.259   -7.046   36.838  1.00 100.00           O
ATOM   1896  CB   ASN A 245     -10.139   -4.792   37.226  1.00 100.00           C
ATOM   1897  CG   ASN A 245     -10.320   -4.358   38.667  1.00 100.00           C
ATOM   1898  OD1  ASN A 245     -11.458   -4.109   39.117  1.00 100.00           O
ATOM   1899  ND2  ASN A 245      -9.204   -4.271   39.405  1.00  98.43           N
ATOM   1900  N    ASP A 246      -6.883   -5.719   38.079  1.00  99.92           N
ATOM   1901  CA   ASP A 246      -6.117   -6.846   38.580  1.00  99.66           C
ATOM   1902  C    ASP A 246      -5.155   -7.478   37.577  1.00 100.00           C
ATOM   1903  O    ASP A 246      -4.623   -8.579   37.776  1.00 100.00           O
ATOM   1904  CB   ASP A 246      -7.087   -7.780   39.378  1.00 100.00           C
ATOM   1905  CG   ASP A 246      -6.952   -9.290   39.300  1.00 100.00           C
ATOM   1906  OD1  ASP A 246      -5.948   -9.905   39.619  1.00 100.00           O
ATOM   1907  OD2  ASP A 246      -8.083   -9.876   38.900  1.00 100.00           O
ATOM   1908  N    GLU A 247      -4.937   -6.742   36.495  1.00 100.00           N
ATOM   1909  CA   GLU A 247      -4.047   -7.131   35.426  1.00 100.00           C
ATOM   1910  C    GLU A 247      -3.031   -5.997   35.417  1.00 100.00           C
ATOM   1911  O    GLU A 247      -3.408   -4.814   35.277  1.00 100.00           O
ATOM   1912  CB   GLU A 247      -4.712   -7.379   34.034  1.00 100.00           C
ATOM   1913  CG   GLU A 247      -5.153   -8.858   33.810  1.00 100.00           C
ATOM   1914  CD   GLU A 247      -4.006   -9.846   33.772  1.00 100.00           C
ATOM   1915  OE1  GLU A 247      -2.831   -9.538   33.686  1.00 100.00           O
ATOM   1916  OE2  GLU A 247      -4.413  -11.089   33.854  1.00 100.00           O
ATOM   1917  N    LYS A 248      -1.752   -6.317   35.617  1.00 100.00           N
ATOM   1918  CA   LYS A 248      -0.682   -5.363   35.660  1.00 100.00           C
ATOM   1919  C    LYS A 248      -0.540   -4.450   34.457  1.00  95.92           C
ATOM   1920  O    LYS A 248      -0.634   -4.874   33.297  1.00  94.48           O
ATOM   1921  CB   LYS A 248       0.643   -5.832   36.248  1.00 100.00           C
ATOM   1922  CG   LYS A 248       1.537   -4.666   36.606  1.00  99.40           C
ATOM   1923  CD   LYS A 248       2.750   -5.064   37.423  1.00 100.00           C
ATOM   1924  CE   LYS A 248       3.795   -3.957   37.436  1.00 100.00           C
ATOM   1925  NZ   LYS A 248       4.643   -3.971   38.635  1.00 100.00           N
ATOM   1926  N    GLU A 249      -0.369   -3.205   34.834  1.00  89.62           N
ATOM   1927  CA   GLU A 249      -0.209   -2.106   33.936  1.00  79.24           C
ATOM   1928  C    GLU A 249       0.762   -2.375   32.803  1.00  69.98           C
ATOM   1929  O    GLU A 249       1.946   -2.708   33.005  1.00  56.76           O
ATOM   1930  CB   GLU A 249       0.317   -0.883   34.698  1.00  75.66           C
ATOM   1931  CG   GLU A 249      -0.740   -0.212   35.580  1.00  73.29           C
ATOM   1932  CD   GLU A 249      -0.570    1.298   35.710  1.00  75.19           C
ATOM   1933  OE1  GLU A 249       0.497    1.896   35.945  1.00  70.38           O
ATOM   1934  OE2  GLU A 249      -1.713    1.925   35.527  1.00  80.18           O
ATOM   1935  N    TYR A 250       0.280   -2.219   31.577  1.00  75.72           N
ATOM   1936  CA   TYR A 250       1.190   -2.433   30.482  1.00  84.39           C
ATOM   1937  C    TYR A 250       2.310   -1.398   30.561  1.00  82.31           C
ATOM   1938  O    TYR A 250       2.514   -0.626   31.515  1.00  86.58           O
ATOM   1939  CB   TYR A 250       0.490   -2.217   29.148  1.00  91.59           C
ATOM   1940  CG   TYR A 250      -0.713   -3.072   28.919  1.00  96.47           C
ATOM   1941  CD1  TYR A 250      -0.604   -4.453   28.740  1.00  96.85           C
```

Figure 22AM

```
ATOM   1942  CD2  TYR A 250     -1.971   -2.475   28.870  1.00 98.60           C
ATOM   1943  CE1  TYR A 250     -1.741   -5.232   28.512  1.00 98.74           C
ATOM   1944  CE2  TYR A 250     -3.116   -3.241   28.637  1.00100.00           C
ATOM   1945  CZ   TYR A 250     -2.997   -4.619   28.459  1.00100.00           C
ATOM   1946  OH   TYR A 250     -4.125   -5.368   28.226  1.00100.00           O
ATOM   1947  N    PRO A 251      3.095   -1.349   29.525  1.00 73.20           N
ATOM   1948  CA   PRO A 251      4.139   -0.372   29.602  1.00 66.35           C
ATOM   1949  C    PRO A 251      3.621    0.855   28.876  1.00 55.77           C
ATOM   1950  O    PRO A 251      2.506    0.817   28.296  1.00 43.29           O
ATOM   1951  CB   PRO A 251      5.393   -1.018   28.970  1.00 67.65           C
ATOM   1952  CG   PRO A 251      4.959   -2.379   28.411  1.00 66.82           C
ATOM   1953  CD   PRO A 251      3.437   -2.436   28.557  1.00 68.13           C
ATOM   1954  N    HIS A 252      4.412    1.930   28.923  1.00 56.88           N
ATOM   1955  CA   HIS A 252      4.013    3.164   28.256  1.00 61.54           C
ATOM   1956  C    HIS A 252      4.676    3.174   26.922  1.00 49.39           C
ATOM   1957  O    HIS A 252      5.907    3.075   26.855  1.00 48.15           O
ATOM   1958  CB   HIS A 252      4.413    4.450   29.003  1.00 68.34           C
ATOM   1959  CG   HIS A 252      3.743    4.815   30.305  1.00 56.80           C
ATOM   1960  ND1  HIS A 252      4.261    4.397   31.521  1.00 52.87           N
ATOM   1961  CD2  HIS A 252      2.650    5.573   30.535  1.00 50.77           C
ATOM   1962  CE1  HIS A 252      3.484    4.890   32.448  1.00 52.89           C
ATOM   1963  NE2  HIS A 252      2.508    5.599   31.885  1.00 57.99           N
ATOM   1964  N    ARG A 253      3.855    3.289   25.899  1.00 45.95           N
ATOM   1965  CA   ARG A 253      4.383    3.273   24.559  1.00 49.45           C
ATOM   1966  C    ARG A 253      4.353    4.520   23.718  1.00 51.20           C
ATOM   1967  O    ARG A 253      3.341    5.217   23.585  1.00 54.39           O
ATOM   1968  CB   ARG A 253      3.665    2.206   23.747  1.00 46.90           C
ATOM   1969  CG   ARG A 253      2.902    1.215   24.588  1.00 47.81           C
ATOM   1970  CD   ARG A 253      3.107   -0.244   24.180  1.00 58.77           C
ATOM   1971  NE   ARG A 253      4.110   -0.986   24.980  1.00 70.69           N
ATOM   1972  CZ   ARG A 253      4.288   -2.326   24.916  1.00 77.73           C
ATOM   1973  NH1  ARG A 253      3.556   -3.104   24.105  1.00 76.16           N
ATOM   1974  NH2  ARG A 253      5.218   -2.908   25.681  1.00 79.52           N
ATOM   1975  N    ARG A 254      5.491    4.750   23.112  1.00 43.19           N
ATOM   1976  CA   ARG A 254      5.634    5.867   22.245  1.00 41.38           C
ATOM   1977  C    ARG A 254      4.569    5.842   21.166  1.00 38.18           C
ATOM   1978  O    ARG A 254      4.193    4.815   20.678  1.00 41.39           O
ATOM   1979  CB   ARG A 254      6.968    5.792   21.563  1.00 45.27           C
ATOM   1980  CG   ARG A 254      8.117    6.309   22.418  1.00 48.45           C
ATOM   1981  CD   ARG A 254      8.207    7.839   22.410  1.00 45.54           C
ATOM   1982  NE   ARG A 254      8.493    8.498   21.129  1.00 40.21           N
ATOM   1983  CZ   ARG A 254      7.526    8.877   20.269  1.00 42.89           C
ATOM   1984  NH1  ARG A 254      6.234    8.656   20.539  1.00 38.13           N
ATOM   1985  NH2  ARG A 254      7.834    9.486   19.100  1.00 39.68           N
ATOM   1986  N    ILE A 255      4.078    6.991   20.785  1.00 38.86           N
ATOM   1987  CA   ILE A 255      3.087    7.109   19.764  1.00 40.99           C
ATOM   1988  C    ILE A 255      3.370    8.411   19.076  1.00 51.91           C
ATOM   1989  O    ILE A 255      4.082    9.229   19.656  1.00 53.97           O
ATOM   1990  CB   ILE A 255      1.698    7.141   20.312  1.00 47.47           C
ATOM   1991  CG1  ILE A 255      0.713    7.372   19.175  1.00 52.36           C
ATOM   1992  CG2  ILE A 255      1.563    8.300   21.284  1.00 53.96           C
ATOM   1993  CD1  ILE A 255     -0.727    7.401   19.699  1.00 55.55           C
ATOM   1994  N    ASP A 256      2.834    8.594   17.852  1.00 55.27           N
ATOM   1995  CA   ASP A 256      3.017    9.796   17.042  1.00 41.94           C
ATOM   1996  C    ASP A 256      1.825    9.934   16.186  1.00 35.63           C
ATOM   1997  O    ASP A 256      1.311    8.974   15.666  1.00 36.39           O
ATOM   1998  CB   ASP A 256      4.283    9.752   16.239  1.00 43.82           C
ATOM   1999  CG   ASP A 256      5.405    9.906   17.201  1.00 58.24           C
ATOM   2000  OD1  ASP A 256      5.522   10.919   17.809  1.00 73.10           O
ATOM   2001  OD2  ASP A 256      6.066    8.813   17.503  1.00 54.81           O
ATOM   2002  N    ILE A 257      1.341   11.113   16.060  1.00 36.82           N
ATOM   2003  CA   ILE A 257      0.189   11.197   15.235  1.00 42.22           C
ATOM   2004  C    ILE A 257      0.575   12.071   14.119  1.00 50.46           C
```

Figure 22AN

```
ATOM   2005  O    ILE A 257       1.484  12.873  14.288  1.00 52.00           O
ATOM   2006  CB   ILE A 257      -0.927  11.816  16.011  1.00 47.02           C
ATOM   2007  CG1  ILE A 257      -0.975  11.083  17.366  1.00 53.83           C
ATOM   2008  CG2  ILE A 257      -2.206  11.673  15.190  1.00 47.31           C
ATOM   2009  CD1  ILE A 257      -2.232  11.283  18.225  1.00 51.28           C
ATOM   2010  N    ARG A 258      -0.078  11.929  12.991  1.00 50.30           N
ATOM   2011  CA   ARG A 258       0.327  12.773  11.923  1.00 47.84           C
ATOM   2012  C    ARG A 258      -0.891  13.287  11.208  1.00 47.07           C
ATOM   2013  O    ARG A 258      -1.750  12.513  10.772  1.00 41.81           O
ATOM   2014  CB   ARG A 258       1.331  12.029  11.052  1.00 54.35           C
ATOM   2015  CG   ARG A 258       2.767  11.930  11.609  1.00 59.38           C
ATOM   2016  CD   ARG A 258       3.574  10.689  11.159  1.00 68.12           C
ATOM   2017  NE   ARG A 258       2.842   9.424  11.457  1.00 76.50           N
ATOM   2018  CZ   ARG A 258       3.204   8.109  11.362  1.00 69.89           C
ATOM   2019  NH1  ARG A 258       4.401   7.659  10.958  1.00 56.68           N
ATOM   2020  NH2  ARG A 258       2.282   7.206  11.712  1.00 73.53           N
ATOM   2021  N    LEU A 259      -0.932  14.625  11.135  1.00 54.39           N
ATOM   2022  CA   LEU A 259      -2.004  15.352  10.494  1.00 53.44           C
ATOM   2023  C    LEU A 259      -1.610  15.815   9.136  1.00 62.31           C
ATOM   2024  O    LEU A 259      -0.636  16.561   8.985  1.00 58.66           O
ATOM   2025  CB   LEU A 259      -2.400  16.618  11.185  1.00 45.52           C
ATOM   2026  CG   LEU A 259      -3.383  17.208  10.211  1.00 41.25           C
ATOM   2027  CD1  LEU A 259      -4.467  16.157   9.980  1.00 39.52           C
ATOM   2028  CD2  LEU A 259      -3.930  18.543  10.711  1.00 36.81           C
ATOM   2029  N    ILE A 260      -2.392  15.383   8.149  1.00 71.16           N
ATOM   2030  CA   ILE A 260      -2.099  15.709   6.755  1.00 71.23           C
ATOM   2031  C    ILE A 260      -3.220  16.359   5.900  1.00 68.35           C
ATOM   2032  O    ILE A 260      -4.407  16.213   6.140  1.00 83.45           O
ATOM   2033  CB   ILE A 260      -1.628  14.354   6.213  1.00 63.61           C
ATOM   2034  CG1  ILE A 260      -0.513  13.846   7.158  1.00 51.11           C
ATOM   2035  CG2  ILE A 260      -1.183  14.495   4.774  1.00 66.18           C
ATOM   2036  CD1  ILE A 260       0.332  12.661   6.719  1.00 41.94           C
ATOM   2037  N    PRO A 261      -2.854  17.110   4.872  0.50 42.84           N
ATOM   2038  CA   PRO A 261      -3.842  17.756   4.004  0.50 33.69           C
ATOM   2039  C    PRO A 261      -4.427  16.754   3.002  0.50 38.39           C
ATOM   2040  O    PRO A 261      -3.685  15.964   2.419  0.50 33.78           O
ATOM   2041  CB   PRO A 261      -3.101  18.858   3.258  0.50 23.92           C
ATOM   2042  CG   PRO A 261      -1.676  18.878   3.803  0.50 27.87           C
ATOM   2043  CD   PRO A 261      -1.562  17.811   4.887  0.50 31.22           C
ATOM   2044  N    LYS A 262      -5.749  16.781   2.799  0.50 47.08           N
ATOM   2045  CA   LYS A 262      -6.408  15.857   1.880  0.50 59.41           C
ATOM   2046  C    LYS A 262      -5.727  15.574   0.555  0.50 58.17           C
ATOM   2047  O    LYS A 262      -5.612  14.415   0.143  0.50 61.76           O
ATOM   2048  CB   LYS A 262      -7.918  15.983   1.739  0.50 70.80           C
ATOM   2049  CG   LYS A 262      -8.471  14.794   0.959  0.50 79.92           C
ATOM   2050  CD   LYS A 262      -9.922  14.452   1.271  0.50 85.77           C
ATOM   2051  CE   LYS A 262     -10.310  13.046   0.818  0.50 88.23           C
ATOM   2052  NZ   LYS A 262     -11.685  12.672   1.185  0.50 89.09           N
ATOM   2053  N    ASP A 263      -5.268  16.625  -0.102  0.50 55.46           N
ATOM   2054  CA   ASP A 263      -4.599  16.451  -1.377  0.50 55.81           C
ATOM   2055  C    ASP A 263      -3.306  15.619  -1.332  0.50 51.72           C
ATOM   2056  O    ASP A 263      -2.854  15.122  -2.354  0.50 52.94           O
ATOM   2057  CB   ASP A 263      -4.467  17.750  -2.220  0.50 53.10           C
ATOM   2058  CG   ASP A 263      -3.605  18.797  -1.589  0.50 48.18           C
ATOM   2059  OD1  ASP A 263      -2.322  18.588  -1.782  0.50 48.46           O
ATOM   2060  OD2  ASP A 263      -4.061  19.702  -0.926  0.50 44.46           O
ATOM   2061  N    GLN A 264      -2.701  15.457  -0.170  0.50 47.54           N
ATOM   2062  CA   GLN A 264      -1.476  14.680  -0.123  0.50 42.45           C
ATOM   2063  C    GLN A 264      -1.383  13.575   0.950  0.50 42.55           C
ATOM   2064  O    GLN A 264      -0.297  13.158   1.397  0.50 41.72           O
ATOM   2065  CB   GLN A 264      -0.209  15.529  -0.331  0.50 37.50           C
ATOM   2066  CG   GLN A 264      -0.166  16.819   0.501  0.50 41.48           C
ATOM   2067  CD   GLN A 264       0.662  17.903  -0.171  0.50 46.08           C
```

Figure 22AO

| | | | | | | | | | |
|---|---|---|---|---|---|---|---|---|---|
| ATOM | 2068 | OE1 | GLN A 264 | 1.778 | 18.234 | 0.267 | 0.50 | 47.99 | O |
| ATOM | 2069 | NE2 | GLN A 264 | 0.117 | 18.450 | -1.253 | 0.50 | 43.06 | N |
| ATOM | 2070 | N | TYR A 265 | -2.550 | 13.091 | 1.358 | 0.50 | 36.20 | N |
| ATOM | 2071 | CA | TYR A 265 | -2.582 | 12.066 | 2.335 | 0.50 | 32.96 | C |
| ATOM | 2072 | C | TYR A 265 | -1.857 | 10.864 | 1.762 | 0.50 | 23.25 | C |
| ATOM | 2073 | O | TYR A 265 | -0.652 | 10.705 | 1.963 | 0.50 | 13.29 | O |
| ATOM | 2074 | CB | TYR A 265 | -4.049 | 11.735 | 2.674 | 0.50 | 45.41 | C |
| ATOM | 2075 | CG | TYR A 265 | -4.241 | 11.114 | 4.037 | 0.50 | 60.64 | C |
| ATOM | 2076 | CD1 | TYR A 265 | -3.254 | 11.225 | 5.016 | 0.50 | 67.84 | C |
| ATOM | 2077 | CD2 | TYR A 265 | -5.417 | 10.440 | 4.364 | 0.50 | 68.21 | C |
| ATOM | 2078 | CE1 | TYR A 265 | -3.427 | 10.666 | 6.284 | 0.50 | 73.69 | C |
| ATOM | 2079 | CE2 | TYR A 265 | -5.609 | 9.873 | 5.625 | 0.50 | 74.35 | C |
| ATOM | 2080 | CZ | TYR A 265 | -4.607 | 9.990 | 6.592 | 0.50 | 79.34 | C |
| ATOM | 2081 | OH | TYR A 265 | -4.779 | 9.437 | 7.845 | 0.50 | 84.38 | O |
| ATOM | 2082 | N | TYR A 266 | -2.618 | 10.086 | 1.010 | 0.50 | 28.62 | N |
| ATOM | 2083 | CA | TYR A 266 | -2.197 | 8.863 | 0.334 | 0.50 | 34.11 | C |
| ATOM | 2084 | C | TYR A 266 | -0.735 | 8.774 | -0.037 | 0.50 | 30.41 | C |
| ATOM | 2085 | O | TYR A 266 | -0.148 | 7.746 | 0.257 | 0.50 | 17.66 | O |
| ATOM | 2086 | CB | TYR A 266 | -3.119 | 8.574 | -0.849 | 0.50 | 37.82 | C |
| ATOM | 2087 | CG | TYR A 266 | -4.507 | 8.477 | -0.283 | 0.50 | 44.01 | C |
| ATOM | 2088 | CD1 | TYR A 266 | -4.930 | 7.289 | 0.308 | 0.50 | 50.17 | C |
| ATOM | 2089 | CD2 | TYR A 266 | -5.383 | 9.563 | -0.311 | 0.50 | 44.68 | C |
| ATOM | 2090 | CE1 | TYR A 266 | -6.207 | 7.152 | 0.854 | 0.50 | 45.87 | C |
| ATOM | 2091 | CE2 | TYR A 266 | -6.664 | 9.442 | 0.233 | 0.50 | 48.87 | C |
| ATOM | 2092 | CZ | TYR A 266 | -7.076 | 8.243 | 0.813 | 0.50 | 45.51 | C |
| ATOM | 2093 | OH | TYR A 266 | -8.331 | 8.122 | 1.356 | 0.50 | 43.29 | O |
| ATOM | 2094 | N | CYS A 267 | -0.159 | 9.827 | -0.660 | 0.50 | 33.44 | N |
| ATOM | 2095 | CA | CYS A 267 | 1.247 | 9.731 | -0.985 | 0.50 | 37.56 | C |
| ATOM | 2096 | C | CYS A 267 | 1.943 | 9.596 | 0.356 | 0.50 | 42.39 | C |
| ATOM | 2097 | O | CYS A 267 | 2.811 | 8.745 | 0.546 | 0.50 | 42.85 | O |
| ATOM | 2098 | CB | CYS A 267 | 1.814 | 10.931 | -1.757 | 0.50 | 38.48 | C |
| ATOM | 2099 | SG | CYS A 267 | 0.675 | 11.561 | -2.995 | 0.50 | 41.42 | S |
| ATOM | 2100 | N | GLY A 268 | 1.520 | 10.460 | 1.283 | 0.50 | 42.57 | N |
| ATOM | 2101 | CA | GLY A 268 | 2.060 | 10.477 | 2.622 | 0.50 | 42.94 | C |
| ATOM | 2102 | C | GLY A 268 | 1.854 | 9.112 | 3.220 | 0.50 | 41.45 | C |
| ATOM | 2103 | O | GLY A 268 | 2.755 | 8.469 | 3.777 | 0.50 | 35.41 | O |
| ATOM | 2104 | N | VAL A 269 | 0.613 | 8.677 | 3.075 | 0.50 | 44.63 | N |
| ATOM | 2105 | CA | VAL A 269 | 0.196 | 7.380 | 3.573 | 0.50 | 40.51 | C |
| ATOM | 2106 | C | VAL A 269 | 1.080 | 6.345 | 2.968 | 0.50 | 37.13 | C |
| ATOM | 2107 | O | VAL A 269 | 1.664 | 5.504 | 3.644 | 0.50 | 27.28 | O |
| ATOM | 2108 | CB | VAL A 269 | -1.222 | 7.095 | 3.146 | 0.50 | 34.70 | C |
| ATOM | 2109 | CG1 | VAL A 269 | -1.474 | 5.602 | 3.268 | 0.50 | 27.68 | C |
| ATOM | 2110 | CG2 | VAL A 269 | -2.135 | 7.883 | 4.075 | 0.50 | 37.61 | C |
| ATOM | 2111 | N | LEU A 270 | 1.148 | 6.475 | 1.652 | 0.50 | 44.97 | N |
| ATOM | 2112 | CA | LEU A 270 | 1.941 | 5.611 | 0.829 | 0.50 | 45.16 | C |
| ATOM | 2113 | C | LEU A 270 | 3.338 | 5.644 | 1.375 | 0.50 | 44.37 | C |
| ATOM | 2114 | O | LEU A 270 | 3.854 | 4.650 | 1.880 | 0.50 | 40.73 | O |
| ATOM | 2115 | CB | LEU A 270 | 1.957 | 6.148 | -0.619 | 0.50 | 42.24 | C |
| ATOM | 2116 | CG | LEU A 270 | 2.792 | 5.319 | -1.580 | 0.50 | 45.76 | C |
| ATOM | 2117 | CD1 | LEU A 270 | 2.373 | 3.846 | -1.535 | 0.50 | 46.95 | C |
| ATOM | 2118 | CD2 | LEU A 270 | 2.607 | 5.868 | -2.995 | 0.50 | 46.07 | C |
| ATOM | 2119 | N | TYR A 271 | 3.917 | 6.833 | 1.281 | 0.50 | 46.29 | N |
| ATOM | 2120 | CA | TYR A 271 | 5.255 | 7.067 | 1.739 | 0.50 | 41.68 | C |
| ATOM | 2121 | C | TYR A 271 | 5.522 | 6.506 | 3.130 | 0.50 | 48.96 | C |
| ATOM | 2122 | O | TYR A 271 | 6.432 | 5.685 | 3.313 | 0.50 | 49.06 | O |
| ATOM | 2123 | CB | TYR A 271 | 5.602 | 8.556 | 1.616 | 0.50 | 36.48 | C |
| ATOM | 2124 | CG | TYR A 271 | 6.860 | 8.883 | 2.387 | 0.50 | 38.00 | C |
| ATOM | 2125 | CD1 | TYR A 271 | 8.047 | 8.219 | 2.082 | 0.50 | 38.01 | C |
| ATOM | 2126 | CD2 | TYR A 271 | 6.855 | 9.833 | 3.408 | 0.50 | 30.74 | C |
| ATOM | 2127 | CE1 | TYR A 271 | 9.222 | 8.499 | 2.778 | 0.50 | 37.74 | C |
| ATOM | 2128 | CE2 | TYR A 271 | 8.018 | 10.124 | 4.118 | 0.50 | 28.18 | C |
| ATOM | 2129 | CZ | TYR A 271 | 9.196 | 9.451 | 3.794 | 0.50 | 36.54 | C |
| ATOM | 2130 | OH | TYR A 271 | 10.348 | 9.729 | 4.475 | 0.50 | 42.82 | O |

Figure 22AP

| ATOM | 2131 | N   | PHE A 272 | 4.719  | 6.929  | 4.112  | 0.50 | 51.82 | N |
|------|------|-----|-----------|--------|--------|--------|------|-------|---|
| ATOM | 2132 | CA  | PHE A 272 | 4.929  | 6.439  | 5.459  | 0.50 | 46.92 | C |
| ATOM | 2133 | C   | PHE A 272 | 5.053  | 4.968  | 5.635  | 0.50 | 45.20 | C |
| ATOM | 2134 | O   | PHE A 272 | 6.051  | 4.529  | 6.191  | 0.50 | 42.07 | O |
| ATOM | 2135 | CB  | PHE A 272 | 4.134  | 7.109  | 6.583  | 0.50 | 41.87 | C |
| ATOM | 2136 | CG  | PHE A 272 | 4.858  | 8.378  | 6.954  | 0.50 | 29.24 | C |
| ATOM | 2137 | CD1 | PHE A 272 | 5.996  | 8.331  | 7.755  | 0.50 | 21.95 | C |
| ATOM | 2138 | CD2 | PHE A 272 | 4.407  | 9.607  | 6.481  | 0.50 | 21.06 | C |
| ATOM | 2139 | CE1 | PHE A 272 | 6.692  | 9.485  | 8.108  | 0.50 | 14.59 | C |
| ATOM | 2140 | CE2 | PHE A 272 | 5.088  | 10.773 | 6.809  | 0.50 | 19.18 | C |
| ATOM | 2141 | CZ  | PHE A 272 | 6.218  | 10.696 | 7.618  | 0.50 | 20.53 | C |
| ATOM | 2142 | N   | THR A 273 | 4.045  | 4.257  | 5.134  | 0.50 | 47.66 | N |
| ATOM | 2143 | CA  | THR A 273 | 3.943  | 2.806  | 5.198  | 0.50 | 47.31 | C |
| ATOM | 2144 | C   | THR A 273 | 5.193  | 2.045  | 4.789  | 0.50 | 54.71 | C |
| ATOM | 2145 | O   | THR A 273 | 5.367  | 0.865  | 5.106  | 0.50 | 49.21 | O |
| ATOM | 2146 | CB  | THR A 273 | 2.709  | 2.343  | 4.429  | 0.50 | 35.34 | C |
| ATOM | 2147 | OG1 | THR A 273 | 1.771  | 3.395  | 4.548  | 0.50 | 30.95 | O |
| ATOM | 2148 | CG2 | THR A 273 | 2.153  | 1.076  | 5.082  | 0.50 | 35.45 | C |
| ATOM | 2149 | N   | GLY A 274 | 6.072  | 2.733  | 4.083  | 0.50 | 63.41 | N |
| ATOM | 2150 | CA  | GLY A 274 | 7.282  | 2.074  | 3.665  | 0.50 | 67.78 | C |
| ATOM | 2151 | C   | GLY A 274 | 6.908  | 0.909  | 2.778  | 0.50 | 66.93 | C |
| ATOM | 2152 | O   | GLY A 274 | 5.893  | 0.960  | 2.079  | 0.50 | 68.04 | O |
| ATOM | 2153 | N   | SER A 275 | 7.732  | -0.129 | 2.809  | 0.50 | 62.79 | N |
| ATOM | 2154 | CA  | SER A 275 | 8.891  | -0.109 | 3.656  | 0.50 | 55.25 | C |
| ATOM | 2155 | C   | SER A 275 | 10.048 | 0.652  | 3.037  | 0.50 | 48.54 | C |
| ATOM | 2156 | O   | SER A 275 | 9.925  | 1.463  | 2.132  | 0.50 | 42.95 | O |
| ATOM | 2157 | CB  | SER A 275 | 9.380  | -1.474 | 4.002  | 0.50 | 58.10 | C |
| ATOM | 2158 | OG  | SER A 275 | 10.352 | -1.771 | 3.026  | 0.50 | 62.34 | O |
| ATOM | 2159 | N   | ASP A 276 | 11.213 | 0.381  | 3.546  | 0.50 | 48.10 | N |
| ATOM | 2160 | CA  | ASP A 276 | 12.347 | 1.073  | 3.046  | 0.50 | 52.24 | C |
| ATOM | 2161 | C   | ASP A 276 | 12.599 | 0.799  | 1.575  | 0.50 | 64.00 | C |
| ATOM | 2162 | O   | ASP A 276 | 12.436 | 1.663  | 0.699  | 0.50 | 69.48 | O |
| ATOM | 2163 | CB  | ASP A 276 | 13.541 | 0.713  | 3.929  | 0.50 | 52.04 | C |
| ATOM | 2164 | CG  | ASP A 276 | 14.386 | 1.907  | 4.188  | 0.50 | 60.10 | C |
| ATOM | 2165 | OD1 | ASP A 276 | 13.746 | 3.041  | 3.971  | 0.50 | 61.05 | O |
| ATOM | 2166 | OD2 | ASP A 276 | 15.534 | 1.815  | 4.564  | 0.50 | 65.35 | O |
| ATOM | 2167 | N   | ILE A 277 | 12.997 | -0.440 | 1.314  | 0.50 | 64.15 | N |
| ATOM | 2168 | CA  | ILE A 277 | 13.294 | -0.892 | -0.023 | 0.50 | 53.57 | C |
| ATOM | 2169 | C   | ILE A 277 | 12.069 | -0.724 | -0.889 | 0.50 | 45.64 | C |
| ATOM | 2170 | O   | ILE A 277 | 12.136 | -0.530 | -2.100 | 0.50 | 45.42 | O |
| ATOM | 2171 | CB  | ILE A 277 | 13.958 | -2.280 | -0.085 | 0.50 | 53.50 | C |
| ATOM | 2172 | CG1 | ILE A 277 | 13.150 | -3.393 | 0.601  | 0.50 | 55.24 | C |
| ATOM | 2173 | CG2 | ILE A 277 | 15.336 | -2.189 | 0.569  | 0.50 | 52.95 | C |
| ATOM | 2174 | CD1 | ILE A 277 | 13.663 | -3.817 | 1.986  | 0.50 | 54.06 | C |
| ATOM | 2175 | N   | PHE A 278 | 10.934 | -0.810 | -0.229 | 0.50 | 42.23 | N |
| ATOM | 2176 | CA  | PHE A 278 | 9.699  | -0.659 | -0.937 | 0.50 | 45.11 | C |
| ATOM | 2177 | C   | PHE A 278 | 9.668  | 0.688  | -1.605 | 0.50 | 56.72 | C |
| ATOM | 2178 | O   | PHE A 278 | 9.228  | 0.825  | -2.739 | 0.50 | 65.97 | O |
| ATOM | 2179 | CB  | PHE A 278 | 8.473  | -0.815 | -0.035 | 0.50 | 39.96 | C |
| ATOM | 2180 | CG  | PHE A 278 | 7.227  | -0.610 | -0.850 | 0.50 | 41.19 | C |
| ATOM | 2181 | CD1 | PHE A 278 | 6.723  | 0.667  | -1.100 | 0.50 | 43.88 | C |
| ATOM | 2182 | CD2 | PHE A 278 | 6.539  | -1.692 | -1.389 | 0.50 | 41.00 | C |
| ATOM | 2183 | CE1 | PHE A 278 | 5.577  | 0.866  | -1.859 | 0.50 | 41.45 | C |
| ATOM | 2184 | CE2 | PHE A 278 | 5.385  | -1.514 | -2.149 | 0.50 | 36.50 | C |
| ATOM | 2185 | CZ  | PHE A 278 | 4.901  | -0.232 | -2.386 | 0.50 | 34.84 | C |
| ATOM | 2186 | N   | ASN A 279 | 10.121 | 1.692  | -0.873 | 0.50 | 57.06 | N |
| ATOM | 2187 | CA  | ASN A 279 | 10.153 | 3.038  | -1.382 | 0.50 | 57.43 | C |
| ATOM | 2188 | C   | ASN A 279 | 11.195 | 3.178  | -2.461 | 0.50 | 64.24 | C |
| ATOM | 2189 | O   | ASN A 279 | 10.975 | 3.808  | -3.496 | 0.50 | 63.81 | O |
| ATOM | 2190 | CB  | ASN A 279 | 10.365 | 4.067  | -0.263 | 0.50 | 53.75 | C |
| ATOM | 2191 | CG  | ASN A 279 | 9.056  | 4.479  | 0.366  | 0.50 | 51.95 | C |
| ATOM | 2192 | OD1 | ASN A 279 | 9.038  | 5.074  | 1.453  | 0.50 | 56.13 | O |
| ATOM | 2193 | ND2 | ASN A 279 | 7.957  | 4.189  | -0.331 | 0.50 | 47.66 | N |

Figure 22AQ

```
ATOM  2194  N    LYS A 280    12.343   2.579   -2.190  0.50  70.92      N
ATOM  2195  CA   LYS A 280    13.457   2.615   -3.117  0.50  80.64      C
ATOM  2196  C    LYS A 280    13.090   2.123   -4.523  0.50  87.35      C
ATOM  2197  O    LYS A 280    13.312   2.823   -5.513  0.50  91.00      O
ATOM  2198  CB   LYS A 280    14.631   1.813   -2.580  0.50  83.11      C
ATOM  2199  CG   LYS A 280    15.098   2.202   -1.190  0.50  83.60      C
ATOM  2200  CD   LYS A 280    16.407   1.516   -0.831  0.50  86.53      C
ATOM  2201  CE   LYS A 280    17.096   2.108    0.388  0.50  88.93      C
ATOM  2202  NZ   LYS A 280    18.481   1.641    0.548  0.50  89.31      N
ATOM  2203  N    ASN A 281    12.540   0.903   -4.595  0.50  88.08      N
ATOM  2204  CA   ASN A 281    12.126   0.246   -5.830  0.50  86.37      C
ATOM  2205  C    ASN A 281    10.939   0.849   -6.570  0.50  85.36      C
ATOM  2206  O    ASN A 281    10.915   0.865   -7.800  0.50  82.07      O
ATOM  2207  CB   ASN A 281    12.103  -1.281   -5.710  0.50  86.29      C
ATOM  2208  CG   ASN A 281    13.505  -1.790   -5.444  0.50  87.19      C
ATOM  2209  OD1  ASN A 281    13.729  -2.601   -4.533  0.50  87.10      O
ATOM  2210  ND2  ASN A 281    14.461  -1.269   -6.217  0.50  87.43      N
ATOM  2211  N    MET A 282     9.952   1.333   -5.810  0.50  89.15      N
ATOM  2212  CA   MET A 282     8.761   1.948   -6.385  0.50  90.60      C
ATOM  2213  C    MET A 282     9.108   3.236   -7.101  0.50  94.12      C
ATOM  2214  O    MET A 282     8.744   3.446   -8.265  0.50  96.97      O
ATOM  2215  CB   MET A 282     7.661   2.280   -5.366  0.50  85.18      C
ATOM  2216  CG   MET A 282     6.639   3.211   -5.998  0.50  79.95      C
ATOM  2217  SD   MET A 282     5.137   3.377   -5.023  0.50  78.39      S
ATOM  2218  CE   MET A 282     4.069   4.324   -6.137  0.50  75.37      C
ATOM  2219  N    ARG A 283     9.821   4.092   -6.363  0.50  90.68      N
ATOM  2220  CA   ARG A 283    10.251   5.371   -6.875  0.50  84.72      C
ATOM  2221  C    ARG A 283    10.968   5.135   -8.177  0.50  76.05      C
ATOM  2222  O    ARG A 283    10.806   5.879   -9.134  0.50  75.56      O
ATOM  2223  CB   ARG A 283    11.097   6.146   -5.874  0.50  89.01      C
ATOM  2224  CG   ARG A 283    10.302   6.546   -4.630  0.50  90.81      C
ATOM  2225  CD   ARG A 283    10.963   7.674   -3.849  0.50  93.11      C
ATOM  2226  NE   ARG A 283    10.124   8.203   -2.779  0.50  94.35      N
ATOM  2227  CZ   ARG A 283    10.416   9.323   -2.130  0.50  94.74      C
ATOM  2228  NH1  ARG A 283    11.498  10.039   -2.433  0.50  97.17      N
ATOM  2229  NH2  ARG A 283     9.604   9.744   -1.164  0.50  91.57      N
ATOM  2230  N    ALA A 284    11.758   4.064   -8.191  0.50  70.64      N
ATOM  2231  CA   ALA A 284    12.495   3.697   -9.375  0.50  65.24      C
ATOM  2232  C    ALA A 284    11.499   3.415  -10.482  0.50  63.16      C
ATOM  2233  O    ALA A 284    11.596   3.967  -11.569  0.50  66.21      O
ATOM  2234  CB   ALA A 284    13.344   2.465   -9.125  0.50  64.60      C
ATOM  2235  N    HIS A 285    10.531   2.553  -10.188  0.50  60.84      N
ATOM  2236  CA   HIS A 285     9.531   2.215  -11.167  0.50  64.02      C
ATOM  2237  C    HIS A 285     8.740   3.412  -11.673  0.50  70.06      C
ATOM  2238  O    HIS A 285     8.671   3.654  -12.883  0.50  66.58      O
ATOM  2239  CB   HIS A 285     8.565   1.122  -10.717  0.50  63.02      C
ATOM  2240  CG   HIS A 285     7.541   0.924  -11.782  0.50  68.62      C
ATOM  2241  ND1  HIS A 285     7.889   0.387  -13.014  0.50  73.64      N
ATOM  2242  CD2  HIS A 285     6.210   1.202  -11.798  0.50  68.65      C
ATOM  2243  CE1  HIS A 285     6.777   0.344  -13.742  0.50  74.25      C
ATOM  2244  NE2  HIS A 285     5.751   0.828  -13.041  0.50  72.09      N
ATOM  2245  N    ALA A 286     8.137   4.146  -10.729  0.50  75.37      N
ATOM  2246  CA   ALA A 286     7.331   5.326  -11.017  0.50  79.83      C
ATOM  2247  C    ALA A 286     8.026   6.255  -11.985  0.50  83.03      C
ATOM  2248  O    ALA A 286     7.405   7.023  -12.716  0.50  78.13      O
ATOM  2249  CB   ALA A 286     7.027   6.084   -9.741  0.50  82.25      C
ATOM  2250  N    LEU A 287     9.345   6.167  -11.938  0.50  90.39      N
ATOM  2251  CA   LEU A 287    10.246   6.942  -12.761  0.50  95.91      C
ATOM  2252  C    LEU A 287    10.163   6.479  -14.222  0.50  99.74      C
ATOM  2253  O    LEU A 287     9.955   7.258  -15.162  0.50 100.00      O
ATOM  2254  CB   LEU A 287    11.672   6.745  -12.198  0.50  96.78      C
ATOM  2255  CG   LEU A 287    12.445   8.038  -11.972  0.50  97.89      C
ATOM  2256  CD1  LEU A 287    12.501   8.847  -13.262  0.50  98.81      C
```

Figure 22AR

| ATOM | 2257 | CD2 | LEU | A | 287 | 11.798 | 8.850 | -10.846 | 0.50 | 98.54 | C |
| --- | --- | --- | --- | --- | --- | --- | --- | --- | --- | --- | --- |
| ATOM | 2258 | N | GLU | A | 288 | 10.328 | 5.167 | -14.396 | 0.50 | 100.00 | N |
| ATOM | 2259 | CA | GLU | A | 288 | 10.293 | 4.537 | -15.701 | 0.50 | 100.00 | C |
| ATOM | 2260 | C | GLU | A | 288 | 9.054 | 4.868 | -16.496 | 0.50 | 100.00 | C |
| ATOM | 2261 | O | GLU | A | 288 | 9.067 | 4.975 | -17.721 | 0.50 | 100.00 | O |
| ATOM | 2262 | CB | GLU | A | 288 | 10.484 | 3.014 | -15.599 | 0.50 | 99.20 | C |
| ATOM | 2263 | CG | GLU | A | 288 | 11.880 | 2.725 | -15.053 | 0.50 | 97.79 | C |
| ATOM | 2264 | CD | GLU | A | 288 | 12.805 | 3.804 | -15.518 | 0.50 | 98.84 | C |
| ATOM | 2265 | OE1 | GLU | A | 288 | 12.873 | 4.167 | -16.682 | 0.50 | 100.00 | O |
| ATOM | 2266 | OE2 | GLU | A | 288 | 13.421 | 4.394 | -14.526 | 0.50 | 99.08 | O |
| ATOM | 2267 | N | LYS | A | 289 | 7.974 | 5.026 | -15.781 | 0.50 | 99.04 | N |
| ATOM | 2268 | CA | LYS | A | 289 | 6.755 | 5.338 | -16.451 | 0.50 | 96.66 | C |
| ATOM | 2269 | C | LYS | A | 289 | 6.675 | 6.815 | -16.751 | 0.50 | 93.73 | C |
| ATOM | 2270 | O | LYS | A | 289 | 5.748 | 7.267 | -17.424 | 0.50 | 95.63 | O |
| ATOM | 2271 | CB | LYS | A | 289 | 5.578 | 4.721 | -15.716 | 0.50 | 96.19 | C |
| ATOM | 2272 | CG | LYS | A | 289 | 5.882 | 3.248 | -15.497 | 0.50 | 94.87 | C |
| ATOM | 2273 | CD | LYS | A | 289 | 6.682 | 2.725 | -16.682 | 0.50 | 97.26 | C |
| ATOM | 2274 | CE | LYS | A | 289 | 7.687 | 1.638 | -16.352 | 0.50 | 99.13 | C |
| ATOM | 2275 | NZ | LYS | A | 289 | 7.126 | 0.292 | -16.517 | 0.50 | 100.00 | N |
| ATOM | 2276 | N | GLY | A | 290 | 7.688 | 7.534 | -16.236 | 0.50 | 90.09 | N |
| ATOM | 2277 | CA | GLY | A | 290 | 7.833 | 8.979 | -16.380 | 0.50 | 90.04 | C |
| ATOM | 2278 | C | GLY | A | 290 | 7.251 | 9.792 | -15.208 | 0.50 | 89.30 | C |
| ATOM | 2279 | O | GLY | A | 290 | 6.449 | 10.706 | -15.411 | 0.50 | 87.40 | O |
| ATOM | 2280 | N | PHE | A | 291 | 7.656 | 9.471 | -13.972 | 0.50 | 88.95 | N |
| ATOM | 2281 | CA | PHE | A | 291 | 7.155 | 10.181 | -12.801 | 0.50 | 90.17 | C |
| ATOM | 2282 | C | PHE | A | 291 | 8.180 | 10.223 | -11.680 | 0.50 | 94.46 | C |
| ATOM | 2283 | O | PHE | A | 291 | 9.113 | 9.423 | -11.647 | 0.50 | 98.26 | O |
| ATOM | 2284 | CB | PHE | A | 291 | 5.861 | 9.551 | -12.267 | 0.50 | 88.46 | C |
| ATOM | 2285 | CG | PHE | A | 291 | 4.921 | 9.117 | -13.367 | 0.50 | 85.94 | C |
| ATOM | 2286 | CD1 | PHE | A | 291 | 4.111 | 10.041 | -14.030 | 0.50 | 82.62 | C |
| ATOM | 2287 | CD2 | PHE | A | 291 | 4.845 | 7.776 | -13.742 | 0.50 | 84.65 | C |
| ATOM | 2288 | CE1 | PHE | A | 291 | 3.251 | 9.642 | -15.051 | 0.50 | 79.75 | C |
| ATOM | 2289 | CE2 | PHE | A | 291 | 3.984 | 7.353 | -14.756 | 0.50 | 81.21 | C |
| ATOM | 2290 | CZ | PHE | A | 291 | 3.187 | 8.294 | -15.408 | 0.50 | 80.09 | C |
| ATOM | 2291 | N | THR | A | 292 | 7.985 | 11.163 | -10.750 | 0.50 | 94.32 | N |
| ATOM | 2292 | CA | THR | A | 292 | 8.869 | 11.332 | -9.602 | 0.50 | 91.96 | C |
| ATOM | 2293 | C | THR | A | 292 | 8.086 | 11.454 | -8.288 | 0.50 | 86.02 | C |
| ATOM | 2294 | O | THR | A | 292 | 7.314 | 12.391 | -8.077 | 0.50 | 86.63 | O |
| ATOM | 2295 | CB | THR | A | 292 | 9.845 | 12.512 | -9.807 | 0.50 | 90.83 | C |
| ATOM | 2296 | OG1 | THR | A | 292 | 10.687 | 12.652 | -8.683 | 0.50 | 92.30 | O |
| ATOM | 2297 | CG2 | THR | A | 292 | 9.080 | 13.800 | -10.064 | 0.50 | 86.61 | C |
| ATOM | 2298 | N | ILE | A | 293 | 8.282 | 10.473 | -7.399 | 0.50 | 76.37 | N |
| ATOM | 2299 | CA | ILE | A | 293 | 7.599 | 10.424 | -6.113 | 0.50 | 63.12 | C |
| ATOM | 2300 | C | ILE | A | 293 | 8.406 | 11.019 | -4.962 | 0.50 | 63.21 | C |
| ATOM | 2301 | O | ILE | A | 293 | 9.629 | 11.214 | -5.055 | 0.50 | 62.12 | O |
| ATOM | 2302 | CB | ILE | A | 293 | 7.137 | 9.017 | -5.738 | 0.50 | 50.06 | C |
| ATOM | 2303 | CG1 | ILE | A | 293 | 6.445 | 8.365 | -6.908 | 0.50 | 52.33 | C |
| ATOM | 2304 | CG2 | ILE | A | 293 | 6.066 | 9.139 | -4.681 | 0.50 | 44.97 | C |
| ATOM | 2305 | CD1 | ILE | A | 293 | 5.098 | 9.033 | -7.174 | 0.50 | 53.04 | C |
| ATOM | 2306 | N | ASN | A | 294 | 7.659 | 11.279 | -3.876 | 0.50 | 59.46 | N |
| ATOM | 2307 | CA | ASN | A | 294 | 8.134 | 11.828 | -2.619 | 0.50 | 52.42 | C |
| ATOM | 2308 | C | ASN | A | 294 | 7.119 | 11.542 | -1.508 | 0.50 | 61.41 | C |
| ATOM | 2309 | O | ASN | A | 294 | 6.414 | 10.530 | -1.535 | 0.50 | 62.68 | O |
| ATOM | 2310 | CB | ASN | A | 294 | 8.464 | 13.326 | -2.742 | 0.50 | 39.01 | C |
| ATOM | 2311 | CG | ASN | A | 294 | 7.274 | 14.097 | -3.241 | 0.50 | 37.65 | C |
| ATOM | 2312 | OD1 | ASN | A | 294 | 7.374 | 15.288 | -3.543 | 0.50 | 40.90 | O |
| ATOM | 2313 | ND2 | ASN | A | 294 | 6.137 | 13.411 | -3.344 | 0.50 | 37.18 | N |
| ATOM | 2314 | N | GLU | A | 295 | 7.039 | 12.426 | -0.515 | 0.50 | 66.60 | N |
| ATOM | 2315 | CA | GLU | A | 295 | 6.106 | 12.244 | 0.577 | 0.50 | 63.69 | C |
| ATOM | 2316 | C | GLU | A | 295 | 4.782 | 12.999 | 0.400 | 0.50 | 57.41 | C |
| ATOM | 2317 | O | GLU | A | 295 | 3.817 | 12.749 | 1.115 | 0.50 | 55.66 | O |
| ATOM | 2318 | CB | GLU | A | 295 | 6.737 | 12.464 | 1.969 | 0.50 | 69.47 | C |
| ATOM | 2319 | CG | GLU | A | 295 | 7.559 | 13.764 | 2.126 | 0.50 | 74.29 | C |

Figure 22AS

```
ATOM   2320  CD   GLU A 295       8.996  13.620   1.714  0.50 76.82           C
ATOM   2321  OE1  GLU A 295       9.243  12.436   1.223  0.50 79.24           O
ATOM   2322  OE2  GLU A 295       9.837  14.500   1.839  0.50 77.37           O
ATOM   2323  N    TYR A 296       4.720  13.931  -0.550  0.50 54.57           N
ATOM   2324  CA   TYR A 296       3.495  14.693  -0.763  0.50 56.42           C
ATOM   2325  C    TYR A 296       2.836  14.505  -2.124  0.50 58.19           C
ATOM   2326  O    TYR A 296       1.617  14.644  -2.273  0.50 55.55           O
ATOM   2327  CB   TYR A 296       3.721  16.198  -0.579  0.50 57.64           C
ATOM   2328  CG   TYR A 296       4.796  16.512   0.420  0.50 62.51           C
ATOM   2329  CD1  TYR A 296       6.135  16.237   0.133  0.50 65.12           C
ATOM   2330  CD2  TYR A 296       4.485  17.090   1.650  0.50 63.83           C
ATOM   2331  CE1  TYR A 296       7.150  16.528   1.043  0.50 63.99           C
ATOM   2332  CE2  TYR A 296       5.487  17.388   2.575  0.50 63.77           C
ATOM   2333  CZ   TYR A 296       6.819  17.103   2.269  0.50 61.46           C
ATOM   2334  OH   TYR A 296       7.799  17.390   3.173  0.50 56.84           O
ATOM   2335  N    THR A 297       3.632  14.209  -3.141  0.50 57.41           N
ATOM   2336  CA   THR A 297       3.023  14.053  -4.429  0.50 52.74           C
ATOM   2337  C    THR A 297       3.723  13.110  -5.341  0.50 55.82           C
ATOM   2338  O    THR A 297       4.578  12.333  -4.917  0.50 57.35           O
ATOM   2339  CB   THR A 297       2.970  15.387  -5.163  0.50 48.62           C
ATOM   2340  OG1  THR A 297       4.249  15.994  -5.112  0.50 47.56           O
ATOM   2341  CG2  THR A 297       1.887  16.264  -4.556  0.50 46.63           C
ATOM   2342  N    ILE A 298       3.279  13.275  -6.607  0.50 56.06           N
ATOM   2343  CA   ILE A 298       3.664  12.594  -7.832  0.50 50.96           C
ATOM   2344  C    ILE A 298       3.533  13.599  -8.949  0.50 49.94           C
ATOM   2345  O    ILE A 298       2.527  14.297  -9.048  0.50 40.11           O
ATOM   2346  CB   ILE A 298       2.774  11.396  -8.170  0.50 48.94           C
ATOM   2347  CG1  ILE A 298       3.335  10.668  -9.390  0.50 52.56           C
ATOM   2348  CG2  ILE A 298       1.342  11.843  -8.456  0.50 43.47           C
ATOM   2349  CD1  ILE A 298       2.497   9.470  -9.831  0.50 54.71           C
ATOM   2350  N    ARG A 299       4.555  13.657  -9.786  0.50 62.87           N
ATOM   2351  CA   ARG A 299       4.556  14.590 -10.884  0.50 74.54           C
ATOM   2352  C    ARG A 299       5.059  14.004 -12.189  0.50 78.59           C
ATOM   2353  O    ARG A 299       5.998  13.195 -12.222  0.50 80.45           O
ATOM   2354  CB   ARG A 299       5.380  15.817 -10.555  0.50 83.50           C
ATOM   2355  CG   ARG A 299       4.829  16.657  -9.408  0.50 90.98           C
ATOM   2356  CD   ARG A 299       5.818  17.733  -8.955  0.50 96.44           C
ATOM   2357  NE   ARG A 299       7.043  17.179  -8.370  0.50 99.77           N
ATOM   2358  CZ   ARG A 299       8.153  17.883  -8.158  0.50100.00           C
ATOM   2359  NH1  ARG A 299       8.231  19.177  -8.469  0.50100.00           N
ATOM   2360  NH2  ARG A 299       9.210  17.277  -7.618  0.50 99.14           N
ATOM   2361  N    PRO A 300       4.401  14.464 -13.257  0.50 78.93           N
ATOM   2362  CA   PRO A 300       4.714  14.063 -14.597  0.50 78.57           C
ATOM   2363  C    PRO A 300       6.124  14.488 -14.921  0.50 78.46           C
ATOM   2364  O    PRO A 300       6.412  15.669 -15.132  0.50 68.06           O
ATOM   2365  CB   PRO A 300       3.736  14.797 -15.515  0.50 80.44           C
ATOM   2366  CG   PRO A 300       2.872  15.690 -14.646  0.50 81.09           C
ATOM   2367  CD   PRO A 300       3.316  15.476 -13.214  0.50 80.49           C
ATOM   2368  N    LEU A 301       7.006  13.498 -14.945  0.50 88.61           N
ATOM   2369  CA   LEU A 301       8.392  13.759 -15.235  0.50 94.34           C
ATOM   2370  C    LEU A 301       8.587  14.314 -16.628  0.50 95.31           C
ATOM   2371  O    LEU A 301       8.347  13.667 -17.653  0.50 93.55           O
ATOM   2372  CB   LEU A 301       9.333  12.602 -14.887  0.50 97.41           C
ATOM   2373  CG   LEU A 301      10.768  13.080 -14.772  0.50 99.06           C
ATOM   2374  CD1  LEU A 301      10.769  14.584 -14.532  0.50100.00           C
ATOM   2375  CD2  LEU A 301      11.398  12.398 -13.565  0.50 99.28           C
ATOM   2376  N    GLY A 302       9.039  15.552 -16.597  0.50 97.57           N
ATOM   2377  CA   GLY A 302       9.319  16.372 -17.750  0.50 99.21           C
ATOM   2378  C    GLY A 302       9.713  15.683 -19.042  0.50 98.39           C
ATOM   2379  O    GLY A 302      10.312  14.597 -19.078  0.50 96.79           O
ATOM   2380  N    VAL A 303       9.333  16.408 -20.097  0.50 96.95           N
ATOM   2381  CA   VAL A 303       9.551  16.080 -21.483  0.50 97.55           C
ATOM   2382  C    VAL A 303      10.929  16.595 -21.865  0.50 96.75           C
```

Figure 22AT

```
ATOM   2383  O    VAL A 303      11.463  16.304 -22.930  0.50 98.87           O
ATOM   2384  CB   VAL A 303       8.464  16.725 -22.348  0.50 98.53           C
ATOM   2385  CG1  VAL A 303       8.233  18.157 -21.891  0.50 98.73           C
ATOM   2386  CG2  VAL A 303       8.848  16.723 -23.826  0.50 99.00           C
ATOM   2387  N    THR A 304      11.496  17.380 -20.954  0.50 96.11           N
ATOM   2388  CA   THR A 304      12.806  17.974 -21.137  0.50 98.38           C
ATOM   2389  C    THR A 304      13.876  17.503 -20.165  0.50 99.80           C
ATOM   2390  O    THR A 304      15.025  17.930 -20.256  0.50100.00           O
ATOM   2391  CB   THR A 304      12.709  19.506 -21.084  0.50100.00           C
ATOM   2392  OG1  THR A 304      12.585  19.932 -19.735  0.50100.00           O
ATOM   2393  CG2  THR A 304      11.496  19.956 -21.896  0.50100.00           C
ATOM   2394  N    GLY A 305      13.509  16.638 -19.225  0.50100.00           N
ATOM   2395  CA   GLY A 305      14.460  16.133 -18.251  0.50100.00           C
ATOM   2396  C    GLY A 305      13.848  16.177 -16.864  0.50100.00           C
ATOM   2397  O    GLY A 305      14.061  15.285 -16.042  0.50100.00           O
ATOM   2398  N    VAL A 306      13.084  17.248 -16.634  0.50 97.69           N
ATOM   2399  CA   VAL A 306      12.387  17.500 -15.394  0.50 95.30           C
ATOM   2400  C    VAL A 306      11.277  18.517 -15.579  0.50 93.62           C
ATOM   2401  O    VAL A 306      11.473  19.574 -16.179  0.50 91.28           O
ATOM   2402  CB   VAL A 306      13.302  17.935 -14.241  0.50 96.46           C
ATOM   2403  CG1  VAL A 306      14.089  16.762 -13.669  0.50 97.44           C
ATOM   2404  CG2  VAL A 306      14.237  19.060 -14.672  0.50 95.07           C
ATOM   2405  N    ALA A 307      10.107  18.170 -15.042  0.50 96.76           N
ATOM   2406  CA   ALA A 307       8.909  18.993 -15.105  0.50 98.51           C
ATOM   2407  C    ALA A 307       8.059  18.826 -13.842  0.50 95.94           C
ATOM   2408  O    ALA A 307       8.001  17.750 -13.248  0.50 98.62           O
ATOM   2409  CB   ALA A 307       8.105  18.730 -16.365  0.50100.00           C
ATOM   2410  N    GLY A 308       7.397  19.905 -13.443  0.50 90.78           N
ATOM   2411  CA   GLY A 308       6.559  19.897 -12.261  0.50 90.95           C
ATOM   2412  C    GLY A 308       5.087  19.564 -12.462  0.50 89.08           C
ATOM   2413  O    GLY A 308       4.702  18.844 -13.389  0.50 90.97           O
ATOM   2414  N    GLU A 309       4.311  20.121 -11.527  0.50 82.68           N
ATOM   2415  CA   GLU A 309       2.875  20.014 -11.424  0.50 77.39           C
ATOM   2416  C    GLU A 309       2.409  18.621 -11.089  0.50 78.91           C
ATOM   2417  O    GLU A 309       2.286  17.746 -11.929  0.50 81.40           O
ATOM   2418  CB   GLU A 309       2.125  20.585 -12.612  0.50 78.26           C
ATOM   2419  CG   GLU A 309       0.653  20.806 -12.256  0.50 80.74           C
ATOM   2420  CD   GLU A 309       0.476  21.785 -11.124  0.50 84.27           C
ATOM   2421  OE1  GLU A 309       1.381  22.119 -10.364  0.50 85.38           O
ATOM   2422  OE2  GLU A 309      -0.734  22.237 -11.056  0.50 85.82           O
ATOM   2423  N    PRO A 310       2.131  18.451  -9.824  0.50 78.95           N
ATOM   2424  CA   PRO A 310       1.675  17.190  -9.300  0.50 77.61           C
ATOM   2425  C    PRO A 310       0.280  16.772  -9.756  0.50 73.08           C
ATOM   2426  O    PRO A 310      -0.549  17.590 -10.151  0.50 69.34           O
ATOM   2427  CB   PRO A 310       1.801  17.297  -7.774  0.50 80.78           C
ATOM   2428  CG   PRO A 310       2.332  18.695  -7.456  0.50 81.05           C
ATOM   2429  CD   PRO A 310       2.496  19.430  -8.775  0.50 79.83           C
ATOM   2430  N    LEU A 311       0.063  15.464  -9.695  0.50 73.17           N
ATOM   2431  CA   LEU A 311      -1.181  14.829 -10.070  0.50 71.28           C
ATOM   2432  C    LEU A 311      -2.080  14.750  -8.867  0.50 77.56           C
ATOM   2433  O    LEU A 311      -1.623  14.912  -7.742  0.50 78.32           O
ATOM   2434  CB   LEU A 311      -0.931  13.409 -10.589  0.50 65.16           C
ATOM   2435  CG   LEU A 311      -0.698  13.323 -12.091  0.50 60.25           C
ATOM   2436  CD1  LEU A 311       0.025  14.557 -12.632  0.50 56.29           C
ATOM   2437  CD2  LEU A 311       0.102  12.058 -12.384  0.50 58.25           C
ATOM   2438  N    PRO A 312      -3.353  14.494  -9.123  0.50 82.59           N
ATOM   2439  CA   PRO A 312      -4.362  14.390  -8.082  0.50 84.78           C
ATOM   2440  C    PRO A 312      -4.578  12.967  -7.568  0.50 85.52           C
ATOM   2441  O    PRO A 312      -5.230  12.164  -8.222  0.50 87.97           O
ATOM   2442  CB   PRO A 312      -5.655  14.919  -8.710  0.50 86.05           C
ATOM   2443  CG   PRO A 312      -5.344  15.364 -10.136  0.50 85.18           C
ATOM   2444  CD   PRO A 312      -3.865  15.118 -10.373  0.50 83.57           C
ATOM   2445  N    VAL A 313      -4.041  12.654  -6.389  0.50 85.75           N
```

Figure 22AU

```
ATOM   2446  CA   VAL A 313      -4.193   11.323   -5.822  0.50 85.03           C
ATOM   2447  C    VAL A 313      -5.267   11.181   -4.759  0.50 83.69           C
ATOM   2448  O    VAL A 313      -5.243   11.841   -3.726  0.50 85.05           O
ATOM   2449  CB   VAL A 313      -2.880   10.786   -5.289  0.50 84.25           C
ATOM   2450  CG1  VAL A 313      -2.980    9.270   -5.110  0.50 85.79           C
ATOM   2451  CG2  VAL A 313      -1.764   11.152   -6.258  0.50 81.98           C
ATOM   2452  N    ASP A 314      -6.209   10.290   -5.014  0.50 82.19           N
ATOM   2453  CA   ASP A 314      -7.270   10.070   -4.064  0.50 80.90           C
ATOM   2454  C    ASP A 314      -7.291    8.705   -3.440  0.50 80.01           C
ATOM   2455  O    ASP A 314      -8.272    8.296   -2.830  0.50 79.35           O
ATOM   2456  CB   ASP A 314      -8.630   10.591   -4.491  0.50 84.02           C
ATOM   2457  CG   ASP A 314      -8.619   12.068   -4.288  0.50 90.29           C
ATOM   2458  OD1  ASP A 314      -7.982   12.682   -5.261  0.50 89.09           O
ATOM   2459  OD2  ASP A 314      -9.026   12.609   -3.268  0.50 94.38           O
ATOM   2460  N    SER A 315      -6.185    8.012   -3.605  0.50 83.78           N
ATOM   2461  CA   SER A 315      -6.034    6.684   -3.067  0.50 86.43           C
ATOM   2462  C    SER A 315      -4.721    6.073   -3.504  0.50 85.29           C
ATOM   2463  O    SER A 315      -4.221    6.360   -4.596  0.50 85.54           O
ATOM   2464  CB   SER A 315      -7.208    5.780   -3.419  0.50 89.59           C
ATOM   2465  OG   SER A 315      -7.113    4.553   -2.723  0.50 90.77           O
ATOM   2466  N    GLU A 316      -4.184    5.229   -2.627  0.50 83.71           N
ATOM   2467  CA   GLU A 316      -2.929    4.539   -2.868  0.50 81.52           C
ATOM   2468  C    GLU A 316      -2.961    3.786   -4.198  0.50 68.96           C
ATOM   2469  O    GLU A 316      -1.929    3.562   -4.839  0.50 59.32           O
ATOM   2470  CB   GLU A 316      -2.591    3.607   -1.691  0.50 86.47           C
ATOM   2471  CG   GLU A 316      -2.939    4.259   -0.344  0.50 89.52           C
ATOM   2472  CD   GLU A 316      -2.350    3.522    0.820  0.50 95.26           C
ATOM   2473  OE1  GLU A 316      -1.229    2.911    0.518  0.50 95.17           O
ATOM   2474  OE2  GLU A 316      -2.842    3.527    1.934  0.50 99.67           O
ATOM   2475  N    LYS A 317      -4.179    3.411   -4.589  0.50 67.40           N
ATOM   2476  CA   LYS A 317      -4.392    2.709   -5.823  0.50 69.37           C
ATOM   2477  C    LYS A 317      -4.102    3.697   -6.920  0.50 65.23           C
ATOM   2478  O    LYS A 317      -3.349    3.384   -7.848  0.50 59.26           O
ATOM   2479  CB   LYS A 317      -5.813    2.182   -5.961  0.50 73.91           C
ATOM   2480  CG   LYS A 317      -6.077    1.538   -7.313  0.50 76.78           C
ATOM   2481  CD   LYS A 317      -5.154    0.361   -7.595  0.50 79.13           C
ATOM   2482  CE   LYS A 317      -5.459   -0.332   -8.913  0.50 80.37           C
ATOM   2483  NZ   LYS A 317      -4.572   -1.471   -9.202  0.50 78.86           N
ATOM   2484  N    ASP A 318      -4.715    4.887   -6.766  0.50 66.27           N
ATOM   2485  CA   ASP A 318      -4.552    5.968   -7.717  0.50 69.04           C
ATOM   2486  C    ASP A 318      -3.089    6.153   -7.998  0.50 68.79           C
ATOM   2487  O    ASP A 318      -2.668    6.276   -9.133  0.50 71.90           O
ATOM   2488  CB   ASP A 318      -5.218    7.284   -7.301  0.50 72.53           C
ATOM   2489  CG   ASP A 318      -6.708    7.179   -7.369  0.50 80.47           C
ATOM   2490  OD1  ASP A 318      -7.293    6.112   -7.457  0.50 83.22           O
ATOM   2491  OD2  ASP A 318      -7.299    8.348   -7.344  0.50 82.93           O
ATOM   2492  N    ILE A 319      -2.305    6.150   -6.950  0.50 67.32           N
ATOM   2493  CA   ILE A 319      -0.889    6.305   -7.129  0.50 70.43           C
ATOM   2494  C    ILE A 319      -0.328    5.166   -7.995  0.50 73.46           C
ATOM   2495  O    ILE A 319       0.281    5.392   -9.045  0.50 71.64           O
ATOM   2496  CB   ILE A 319      -0.206    6.317   -5.763  0.50 70.99           C
ATOM   2497  CG1  ILE A 319      -0.460    7.604   -4.998  0.50 65.80           C
ATOM   2498  CG2  ILE A 319       1.290    6.023   -5.851  0.50 74.00           C
ATOM   2499  CD1  ILE A 319       0.212    7.562   -3.627  0.50 63.90           C
ATOM   2500  N    PHE A 320      -0.550    3.931   -7.533  0.50 75.92           N
ATOM   2501  CA   PHE A 320      -0.088    2.735   -8.211  0.50 78.17           C
ATOM   2502  C    PHE A 320      -0.396    2.755   -9.689  0.50 73.98           C
ATOM   2503  O    PHE A 320       0.432    2.350  -10.509  0.50 71.23           O
ATOM   2504  CB   PHE A 320      -0.755    1.480   -7.631  0.50 87.30           C
ATOM   2505  CG   PHE A 320      -0.238    1.081   -6.279  0.50 94.52           C
ATOM   2506  CD1  PHE A 320       1.127    0.874   -6.082  0.50 97.40           C
ATOM   2507  CD2  PHE A 320      -1.109    0.912   -5.202  0.50 97.15           C
ATOM   2508  CE1  PHE A 320       1.618    0.502   -4.832  0.50 99.10           C
```

Figure 22AV

```
ATOM   2509  CE2 PHE A 320      -0.637    0.538   -3.945  0.50 99.34           C
ATOM   2510  CZ  PHE A 320       0.732    0.335   -3.768  0.50100.00           C
ATOM   2511  N   ASP A 321      -1.615    3.227   -9.981  0.50 70.15           N
ATOM   2512  CA  ASP A 321      -2.173    3.344  -11.320  0.50 66.51           C
ATOM   2513  C   ASP A 321      -1.397    4.222  -12.301  0.50 63.20           C
ATOM   2514  O   ASP A 321      -1.333    3.926  -13.492  0.50 59.54           O
ATOM   2515  CB  ASP A 321      -3.696    3.569  -11.324  0.50 66.70           C
ATOM   2516  CG  ASP A 321      -4.436    2.548  -10.492  0.50 66.91           C
ATOM   2517  OD1 ASP A 321      -3.930    1.916   -9.576  0.50 63.30           O
ATOM   2518  OD2 ASP A 321      -5.692    2.424  -10.842  0.50 70.95           O
ATOM   2519  N   TYR A 322      -0.814    5.307  -11.800  0.50 63.22           N
ATOM   2520  CA  TYR A 322      -0.041    6.218  -12.628  0.50 58.94           C
ATOM   2521  C   TYR A 322       1.226    5.589  -13.174  0.50 61.13           C
ATOM   2522  O   TYR A 322       1.584    5.788  -14.337  0.50 59.39           O
ATOM   2523  CB  TYR A 322       0.379    7.475  -11.867  0.50 51.93           C
ATOM   2524  CG  TYR A 322      -0.795    8.232  -11.356  0.50 49.82           C
ATOM   2525  CD1 TYR A 322      -2.000    8.217  -12.057  0.50 49.40           C
ATOM   2526  CD2 TYR A 322      -0.699    8.971  -10.178  0.50 47.72           C
ATOM   2527  CE1 TYR A 322      -3.104    8.925  -11.588  0.50 47.98           C
ATOM   2528  CE2 TYR A 322      -1.795    9.684   -9.698  0.50 45.98           C
ATOM   2529  CZ  TYR A 322      -2.993    9.660  -10.408  0.50 44.77           C
ATOM   2530  OH  TYR A 322      -4.066   10.354   -9.944  0.50 45.17           O
ATOM   2531  N   ILE A 323       1.909    4.845  -12.307  0.50 63.29           N
ATOM   2532  CA  ILE A 323       3.149    4.179  -12.665  0.50 67.62           C
ATOM   2533  C   ILE A 323       2.922    2.816  -13.325  0.50 77.58           C
ATOM   2534  O   ILE A 323       3.874    2.096  -13.657  0.50 78.43           O
ATOM   2535  CB  ILE A 323       4.089    4.077  -11.462  0.50 58.23           C
ATOM   2536  CG1 ILE A 323       3.461    3.213  -10.375  0.50 59.76           C
ATOM   2537  CG2 ILE A 323       4.343    5.464  -10.914  0.50 49.17           C
ATOM   2538  CD1 ILE A 323       4.485    2.717   -9.368  0.50 61.14           C
ATOM   2539  N   GLN A 324       1.641    2.467  -13.510  0.50 81.57           N
ATOM   2540  CA  GLN A 324       1.254    1.199  -14.111  0.50 81.23           C
ATOM   2541  C   GLN A 324       1.765   -0.007  -13.320  0.50 81.08           C
ATOM   2542  O   GLN A 324       2.480   -0.861  -13.828  0.50 76.95           O
ATOM   2543  CB  GLN A 324       1.399    1.143  -15.647  0.50 81.74           C
ATOM   2544  CG  GLN A 324       2.666    1.865  -16.162  0.50 84.36           C
ATOM   2545  CD  GLN A 324       2.479    2.644  -17.461  0.50 85.14           C
ATOM   2546  OE1 GLN A 324       3.421    3.284  -17.950  0.50 83.33           O
ATOM   2547  NE2 GLN A 324       1.252    2.652  -17.991  0.50 86.46           N
ATOM   2548  N   TRP A 325       1.364   -0.028  -12.035  0.50 84.13           N
ATOM   2549  CA  TRP A 325       1.714   -1.056  -11.064  0.50 82.84           C
ATOM   2550  C   TRP A 325       0.529   -1.636  -10.314  0.50 81.38           C
ATOM   2551  O   TRP A 325      -0.434   -0.956   -9.980  0.50 76.20           O
ATOM   2552  CB  TRP A 325       2.714   -0.501  -10.054  0.50 84.86           C
ATOM   2553  CG  TRP A 325       4.093   -0.913  -10.391  0.50 87.58           C
ATOM   2554  CD1 TRP A 325       4.489   -1.388  -11.588  0.50 91.08           C
ATOM   2555  CD2 TRP A 325       5.236   -0.929   -9.539  0.50 88.44           C
ATOM   2556  NE1 TRP A 325       5.821   -1.689  -11.553  0.50 93.28           N
ATOM   2557  CE2 TRP A 325       6.309   -1.414  -10.307  0.50 90.60           C
ATOM   2558  CE3 TRP A 325       5.459   -0.565   -8.218  0.50 87.43           C
ATOM   2559  CZ2 TRP A 325       7.588   -1.552   -9.781  0.50 90.39           C
ATOM   2560  CZ3 TRP A 325       6.722   -0.699   -7.697  0.50 87.59           C
ATOM   2561  CH2 TRP A 325       7.774   -1.184   -8.472  0.50 89.52           C
ATOM   2562  N   LYS A 326       0.623   -2.927  -10.046  0.50 88.74           N
ATOM   2563  CA  LYS A 326      -0.428   -3.621   -9.333  0.50 96.25           C
ATOM   2564  C   LYS A 326      -0.634   -3.048   -7.943  0.50 96.48           C
ATOM   2565  O   LYS A 326       0.336   -2.882   -7.201  0.50 96.49           O
ATOM   2566  CB  LYS A 326      -0.140   -5.116   -9.223  0.50 99.86           C
ATOM   2567  CG  LYS A 326       0.898   -5.448   -8.152  0.50100.00           C
ATOM   2568  CD  LYS A 326       0.735   -6.834   -7.530  0.50100.00           C
ATOM   2569  CE  LYS A 326      -0.548   -7.012   -6.719  1.00100.00           C
ATOM   2570  NZ  LYS A 326      -0.700   -6.058   -5.602  1.00100.00           N
ATOM   2571  N   TYR A 327      -1.895   -2.751   -7.589  0.50 95.73           N
```

Figure 22AW

```
ATOM   2572  CA   TYR A 327      -2.178  -2.210  -6.272  0.50 91.11           C
ATOM   2573  C    TYR A 327      -1.631  -3.184  -5.249  0.50 90.78           C
ATOM   2574  O    TYR A 327      -2.269  -4.146  -4.832  0.50 94.62           O
ATOM   2575  CB   TYR A 327      -3.679  -1.964  -6.036  0.50 86.44           C
ATOM   2576  CG   TYR A 327      -4.017  -1.245  -4.748  0.50 84.40           C
ATOM   2577  CD1  TYR A 327      -3.171  -1.243  -3.637  0.50 81.14           C
ATOM   2578  CD2  TYR A 327      -5.234  -0.572  -4.639  0.50 86.00           C
ATOM   2579  CE1  TYR A 327      -3.492  -0.589  -2.452  0.50 81.62           C
ATOM   2580  CE2  TYR A 327      -5.583   0.089  -3.460  0.50 85.77           C
ATOM   2581  CZ   TYR A 327      -4.711   0.079  -2.372  0.50 83.44           C
ATOM   2582  OH   TYR A 327      -5.052   0.727  -1.219  0.50 83.77           O
ATOM   2583  N    ARG A 328      -0.427  -2.896  -4.845  0.50 86.99           N
ATOM   2584  CA   ARG A 328       0.228  -3.715  -3.880  0.50 85.54           C
ATOM   2585  C    ARG A 328      -0.368  -3.542  -2.516  0.50 85.95           C
ATOM   2586  O    ARG A 328      -0.698  -2.438  -2.098  0.50 83.42           O
ATOM   2587  CB   ARG A 328       1.677  -3.322  -3.812  0.50 85.19           C
ATOM   2588  CG   ARG A 328       2.521  -3.969  -4.891  0.50 83.25           C
ATOM   2589  CD   ARG A 328       3.457  -4.986  -4.270  0.50 81.93           C
ATOM   2590  NE   ARG A 328       4.690  -5.127  -5.025  0.50 79.71           N
ATOM   2591  CZ   ARG A 328       5.854  -5.368  -4.443  0.50 79.32           C
ATOM   2592  NH1  ARG A 328       5.968  -5.492  -3.122  0.50 80.17           N
ATOM   2593  NH2  ARG A 328       6.932  -5.488  -5.203  0.50 79.76           N
ATOM   2594  N    GLU A 329      -0.494  -4.664  -1.839  0.50 90.07           N
ATOM   2595  CA   GLU A 329      -1.028  -4.660  -0.510  0.50 95.06           C
ATOM   2596  C    GLU A 329       0.101  -4.190   0.387  0.50 96.70           C
ATOM   2597  O    GLU A 329       1.276  -4.318   0.018  0.50 95.16           O
ATOM   2598  CB   GLU A 329      -1.496  -6.055  -0.056  0.50 98.07           C
ATOM   2599  CG   GLU A 329      -2.921  -6.443  -0.501  0.50 99.91           C
ATOM   2600  CD   GLU A 329      -3.403  -7.710   0.170  0.50100.00           C
ATOM   2601  OE1  GLU A 329      -2.663  -8.469   0.783  0.50100.00           O
ATOM   2602  OE2  GLU A 329      -4.695  -7.910   0.037  0.50100.00           O
ATOM   2603  N    PRO A 330      -0.259  -3.647   1.550  0.50 97.54           N
ATOM   2604  CA   PRO A 330       0.726  -3.163   2.499  0.50 95.16           C
ATOM   2605  C    PRO A 330       1.551  -4.323   3.008  0.50 90.48           C
ATOM   2606  O    PRO A 330       2.755  -4.217   3.233  0.50 87.07           O
ATOM   2607  CB   PRO A 330      -0.069  -2.599   3.679  0.50 97.76           C
ATOM   2608  CG   PRO A 330      -1.518  -3.042   3.507  0.50 98.84           C
ATOM   2609  CD   PRO A 330      -1.640  -3.621   2.109  0.50 97.73           C
ATOM   2610  N    LYS A 331       0.848  -5.438   3.178  0.50 91.45           N
ATOM   2611  CA   LYS A 331       1.412  -6.677   3.664  0.50 92.31           C
ATOM   2612  C    LYS A 331       2.653  -7.082   2.891  0.50 92.69           C
ATOM   2613  O    LYS A 331       3.629  -7.571   3.470  0.50 96.73           O
ATOM   2614  CB   LYS A 331       0.379  -7.803   3.673  0.50 90.56           C
ATOM   2615  CG   LYS A 331       0.599  -8.819   4.791  0.50 91.50           C
ATOM   2616  CD   LYS A 331       1.460 -10.024   4.434  0.50 91.85           C
ATOM   2617  CE   LYS A 331       0.663 -11.163   3.808  0.50 93.09           C
ATOM   2618  NZ   LYS A 331      -0.322 -11.766   4.720  0.50 92.97           N
ATOM   2619  N    ASP A 332       2.601  -6.869   1.579  0.50 86.46           N
ATOM   2620  CA   ASP A 332       3.704  -7.214   0.706  0.50 83.79           C
ATOM   2621  C    ASP A 332       4.543  -6.085   0.158  0.50 72.92           C
ATOM   2622  O    ASP A 332       5.114  -6.200  -0.924  0.50 68.16           O
ATOM   2623  CB   ASP A 332       3.320  -8.247  -0.351  0.50 92.33           C
ATOM   2624  CG   ASP A 332       1.881  -8.085  -0.715  0.50 98.48           C
ATOM   2625  OD1  ASP A 332       1.420  -6.901  -0.385  0.50100.00           O
ATOM   2626  OD2  ASP A 332       1.215  -8.967  -1.229  0.50100.00           O
ATOM   2627  N    ARG A 333       4.610  -4.999   0.917  0.50 68.14           N
ATOM   2628  CA   ARG A 333       5.394  -3.839   0.534  0.50 57.83           C
ATOM   2629  C    ARG A 333       6.818  -4.022   0.997  0.50 57.42           C
ATOM   2630  O    ARG A 333       7.496  -3.085   1.405  0.50 55.58           O
ATOM   2631  CB   ARG A 333       4.779  -2.499   0.929  0.50 50.65           C
ATOM   2632  CG   ARG A 333       3.535  -2.280   0.082  0.50 50.43           C
ATOM   2633  CD   ARG A 333       2.759  -1.008   0.337  0.50 50.94           C
ATOM   2634  NE   ARG A 333       1.495  -1.039  -0.396  0.50 55.10           N
```

Figure 22AX

```
ATOM   2635  CZ   ARG A 333      0.561   -0.092   -0.301  0.50 61.11           C
ATOM   2636  NH1  ARG A 333      0.724    0.969    0.489  0.50 59.00           N
ATOM   2637  NH2  ARG A 333     -0.564   -0.207   -1.018  0.50 65.08           N
ATOM   2638  N    SER A 334      7.231   -5.280    0.921  0.50 65.29           N
ATOM   2639  CA   SER A 334      8.552   -5.748    1.293  0.50 76.62           C
ATOM   2640  C    SER A 334      9.651   -5.002    0.526  0.50 78.34           C
ATOM   2641  O    SER A 334     10.772   -4.801    1.008  0.50 76.68           O
ATOM   2642  CB   SER A 334      8.636   -7.237    0.988  0.50 82.33           C
ATOM   2643  OG   SER A 334      8.214   -7.473   -0.354  0.50 83.85           O
ATOM   2644  N    GLU A 335      9.300   -4.603   -0.693  0.50 77.31           N
ATOM   2645  CA   GLU A 335     10.188   -3.884   -1.577  0.50 76.65           C
ATOM   2646  C    GLU A 335      9.519   -3.665   -2.919  0.50 78.09           C
ATOM   2647  O    GLU A 335      9.811   -2.610   -3.542  0.50 76.45           O
ATOM   2648  CB   GLU A 335     11.586   -4.524   -1.684  0.50 77.10           C
ATOM   2649  CG   GLU A 335     11.569   -6.065   -1.750  0.50 82.92           C
ATOM   2650  CD   GLU A 335     12.869   -6.716   -1.335  0.50 85.74           C
ATOM   2651  OE1  GLU A 335     13.939   -6.135   -1.334  0.50 85.90           O
ATOM   2652  OE2  GLU A 335     12.723   -7.969   -0.953  0.50 86.11           O
ATOM   2653  OXT  GLU A 335      8.653   -4.518   -3.243  0.50 79.38           O
TER    2654       GLU A 335
ATOM   2655  O5*   C  T   1     42.605   11.529   -5.769  1.00 66.56           O
ATOM   2656  C5*   C  T   1     43.031   12.692   -6.519  1.00 64.79           C
ATOM   2657  C4*   C  T   1     42.006   13.802   -6.387  1.00 61.90           C
ATOM   2658  O4*   C  T   1     40.780   13.346   -6.965  1.00 52.74           O
ATOM   2659  C3*   C  T   1     41.664   14.195   -4.948  1.00 68.28           C
ATOM   2660  O3*   C  T   1     41.308   15.633   -4.955  1.00 80.77           O
ATOM   2661  C2*   C  T   1     40.419   13.351   -4.622  1.00 59.79           C
ATOM   2662  C1*   C  T   1     39.790   13.160   -5.983  1.00 48.54           C
ATOM   2663  N1    C  T   1     39.266   11.905   -6.343  1.00 37.93           N
ATOM   2664  C2    C  T   1     38.027   11.938   -6.991  1.00 36.64           C
ATOM   2665  O2    C  T   1     37.494   13.046   -7.151  1.00 36.08           O
ATOM   2666  N3    C  T   1     37.472   10.780   -7.426  1.00 26.83           N
ATOM   2667  C4    C  T   1     38.112    9.648   -7.215  1.00 24.29           C
ATOM   2668  N4    C  T   1     37.531    8.553   -7.653  1.00 24.81           N
ATOM   2669  C5    C  T   1     39.390    9.594   -6.514  1.00 24.97           C
ATOM   2670  C6    C  T   1     39.953   10.748   -6.123  1.00 27.59           C
ATOM   2671  P     C  T   2     40.894   16.440   -3.606  1.00 84.28           P
ATOM   2672  O1P   C  T   2     41.174   17.893   -3.845  1.00 88.48           O
ATOM   2673  O2P   C  T   2     41.535   15.746   -2.442  1.00 83.60           O
ATOM   2674  O5*   C  T   2     39.288   16.264   -3.468  1.00 68.27           O
ATOM   2675  C5*   C  T   2     38.369   16.767   -4.427  1.00 57.16           C
ATOM   2676  C4*   C  T   2     36.945   16.255   -4.181  1.00 49.17           C
ATOM   2677  O4*   C  T   2     36.788   14.882   -4.660  1.00 47.37           O
ATOM   2678  C3*   C  T   2     36.587   16.145   -2.727  1.00 49.13           C
ATOM   2679  O3*   C  T   2     36.142   17.293   -2.023  1.00 46.67           O
ATOM   2680  C2*   C  T   2     35.928   14.805   -2.462  1.00 47.16           C
ATOM   2681  C1*   C  T   2     35.925   14.151   -3.823  1.00 42.13           C
ATOM   2682  N1    C  T   2     36.269   12.752   -3.842  1.00 24.99           N
ATOM   2683  C2    C  T   2     35.350   11.898   -4.405  1.00 27.54           C
ATOM   2684  O2    C  T   2     34.322   12.404   -4.859  1.00 34.08           O
ATOM   2685  N3    C  T   2     35.631   10.568   -4.482  1.00 24.61           N
ATOM   2686  C4    C  T   2     36.806   10.065   -3.975  1.00 36.02           C
ATOM   2687  N4    C  T   2     37.101    8.722   -4.045  1.00 32.05           N
ATOM   2688  C5    C  T   2     37.761   10.979   -3.378  1.00 27.81           C
ATOM   2689  C6    C  T   2     37.462   12.310   -3.371  1.00 24.42           C
ATOM   2690  P     G  T   3     34.855   18.205   -2.156  1.00 50.14           P
ATOM   2691  O1P   G  T   3     35.176   19.333   -3.099  1.00 58.39           O
ATOM   2692  O2P   G  T   3     34.512   18.494   -0.759  1.00 56.53           O
ATOM   2693  O5*   G  T   3     33.585   17.457   -2.724  1.00 42.35           O
ATOM   2694  C5*   G  T   3     32.457   18.292   -2.880  1.00 34.18           C
ATOM   2695  C4*   G  T   3     31.230   17.517   -3.232  1.00 44.16           C
ATOM   2696  O4*   G  T   3     31.648   16.206   -3.712  1.00 52.47           O
ATOM   2697  C3*   G  T   3     30.187   17.308   -2.116  1.00 43.12           C
```

Figure 22AY

```
ATOM   2698  O3*   G T  3    28.975  17.627  -2.736  1.00 37.32           O
ATOM   2699  C2*   G T  3    30.172  15.803  -1.825  1.00 49.33           C
ATOM   2700  C1*   G T  3    30.963  15.156  -2.979  1.00 48.26           C
ATOM   2701  N9    G T  3    31.851  14.020  -2.622  1.00 28.86           N
ATOM   2702  C8    G T  3    33.081  14.121  -1.975  1.00 20.18           C
ATOM   2703  N7    G T  3    33.653  12.944  -1.805  1.00 13.58           N
ATOM   2704  C5    G T  3    32.711  12.031  -2.364  1.00  6.12           C
ATOM   2705  C6    G T  3    32.805  10.647  -2.464  1.00 21.02           C
ATOM   2706  O6    G T  3    33.723   9.938  -2.053  1.00 26.08           O
ATOM   2707  N1    G T  3    31.705  10.062  -3.085  1.00 17.17           N
ATOM   2708  C2    G T  3    30.646  10.772  -3.585  1.00 19.36           C
ATOM   2709  N2    G T  3    29.675   9.998  -4.127  1.00 24.51           N
ATOM   2710  N3    G T  3    30.517  12.121  -3.495  1.00 16.02           N
ATOM   2711  C4    G T  3    31.595  12.666  -2.860  1.00 11.14           C
ATOM   2712  P     A T  4    27.599  17.359  -2.037  1.00 36.99           P
ATOM   2713  O1P   A T  4    26.557  18.214  -2.630  1.00 26.99           O
ATOM   2714  O2P   A T  4    27.970  17.432  -0.617  1.00 40.08           O
ATOM   2715  O5*   A T  4    27.096  15.878  -2.354  1.00 48.73           O
ATOM   2716  C5*   A T  4    26.588  15.344  -3.582  1.00 48.76           C
ATOM   2717  C4*   A T  4    25.793  14.051  -3.245  1.00 48.63           C
ATOM   2718  O4*   A T  4    26.624  12.891  -2.944  1.00 43.94           O
ATOM   2719  C3*   A T  4    24.847  14.180  -2.054  1.00 45.86           C
ATOM   2720  O3*   A T  4    23.604  13.571  -2.439  1.00 49.41           O
ATOM   2721  C2*   A T  4    25.504  13.389  -0.925  1.00 35.93           C
ATOM   2722  C1*   A T  4    26.355  12.349  -1.655  1.00 25.85           C
ATOM   2723  N9    A T  4    27.625  12.153  -1.070  1.00  7.81           N
ATOM   2724  C8    A T  4    28.442  13.139  -0.633  1.00 14.98           C
ATOM   2725  N7    A T  4    29.632  12.644  -0.152  1.00 19.96           N
ATOM   2726  C5    A T  4    29.543  11.246  -0.289  1.00  1.00           C
ATOM   2727  C6    A T  4    30.421  10.219   0.023  1.00  7.92           C
ATOM   2728  N6    A T  4    31.686  10.330   0.604  1.00 16.05           N
ATOM   2729  N1    A T  4    29.951   8.979  -0.276  1.00 15.00           N
ATOM   2730  C2    A T  4    28.745   8.805  -0.855  1.00 13.29           C
ATOM   2731  N3    A T  4    27.819   9.699  -1.199  1.00 16.85           N
ATOM   2732  C4    A T  4    28.285  10.927  -0.849  1.00  9.62           C
ATOM   2733  P     C T  5    22.361  13.940  -1.551  1.00 54.96           P
ATOM   2734  O1P   C T  5    21.075  14.015  -2.320  1.00 47.50           O
ATOM   2735  O2P   C T  5    22.844  15.087  -0.770  1.00 57.96           O
ATOM   2736  O5*   C T  5    22.335  12.643  -0.622  1.00 67.26           O
ATOM   2737  C5*   C T  5    22.171  11.358  -1.214  1.00 55.38           C
ATOM   2738  C4*   C T  5    22.715  10.261  -0.312  1.00 37.17           C
ATOM   2739  O4*   C T  5    24.076  10.569   0.014  1.00 33.08           O
ATOM   2740  C3*   C T  5    22.083  10.054   1.015  1.00 40.58           C
ATOM   2741  O3*   C T  5    20.964   9.178   0.944  1.00 60.94           O
ATOM   2742  C2*   C T  5    23.232   9.597   1.909  1.00 32.19           C
ATOM   2743  C1*   C T  5    24.467   9.881   1.097  1.00 15.31           C
ATOM   2744  N1    C T  5    25.784  10.370   1.680  1.00  7.68           N
ATOM   2745  C2    C T  5    26.710   9.420   2.025  1.00 22.96           C
ATOM   2746  O2    C T  5    26.368   8.265   1.781  1.00 42.02           O
ATOM   2747  N3    C T  5    27.930   9.702   2.566  1.00 11.40           N
ATOM   2748  C4    C T  5    28.202  10.934   2.776  1.00 13.10           C
ATOM   2749  N4    C T  5    29.419  11.156   3.327  1.00 28.03           N
ATOM   2750  C5    C T  5    27.299  11.927   2.496  1.00  4.35           C
ATOM   2751  C6    C T  5    26.099  11.618   1.937  1.00 11.89           C
ATOM   2752  P     C T  6    20.088   8.973   2.271  1.00 79.02           P
ATOM   2753  O1P   C T  6    20.843   9.616   3.382  1.00 81.76           O
ATOM   2754  O2P   C T  6    19.735   7.539   2.358  1.00 86.21           O
ATOM   2755  O5*   C T  6    18.722   9.797   1.994  1.00 81.11           O
ATOM   2756  C5*   C T  6    18.064   9.769   0.716  1.00 88.12           C
ATOM   2757  C4*   C T  6    16.892  10.742   0.713  1.00 91.53           C
ATOM   2758  O4*   C T  6    15.977  10.271   1.717  1.00 92.27           O
ATOM   2759  C3*   C T  6    17.283  12.182   1.095  1.00 97.53           C
ATOM   2760  O3*   C T  6    16.752  13.189   0.138  1.00100.00           O
```

Figure 22AZ

```
ATOM   2761  C2*   C T  6   16.761  12.391   2.515  1.00 99.52        C
ATOM   2762  C1*   C T  6   15.871  11.187   2.811  1.00 99.63        C
ATOM   2763  N1    C T  6   16.190  10.464   4.138  1.00 99.67        N
ATOM   2764  C2    C T  6   15.117   9.916   4.852  1.00 97.06        C
ATOM   2765  O2    C T  6   13.990  10.054   4.382  1.00100.00        O
ATOM   2766  N3    C T  6   15.338   9.237   5.998  1.00 87.60        N
ATOM   2767  C4    C T  6   16.566   9.112   6.452  1.00 84.45        C
ATOM   2768  N4    C T  6   16.680   8.428   7.596  1.00 83.20        N
ATOM   2769  C5    C T  6   17.701   9.642   5.756  1.00 86.82        C
ATOM   2770  C6    C T  6   17.471  10.303   4.603  1.00 93.72        C
ATOM   2771  P     A T  7   16.942  14.811   0.291  1.00100.00        P
ATOM   2772  O1P   A T  7   16.901  15.456  -1.055  1.00 96.63        O
ATOM   2773  O2P   A T  7   18.120  15.074   1.161  1.00100.00        O
ATOM   2774  O5*   A T  7   15.590  15.208   1.097  1.00100.00        O
ATOM   2775  C5*   A T  7   14.328  14.476   0.861  1.00 98.97        C
ATOM   2776  C4*   A T  7   13.229  14.844   1.863  1.00 93.63        C
ATOM   2777  O4*   A T  7   13.285  14.153   3.131  1.00 86.94        O
ATOM   2778  C3*   A T  7   13.179  16.310   2.190  1.00 91.86        C
ATOM   2779  O3*   A T  7   11.855  16.649   2.057  1.00 91.55        O
ATOM   2780  C2*   A T  7   13.610  16.456   3.654  1.00 85.68        C
ATOM   2781  C1*   A T  7   13.275  15.085   4.220  1.00 89.24        C
ATOM   2782  N9    A T  7   14.189  14.539   5.202  1.00 97.94        N
ATOM   2783  C8    A T  7   15.552  14.645   5.240  1.00 97.42        C
ATOM   2784  N7    A T  7   16.064  13.980   6.281  1.00 95.15        N
ATOM   2785  C5    A T  7   14.944  13.407   6.917  1.00 91.73        C
ATOM   2786  C6    A T  7   14.777  12.600   8.065  1.00 75.38        C
ATOM   2787  N6    A T  7   15.781  12.151   8.807  1.00 60.56        N
ATOM   2788  N1    A T  7   13.515  12.255   8.414  1.00 77.27        N
ATOM   2789  C2    A T  7   12.483  12.648   7.635  1.00 92.97        C
ATOM   2790  N3    A T  7   12.502  13.419   6.548  1.00 99.90        N
ATOM   2791  C4    A T  7   13.774  13.772   6.260  1.00100.00        C
ATOM   2792  P     C T  8   11.451  18.040   2.665  1.00 95.66        P
ATOM   2793  O1P   C T  8   10.182  18.425   2.003  1.00 98.66        O
ATOM   2794  O2P   C T  8   12.648  18.921   2.763  1.00 89.12        O
ATOM   2795  O5*   C T  8   11.118  17.654   4.149  1.00 97.44        O
ATOM   2796  C5*   C T  8   10.183  16.665   4.416  1.00 87.85        C
ATOM   2797  C4*   C T  8    9.973  16.767   5.892  1.00 70.32        C
ATOM   2798  O4*   C T  8   11.093  16.190   6.601  1.00 60.78        O
ATOM   2799  C3*   C T  8    9.871  18.221   6.326  1.00 59.64        C
ATOM   2800  O3*   C T  8    8.600  18.380   6.890  1.00 64.47        O
ATOM   2801  C2*   C T  8   11.016  18.466   7.306  1.00 50.36        C
ATOM   2802  C1*   C T  8   11.403  17.053   7.664  1.00 55.42        C
ATOM   2803  N1    C T  8   12.717  16.773   8.071  1.00 58.05        N
ATOM   2804  C2    C T  8   12.857  15.968   9.197  1.00 60.15        C
ATOM   2805  O2    C T  8   11.833  15.539   9.752  1.00 59.60        O
ATOM   2806  N3    C T  8   14.085  15.672   9.652  1.00 52.34        N
ATOM   2807  C4    C T  8   15.151  16.177   9.027  1.00 60.57        C
ATOM   2808  N4    C T  8   16.369  15.862   9.487  1.00 59.72        N
ATOM   2809  C5    C T  8   15.008  17.042   7.889  1.00 63.64        C
ATOM   2810  C6    C T  8   13.775  17.328   7.457  1.00 61.51        C
ATOM   2811  P     G T  9    8.096  19.816   7.393  1.00 77.72        P
ATOM   2812  O1P   G T  9    6.791  20.059   6.701  1.00 80.38        O
ATOM   2813  O2P   G T  9    9.216  20.787   7.275  1.00 80.27        O
ATOM   2814  O5*   G T  9    7.847  19.627   8.972  1.00 71.74        O
ATOM   2815  C5*   G T  9    6.860  18.699   9.457  1.00 57.26        C
ATOM   2816  C4*   G T  9    6.921  18.581  10.964  1.00 39.99        C
ATOM   2817  O4*   G T  9    8.171  18.036  11.400  1.00 36.12        O
ATOM   2818  C3*   G T  9    6.698  19.848  11.735  1.00 40.78        C
ATOM   2819  O3*   G T  9    5.667  19.475  12.638  1.00 54.08        O
ATOM   2820  C2*   G T  9    8.029  20.132  12.455  1.00 36.15        C
ATOM   2821  C1*   G T  9    8.719  18.764  12.462  1.00 35.58        C
ATOM   2822  N9    G T  9   10.086  18.717  12.135  1.00 39.53        N
ATOM   2823  C8    G T  9   10.556  19.236  10.982  1.00 54.83        C
```

Figure 22BA

| ATOM | 2824 | N7  | G T | 9  | 11.839 | 19.089 | 10.860 | 1.00 | 52.64 | N |
|------|------|-----|-----|----|--------|--------|--------|------|-------|---|
| ATOM | 2825 | C5  | G T | 9  | 12.194 | 18.431 | 12.006 | 1.00 | 40.44 | C |
| ATOM | 2826 | C6  | G T | 9  | 13.451 | 18.038 | 12.366 | 1.00 | 45.01 | C |
| ATOM | 2827 | O6  | G T | 9  | 14.501 | 18.157 | 11.747 | 1.00 | 47.95 | O |
| ATOM | 2828 | N1  | G T | 9  | 13.437 | 17.414 | 13.567 | 1.00 | 41.06 | N |
| ATOM | 2829 | C2  | G T | 9  | 12.380 | 17.199 | 14.341 | 1.00 | 37.20 | C |
| ATOM | 2830 | N2  | G T | 9  | 12.719 | 16.581 | 15.453 | 1.00 | 30.50 | N |
| ATOM | 2831 | N3  | G T | 9  | 11.132 | 17.561 | 14.044 | 1.00 | 37.43 | N |
| ATOM | 2832 | C4  | G T | 9  | 11.128 | 18.191 | 12.836 | 1.00 | 37.81 | C |
| ATOM | 2833 | P   | C T | 10 | 4.846  | 20.563 | 13.502 | 1.00 | 56.69 | P |
| ATOM | 2834 | O1P | C T | 10 | 3.570  | 19.916 | 13.972 | 1.00 | 49.34 | O |
| ATOM | 2835 | O2P | C T | 10 | 4.808  | 21.851 | 12.779 | 1.00 | 69.15 | O |
| ATOM | 2836 | O5* | C T | 10 | 5.847  | 20.754 | 14.701 | 1.00 | 43.58 | O |
| ATOM | 2837 | C5* | C T | 10 | 5.899  | 19.739 | 15.591 | 1.00 | 43.49 | C |
| ATOM | 2838 | C4* | C T | 10 | 7.075  | 19.933 | 16.487 | 1.00 | 35.64 | C |
| ATOM | 2839 | O4* | C T | 10 | 8.251  | 19.768 | 15.727 | 1.00 | 28.13 | O |
| ATOM | 2840 | C3* | C T | 10 | 7.237  | 21.158 | 17.408 | 1.00 | 30.79 | C |
| ATOM | 2841 | O3* | C T | 10 | 7.245  | 20.652 | 18.774 | 1.00 | 41.80 | O |
| ATOM | 2842 | C2* | C T | 10 | 8.673  | 21.580 | 17.150 | 1.00 | 31.39 | C |
| ATOM | 2843 | C1* | C T | 10 | 9.266  | 20.354 | 16.479 | 1.00 | 25.68 | C |
| ATOM | 2844 | N1  | C T | 10 | 10.398 | 20.505 | 15.669 | 1.00 | 25.14 | N |
| ATOM | 2845 | C2  | C T | 10 | 11.659 | 20.143 | 16.174 | 1.00 | 29.66 | C |
| ATOM | 2846 | O2  | C T | 10 | 11.716 | 19.677 | 17.315 | 1.00 | 32.55 | O |
| ATOM | 2847 | N3  | C T | 10 | 12.743 | 20.269 | 15.374 | 1.00 | 26.94 | N |
| ATOM | 2848 | C4  | C T | 10 | 12.530 | 20.773 | 14.174 | 1.00 | 35.92 | C |
| ATOM | 2849 | N4  | C T | 10 | 13.604 | 20.875 | 13.437 | 1.00 | 39.88 | N |
| ATOM | 2850 | C5  | C T | 10 | 11.281 | 21.166 | 13.630 | 1.00 | 38.63 | C |
| ATOM | 2851 | C6  | C T | 10 | 10.226 | 21.009 | 14.410 | 1.00 | 36.92 | C |
| ATOM | 2852 | P   | A T | 11 | 7.143  | 21.513 | 20.132 | 1.00 | 36.27 | P |
| ATOM | 2853 | O1P | A T | 11 | 6.568  | 20.599 | 21.118 | 1.00 | 43.89 | O |
| ATOM | 2854 | O2P | A T | 11 | 6.460  | 22.787 | 19.810 | 1.00 | 45.54 | O |
| ATOM | 2855 | O5* | A T | 11 | 8.625  | 21.719 | 20.639 | 1.00 | 14.07 | O |
| ATOM | 2856 | C5* | A T | 11 | 9.231  | 20.585 | 21.021 | 1.00 | 8.55  | C |
| ATOM | 2857 | C4* | A T | 11 | 10.561 | 20.854 | 21.610 | 1.00 | 19.30 | C |
| ATOM | 2858 | O4* | A T | 11 | 11.551 | 20.963 | 20.669 | 1.00 | 30.76 | O |
| ATOM | 2859 | C3* | A T | 11 | 10.750 | 22.030 | 22.502 | 1.00 | 37.54 | C |
| ATOM | 2860 | O3* | A T | 11 | 11.725 | 21.543 | 23.472 | 1.00 | 48.77 | O |
| ATOM | 2861 | C2* | A T | 11 | 11.419 | 23.082 | 21.614 | 1.00 | 39.08 | C |
| ATOM | 2862 | C1* | A T | 11 | 12.262 | 22.179 | 20.765 | 1.00 | 36.22 | C |
| ATOM | 2863 | N9  | A T | 11 | 12.472 | 22.540 | 19.386 | 1.00 | 32.13 | N |
| ATOM | 2864 | C8  | A T | 11 | 11.509 | 22.844 | 18.482 | 1.00 | 25.51 | C |
| ATOM | 2865 | N7  | A T | 11 | 12.044 | 23.082 | 17.317 | 1.00 | 29.76 | N |
| ATOM | 2866 | C5  | A T | 11 | 13.405 | 22.877 | 17.506 | 1.00 | 27.13 | C |
| ATOM | 2867 | C6  | A T | 11 | 14.485 | 22.992 | 16.637 | 1.00 | 40.98 | C |
| ATOM | 2868 | N6  | A T | 11 | 14.262 | 23.292 | 15.340 | 1.00 | 56.31 | N |
| ATOM | 2869 | N1  | A T | 11 | 15.771 | 22.736 | 17.099 | 1.00 | 33.25 | N |
| ATOM | 2870 | C2  | A T | 11 | 15.879 | 22.396 | 18.391 | 1.00 | 38.48 | C |
| ATOM | 2871 | N3  | A T | 11 | 14.906 | 22.262 | 19.311 | 1.00 | 41.40 | N |
| ATOM | 2872 | C4  | A T | 11 | 13.691 | 22.532 | 18.778 | 1.00 | 30.49 | C |
| ATOM | 2873 | P   | T T | 12 | 11.918 | 22.362 | 24.814 | 1.00 | 43.67 | P |
| ATOM | 2874 | O1P | T T | 12 | 11.889 | 21.442 | 25.979 | 1.00 | 51.36 | O |
| ATOM | 2875 | O2P | T T | 12 | 10.909 | 23.410 | 24.598 | 1.00 | 40.46 | O |
| ATOM | 2876 | O5* | T T | 12 | 13.352 | 23.032 | 24.774 | 1.00 | 36.12 | O |
| ATOM | 2877 | C5* | T T | 12 | 14.431 | 22.235 | 24.750 | 1.00 | 28.87 | C |
| ATOM | 2878 | C4* | T T | 12 | 15.542 | 22.990 | 24.070 | 1.00 | 35.99 | C |
| ATOM | 2879 | O4* | T T | 12 | 15.342 | 23.294 | 22.668 | 1.00 | 41.80 | O |
| ATOM | 2880 | C3* | T T | 12 | 16.085 | 24.225 | 24.738 | 1.00 | 36.09 | C |
| ATOM | 2881 | O3* | T T | 12 | 17.386 | 23.815 | 24.998 | 1.00 | 35.60 | O |
| ATOM | 2882 | C2* | T T | 12 | 16.112 | 25.291 | 23.642 | 1.00 | 42.65 | C |
| ATOM | 2883 | C1* | T T | 12 | 16.059 | 24.471 | 22.350 | 1.00 | 39.95 | C |
| ATOM | 2884 | N1  | T T | 12 | 15.447 | 25.023 | 21.104 | 1.00 | 34.75 | N |
| ATOM | 2885 | C2  | T T | 12 | 16.227 | 25.234 | 19.987 | 1.00 | 29.38 | C |
| ATOM | 2886 | O2  | T T | 12 | 17.429 | 25.039 | 20.006 | 1.00 | 35.30 | O |

Figure 22BB

| ATOM | 2887 | N3   | T | T | 12 | 15.541 | 25.690 | 18.867 | 1.00 | 21.98 | N |
| ATOM | 2888 | C4   | T | T | 12 | 14.169 | 25.967 | 18.814 | 1.00 | 31.16 | C |
| ATOM | 2889 | O4   | T | T | 12 | 13.644 | 26.350 | 17.751 | 1.00 | 39.18 | O |
| ATOM | 2890 | C5   | T | T | 12 | 13.436 | 25.696 | 20.020 | 1.00 | 27.54 | C |
| ATOM | 2891 | C5M  | T | T | 12 | 11.964 | 25.921 | 20.049 | 1.00 | 26.62 | C |
| ATOM | 2892 | C6   | T | T | 12 | 14.094 | 25.231 | 21.074 | 1.00 | 31.33 | C |
| ATOM | 2893 | P    | C | T | 13 | 18.482 | 24.829 | 25.483 | 1.00 | 49.34 | P |
| ATOM | 2894 | O1P  | C | T | 13 | 19.527 | 24.067 | 26.236 | 1.00 | 43.63 | O |
| ATOM | 2895 | O2P  | C | T | 13 | 17.807 | 26.032 | 25.978 | 1.00 | 51.91 | O |
| ATOM | 2896 | O5*  | C | T | 13 | 19.173 | 25.351 | 24.161 | 1.00 | 65.02 | O |
| ATOM | 2897 | C5*  | C | T | 13 | 20.139 | 24.585 | 23.506 | 1.00 | 62.77 | C |
| ATOM | 2898 | C4*  | C | T | 13 | 20.812 | 25.479 | 22.508 | 1.00 | 52.38 | C |
| ATOM | 2899 | O4*  | C | T | 13 | 19.799 | 25.916 | 21.559 | 1.00 | 49.27 | O |
| ATOM | 2900 | C3*  | C | T | 13 | 21.410 | 26.734 | 23.148 | 1.00 | 48.87 | C |
| ATOM | 2901 | O3*  | C | T | 13 | 22.801 | 26.695 | 22.953 | 1.00 | 53.98 | O |
| ATOM | 2902 | C2*  | C | T | 13 | 20.693 | 27.949 | 22.500 | 1.00 | 43.84 | C |
| ATOM | 2903 | C1*  | C | T | 13 | 19.830 | 27.323 | 21.397 | 1.00 | 37.53 | C |
| ATOM | 2904 | N1   | C | T | 13 | 18.447 | 27.719 | 21.020 | 1.00 | 32.69 | N |
| ATOM | 2905 | C2   | C | T | 13 | 18.345 | 28.146 | 19.728 | 1.00 | 38.91 | C |
| ATOM | 2906 | O2   | C | T | 13 | 19.395 | 28.200 | 19.071 | 1.00 | 48.41 | O |
| ATOM | 2907 | N3   | C | T | 13 | 17.166 | 28.524 | 19.215 | 1.00 | 24.16 | N |
| ATOM | 2908 | C4   | C | T | 13 | 16.069 | 28.494 | 19.943 | 1.00 | 36.72 | C |
| ATOM | 2909 | N4   | C | T | 13 | 14.928 | 28.840 | 19.359 | 1.00 | 35.75 | N |
| ATOM | 2910 | C5   | C | T | 13 | 16.120 | 28.041 | 21.320 | 1.00 | 38.70 | C |
| ATOM | 2911 | C6   | C | T | 13 | 17.337 | 27.667 | 21.812 | 1.00 | 35.95 | C |
| ATOM | 2912 | P    | A | T | 14 | 23.736 | 27.880 | 23.456 | 1.00 | 72.11 | P |
| ATOM | 2913 | O1P  | A | T | 14 | 25.102 | 27.339 | 23.697 | 1.00 | 72.78 | O |
| ATOM | 2914 | O2P  | A | T | 14 | 23.049 | 28.616 | 24.543 | 1.00 | 84.10 | O |
| ATOM | 2915 | O5*  | A | T | 14 | 23.756 | 28.860 | 22.182 | 1.00 | 64.78 | O |
| ATOM | 2916 | C5*  | A | T | 14 | 24.477 | 28.520 | 21.016 | 1.00 | 52.43 | C |
| ATOM | 2917 | C4*  | A | T | 14 | 24.392 | 29.638 | 20.004 | 1.00 | 47.97 | C |
| ATOM | 2918 | O4*  | A | T | 14 | 23.063 | 29.889 | 19.534 | 1.00 | 43.07 | O |
| ATOM | 2919 | C3*  | A | T | 14 | 24.939 | 30.966 | 20.432 | 1.00 | 50.60 | C |
| ATOM | 2920 | O3*  | A | T | 14 | 25.917 | 31.145 | 19.524 | 1.00 | 65.38 | O |
| ATOM | 2921 | C2*  | A | T | 14 | 23.828 | 32.014 | 20.245 | 1.00 | 36.27 | C |
| ATOM | 2922 | C1*  | A | T | 14 | 22.819 | 31.265 | 19.402 | 1.00 | 32.89 | C |
| ATOM | 2923 | N9   | A | T | 14 | 21.423 | 31.293 | 19.681 | 1.00 | 25.60 | N |
| ATOM | 2924 | C8   | A | T | 14 | 20.803 | 30.843 | 20.787 | 1.00 | 27.76 | C |
| ATOM | 2925 | N7   | A | T | 14 | 19.467 | 30.985 | 20.677 | 1.00 | 33.61 | N |
| ATOM | 2926 | C5   | A | T | 14 | 19.266 | 31.518 | 19.406 | 1.00 | 27.21 | C |
| ATOM | 2927 | C6   | A | T | 14 | 18.127 | 31.912 | 18.667 | 1.00 | 37.48 | C |
| ATOM | 2928 | N6   | A | T | 14 | 16.871 | 31.793 | 19.061 | 1.00 | 39.63 | N |
| ATOM | 2929 | N1   | A | T | 14 | 18.324 | 32.451 | 17.455 | 1.00 | 41.83 | N |
| ATOM | 2930 | C2   | A | T | 14 | 19.573 | 32.554 | 16.973 | 1.00 | 37.95 | C |
| ATOM | 2931 | N3   | A | T | 14 | 20.726 | 32.229 | 17.565 | 1.00 | 28.54 | N |
| ATOM | 2932 | C4   | A | T | 14 | 20.492 | 31.716 | 18.782 | 1.00 | 25.52 | C |
| ATOM | 2933 | P    | G | T | 15 | 26.846 | 32.379 | 19.724 | 1.00 | 75.77 | P |
| ATOM | 2934 | O1P  | G | T | 15 | 28.054 | 32.122 | 18.905 | 1.00 | 78.30 | O |
| ATOM | 2935 | O2P  | G | T | 15 | 26.982 | 32.540 | 21.190 | 1.00 | 83.60 | O |
| ATOM | 2936 | O5*  | G | T | 15 | 25.878 | 33.550 | 19.122 | 1.00 | 69.71 | O |
| ATOM | 2937 | C5*  | G | T | 15 | 25.372 | 33.557 | 17.749 | 1.00 | 59.09 | C |
| ATOM | 2938 | C4*  | G | T | 15 | 24.429 | 34.731 | 17.340 | 1.00 | 58.16 | C |
| ATOM | 2939 | O4*  | G | T | 15 | 23.010 | 34.459 | 17.425 | 1.00 | 58.93 | O |
| ATOM | 2940 | C3*  | G | T | 15 | 24.661 | 36.175 | 17.766 | 1.00 | 60.66 | C |
| ATOM | 2941 | O3*  | G | T | 15 | 25.053 | 36.973 | 16.609 | 1.00 | 62.24 | O |
| ATOM | 2942 | C2*  | G | T | 15 | 23.283 | 36.653 | 18.232 | 1.00 | 59.20 | C |
| ATOM | 2943 | C1*  | G | T | 15 | 22.296 | 35.595 | 17.778 | 1.00 | 50.74 | C |
| ATOM | 2944 | N9   | G | T | 15 | 21.366 | 35.224 | 18.805 | 1.00 | 39.76 | N |
| ATOM | 2945 | C8   | G | T | 15 | 21.630 | 34.706 | 20.051 | 1.00 | 45.15 | C |
| ATOM | 2946 | N7   | G | T | 15 | 20.499 | 34.518 | 20.746 | 1.00 | 39.61 | N |
| ATOM | 2947 | C5   | G | T | 15 | 19.496 | 34.971 | 19.872 | 1.00 | 35.31 | C |
| ATOM | 2948 | C6   | G | T | 15 | 18.068 | 35.044 | 20.002 | 1.00 | 46.62 | C |
| ATOM | 2949 | O6   | G | T | 15 | 17.302 | 34.706 | 20.944 | 1.00 | 53.01 | O |

Figure 22BC

```
ATOM   2950  N1   G T  15    17.506  35.583  18.866  1.00 38.36      N
ATOM   2951  C2   G T  15    18.212  35.951  17.782  1.00 31.58      C
ATOM   2952  N2   G T  15    17.504  36.481  16.796  1.00 43.07      N
ATOM   2953  N3   G T  15    19.510  35.875  17.658  1.00 19.11      N
ATOM   2954  C4   G T  15    20.057  35.418  18.705  1.00 24.77      C
ATOM   2955  P    C T  16    25.386  38.551  16.755  1.00 48.70      P
ATOM   2956  O1P  C T  16    26.181  38.963  15.583  1.00 48.42      O
ATOM   2957  O2P  C T  16    25.867  38.847  18.134  1.00 44.36      O
ATOM   2958  O5*  C T  16    23.910  39.078  16.550  1.00 34.70      O
ATOM   2959  C5*  C T  16    23.364  38.587  15.359  1.00 27.87      C
ATOM   2960  C4*  C T  16    22.101  39.324  15.172  1.00 44.30      C
ATOM   2961  O4*  C T  16    21.150  38.815  16.079  1.00 48.19      O
ATOM   2962  C3*  C T  16    22.229  40.801  15.512  1.00 56.68      C
ATOM   2963  O3*  C T  16    21.159  41.441  14.803  1.00 67.16      O
ATOM   2964  C2*  C T  16    21.867  40.897  16.973  1.00 46.08      C
ATOM   2965  C1*  C T  16    20.838  39.806  17.003  1.00 37.92      C
ATOM   2966  N1   C T  16    20.489  39.241  18.266  1.00 27.32      N
ATOM   2967  C2   C T  16    19.154  39.266  18.508  1.00 31.04      C
ATOM   2968  O2   C T  16    18.413  39.735  17.651  1.00 35.38      O
ATOM   2969  N3   C T  16    18.701  38.769  19.641  1.00 39.33      N
ATOM   2970  C4   C T  16    19.538  38.290  20.501  1.00 39.58      C
ATOM   2971  N4   C T  16    18.913  37.842  21.595  1.00 39.79      N
ATOM   2972  C5   C T  16    20.950  38.263  20.300  1.00 26.55      C
ATOM   2973  C6   C T  16    21.393  38.767  19.165  1.00 25.37      C
TER    2974       C T  16
ATOM   2975  O5*  G P   1     8.125  38.506  23.519  1.00 92.51      O
ATOM   2976  C5*  G P   1     9.213  39.344  23.123  1.00 83.60      C
ATOM   2977  C4*  G P   1     9.217  39.658  21.623  1.00 69.91      C
ATOM   2978  O4*  G P   1    10.542  40.119  21.356  1.00 57.26      O
ATOM   2979  C3*  G P   1     9.011  38.473  20.684  1.00 70.79      C
ATOM   2980  O3*  G P   1     8.094  38.696  19.669  1.00 82.69      O
ATOM   2981  C2*  G P   1    10.297  38.225  19.962  1.00 63.56      C
ATOM   2982  C1*  G P   1    11.195  39.310  20.430  1.00 53.80      C
ATOM   2983  N9   G P   1    12.257  38.782  21.182  1.00 47.83      N
ATOM   2984  C8   G P   1    12.206  38.183  22.385  1.00 51.68      C
ATOM   2985  N7   G P   1    13.408  37.830  22.771  1.00 41.15      N
ATOM   2986  C5   G P   1    14.210  38.204  21.757  1.00 21.26      C
ATOM   2987  C6   G P   1    15.539  38.110  21.674  1.00 29.08      C
ATOM   2988  O6   G P   1    16.272  37.662  22.509  1.00 35.75      O
ATOM   2989  N1   G P   1    15.983  38.672  20.507  1.00 36.44      N
ATOM   2990  C2   G P   1    15.161  39.246  19.546  1.00 45.39      C
ATOM   2991  N2   G P   1    15.728  39.703  18.436  1.00 51.43      N
ATOM   2992  N3   G P   1    13.868  39.359  19.631  1.00 35.02      N
ATOM   2993  C4   G P   1    13.501  38.820  20.772  1.00 33.97      C
ATOM   2994  P    C P   2     7.834  37.407  18.743  1.00 93.61      P
ATOM   2995  O1P  C P   2     6.470  37.513  18.151  1.00 92.11      O
ATOM   2996  O2P  C P   2     8.200  36.201  19.541  1.00 95.51      O
ATOM   2997  O5*  C P   2     8.954  37.516  17.605  1.00 88.44      O
ATOM   2998  C5*  C P   2     8.943  38.523  16.650  1.00 82.47      C
ATOM   2999  C4*  C P   2    10.036  38.201  15.656  1.00 77.03      C
ATOM   3000  O4*  C P   2    11.309  38.400  16.328  1.00 67.50      O
ATOM   3001  C3*  C P   2    10.040  36.755  15.160  1.00 81.29      C
ATOM   3002  O3*  C P   2     9.413  36.526  13.866  1.00 92.17      O
ATOM   3003  C2*  C P   2    11.501  36.327  15.221  1.00 74.27      C
ATOM   3004  C1*  C P   2    12.212  37.370  16.050  1.00 58.65      C
ATOM   3005  N1   C P   2    12.752  36.778  17.295  1.00 45.55      N
ATOM   3006  C2   C P   2    14.111  36.607  17.386  1.00 45.55      C
ATOM   3007  O2   C P   2    14.764  36.971  16.433  1.00 52.58      O
ATOM   3008  N3   C P   2    14.661  36.055  18.486  1.00 42.83      N
ATOM   3009  C4   C P   2    13.877  35.667  19.470  1.00 42.26      C
ATOM   3010  N4   C P   2    14.510  35.153  20.531  1.00 52.12      N
ATOM   3011  C5   C P   2    12.466  35.802  19.420  1.00 35.26      C
ATOM   3012  C6   C P   2    11.944  36.358  18.311  1.00 42.98      C
```

Figure 22BD

| ATOM | 3013 | P | T | P | 3 | 10.111 | 36.748 | 12.423 | 1.00 | 99.64 | P |
| --- | --- | --- | --- | --- | --- | --- | --- | --- | --- | --- | --- |
| ATOM | 3014 | O1P | T | P | 3 | 10.318 | 38.214 | 12.222 | 1.00 | 100.00 | O |
| ATOM | 3015 | O2P | T | P | 3 | 9.284 | 36.021 | 11.425 | 1.00 | 98.40 | O |
| ATOM | 3016 | O5* | T | P | 3 | 11.563 | 36.053 | 12.470 | 1.00 | 88.27 | O |
| ATOM | 3017 | C5* | T | P | 3 | 12.595 | 36.745 | 11.762 | 1.00 | 81.99 | C |
| ATOM | 3018 | C4* | T | P | 3 | 13.955 | 36.055 | 11.731 | 1.00 | 76.41 | C |
| ATOM | 3019 | O4* | T | P | 3 | 14.513 | 35.929 | 13.061 | 1.00 | 73.89 | O |
| ATOM | 3020 | C3* | T | P | 3 | 14.070 | 34.698 | 11.023 | 1.00 | 73.29 | C |
| ATOM | 3021 | O3* | T | P | 3 | 14.907 | 34.835 | 9.893 | 1.00 | 67.20 | O |
| ATOM | 3022 | C2* | T | P | 3 | 14.793 | 33.791 | 12.012 | 1.00 | 75.83 | C |
| ATOM | 3023 | C1* | T | P | 3 | 15.179 | 34.682 | 13.198 | 1.00 | 69.62 | C |
| ATOM | 3024 | N1 | T | P | 3 | 14.926 | 34.027 | 14.559 | 1.00 | 49.27 | N |
| ATOM | 3025 | C2 | T | P | 3 | 16.003 | 33.656 | 15.343 | 1.00 | 46.30 | C |
| ATOM | 3026 | O2 | T | P | 3 | 17.197 | 33.793 | 15.067 | 1.00 | 50.04 | O |
| ATOM | 3027 | N3 | T | P | 3 | 15.648 | 33.068 | 16.505 | 1.00 | 40.13 | N |
| ATOM | 3028 | C4 | T | P | 3 | 14.404 | 32.835 | 17.037 | 1.00 | 34.54 | C |
| ATOM | 3029 | O4 | T | P | 3 | 14.245 | 32.314 | 18.128 | 1.00 | 45.18 | O |
| ATOM | 3030 | C5 | T | P | 3 | 13.337 | 33.257 | 16.207 | 1.00 | 27.26 | C |
| ATOM | 3031 | C5M | T | P | 3 | 11.941 | 32.974 | 16.657 | 1.00 | 14.53 | C |
| ATOM | 3032 | C6 | T | P | 3 | 13.628 | 33.813 | 15.010 | 1.00 | 37.31 | C |
| ATOM | 3033 | P | G | P | 4 | 15.173 | 33.641 | 8.849 | 1.00 | 63.34 | P |
| ATOM | 3034 | O1P | G | P | 4 | 15.541 | 34.352 | 7.597 | 1.00 | 68.36 | O |
| ATOM | 3035 | O2P | G | P | 4 | 14.038 | 32.670 | 8.837 | 1.00 | 55.94 | O |
| ATOM | 3036 | O5* | G | P | 4 | 16.480 | 32.873 | 9.440 | 1.00 | 48.22 | O |
| ATOM | 3037 | C5* | G | P | 4 | 17.717 | 33.567 | 9.570 | 1.00 | 43.31 | C |
| ATOM | 3038 | C4* | G | P | 4 | 18.762 | 32.669 | 10.195 | 1.00 | 46.13 | C |
| ATOM | 3039 | O4* | G | P | 4 | 18.505 | 32.365 | 11.582 | 1.00 | 54.82 | O |
| ATOM | 3040 | C3* | G | P | 4 | 18.735 | 31.336 | 9.499 | 1.00 | 53.83 | C |
| ATOM | 3041 | O3* | G | P | 4 | 20.055 | 30.927 | 9.618 | 1.00 | 55.96 | O |
| ATOM | 3042 | C2* | G | P | 4 | 17.832 | 30.432 | 10.331 | 1.00 | 55.67 | C |
| ATOM | 3043 | C1* | G | P | 4 | 18.186 | 30.956 | 11.721 | 1.00 | 53.96 | C |
| ATOM | 3044 | N9 | G | P | 4 | 17.171 | 30.721 | 12.747 | 1.00 | 30.04 | N |
| ATOM | 3045 | C8 | G | P | 4 | 15.801 | 30.902 | 12.616 | 1.00 | 26.13 | C |
| ATOM | 3046 | N7 | G | P | 4 | 15.191 | 30.583 | 13.737 | 1.00 | 28.09 | N |
| ATOM | 3047 | C5 | G | P | 4 | 16.244 | 30.155 | 14.599 | 1.00 | 22.03 | C |
| ATOM | 3048 | C6 | G | P | 4 | 16.195 | 29.714 | 15.949 | 1.00 | 16.68 | C |
| ATOM | 3049 | O6 | G | P | 4 | 15.194 | 29.637 | 16.665 | 1.00 | 25.65 | O |
| ATOM | 3050 | N1 | G | P | 4 | 17.451 | 29.405 | 16.462 | 1.00 | 5.81 | N |
| ATOM | 3051 | C2 | G | P | 4 | 18.618 | 29.521 | 15.747 | 1.00 | 20.67 | C |
| ATOM | 3052 | N2 | G | P | 4 | 19.743 | 29.122 | 16.379 | 1.00 | 28.72 | N |
| ATOM | 3053 | N3 | G | P | 4 | 18.688 | 29.950 | 14.467 | 1.00 | 22.60 | N |
| ATOM | 3054 | C4 | G | P | 4 | 17.467 | 30.237 | 13.976 | 1.00 | 16.58 | C |
| ATOM | 3055 | P | A | P | 5 | 20.407 | 29.466 | 9.139 | 1.00 | 50.85 | P |
| ATOM | 3056 | O1P | A | P | 5 | 21.799 | 29.509 | 8.622 | 1.00 | 38.73 | O |
| ATOM | 3057 | O2P | A | P | 5 | 19.192 | 28.973 | 8.394 | 1.00 | 47.19 | O |
| ATOM | 3058 | O5* | A | P | 5 | 20.635 | 28.719 | 10.506 | 1.00 | 54.87 | O |
| ATOM | 3059 | C5* | A | P | 5 | 21.862 | 29.148 | 11.092 | 1.00 | 50.78 | C |
| ATOM | 3060 | C4* | A | P | 5 | 22.312 | 28.113 | 12.073 | 1.00 | 45.51 | C |
| ATOM | 3061 | O4* | A | P | 5 | 21.221 | 27.887 | 12.990 | 1.00 | 46.74 | O |
| ATOM | 3062 | C3* | A | P | 5 | 22.641 | 26.786 | 11.427 | 1.00 | 37.83 | C |
| ATOM | 3063 | O3* | A | P | 5 | 23.840 | 26.464 | 12.096 | 1.00 | 38.56 | O |
| ATOM | 3064 | C2* | A | P | 5 | 21.443 | 25.869 | 11.740 | 1.00 | 41.78 | C |
| ATOM | 3065 | C1* | A | P | 5 | 20.747 | 26.576 | 12.922 | 1.00 | 43.32 | C |
| ATOM | 3066 | N9 | A | P | 5 | 19.300 | 26.701 | 13.069 | 1.00 | 37.12 | N |
| ATOM | 3067 | C8 | A | P | 5 | 18.376 | 27.110 | 12.160 | 1.00 | 38.46 | C |
| ATOM | 3068 | N7 | A | P | 5 | 17.144 | 27.118 | 12.700 | 1.00 | 41.79 | N |
| ATOM | 3069 | C5 | A | P | 5 | 17.314 | 26.728 | 14.067 | 1.00 | 39.53 | C |
| ATOM | 3070 | C6 | A | P | 5 | 16.440 | 26.502 | 15.216 | 1.00 | 25.43 | C |
| ATOM | 3071 | N6 | A | P | 5 | 15.101 | 26.721 | 15.296 | 1.00 | 31.18 | N |
| ATOM | 3072 | N1 | A | P | 5 | 17.010 | 26.129 | 16.346 | 1.00 | 15.01 | N |
| ATOM | 3073 | C2 | A | P | 5 | 18.316 | 25.949 | 16.406 | 1.00 | 24.08 | C |
| ATOM | 3074 | N3 | A | P | 5 | 19.232 | 26.063 | 15.466 | 1.00 | 38.79 | N |
| ATOM | 3075 | C4 | A | P | 5 | 18.657 | 26.462 | 14.289 | 1.00 | 43.69 | C |

Figure 22BE

| ATOM | 3076 | P    | T P | 6 | 24.424 | 25.019 | 11.981 | 1.00 | 44.36 | P |
| --- | --- | --- | --- | --- | --- | --- | --- | --- | --- | --- |
| ATOM | 3077 | O1P  | T P | 6 | 25.873 | 24.990 | 12.334 | 1.00 | 36.27 | O |
| ATOM | 3078 | O2P  | T P | 6 | 23.842 | 24.471 | 10.746 | 1.00 | 42.39 | O |
| ATOM | 3079 | O5*  | T P | 6 | 23.762 | 24.350 | 13.254 | 1.00 | 55.25 | O |
| ATOM | 3080 | C5*  | T P | 6 | 24.330 | 24.586 | 14.556 | 1.00 | 44.87 | C |
| ATOM | 3081 | C4*  | T P | 6 | 23.562 | 23.715 | 15.519 | 1.00 | 28.97 | C |
| ATOM | 3082 | O4*  | T P | 6 | 22.200 | 23.902 | 15.148 | 1.00 | 28.81 | O |
| ATOM | 3083 | C3*  | T P | 6 | 23.789 | 22.217 | 15.336 | 1.00 | 25.28 | C |
| ATOM | 3084 | O3*  | T P | 6 | 24.300 | 21.688 | 16.516 | 1.00 | 44.49 | O |
| ATOM | 3085 | C2*  | T P | 6 | 22.472 | 21.562 | 14.950 | 1.00 | 11.88 | C |
| ATOM | 3086 | C1*  | T P | 6 | 21.538 | 22.694 | 15.111 | 1.00 | 13.64 | C |
| ATOM | 3087 | N1   | T P | 6 | 20.233 | 22.865 | 14.579 | 1.00 | 16.30 | N |
| ATOM | 3088 | C2   | T P | 6 | 19.229 | 22.736 | 15.512 | 1.00 | 36.12 | C |
| ATOM | 3089 | O2   | T P | 6 | 19.473 | 22.448 | 16.685 | 1.00 | 49.07 | O |
| ATOM | 3090 | N3   | T P | 6 | 17.948 | 22.944 | 15.085 | 1.00 | 31.67 | N |
| ATOM | 3091 | C4   | T P | 6 | 17.627 | 23.236 | 13.814 | 1.00 | 30.22 | C |
| ATOM | 3092 | O4   | T P | 6 | 16.461 | 23.419 | 13.532 | 1.00 | 46.25 | O |
| ATOM | 3093 | C5   | T P | 6 | 18.709 | 23.368 | 12.885 | 1.00 | 24.66 | C |
| ATOM | 3094 | C5M  | T P | 6 | 18.354 | 23.737 | 11.464 | 1.00 | 29.13 | C |
| ATOM | 3095 | C6   | T P | 6 | 19.977 | 23.205 | 13.305 | 1.00 | 14.28 | C |
| ATOM | 3096 | P    | G P | 7 | 24.617 | 20.143 | 16.480 | 1.00 | 60.20 | P |
| ATOM | 3097 | O1P  | G P | 7 | 25.821 | 19.856 | 17.315 | 1.00 | 57.57 | O |
| ATOM | 3098 | O2P  | G P | 7 | 24.610 | 19.776 | 15.043 | 1.00 | 63.29 | O |
| ATOM | 3099 | O5*  | G P | 7 | 23.307 | 19.535 | 17.194 | 1.00 | 60.59 | O |
| ATOM | 3100 | C5*  | G P | 7 | 23.048 | 19.770 | 18.568 | 1.00 | 44.83 | C |
| ATOM | 3101 | C4*  | G P | 7 | 21.858 | 18.955 | 18.955 | 1.00 | 33.68 | C |
| ATOM | 3102 | O4*  | G P | 7 | 20.635 | 19.368 | 18.336 | 1.00 | 32.02 | O |
| ATOM | 3103 | C3*  | G P | 7 | 21.953 | 17.481 | 18.749 | 1.00 | 33.93 | C |
| ATOM | 3104 | O3*  | G P | 7 | 21.885 | 17.067 | 20.011 | 1.00 | 34.74 | O |
| ATOM | 3105 | C2*  | G P | 7 | 20.651 | 17.083 | 17.998 | 1.00 | 37.53 | C |
| ATOM | 3106 | C1*  | G P | 7 | 19.749 | 18.289 | 18.099 | 1.00 | 31.01 | C |
| ATOM | 3107 | N9   | G P | 7 | 19.106 | 18.732 | 16.895 | 1.00 | 27.81 | N |
| ATOM | 3108 | C8   | G P | 7 | 19.810 | 19.098 | 15.784 | 1.00 | 27.44 | C |
| ATOM | 3109 | N7   | G P | 7 | 19.006 | 19.540 | 14.854 | 1.00 | 21.23 | N |
| ATOM | 3110 | C5   | G P | 7 | 17.745 | 19.476 | 15.400 | 1.00 |  6.65 | C |
| ATOM | 3111 | C6   | G P | 7 | 16.562 | 19.842 | 14.823 | 1.00 | 23.01 | C |
| ATOM | 3112 | O6   | G P | 7 | 16.346 | 20.316 | 13.719 | 1.00 | 32.11 | O |
| ATOM | 3113 | N1   | G P | 7 | 15.536 | 19.685 | 15.697 | 1.00 | 28.78 | N |
| ATOM | 3114 | C2   | G P | 7 | 15.615 | 19.215 | 16.936 | 1.00 | 23.94 | C |
| ATOM | 3115 | N2   | G P | 7 | 14.442 | 19.167 | 17.515 | 1.00 | 25.85 | N |
| ATOM | 3116 | N3   | G P | 7 | 16.730 | 18.860 | 17.539 | 1.00 | 19.72 | N |
| ATOM | 3117 | C4   | G P | 7 | 17.769 | 19.015 | 16.683 | 1.00 | 15.72 | C |
| ATOM | 3118 | P    | C P | 8 | 22.009 | 15.550 | 20.442 | 1.00 | 38.35 | P |
| ATOM | 3119 | O1P  | C P | 8 | 22.087 | 15.502 | 21.944 | 1.00 | 48.29 | O |
| ATOM | 3120 | O2P  | C P | 8 | 23.095 | 14.928 | 19.674 | 1.00 | 33.04 | O |
| ATOM | 3121 | O5*  | C P | 8 | 20.561 | 15.118 | 19.919 | 1.00 | 13.23 | O |
| ATOM | 3122 | C5*  | C P | 8 | 19.483 | 15.368 | 20.614 | 1.00 | 13.89 | C |
| ATOM | 3123 | C4*  | C P | 8 | 18.244 | 14.750 | 20.011 | 1.00 | 20.98 | C |
| ATOM | 3124 | O4*  | C P | 8 | 17.691 | 15.520 | 18.957 | 1.00 | 25.28 | O |
| ATOM | 3125 | C3*  | C P | 8 | 18.256 | 13.292 | 19.566 | 1.00 | 36.37 | C |
| ATOM | 3126 | O3*  | C P | 8 | 17.316 | 12.509 | 20.329 | 1.00 | 45.40 | O |
| ATOM | 3127 | C2*  | C P | 8 | 17.724 | 13.304 | 18.147 | 1.00 | 38.34 | C |
| ATOM | 3128 | C1*  | C P | 8 | 17.016 | 14.654 | 18.049 | 1.00 | 34.78 | C |
| ATOM | 3129 | N1   | C P | 8 | 16.957 | 15.266 | 16.690 | 1.00 | 28.46 | N |
| ATOM | 3130 | C2   | C P | 8 | 15.738 | 15.689 | 16.216 | 1.00 | 28.83 | C |
| ATOM | 3131 | O2   | C P | 8 | 14.797 | 15.474 | 16.960 | 1.00 | 31.63 | O |
| ATOM | 3132 | N3   | C P | 8 | 15.647 | 16.293 | 15.006 | 1.00 | 30.51 | N |
| ATOM | 3133 | C4   | C P | 8 | 16.777 | 16.434 | 14.310 | 1.00 | 33.84 | C |
| ATOM | 3134 | N4   | C P | 8 | 16.705 | 17.045 | 13.104 | 1.00 | 35.95 | N |
| ATOM | 3135 | C5   | C P | 8 | 18.044 | 16.023 | 14.807 | 1.00 | 28.20 | C |
| ATOM | 3136 | C6   | C P | 8 | 18.097 | 15.452 | 15.999 | 1.00 | 24.27 | C |
| ATOM | 3137 | P    | G P | 9 | 17.309 | 10.942 | 20.078 | 1.00 | 34.03 | P |
| ATOM | 3138 | O1P  | G P | 9 | 16.868 | 10.111 | 21.243 | 1.00 | 34.35 | O |

Figure 22BF

```
ATOM   3139  O2P   G P    9      18.674   10.738   19.548  1.00 35.84           O
ATOM   3140  O5*   G P    9      16.066   10.969   19.084  1.00 10.06           O
ATOM   3141  C5*   G P    9      14.883   11.468   19.608  1.00 10.87           C
ATOM   3142  C4*   G P    9      13.671   11.271   18.728  1.00 17.48           C
ATOM   3143  O4*   G P    9      13.775   12.034   17.506  1.00 40.76           O
ATOM   3144  C3*   G P    9      13.586    9.843   18.274  1.00 30.92           C
ATOM   3145  O3*   G P    9      12.178    9.559   18.106  1.00 41.87           O
ATOM   3146  C2*   G P    9      14.271    9.832   16.910  1.00 39.79           C
ATOM   3147  C1*   G P    9      13.808   11.174   16.344  1.00 39.76           C
ATOM   3148  N9    G P    9      14.679   11.774   15.380  1.00 18.78           N
ATOM   3149  C8    G P    9      16.034   11.726   15.475  1.00 19.54           C
ATOM   3150  N7    G P    9      16.585   12.378   14.466  1.00 27.39           N
ATOM   3151  C5    G P    9      15.467   12.888   13.686  1.00 22.03           C
ATOM   3152  C6    G P    9      15.427   13.720   12.475  1.00 29.80           C
ATOM   3153  O6    G P    9      16.360   14.218   11.812  1.00 41.23           O
ATOM   3154  N1    G P    9      14.154   14.016   12.064  1.00 29.31           N
ATOM   3155  C2    G P    9      13.055   13.570   12.700  1.00 36.42           C
ATOM   3156  N2    G P    9      11.921   13.957   12.102  1.00 45.12           N
ATOM   3157  N3    G P    9      13.041   12.815   13.849  1.00 34.10           N
ATOM   3158  C4    G P    9      14.295   12.509   14.265  1.00 17.75           C
ATOM   3159  P     T P   10      11.806    8.072   17.683  1.00 44.03           P
ATOM   3160  O1P   T P   10      10.462    7.676   18.177  1.00 39.02           O
ATOM   3161  O2P   T P   10      13.072    7.333   17.918  1.00 42.73           O
ATOM   3162  O5*   T P   10      11.368    8.171   16.176  1.00 51.55           O
ATOM   3163  C5*   T P   10      10.012    8.577   16.146  1.00 57.49           C
ATOM   3164  C4*   T P   10       9.478    8.647   14.748  1.00 71.12           C
ATOM   3165  O4*   T P   10      10.171    9.662   13.981  1.00 68.91           O
ATOM   3166  C3*   T P   10       9.679    7.331   14.057  1.00 79.23           C
ATOM   3167  O3*   T P   10       8.454    6.691   13.926  1.00 89.12           O
ATOM   3168  C2*   T P   10      10.290    7.660   12.716  1.00 72.99           C
ATOM   3169  C1*   T P   10      10.472    9.152   12.720  1.00 62.33           C
ATOM   3170  N1    T P   10      11.792    9.505   12.311  1.00 47.03           N
ATOM   3171  C2    T P   10      11.831   10.323   11.219  1.00 51.04           C
ATOM   3172  O2    T P   10      10.781   10.719   10.661  1.00 49.31           O
ATOM   3173  N3    T P   10      13.117   10.630   10.811  1.00 55.07           N
ATOM   3174  C4    T P   10      14.273   10.217   11.452  1.00 39.53           C
ATOM   3175  O4    T P   10      15.416   10.505   11.096  1.00 51.62           O
ATOM   3176  C5    T P   10      14.153    9.414   12.538  1.00 21.96           C
ATOM   3177  C5M   T P   10      15.515    9.013   13.045  1.00 18.19           C
ATOM   3178  C6    T P   10      12.930    9.035   12.949  1.00 30.26           C
ATOM   3179  P     G P   11       8.438    5.107   13.711  1.00 95.46           P
ATOM   3180  O1P   G P   11       7.335    4.580   14.537  1.00100.00           O
ATOM   3181  O2P   G P   11       9.831    4.597   13.922  1.00 85.72           O
ATOM   3182  O5*   G P   11       7.970    4.981   12.173  1.00100.00           O
ATOM   3183  C5*   G P   11       6.724    5.617   11.729  1.00100.00           C
ATOM   3184  C4*   G P   11       6.736    6.047   10.247  1.00100.00           C
ATOM   3185  O4*   G P   11       7.886    6.912   10.012  1.00 98.36           O
ATOM   3186  C3*   G P   11       6.774    4.937    9.178  1.00 98.80           C
ATOM   3187  O3*   G P   11       5.560    4.938    8.385  1.00 95.67           O
ATOM   3188  C2*   G P   11       8.034    5.207    8.326  1.00 94.60           C
ATOM   3189  C1*   G P   11       8.668    6.466    8.926  1.00 91.74           C
ATOM   3190  N9    G P   11      10.091    6.418    9.325  1.00 85.41           N
ATOM   3191  C8    G P   11      10.679    5.796   10.399  1.00 82.12           C
ATOM   3192  N7    G P   11      11.995    5.975   10.414  1.00 82.22           N
ATOM   3193  C5    G P   11      12.268    6.736    9.276  1.00 82.21           C
ATOM   3194  C6    G P   11      13.494    7.247    8.740  1.00 84.16           C
ATOM   3195  O6    G P   11      14.672    7.150    9.165  1.00 81.70           O
ATOM   3196  N1    G P   11      13.239    7.961    7.567  1.00 89.39           N
ATOM   3197  C2    G P   11      11.995    8.152    7.003  1.00 93.93           C
ATOM   3198  N2    G P   11      11.928    8.844    5.876  1.00 99.54           N
ATOM   3199  N3    G P   11      10.875    7.681    7.484  1.00 89.94           N
ATOM   3200  C4    G P   11      11.085    6.992    8.602  1.00 85.24           C
TER    3201        G P   11
```

Figure 22BG

| ATOM | 3202 | O3P | G | D | 1 | 36.570 | 3.831 | 9.128 | 1.00 | 59.87 | O |
|---|---|---|---|---|---|---|---|---|---|---|---|
| ATOM | 3203 | P | G | D | 1 | 36.531 | 3.621 | 7.658 | 1.00 | 61.76 | P |
| ATOM | 3204 | O1P | G | D | 1 | 37.383 | 4.516 | 6.829 | 1.00 | 69.80 | O |
| ATOM | 3205 | O2P | G | D | 1 | 36.806 | 2.182 | 7.549 | 1.00 | 59.32 | O |
| ATOM | 3206 | O5* | G | D | 1 | 35.035 | 3.877 | 7.075 | 1.00 | 49.39 | O |
| ATOM | 3207 | C5* | G | D | 1 | 33.996 | 3.007 | 7.391 | 1.00 | 36.51 | C |
| ATOM | 3208 | C4* | G | D | 1 | 33.288 | 2.454 | 6.198 | 1.00 | 32.80 | C |
| ATOM | 3209 | O4* | G | D | 1 | 32.372 | 3.409 | 5.703 | 1.00 | 35.74 | O |
| ATOM | 3210 | C3* | G | D | 1 | 34.086 | 1.993 | 5.018 | 1.00 | 38.82 | C |
| ATOM | 3211 | O3* | G | D | 1 | 33.346 | 0.816 | 4.394 | 1.00 | 43.03 | O |
| ATOM | 3212 | C2* | G | D | 1 | 34.005 | 3.219 | 4.087 | 1.00 | 41.15 | C |
| ATOM | 3213 | C1* | G | D | 1 | 32.636 | 3.763 | 4.368 | 1.00 | 32.34 | C |
| ATOM | 3214 | N9 | G | D | 1 | 32.684 | 5.161 | 4.445 | 1.00 | 21.91 | N |
| ATOM | 3215 | C8 | G | D | 1 | 33.766 | 5.831 | 4.960 | 1.00 | 23.00 | C |
| ATOM | 3216 | N7 | G | D | 1 | 33.463 | 7.125 | 4.927 | 1.00 | 31.14 | N |
| ATOM | 3217 | C5 | G | D | 1 | 32.140 | 7.223 | 4.367 | 1.00 | 11.23 | C |
| ATOM | 3218 | C6 | G | D | 1 | 31.340 | 8.334 | 4.046 | 1.00 | 30.33 | C |
| ATOM | 3219 | O6 | G | D | 1 | 31.606 | 9.551 | 4.230 | 1.00 | 45.89 | O |
| ATOM | 3220 | N1 | G | D | 1 | 30.095 | 7.976 | 3.459 | 1.00 | 19.98 | N |
| ATOM | 3221 | C2 | G | D | 1 | 29.697 | 6.717 | 3.224 | 1.00 | 12.32 | C |
| ATOM | 3222 | N2 | G | D | 1 | 28.498 | 6.590 | 2.657 | 1.00 | 16.30 | N |
| ATOM | 3223 | N3 | G | D | 1 | 30.441 | 5.688 | 3.493 | 1.00 | 5.87 | N |
| ATOM | 3224 | C4 | G | D | 1 | 31.659 | 6.029 | 4.042 | 1.00 | 5.13 | C |
| ATOM | 3225 | P | T | D | 2 | 33.839 | 0.119 | 3.002 | 1.00 | 31.07 | P |
| ATOM | 3226 | O1P | T | D | 2 | 33.203 | -1.233 | 2.831 | 1.00 | 24.25 | O |
| ATOM | 3227 | O2P | T | D | 2 | 35.298 | 0.383 | 2.952 | 1.00 | 20.08 | O |
| ATOM | 3228 | O5* | T | D | 2 | 33.000 | 0.923 | 1.979 | 1.00 | 10.31 | O |
| ATOM | 3229 | C5* | T | D | 2 | 31.682 | 0.432 | 2.132 | 1.00 | 11.29 | C |
| ATOM | 3230 | C4* | T | D | 2 | 30.826 | 1.011 | 1.104 | 1.00 | 20.56 | C |
| ATOM | 3231 | O4* | T | D | 2 | 30.883 | 2.446 | 1.224 | 1.00 | 32.60 | O |
| ATOM | 3232 | C3* | T | D | 2 | 31.323 | 0.665 | -0.297 | 1.00 | 29.62 | C |
| ATOM | 3233 | O3* | T | D | 2 | 30.174 | 0.218 | -0.957 | 1.00 | 42.83 | O |
| ATOM | 3234 | C2* | T | D | 2 | 31.882 | 1.955 | -0.912 | 1.00 | 22.27 | C |
| ATOM | 3235 | C1* | T | D | 2 | 31.098 | 3.036 | -0.097 | 1.00 | 27.85 | C |
| ATOM | 3236 | N1 | T | D | 2 | 31.680 | 4.386 | 0.171 | 1.00 | 9.17 | N |
| ATOM | 3237 | C2 | T | D | 2 | 30.954 | 5.475 | -0.067 | 1.00 | 6.39 | C |
| ATOM | 3238 | O2 | T | D | 2 | 29.838 | 5.419 | -0.523 | 1.00 | 15.49 | O |
| ATOM | 3239 | N3 | T | D | 2 | 31.553 | 6.615 | 0.284 | 1.00 | 5.30 | N |
| ATOM | 3240 | C4 | T | D | 2 | 32.833 | 6.781 | 0.831 | 1.00 | 13.45 | C |
| ATOM | 3241 | O4 | T | D | 2 | 33.247 | 7.955 | 1.102 | 1.00 | 32.57 | O |
| ATOM | 3242 | C5 | T | D | 2 | 33.525 | 5.576 | 1.043 | 1.00 | 1.00 | C |
| ATOM | 3243 | C5M | T | D | 2 | 34.907 | 5.492 | 1.634 | 1.00 | 9.11 | C |
| ATOM | 3244 | C6 | T | D | 2 | 32.915 | 4.463 | 0.729 | 1.00 | 2.01 | C |
| ATOM | 3245 | P | C | D | 3 | 30.372 | -0.379 | -2.388 | 1.00 | 37.30 | P |
| ATOM | 3246 | O1P | C | D | 3 | 29.600 | -1.636 | -2.621 | 1.00 | 40.96 | O |
| ATOM | 3247 | O2P | C | D | 3 | 31.849 | -0.388 | -2.424 | 1.00 | 16.94 | O |
| ATOM | 3248 | O5* | C | D | 3 | 29.687 | 0.785 | -3.193 | 1.00 | 32.48 | O |
| ATOM | 3249 | C5* | C | D | 3 | 28.361 | 1.243 | -3.112 | 1.00 | 27.07 | C |
| ATOM | 3250 | C4* | C | D | 3 | 28.317 | 2.517 | -4.013 | 1.00 | 44.62 | C |
| ATOM | 3251 | O4* | C | D | 3 | 29.091 | 3.668 | -3.522 | 1.00 | 51.94 | O |
| ATOM | 3252 | C3* | C | D | 3 | 28.810 | 2.357 | -5.445 | 1.00 | 42.40 | C |
| ATOM | 3253 | O3* | C | D | 3 | 27.742 | 2.865 | -6.139 | 1.00 | 50.72 | O |
| ATOM | 3254 | C2* | C | D | 3 | 30.067 | 3.243 | -5.614 | 1.00 | 30.54 | C |
| ATOM | 3255 | C1* | C | D | 3 | 29.822 | 4.321 | -4.566 | 1.00 | 28.07 | C |
| ATOM | 3256 | N1 | C | D | 3 | 30.984 | 5.083 | -3.932 | 1.00 | 6.26 | N |
| ATOM | 3257 | C2 | C | D | 3 | 30.924 | 6.489 | -3.797 | 1.00 | 14.46 | C |
| ATOM | 3258 | O2 | C | D | 3 | 29.928 | 7.135 | -4.226 | 1.00 | 27.32 | O |
| ATOM | 3259 | N3 | C | D | 3 | 31.957 | 7.156 | -3.230 | 1.00 | 8.55 | N |
| ATOM | 3260 | C4 | C | D | 3 | 33.024 | 6.487 | -2.843 | 1.00 | 11.60 | C |
| ATOM | 3261 | N4 | C | D | 3 | 34.007 | 7.143 | -2.249 | 1.00 | 10.38 | N |
| ATOM | 3262 | C5 | C | D | 3 | 33.097 | 5.072 | -2.967 | 1.00 | 9.89 | C |
| ATOM | 3263 | C6 | C | D | 3 | 32.064 | 4.418 | -3.520 | 1.00 | 4.66 | C |
| ATOM | 3264 | P | G | D | 4 | 27.713 | 2.761 | -7.712 | 1.00 | 58.96 | P |

Figure 22BH

| | | | | | | | | | | |
|---|---|---|---|---|---|---|---|---|---|---|
| ATOM | 3265 | O1P | G | D | 4 | 26.272 | 2.527 | -8.121 | 1.00 46.23 | O |
| ATOM | 3266 | O2P | G | D | 4 | 28.894 | 1.940 | -8.137 | 1.00 52.31 | O |
| ATOM | 3267 | O5* | G | D | 4 | 28.072 | 4.235 | -8.153 | 1.00 62.68 | O |
| ATOM | 3268 | C5* | G | D | 4 | 27.065 | 5.168 | -8.129 | 1.00 56.61 | C |
| ATOM | 3269 | C4* | G | D | 4 | 27.702 | 6.450 | -8.528 | 1.00 52.65 | C |
| ATOM | 3270 | O4* | G | D | 4 | 28.751 | 6.672 | -7.581 | 1.00 44.34 | O |
| ATOM | 3271 | C3* | G | D | 4 | 28.354 | 6.471 | -9.914 | 1.00 57.92 | C |
| ATOM | 3272 | O3* | G | D | 4 | 27.598 | 7.361 | -10.797 | 1.00 66.32 | O |
| ATOM | 3273 | C2* | G | D | 4 | 29.801 | 6.935 | -9.673 | 1.00 49.36 | C |
| ATOM | 3274 | C1* | G | D | 4 | 29.859 | 7.205 | -8.198 | 1.00 30.02 | C |
| ATOM | 3275 | N9 | G | D | 4 | 31.070 | 6.809 | -7.583 | 1.00 19.87 | N |
| ATOM | 3276 | C8 | G | D | 4 | 31.693 | 5.593 | -7.498 | 1.00 19.31 | C |
| ATOM | 3277 | N7 | G | D | 4 | 32.882 | 5.704 | -6.854 | 1.00 20.25 | N |
| ATOM | 3278 | C5 | G | D | 4 | 32.971 | 7.084 | -6.534 | 1.00 11.60 | C |
| ATOM | 3279 | C6 | G | D | 4 | 33.942 | 7.829 | -5.892 | 1.00 17.51 | C |
| ATOM | 3280 | O6 | G | D | 4 | 35.007 | 7.465 | -5.390 | 1.00 28.52 | O |
| ATOM | 3281 | N1 | G | D | 4 | 33.596 | 9.155 | -5.841 | 1.00 17.21 | N |
| ATOM | 3282 | C2 | G | D | 4 | 32.433 | 9.719 | -6.340 | 1.00 33.48 | C |
| ATOM | 3283 | N2 | G | D | 4 | 32.261 | 11.057 | -6.198 | 1.00 37.08 | N |
| ATOM | 3284 | N3 | G | D | 4 | 31.493 | 9.036 | -6.953 | 1.00 25.32 | N |
| ATOM | 3285 | C4 | G | D | 4 | 31.854 | 7.751 | -7.016 | 1.00 16.54 | C |
| ATOM | 3286 | P | G | D | 5 | 28.146 | 7.875 | -12.225 | 1.00 69.65 | P |
| ATOM | 3287 | O1P | G | D | 5 | 27.013 | 7.921 | -13.213 | 1.00 74.48 | O |
| ATOM | 3288 | O2P | G | D | 5 | 29.395 | 7.175 | -12.613 | 1.00 70.27 | O |
| ATOM | 3289 | O5* | G | D | 5 | 28.570 | 9.369 | -11.839 | 1.00 55.65 | O |
| ATOM | 3290 | C5* | G | D | 5 | 27.596 | 10.352 | -11.551 | 1.00 43.47 | C |
| ATOM | 3291 | C4* | G | D | 5 | 28.400 | 11.592 | -11.300 | 1.00 44.62 | C |
| ATOM | 3292 | O4* | G | D | 5 | 29.479 | 11.238 | -10.416 | 1.00 41.85 | O |
| ATOM | 3293 | C3* | G | D | 5 | 29.061 | 12.172 | -12.537 | 1.00 48.37 | C |
| ATOM | 3294 | O3* | G | D | 5 | 28.761 | 13.547 | -12.566 | 1.00 62.30 | O |
| ATOM | 3295 | C2* | G | D | 5 | 30.561 | 12.013 | -12.349 | 1.00 42.32 | C |
| ATOM | 3296 | C1* | G | D | 5 | 30.708 | 11.672 | -10.885 | 1.00 33.28 | C |
| ATOM | 3297 | N9 | G | D | 5 | 31.568 | 10.587 | -10.629 | 1.00 26.11 | N |
| ATOM | 3298 | C8 | G | D | 5 | 31.336 | 9.267 | -10.910 | 1.00 21.68 | C |
| ATOM | 3299 | N7 | G | D | 5 | 32.386 | 8.539 | -10.479 | 1.00 26.27 | N |
| ATOM | 3300 | C5 | G | D | 5 | 33.265 | 9.478 | -9.909 | 1.00 13.99 | C |
| ATOM | 3301 | C6 | G | D | 5 | 34.489 | 9.290 | -9.290 | 1.00 26.83 | C |
| ATOM | 3302 | O6 | G | D | 5 | 35.118 | 8.237 | -9.078 | 1.00 33.47 | O |
| ATOM | 3303 | N1 | G | D | 5 | 34.980 | 10.489 | -8.846 | 1.00 22.00 | N |
| ATOM | 3304 | C2 | G | D | 5 | 34.383 | 11.699 | -8.999 | 1.00 25.03 | C |
| ATOM | 3305 | N2 | G | D | 5 | 35.065 | 12.718 | -8.485 | 1.00 29.30 | N |
| ATOM | 3306 | N3 | G | D | 5 | 33.204 | 11.904 | -9.554 | 1.00 15.04 | N |
| ATOM | 3307 | C4 | G | D | 5 | 32.747 | 10.737 | -9.983 | 1.00 13.48 | C |
| TER | 3308 | | G | D | 5 | | | | | |
| HETATM | 3309 | NA | | NA | 341 | 18.765 | 8.832 | 22.075 | 1.00 22.70 | NA |
| HETATM | 3310 | NA | | NA | 342 | 31.203 | -4.052 | -3.083 | 1.00 21.40 | NA |
| HETATM | 3311 | O | | HOH | 500 | 17.305 | 7.251 | 21.652 | 1.00 28.59 | O |
| HETATM | 3312 | O | | HOH | 501 | 12.235 | 18.598 | 25.497 | 1.00 22.01 | O |
| HETATM | 3313 | O | | HOH | 502 | 29.545 | -4.153 | -4.372 | 1.00 29.28 | O |
| HETATM | 3314 | O | | HOH | 504 | 9.908 | 18.404 | 25.168 | 1.00 28.22 | O |
| HETATM | 3315 | O | | HOH | 505 | 22.127 | 4.181 | 20.295 | 1.00 47.91 | O |
| HETATM | 3316 | O | | HOH | 506 | 13.285 | 29.961 | 14.970 | 1.00 37.94 | O |
| HETATM | 3317 | O | | HOH | 507 | 4.780 | 1.709 | 32.326 | 1.00 52.10 | O |
| HETATM | 3318 | O | | HOH | 508 | 10.482 | 13.095 | 13.962 | 1.00 36.14 | O |
| HETATM | 3319 | O | | HOH | 509 | 28.535 | 12.030 | -4.921 | 1.00 44.32 | O |
| HETATM | 3320 | O | | HOH | 510 | 26.015 | 15.764 | 6.099 | 1.00 43.23 | O |
| HETATM | 3321 | O | | HOH | 511 | 23.293 | 9.363 | 5.061 | 1.00 34.41 | O |
| HETATM | 3322 | O | | HOH | 512 | 16.254 | 2.983 | 23.136 | 1.00 33.40 | O |
| HETATM | 3323 | O | | HOH | 513 | 35.516 | 9.833 | -0.291 | 1.00 52.11 | O |
| HETATM | 3324 | O | | HOH | 514 | 36.049 | 6.459 | -1.586 | 1.00 32.13 | O |
| HETATM | 3325 | O | | HOH | 515 | 19.240 | 34.748 | 13.051 | 1.00 38.04 | O |
| HETATM | 3326 | O | | HOH | 516 | 6.977 | 1.939 | 22.837 | 1.00 47.71 | O |
| HETATM | 3327 | O | | HOH | 517 | 6.837 | 1.444 | 14.051 | 1.00 58.34 | O |

Figure 22BI

```
HETATM 3328  O   HOH   518     -3.051  11.845  -1.334  1.00 52.72           O
HETATM 3329  O   HOH   519      8.269  20.105   1.982  1.00 61.56           O
HETATM 3330  O   HOH   520     14.369  19.332  34.672  1.00 50.12           O
HETATM 3331  O   HOH   521     17.035   6.135  10.250  1.00 60.37           O
HETATM 3332  O   HOH   522     26.512  15.874   1.591  1.00 51.30           O
HETATM 3333  O   HOH   523     24.381  17.471  -2.881  1.00 48.80           O
HETATM 3334  O   HOH   524     10.866  25.034  16.358  1.00 52.16           O
HETATM 3335  O   HOH   525      8.611  11.516  13.419  1.00 54.70           O
HETATM 3336  O   HOH   526     31.660  10.696  37.103  1.00 46.80           O
HETATM 3337  O   HOH   527     17.419  19.842  11.300  1.00 38.86           O
MASTER      270    0    2   16    9    0    1    6 3333    4    0   30
END
```

COMPOSITIONS AND METHODS OF TREATING NEOPLASIA

STATEMENT OF RIGHTS TO INVENTIONS MADE UNDER FEDERALLY SPONSORED RESEARCH

This work was supported by the following grants from the National Institutes of Health, Grant Nos: RO1-CA097031 and RO1-CA100247. The government may have certain rights in the invention.

CROSS REFERENCE TO RELATED APPLICATIONS

This application is the U.S. national phase application, pursuant to 35 U.S.C. §371, of PCT international application Ser. No. PCT/US2008/001991, filed 14 Feb. 2008, and published in English, which claims the benefit of the following U.S. Provisional Application Nos. 60/901,613 and 60/904,214, filed on Feb. 14, 2007 and Feb. 28, 2007, respectively, the entire contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Aug. 2, 2012, is named 67434.txt and is 35,177 bytes in size.

BACKGROUND OF THE INVENTION

Colorectal cancer is the second most common cause of cancer-related death in both men and women in the Western hemisphere. According to American. Cancer Society, an estimated 106,680 new cases of colon cancer with 57,460 deaths of both males and females would occur in the U.S. in the year 2006. Prognosis depends on the stage of the tumor at the time of diagnosis, with surgery being the most effective treatment. Colorectal cancers develop through a series of histological distinct stages from "adenoma to carcinoma." The temporal order in which mutations occur in different genes relates to the progression through the histological stages of cancer from adenoma to carcinoma. Mutations of the adenomatous polyposis coli (APC)*, Ki-ras, deleted in colorectal cancer (DCC), and p53 genes play important roles at different stages of colorectal tumorigenesis. Mutation of the APC gene is an early event in familial adenomatous polyposis (FAP), a syndrome of inherited predisposition to colon cancer. Notably, mutations in the APC gene also are found in 60 to 80% of sporadic colorectal cancers and adenomas.

APC is expressed constitutively within the normal colonic epithelium; however, little is known about how mutations of (or abnormal expression of) APC contribute to the development of colon cancer. The APC gene product is a 310-kDa-homodimeric protein localized in both the cytoplasm and the nucleus. Previous studies indicate that the cellular level of wild-type APC is critical to cytoskeletal integrity, cellular adhesion, and Wingless/Wnt signaling. Wild-type APC binds to EB1 and a tumor suppressor protein, DLG that regulates microtubule polymerization and cell cycle progression from $G_o/G_1$ to S phase, respectively. In addition, APC may act as a negative regulator of β-catenin signaling in the transformation of colonic epithelial cells and in melanoma progression. The β-catenin/Tcf4 complex regulates the proto-oncogene and cell cycle regulator c-myc, the $G_1$/S-regulating cyclin D1, the gene encoding the matrix-degrading metalloproteinase, matrysin, the AP-1 transcription factors c-jun and fra-1 and the urokinase-type plasminogen activator receptor gene.

An association has been shown between the severe polyposis phenotype and germline mutations in the mutation cluster region (MCR) of APC. Selective pressure for an MCR mutant has been proposed based on the germline mutation in FAP. Patients with mutations outside of the MCR region have a milder phenotype. The mechanism(s) by which APC mutations may contribute to the accumulation of mutations in other genes that are associated with the colon cancer progression remains unclear.

SUMMARY OF THE INVENTION

As described below, the present invention features methods of treating neoplasia by inhibiting DNA repair by polβ.

In one aspect, the invention generally provides a method for treating neoplasia (e.g., colon cancer, lung cancer, or glioblastoma) in a subject (e.g., a human), the method involving administering to the subject an effective amount of an agent that binds to pol-β at an adenomatous polyposis coli (APC) binding site and reduces base extension repair relative to a reference, thereby treating the neoplasia.

In another aspect, the invention provides a method for treating neoplasia in a subject, the method involving administering to the subject an agent that binds pol-β at an adenomatous polyposis coli (APC) binding site containing amino acids Thr79, Lys81 and Arg83, and reduces pol-β-directed dRP-lyase activity or pol-β-directed strand-displacement synthesis, thereby treating the neoplasia.

In yet another aspect, the invention provides a method for treating a subject having a neoplasm, the method involving administering to the subject an effective amount of a pharmaceutical composition containing a compound that is one or more of NSC124854, NSC666715, NSC21371 and NSC91855, or an analog thereof.

In yet another aspect, the invention provides a method for treating a subject having a neoplasm, the method involving administering to the subject a pharmaceutical composition containing an effective amount of NSC124854 or NSC666715 and an alkylating agent.

In yet another aspect, the invention provides a method for treating a neoplasia in a subject, the method involving administering to the subject a combination that includes an effective amount of a DNA alkylating agent; and a pharmaceutical composition containing a compound that is one or more of NSC124854, NSC666715, NSC21371 and NSC91855, or an analog thereof, where the administration of the composition reduces the amount of the DNA alkylating agent required to treat the neoplasm, relative to the amount required to treat a neoplasm in a control subject. In one embodiment, the method further involves the step of identifying the subject as having an MMR-deficient neoplasia or a neoplasia that does not respond to conventional chemotherapeutics. In another embodiment, an effective amount of the combination has reduced toxicity relative to the administration of an effective amount of a DNA alklyating agent (e.g., Temozolomide) alone.

In yet another aspect, the invention provides a method of selecting an effective therapy for treating a neoplasia in a subject, the method involves identifying the subject as having an MMR-deficient neoplasia or a neoplasia that fails to respond to conventional chemotherapeutics; and administering to the subject an alkylating agent and an agent that binds to pol-β at an adenomatous polyposis coli (APC) binding site and reduces base extension repair.

In yet another aspect, the invention provides a pharmaceutical composition for the treatment of a neoplasia, the composition containing an effective amount of a compound that is one or more of NSC124854, NSC666715, NSC21371 and NSC91855, or an analog thereof. In one embodiment, the composition further comprises a DNA alkylating agent (e.g., temozolamide). In another embodiment, the composition is labeled for the treatment of an MMR-deficient neoplasia.

In yet another aspect, the invention provides an isolated polypeptide containing an amino acid sequence having at least 85%, 90%, 95%, or 100% amino acid sequence identity to at least a fragment of polβ, where the fragment contains, is or is essentially pol-β amino acids linking an amino-terminal lyase domain and a carboxyl-terminal polymerase domain of polβ that are any one or more of polβ amino acids 60-170, polβ amino acids 60-120, polβ amino acids 80-170, polβ amino acids 80-120, and where the polypeptide binds APC. In one embodiment, APC binding to the fragment reduces pol-β-directed long patch- and/or single nucleotide-base extension repair pathways relative to a reference. In one embodiment, the fragment contains one or more of pol-β amino acids Thr79, Lys81 and Arg83. In another embodiment, the polypeptide comprises a mutation at an amino acid position corresponding to polβ amino acid Thr79, Lys81 and/or Arg83.

In yet another aspect, the invention provides an isolated fragment of APC containing an amino acid sequence having at least 85%, 90%, 95%, or 100% amino acid sequence identity to at least a fragment of APC that interacts with an APC binding site of pol-β, thereby reducing base excision repair.

In yet another aspect, the invention provides an isolated nucleic acid molecule encoding the polypeptide or fragment the previous aspects.

In yet another aspect, the invention provides a vector containing the isolated nucleic acid molecule the previous aspect.

In yet another aspect, the invention provides a cell containing the vector of a previous aspect or the polypeptide of a previous aspect.

In yet another aspect, the invention provides a method for identifying an agent that binds a polypeptide of a previous aspect, the method involving contacting the polypeptide with a candidate agent; and measuring DNA repair activity following contact with the candidate compound. In one embodiment, the DNA repair activity is in the long patch- and/or single nucleotide-base extension repair pathways.

In yet another aspect, the invention provides a method of identifying a compound for the treatment of a neoplasm, the method involving providing a three-dimensional structure of pol-β having at least one atomic coordinate, or surrogate thereof, from FIGS. 22A-22BI for each of the following residues Thr79, Lys81 and Arg83 of pol-β: or atomic coordinates that have a root mean square deviation of the coordinates of less than 3 angstroms; and producing a structure for a candidate compound where the structure defines a molecule having sufficient surface complementary to the pol-β structure to bind the domain in an aqueous solution. In one embodiment, the candidate compound is an APC mimetic, a small molecule, or a peptidomimetic.

In yet another aspect, the invention provides a compound identified by the method of a previous aspect.

In yet another aspect, the invention provides a kit for the treatment of a neoplasia, the kit containing an effective amount of NSC124854 or NSC666715 and directions for the use of the kit for the treatment of a neoplasia. In one embodiment, the kit further comprises an effective amount of an alkylating agent, where the amount of alkylating agent required to treat the neoplasia when administered in combination NSC124854 or NSC666715 is less than the amount of alkylating agent administered alone.

In yet another aspect, the invention provides a method for increasing cytotoxicity in a subject of a chemotherapeutic agent, the method involving administering to the subject NSC124854 or NSC666715 and an alkylating agent. In one embodiment, NSC124854 or NSC666715 and the alkylating agent are administered within about 7-14 days, within about 3-5 days or are administered concurrently.

In various embodiments of the above aspects, the agent is APC or an APC mimetic (e.g., an agent having structural or functional homology with APC). In one embodiment of the above aspects, the agent is NSC-124854 or NSC-666715. In other embodiments, the APC binding site comprises pol-β amino acids that are 60-120, 60-170, or 80-170. In still other embodiments, the agent binds pol-β amino acids linking an amino-terminal lyase domain and a carboxyl-terminal polymerase domain of pol-β. In still other embodiments, the method further comprises administering an effective amount of an alkylating agent. In one embodiment of the above aspects, the alkylating agent is temozolamide. In other embodiments, the agent that binds to pol-13 reduces long patch-BER by reducing Fen-1 activity relative to a reference. In still other embodiments, the agent that binds to pol-β reduces the activity of long patch- or single nucleotide-BER pathways relative to a reference pr reduces long patch- or single nucleotide-BER pathways. In various embodiments of the above aspects, the composition reduces pol-β-directed dRP-lyase activity or pol-β-directed strand-displacement synthesis by at least 10% in a cell relative to an untreated control cell.

In various embodiments of the above aspects, the subject is identified as having a neoplasia that does not respond to a conventional chemotherapeutic or that is DNA mismatch repair deficient. In other embodiments of the above aspects, the agent that binds to pol-β is NSC124854 or NSC666715, or an analog thereof. In other embodiments, administration of NSC124854 or NSC666715 reduces the amount of DNA alkylating agent (e.g., Temozolomide) required to treat the neoplasm, relative to the amount required to treat an MMR-deficient neoplasm in a control subject.

Other features and advantages of the invention will be apparent from the detailed description, and from the claims.

DEFINITIONS

By "alkylating agent" is meant a cytotoxic agent that transfers an alkyl group to a nucleophilic group on a molecule. Exemplary alkylating agents include, but are not limited to temozolamide, mechlorethamine, cyclophosphamide, chlorambucil, melphalan, ifosfamide, thiotepa, hexamethylmelamine, busulfan, altretamine, procarbazine, dacarbazine temozolomide, carmustine, lomustine, streptozocin, carboplatin, cisplatin, and oxaliplatin.

By "adenomatous polyposis coli (APC) binding site" is meant a portion of a pol-β polypeptide that interacts with an APC polypeptide.

By "binding to" a molecule is meant having a physicochemical affinity for that molecule.

By "computer modeling" is meant the application of a computational program to determine one or more of the following: the location and binding proximity of a ligand to a binding moiety, the occupied space of a bound ligand, the amount of complementary contact surface between a binding moiety and a ligand, the deformation energy of binding of a given ligand to a binding moiety, and some estimate of hydrogen bonding strength, van der Waals interaction, hydrophobic interaction, and/or electrostatic interaction energies between ligand and binding moiety. Computer modeling can also provide comparisons between the features of a model system and a candidate compound. For example, a computer modeling experiment can compare a pharmacophore model of the invention with a candidate compound to assess the fit of the candidate compound with the model.

By "conventional chemotherapeutic agent" is meant one or more chemical agents used in the treatment or control of proliferative diseases, including cancer. Chemotherapeutic agents include cytotoxic and cytostatic agents.

By "pol-β protein" is meant a polypeptide having at least about 85% identity to NCBI Accession No. P06746, or a fragment thereof having APC binding activity. An exemplary sequence for a human pol-β protein is provided at FIG. 9. Exemplary fragments useful in the methods of the invention include those comprising amino acids By "ameliorate" is meant decrease, suppress, attenuate, diminish, arrest, or stabilize the development or progression of a disease.

By "compound" is meant any small molecule chemical compound, antibody, nucleic acid molecule, or polypeptide, or fragments thereof.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "marker" is meant any protein or polynucleotide having an alteration in expression level or activity that is associated with a disease or disorder.

By "neoplasia" is meant a disease or disorder characterized by excess proliferation or reduced apoptosis. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

By "subject" is meant a mammal, including, but not limited to, a human or non-human mammal, such as a bovine, equine, canine, ovine, or feline.

By "reference" is meant a standard or control condition. In one embodiment, the effect of an agent on a cell is compared to the effect of the agent on a control cell.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

"Therapeutic agent" means a substance that has the potential of affecting the function of an organism. Such a compound may be, for example, a naturally occurring, semi-synthetic, or synthetic agent. For example, an agent may be a drug that targets a specific function of an organism or an antibiotic. A therapeutic agent may decrease, suppress, attenuate, diminish, arrest, or stabilize the development or progression of disease, disorder, or infection in a eukaryotic host organism.

BRIEF DESCRIPTION OF THE DRAWINGS

FIGS. 5A and 5B show the determination of interaction of APC with pol-β by yeast two-hybrid analysis. The yeast two-hybrid constructs are described below. FIG. 5A shows the deletion constructs of pol-β, APCwt (SEQ ID NO: 22) and APC(I-A,Y-A) plasmids used in the yeast two-hybrid analysis. Mutational position of isoleucine (I) and tyrosine (Y) are italicized and shown with arrows in the diagram. FIG. 5B shows the interaction of APC with deletion constructs of pol-β. The yeast PJ69-4A cells were co-transformed with pGBDU-C3-APCwt (amino acids 1190-1328) or pGBDU-C3-APC(I-A,Y-A) (amino acids 1200-1324; I1259A, Y1262A) plasmids with either pGAD-C3-pol-βwt or different deletion construct plasmids. For a positive control, proliferating cell nuclear antigen (PCNA)/pol-β interaction is shown. Data is representative of three different experiments.

FIGS. 6A and 6B show an analysis of residues of pol-β involved in the interaction with APC. FIG. 6A shows the yeast two-hybrid constructs which were prepared by site-directed mutagenesis at the Set-1 and Set-2 amino acids, which are italicized and shown with arrows in the diagram (SEQ ID NOS 23-25, respectively, in order of appearance). FIG. 6B shows the interaction of APC with Set-1 and Set-2 pol-β mutant plasmids. The yeast PJ69-4A cells were co-transformed with pGBDU-C3-APCwt plasmid (residues 1190-1328) with pGAD-C3-pol-βwt, pGAD-C3-pol-βMut(Set-1), or pGAD-C3-pol-βMut(Set-2) plasmids. For a positive control, PCNA/pol-β interaction is shown. Data is the representative of three different experiments.

FIGS. 7A and 7B show that APC blocks pol-β-directed strand-displacement synthesis. FIG. 7A shows a schematic representation of the protocol. FIG. 7B shows the effect of APC peptide on the strand-displacement synthesis. In this experiment, the $^{32}$P-F-DNA (2.5 nM) was precut with apurinic/apyrimidinic endonuclease (1 nM) and mixed with separately preincubated mixture of pol-β (1 nM) and different concentrations of APC. Lane 4-6 and 7-9 contains 0.5, 1.0 and 2.0 μM APCwt and APC(I-A,Y-A) peptides, respectively. The repair was initiated by the addition of dNTPs and DNA ligase I (0.2 nM). Lane 1 shows $^{32}$P-labeled 63-mer F-DNA and Lane 2 shows the 23-mer product after apurinic/apyrimidinic endonuclease incision. Data are the representative of three different experiments.

FIG. 8A shows a schematic representation of the protocol. FIG. 8B shows the effect of pol-βwt and pol-βMut-1 proteins on the strand-displacement synthesis. The $^{32}$P-F-DNA (2.5 nM) was precut with apurinic/apyrimidinic endonuclease (1 nM) and mixed with 1.0 nM of either pol-βwt or pol-βMut-1 protein, respectively, and dNTPs. The reaction was terminated at different time intervals and processed for electrophoresis and autoradiography. Lane 1 shows $^{32}$P-labeled 63-mer F-DNA and Lane 2 shows the 23-mer product after apurinic/apyrimidinic endonuclease incision. Data are the representative of three different experiments.

FIG. 9 provides the amino acid sequence for a human DNA polymerase beta, which corresponds to NCBI Accession No. P06746 (SEQ ID NO: 26).

FIG. 10A shows a schematic representation of the protocol. FIG. 10B shows the effect of pol-βwt and pol-βMut-1 proteins on the base excision repair activity. The reaction was assembled separately with $^{32}$P-F-DNA (2.5 nM), apurinic/apyrimidinic endonuclease (1 nM) and pol-β (1.0 nM), Fen-1 (0.3 nM) and APC for 5 minutes at 23° C. Then they were mixed together with dNTPs and DNA ligase I (0.2 nM) and incubated for 30 minutes at 37° C. Lane 6-8 and 9-11 contained 0.5, 1.0 and 2.0 μM APCwt and APC(I-A,Y-A) peptides, respectively. Lane 1 shows $^{32}$P-labeled 63-mer F-DNA and Lane 2 shows the 23-mer product after apurinic/apyrimidinic endonuclease incision. Data are the representative of three different experiments.

FIG. 11A shows a schematic representation of the protocol. FIG. 11B shows the effect of Fen-1 on the pol-βMut-1-directed base excision repair activity. The reaction was assembled separately with $^{32}$P-F-DNA (2.5 nM), apurinic/apyrimidinic endonuclease (1 nM) and pol-β (1.0 nM) and Fen-1 (0.3 nM) for 5 minutes at 23° C. Then they were mixed together with dNTPs and DNA ligase I (0.2 nM) and incubated for additional 30 minutes at 37° C. Lane 1 shows $^{32}$P-labeled 63-mer F-DNA and Lane 2 shows the 23-mer product after apurinic/apyrimidinic endonuclease incision. Data are the representative of three different experiments.

FIG. 12A shows a schematic representation of the protocol. FIG. 12B shows the effect of pol-βwt and pol-βMut-1 proteins on the base excision repair activity. The reaction was assembled separately with $^{32}$P-U-DNA (2.5 nM), UDG (40 nM), apurinic/apyrimidinic endonuclease (1 nM) and pol-β (1.0 nM), Fen-1 (0.3 nM) and APCwt or APC(I-A,Y-A) (2.0 µM) for 5 minutes at 23° C. Then they were mixed together with dNTPs and DNA ligase I (0.2 nM) and incubated for additional 30 minutes at 37° C. Lane 1 shows $^{32}$P-labeled 63-mer F-DNA and Lane 2 shows the 23-mer product after apurinic/apyrimidinic endonuclease incision. Data are the representative of three different experiments.

FIG. 13A shows a schematic representation of dRP-lyase DNA substrate and its activity. FIG. 13B shows an autoradiogram illustrating the dRP-lyase activity of pol-βwt and pol-βMut-1 proteins. As described in methods, reactions were performed using 1 nM of pol-βwt and pol-βMut-1 proteins and 0.5, 1.0, and 2.0 µM APCwt and APC (I-A,Y-A) peptides, respectively. A 2.5 nM of 3'-end labeled U-DNA was treated with 40 nM UDG and 1.0 nM apurinic/apyrimidinic endonuclease to generate the dRP-lyase substrate. Then the dRP-lyase substrate was mixed with APC and pol-β proteins, which were preincubated for 5 minutes at 22° C. The reactions were further incubated at 37° C. for 15 minutes. The dRP substrates and products were stabilized with sodium borohydride and analyzed by electrophoresis. Data are the representation of three different experiments.

FIG. 14A shows a schematic representation of the protocol. FIG. 14B shows the effect of APC peptide on the strand-displacement synthesis. In this experiment, the $^{32}$P-F-DNA (2.5 nM) was precut with APE (1 nM) and mixed with separately preincubated mixture of pol-β (1 nM) and different concentrations of APC. Lane 4-6 and 7-9 contains 0.5, 1.0 and 2.0 µM APCwt and APC(I-A,Y-A) peptides, respectively. The repair was initiated by the addition of dNTPs and DNA ligase I (0.2 nM). Lane 1 shows $^{32}$P-labeled 63-mer F-DNA and Lane 2 shows the 23-mer product after APE incision. Data are the representative of three different experiments.

FIGS. 15A and 15B show the site selected for molecular docking (spheres in gold) is a cleft in the human pol-β structure (blue and salmon) with appropriate chemical and geometric characteristics for binding small drug-like molecules. FIG. 15A and FIG. 15B show the interaction of NSC-124584 and NSC-666715 molecules with Pol-β, respectively. The residue Lys72 is shown in magenta.

FIGS. 16A and 16B show that NSC-124584 and NSC-666715 block pol-β-directed dRP-lyase activity. FIG. 16A shows a schematic representation of dRP-lyase DNA substrate and its activity. FIG. 16B shows an autoradiogram illustrating the dRP-lyase activity of pol-βwt in the presence of various concentrations of CN3 (lane 4-8), CN4 (lane 9-13), NSC-124584 (lane 14-18) and NSC-666715 (lane 19-23), respectively. The reaction conditions were same as described in FIG. 6. Data are the representation of three different experiments.

FIG. 17A shows a schematic representation of the protocol. FIG. 17B shows the effect of various concentrations of CN3 (lane 8-11), CN4 (lane 12-14), NSC-124584 (lane 15-20) and NSC-666715 (lane 21-24), respectively, on the strand-displacement synthesis. The reaction conditions were same as described in FIG. 7. Data are the representative of three different experiments.

FIG. 18B depicts the effect of TMZ on the APC and β-tubulin protein levels in HCT-116(APC$^{+/+}$) cells. Data are the mean±SE of three different estimations.

FIG. 19A-D, cells were pretreated for 2 hours with different concentrations of NSC-124584 and NSC-666715 followed by the treatment with different concentrations of TMZ. After 48 hours, cells were harvested and processed for cytotoxicity determination as described herein. FIGS. 19E and F, cells were treated with NSC-124584 and NSC-666715, respectively, to determine their individual cytotoxicity of these compounds. Data are the mean±SE of three different estimations.

FIG. 21 shows the structures of CN1=NSC124854; CN2=NSC666715; CN3=NSC21371; and CN4=NSC91855.

FIGS. 22A-22BI provides human pol-β (PDB code 1BPZ) atomic coordinates and structure factors that are available in the Protein Data Bank code 1BPZ, which is hereby incorporated by reference in its entirety (SEQ ID NOS 26-28, residues 5-335 of SEQ ID NO: 26 and SEQ ID NOS 27-28, respectively, in order of appearance).

FIG. 23A shows a BER assay protocol. FIG. 23B shows an autoradiogram illustrating the effect of NSC-124854 and NSC-666715 on SN- and LP-BER activities. Data are representative of three different experiments.

DETAILED DESCRIPTION OF THE INVENTION

Figure 1:
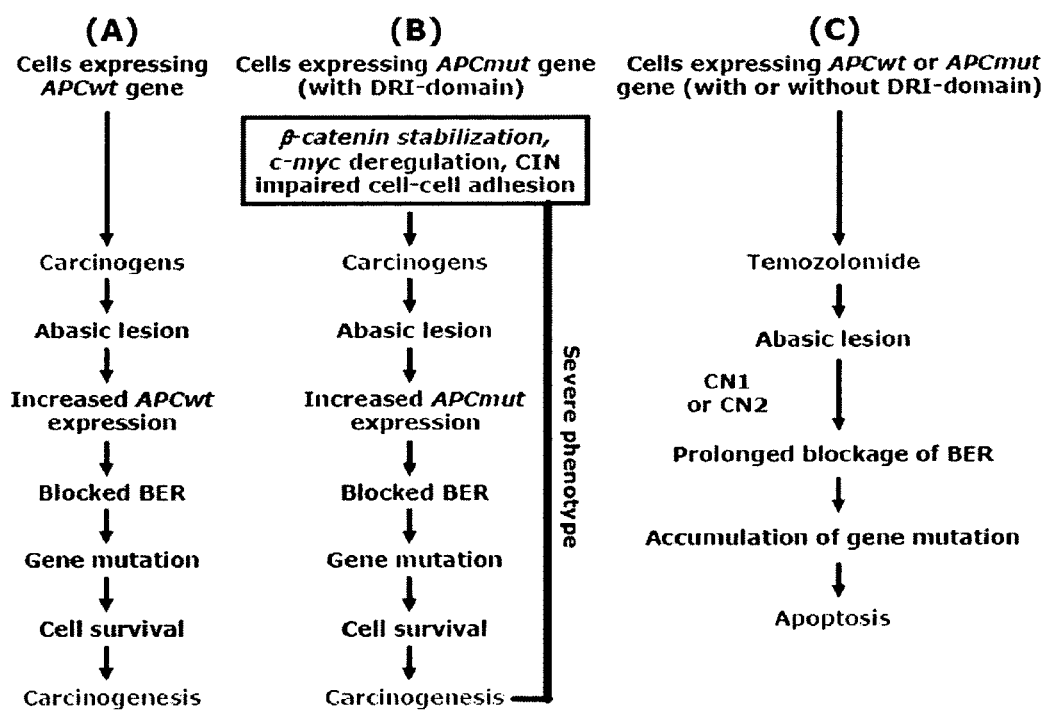
FIG. 1 is a schematic diagram showing a model for the role of adenomatous polyposis coli (APC) in base excision repair and chemoprevention.

The invention features compositions and methods that are useful for the treatment of neoplasia by reducing DNA repair. The invention is based, at least in part, on the observations that APC modulated DNA base excision repair (BER) and that it blocked both single nucleotide (SN)- and long-patch (LP)-BER. Moreover, as reported herein, APC does so, in large part, through its interaction with DNA polymerase β (Pol-β). This interaction inhibited Pol-β-directed dRP-lyase and strand-displacement activities. The Thr79, Lys81 and Arg83 amino acid residues of Pol-β function in mediating the interaction of Pol-β with APC. Mutation of these residues mimicked the effects of the interaction of Pol-β with APC and blocked Pol-β-directed single nucleotide—and long patch-BER. Without wishing to be bound by theory, it appears that under normal physiological conditions APC performs tumor suppressor function by controlling β-catenin levels, maintaining cell-cell adhesion, cell migration and chromosomal stability.

Using structure-based molecular docking of Pol-β targeting to these amino acids, two potent small chemical compounds were identified that block Pol-β-directed single nucleotide—and long patch-BER. These compounds are promising therapeutics that are useful for the treatment of neoplasia alone, or in combination with conventional chemotherapeutic agents, including DNA-alkylating agents. Analysis of the function of APC indicated that APC gene expression was induced in human colon cancer cell lines upon exposure to several DNA-alkylating agents and, depending on various factors, either promoted or inhibited tumorigenesis. In particular embodiments, the invention provides therapies for subjects that have neoplasias that are deficient in DNA mismatch repair (MMR) activity. A neoplasia that is "MMR-deficient" has a reduced level of mismatch repair relative to a the level in a wild-type control cell. Methods for identifying such cells include measuring microsatellite stability, measuring the fidelity of DNA replication by identifying single-base mismatches and insertion-deletion loops arising during DNA replication, or by identifying mutations in a protein associated with mismatch repair (e.g., hMSH2, hMLH1, hPMS1, hPMS2, hMSH3, and hMSH6). Because MMR-deficient cells are resistant to treatment with alkylating agents, subjects that have MMR-deficient neoplasias do not respond to convention therapeutics. As reported herein, APC blocks BER and increases cellular toxicity in response to DNA-alkylation damage. The blockage of BER decreases the resistance and increases the cytotoxicity of DNA-alkylation damage in MMR-deficient cells. Thus, the invention provides an important new therapy for patients that do not respond to conventional chemotherapeutics.

The Base Excision Repair (BER) Pathway

The BER pathway plays a key role in the responses of cells to alklyating agents that damage DNA. Indeed, the extent and type of DNA damage incurred on exposure to the alkylating agents plays a role in determining the type of BER response. It also determines whether the cell continues to attempt to repair the damage, or in the face of extensive damage, switches to an apoptotic response to eliminate the cell. The latter phenomenon is exploited in the use of alkylating agents as chemotherapeutic agents. It is well established that APC plays a key role in colorectal carcinogenesis, and it is generally considered to act as a tumor suppressor. As reported in more detail below, the treatment of human colon cancer cells and mouse embryonic fibroblast cells with the DNA alkylating agent methylmethane sulfonate (MMS) enhances the levels of APC and blocks BER resulting in increased sensitivity and apoptosis of cells harboring damaged DNA. In addition, exposure of human colon cancer and spontaneously immortalized normal human breast epithelial cell lines to DNA-alkylating agents, including N-methyl-N'-nitro-N-nitrosoguanine (MNNG), and dimethylhyrdazine (DMH), as well as the cigarette smoke carcinogen, DMBA enhanced the expression of APC and that this is associated with carcinogenesis.

Adenomatous Polyposis Coli

Mutation of the adenomatous polyposis coli (APC), a tumor suppressor gene is an early event in familial adenomatous polyposis (FAP), a syndrome in which there is an inherited predisposition to colon cancer. The amino acid sequence of APC is provided at NCBI Reference No. NP_000029 (SEQ ID NO: 1), which is reproduced below:

```
   1 maaasydqll kqvealkmen snlrqeledn snhltklete asnmkevlkq lqgsiedeam 61 assgqidlle rlkelnldss nfpgvklrsk mslrsygsre gsvssrsgec spvpmgsfpr 121 rgfvngsres tgyleeleke rsllladldk eekekdwyya qlqnltkrid sipltenfsl 181 qtdmtrrqle yearqirvam eeqlgtcgdm ekraqrriar iqqiekdilr irqllqsqat 241 eaerssqnkh etgshdaerq negqgvgein matsgngqgs ttrmdhetas vlssssthsa 301 prrltshlgt kvemvyslls mlgthdkddm srtllamsss qdscismrqs gclplliqll 361 hgndkdsvll gnsrgskear arasaalhni ihsqpddkrg rreirvlhll eqiraycetc 421 wewqeahepg mdqdknpmpa pvehqicpav cvlmklsfde ehrhamnelg glqaiaellq 481 vdcemygltn dhysitlrry agmaltnltf gdvankatlc smkgcmralv aqlksesedl 541 qqviasvlrn lswradvnsk ktlrevgsvk almecalevk kestlksvls alwnlsahct 601 enkadicavd galaflvgtl tyrsqtntla iiesgggilr nvssliatne dhrqilrenn 661 clqtllqhlk shsltivsna cgtlwnlsar npkdqealwd mgavsmlknl ihskhkmiam 721 gsaaalrnlm anrpakykda nimspgsslp slhvrkqkal eaeldaqhls etfdnidnls 781 pkashrskqr hkqslygdyv fdtnrhddnr sdnfntgnmt vlspylnttv lpssssrgs 841 ldssrsekdr slerergigl gnyhpatenp gtsskrglqi sttaaqiakv meevsaihts 901 qedrssgstt elhcvtdern alrrssaaht hsntynftks ensnrtcsmp yakleykrss 961 ndslnsvsss dgygkrgqmk psiesysedd eskfcsygqy padlahkihs anhmddndge 1021 ldtpinyslk ysdeqlnsgr qspsqnerwa rpkhiiedei kqseqrqsrn qsttypvyte
```

```
-continued
1081  stddkhlkfq  phfgqqecvs  pyrsrgangs  etnrvgsnhg  inqnvsqslc  qeddyeddkp 1141  tnyserysee  eqheeeerpt  nysikyneek  rhvdqpidys  lkyatdipss  qkqsfsfsks 1201  ssgqssksteh  mssssentst  pssnakrqnq  lhpssaqsrs  gqpqkaatck  vssinqetiq 1261  tycvedtpic  fsrcsslssl  ssaedeigcn  qttqeadsan  tlqiaeikek  igtrsaedpv 1321  sevpavsqhp  rtkssrlqgs  slssesarhk  avefssgaks  psksgaqtpk  sppehyvqet 1381  plmfsrctsv  ssldsfesrs  iassvqsepc  sgmvsgiisp  sdlpdspgqt  mppsrsktpp 1441  pppqtaqtkr  evpknkapta  ekresgpkqa  avnaavqrvq  vlpdadtllh  fatestpdgf 1501  scssslsals  ldepfiqkdv  elrimppvqe  ndngnetese  qpkesnenqe  keaektidse 1561  kdllddsddd  dieileecii  samptkssrk  akkpaqtask  lpppvarkps  qlpvykllps 1621  gnrlqpqkhv  sftpgddmpr  vycvegtpin  fstatslsdl  tiesppnela  agegvrggaq 1681  sgefekrdti  ptegrstdea  qggktssvti  pelddnkaee  gdilaecins  ampkgkshkp 1741  frvkkimdqv  qqasasssap  nknqldgkkk  kptspvkpip  qnteyrtrvr  knadsknnln 1801  aervfsdnkd  skkqnlknns  kvfndklpnn  edrvrgsfaf  dsphhytpie  gtpycfsrnd 1861  slssldfddd  dvdlsrekae  irkakenkes  eakvtshtel  tsnqqsankt  qaiakqpinr 1921  gqpkpilqkq  stfpqsskdi  pdrgaatdek  lqnfaientp  vcfshnssls  slsdidqenn 1981  nkenepiket  eppdsqgeps  kpqasgyapk  sfhvedtpvc  fsrnsslssl  sidseddllq 2041  ecissampkk  kkpsrlkgdn  ekhsprnmgg  ilgedltldl  kdiqrpdseh  glspdsenfd 2101  wkaiqegans  ivsslhqaaa  aaclsrgass  dsdsilslks  gislgspfhl  tpdqeekpft 2161  snkgprilkp  gekstletkk  ieseskgikg  gkkvykslit  gkvrsnseis  gqmkqplqan 2221  mpsisrgrtm  ihipgvrnss  sstspvskkg  pplktpasks  psegqtatts  prgakpsvks 2281  elspvarqts  qiggsskaps  rsgsrdstps  rpaqqplsrp  iqspgrnsis  pgrngisppn 2341  klsqlprtss  pstastkssg  sgkmsytspg  rqmsqqnltk  qtglsknass  iprsesaskg 2401  lnqmnngnga  nkkvelsrms  stkssgsesd  rserpvlvrq  stfikeapsp  tlrrkleesa 2461  sfeslspssr  pasptrsqaq  tpvlspslpd  mslsthssvq  aggwrklppn  lsptieyndg 2521  rpakrhdiar  shsespsrlp  inrsgtwkre  hskhssslpr  vstwrrtgss  ssilsasses 2581  sekaksedek  hvnsisgtkq  skenqvsakg  twrkikenef  sptnstsqtv  ssgatngaes 2641  ktliyqmapa  vsktedvwvr  iedcpinnpr  sgrsptgntp  pvidsvseka  npnikdskdn 2701  qakqnvgngs  vpmrtvglen  rlnsfiqvda  pdqkgteikp  gqnnpvpvse  tnessivert 2761  pfssssskh  sspsgtvaar  vtpfnynpsp  rkssadstsa  rpsqiptpvn  nntkkrdskt 2821  dstessgtqs  pkrhsgsylv  tsv
```

APC is expressed constitutively within the normal colonic epithelium. Little is known about how mutations of (or abnormal expression of) APC contribute to the development of colon cancer. The APC gene product is a 310-kDa-homodimeric protein localized in both the cytoplasm and the nucleus. APC is known to play a diversified role in cell migration, cell-cell adhesion, β-catenin regulation, cellular proliferation and chromosomal segregation. Notably, mutations in the APC gene also are found in 60 to 80% of sporadic colorectal cancers and adenomas. Thus, it is now established that mutations in APC may be necessary for the early onset of polyposis. Whether APC mutations may contribute to the accumulation of mutations in other genes that are associated with colon cancer progression remains unclear. Mutations in the APC gene are associated with an early onset of colorectal carcinogenesis.

The present report describes a role of APC in base excision repair. Abasic sites in DNA are induced by stressors such as spontaneous oxidation/reduction, alkylation and temperature changes and are repaired primarily by single-nucleotide (SN)- or long-patch (LP)-base excision repair pathways. APC interacts with DNA polymerase β (pol-β) and flap endonuclease 1 (Fen-1) and blocks pol-β-directed strand-displacement synthesis. The APC interaction site in pol-β has now been mapped and the mechanism by which APC blocks single nucleotide- and long patch-base excision repair pathways has now been described. The amino acid residues Thr79, Lys81 and Arg83 of pol-β are interaction sites for APC. The pol-βMut-1 protein (T79A/K81A/R83A) blocked strand-displacement DNA synthesis and long patch-base excision repair with both uracil and tetrahydrofuran DNA substrates. The APC-mediated blockage of long patch-base excision repair is due to blockage of Fen-1 activity. Furthermore, the interaction of APC with pol-β blocked single nucleotide-base excision repair by inhibiting the deoxyribose phosphate-lyase activity of pol-β. These findings suggest a mechanism by which APC blocks pol-β-directed long patch- and single nucleotide-base excision repair pathways. Moreover, these results suggest a role for APC in base excision repair and chemoprevention (FIG. 1).

Base Excision Repair

Figure 2:
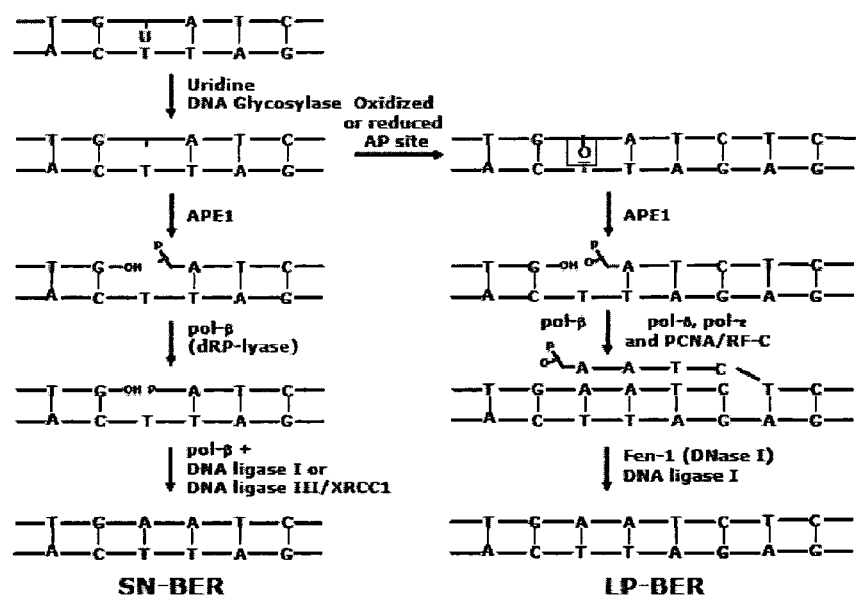
FIG. 2 is a schematic diagram showing a model of base excision repair pathways. DNA repair of abasic sites diverge after the generation of the 3'-hydroxyl required for replacement synthesis. The single nucleotide- or long patch-base excision repair pathways and their known protein components are summarized.

Exogenous and endogenous mutagenic agents attack the genomes of all living cells. DNA bases damaged by these agents may be cytotoxic and/or miscoding, and are thought to be a major source of intermediates in tumorigenesis. DNA repair systems efficiently remove damaged DNA via several different pathways that reverse the vast majority of genetic lesions formed during the life span of a cell. Most DNA repair mechanisms, including the base excision repair pathway, involve the participation of enzymes and other proteins that recognize structural alterations in DNA. Estimates of the number of abasic sites generated by mammalian cells are approximately $10^6$/cell/day. Abasic sites are unstable and degrade spontaneously into DNA-strand breaks by β-elimination that retards DNA polymerases. They are highly mutagenic because of non-template DNA and RNA synthesis. Despite the large number of abasic sites generated per cell per day, the number of resulting mutations is extremely low. This disparity underscores the importance of the elaborate mechanisms that the cell has devised to repair abasic sites. A schematic diagram showing different base excision repair steps is shown in FIG. 2. Deficiencies in the DNA repair pathways usually have catastrophic consequences for the affected organisms. In humans, deficiency in DNA repair has been linked to a number of genetic diseases characterized by radiation sensitivity and cancer-prone syndromes. In recent studies, evidence is provided that predisposition of certain colon tumors result from defects in DNA mismatch repair (MMR) system. About 15% of hereditary nonpolyposis colon cancers (HNPCC) have defects in one or more proteins in the MMR pathway. Also, mutations and/or different levels of expression of DNA polymerase β, pol-β gene have been observed in many colon and lung tumors and cell lines, indicating that a base excision repair-defective pathway is associated with cancer development. In a recent study, a significant concordance between the in vitro replication errors of pol-β and in vivo point mutations of the APC gene has been suggested as a leading cause of colon cancer.

In mammalian cells, base excision repair can proceed through at least two pathways distinguished by the repair patch size as well as by the contribution of different proteins involved in the pathway. These are designated as "single nucleotide (SN)-base excision repair" and "multinucleotide or long-patch (LP)-base excision repair" pathways. In both pathways, repair is initiated by the initial recognition and removal of the modified base by a DNA glycosylase generating an abasic site (AP-site). There are two types of DNA glycosylases—monofunctional and bifunctional. Monofunctional DNA glycosylases cleave only the glycosidic bond between N and C1' and then protect the abasic site until apurinic/apyrimidinic (AP) endonuclease 1 (APE-1) cleaves the DNA backbone at the 5'-end of the AP-site. The bifunctional DNA glycosylases have additional AP-lyase activity. The DNA glycosylase cleaves a glycosidic bond between the sugar and the base to establish an abasic-site. Subsequently, APE-1 cleaves the DNA backbone generating a 3'-OH and 5'-deoxyribose phosphate (5'-dRP) ends. Subsequently, the remaining 5'-dRP residue is cleaved by a 5'-deoxyribose phosphate lyase (dRP-lyase) activity of pol-β to yield a 5'-phosphorylated gapped-DNA strand. Pol-β then incorporates the correct base at the site of the damaged base with its polymerizing activity and DNA ligase-I or III seals the nick. This repair process becomes complicated once the AP-site is oxidized or reduced. In this case, the dRP-lyase activity of pol-β is interrupted and the repair of DNA is accomplished through long patch-base excision repair. Under these circumstances, the pol-β-dependent strand-displacement synthesis generates longer repair patch and a 5'-overhang of a single-stranded DNA-flap with a modified sugar at its 5'-end. The 5'-overhang DNA-flap is cleaved by flap endonuclease 1 (Fen-1), and finally the nick is sealed by DNA ligase I or III.

Pol-β

Pol-β is the smallest eukaryotic DNA polymerase. It is a 39-kDa protein and consists of an 8-kDa amino-terminal domain with dRP-lyase and 5'-phosphate recognition activities, and a 31-kDa carboxyl-terminal domain with nucleotidyltransferase activity (Beard et al., (2006) *Chem. Rev.* 106, 361-382). The 8- and 31-kDa domains of poi-β are connected by a protease-hypersensitive region, known as the linker-region (Kumar et al., (1990) *Biochemistry* 29, 7156-7159; Beard, W. A., and Wilson, S. H. (1995) *Methods Enzymol.* 262, 98-107). Pol-β has the ability to fill short DNA gaps, but lacks an associated exonuclease or proofreading activity (Singhal, R. K., and Wilson, S. H. (1993) *J. Biol. Chem.* 268, 15906-15911). The 31-kDa carboxyl-terminal polymerase domain is composed of three functionally distinguishable subdomains. First, the catalytic C-subdomain, which coordinates two divalent metal cations, assists the nucleotidyl transferase reaction in base excision repair. Second, the D-subdomain which has a primary role in duplex DNA-binding; and the N-subdomain provides interactions with the nascent base pair (nucleoside 5'-triphosphate and templating nucleotide) (Beard et al., (2006) *Chem. Rev.* 106, 361-382). These subdomains correspond to the palm, thumb, and fingers subdomains, respectively, for right-handed DNA polymerases (Beard et al., (2006) *Chem. Rev.* 106, 361-382, 35).

The crystal and solution structures of the amino-terminal 8-kDa lyase domain (amino acids 1-87) have been determined (Pelletier et al., (1994) *Science* 264, 1891-1903, Liu et al., (1996) *Biochemistry* 35, 6188-6200). This domain is composed of two pairs of antiparallel α-helices and possesses the dRP-lyase activity. The lyase domain also contains a motif termed "Helix-hairpin-Helix (HhH)", which is common in many other DNA repair proteins (Pelletier, H., and Sawaya, M. R. (1996) *Biochemistry* 35, 12778-12787). Biochemical and crystallography studies indicate that Lys72 plays a role in the lyase reaction mechanism. This reaction proceeds via a Schiff-base intermediate between pol-β and the 5'-dRP residue of the substrate, whereby the side chain of Lys72 provides the nucleophile for the completion of the reaction. The involvement of the lyase domain in strand-displacement synthesis of pol-β remains to be identified.

As reported in more detail below, the interaction of APC with pol-β was characterized. This characterization suggested a role for APC in regulating both long patch- and single nucleotide-base excision repair pathways. The interaction of APC with pol-β was mapped, and residues Thr79, Lys81 and Arg83 of the linker-region of pol-β protein were discovered to function in the interaction with APC. Interaction of APC with pol-β blocks both strand-displacement DNA synthesis as well as the dRP-lyase activity of pol-β. The mutational analysis of pol-β identified the role of APC in the base excision repair function of pol-β. These findings describe a novel role for APC in the control of both long patch- and single nucleotide-base excision repair activities and suggest a function of the linker-region of pol-β in base excision repair activity.

Base Excision Repair as a Chemotherapeutic Target

Defects in the base excision repair pathway can cause cytotoxic accumulation of lesions in cell genomic DNA. This accumulation of lesions has been exploited as a chemotherapeutic target for killing cancer cells. DNA-alkylating agents are commonly used to induce genetic lesions in cancer cells for the treatment of brain tumors, ovarian cancer, malignant melanomas, and various hematological tumors. These DNA-alkylating agents have either one or two reactive groups that interact covalently with nucleophilic centers in DNA. Such reactive sites are present in all four bases, and they are attacked with different affinities and specificities. Most reactive sites are the ring nitrogen atoms—in particular $N^7$ of guanine ($N^7$mG) and $N^3$ of adenine ($N^3$mA), but alkylation also occurs at less nucleophilic oxygens, such as the $O^6$ position of guanine ($O^6$mG). The $N^7$mG and $N^3$ mA are very common lesions and under normal circumstances they are repaired by base excision repair. Although a number of pol-β inhibitors have been reported, more potent and selective inhibitors of DNA pol-β are still needed. One approach to the identification of such agents is to sensitize cancer cells to DNA-damaging agents by inhibiting various proteins in the DNA repair pathways. Small chemical compounds have been identified by molecular docking or NMR studies to target the base excision repair pathway by inhibiting apurinic/apyrimidinic endonuclease and pol-β activities. For pol-β, the most active compound identified by NMR chemical shift mapping is pamoic acid. This compound inhibits dRP-lyase activity, blocks only single nucleotide-base excision repair of pol-β, which occurs at a high concentration. Since abasic DNA damage can also be repaired by long patch-BER, there is a need for agents that can block both pol-β directed single nucleotide- and long patch-base excision repair pathways. As reported below, APC interacts with pol-β and blocks both SN- and LP-BER pathways. Thus, APC and APC mimetics may be used to target pol-β-mediated sensitization of colon cancer cells.

Compounds of the Invention

Compounds, such as NSC-124854 and NSC-666715, and other compounds that bind to amino acid residues of Pol-β that function in mediating the interaction of Pol-β with APC (e.g., Thr79, Lys81 and Arg83) are useful for the treatment of neoplasias, such as glioblastomas, lung cancer, and colon cancer, alone or in combination with an alkylating agent, such as temozolamide. Without wishing to be bound by theory, these compounds may be particularly effective against neoplastic cells because they are capable of interacting with and reducing the activity of pol-β. In one approach, compounds useful for the treatment of neoplasia are selected using a molecular docking program to identify compounds that bind to pol-β at an APC binding site (e.g., a pol-β site comprising at least amino acid residues Thr79, Lys81 and Arg83). In certain embodiments, a compound of the invention binds to pol-β and reduces BER activity, pol-β-directed dRP-lyase activity, or pol-β-directed strand-displacement synthesis.

In certain embodiments, a compound of the invention can prevent, inhibit, or disrupt, or reduce by at least 10%, 25%, 50%, 75%, or 100% the activity of a BER pathway by binding to an APC binding site in pol-β.

In certain embodiments, a compound of the invention is a small molecule having a molecular weight less than about 1000 daltons, less than 800, less than 600, less than 500, less than 400, or less than about 300 daltons. Examples of compounds of the invention include NSC-124854 and NSC-666715, and pharmaceutically acceptable salts thereof.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, e.g., NSC-124854 and NSC-666715 having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

In Silico Screening Methods and Systems

In another aspect, the invention provides a machine readable storage medium which comprises the structural coordinates of an APC binding site in pol-β identified herein (e.g., aminio acids 60-120, 60-170, 80-170, or another fragment containing Thr79, Lys81 and Arg83). A storage medium encoded with these data is capable of displaying a three-dimensional graphical representation of a molecule or molecular complex which comprises such binding sites on a computer screen or similar viewing device.

The invention also provides methods for designing, evaluating and identifying compounds that bind to the aforementioned binding site. Such compounds are expected to be cytotoxic, to inhibit pol-β biological activity (e.g., pol-β-directed dRP-lyase activity, pol-β-directed strand-displacement synthesis) and/or to reduce the activity of a BER pathway. The invention provides a computer for producing a) a three-dimensional representation of a molecule or molecular complex, wherein said molecule or molecular complex comprises a binding site; or b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms, wherein said computer comprises:

(i) a machine-readable data storage medium comprising a data storage material encoded with machine-readable data, wherein said data comprises the structure coordinates of amino acid residues in the pol-β APC binding site;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding site.

In another embodiment, the invention provides a computer for producing a three-dimensional representation of a molecule or molecular complex defined by structure coordinates of all of the pol-β amino acids, or a three-dimensional representation of a homologue of said molecule or molecular complex, wherein said homologue comprises a binding site that has a root mean square deviation from the backbone atoms of said amino acids of not more than 2.0 (more preferably not more than 1.5) angstroms In exemplary embodiments, the computer or computer system can include components that are conventional in the art, e.g., as disclosed in U.S. Pat. Nos. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in a manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising an APC binding site may be used for a variety of purposes, such as drug discovery.

For example, the structure encoded by the data may be computationally evaluated for its ability to associate with chemical entities. Chemical entities that associate with a binding site of a pol-β protein are expected to be toxic to neoplastic cells (e.g., glioblastoma, lung cancer, colon cancer cells), to inhibit base excision repair, or to enhance the efficacy of an alkylating agent. Such compounds are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding site defined by structure coordinates of pol-β, as described herein, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:
i) employing computational means to perform a fitting operation between the chemical entity and a binding site of the pol-β polypeptide or fragment thereof or molecular complex; and
ii) analyzing the results of the fitting operation to quantify the association between the chemical entity and the APC binding site. This embodiment relates to evaluating the potential of a chemical entity to associate with or bind to a binding site of a pol-β polypeptide or fragment thereof.

The term "chemical entity", as used herein, refers to chemical compounds, complexes of at least two chemical compounds, and fragments of such compounds or complexes.

In certain embodiments, the method evaluates the potential of a chemical entity to associate with a molecule or molecular complex defined by structure coordinates of all of the amino acids of pol-β protein, as described herein, or a homologue of said molecule or molecular complex having a root mean square deviation from the backbone atoms of said amino acids of not more than 2.0 (more preferably not more than 1.5) angstroms.

In a further embodiment, the structural coordinates one of the binding sites described herein can be utilized in a method for identifying an antagonist of a molecule comprising a APC binding site (e.g., a binding site within the pol-β sequence). This method comprises the steps of:
a) using the atomic coordinates of pol-β;
b) employing the three-dimensional structure to design or select the potential agonist or antagonist. The method further includes the optional steps of c) synthesizing the agonist or antagonist; and d) contacting the agonist or antagonist with the molecule to determine the ability of the potential agonist or antagonist to interact with the molecule. If desired, the method further involves the step of contacting a neoplastic cell (e.g., glioblastoma cell) with a pol-β binding compound and evaluating cytotoxicity in the presence or the absence of an alkylating agent, evaluating neoplastic cell proliferation, cell death, or BER activity.

In another embodiment, the invention provides a method for identifying a potential antagonist of pol-β polypeptide, the method comprising the steps of:

a) using the atomic coordinates of the pol-β polypeptide (e.g., APC binding site sequence, including at least about Thr79, Lys81 and Arg83 amino acid residues of Pol-β, or other residues that mediate the interaction of Pol-β with APC); and b) employing the three-dimensional structure to design or select the potential antagonist.

The present inventors' elucidation of a heretofore unknown APC binding site of a pol-β polypeptide provides the necessary information for designing new chemical entities and compounds that may interact with pol-β proteins, in whole or in part, and may therefore modulate (e.g., inhibit) the activity of pol-β proteins.

The design of compounds that bind to a pol-β sequence, that are cytotoxic to a neoplastic cell, or that reduce pol-β expression or biological activity, according to this invention generally involves consideration of several factors. In one embodiment, the compound physically and/or structurally associates with at least a fragment of a pol-β polypeptide, such as an APC binding site within a pol-β sequence. Non-covalent molecular interactions important in this association include hydrogen bonding, van der Waals interactions, hydrophobic interactions and electrostatic interactions. Desirably, the compound assumes a conformation that allows it to associate with the APC binding site(s) directly. Although certain portions of the compound may not directly participate in these associations, those portions of the entity may still influence the overall conformation of the molecule. This, in turn, may have a significant impact on the compound's potency. Such conformational requirements include the overall three-dimensional structure and orientation of the chemical compound in relation to all or a portion of the binding site, or the spacing between functional groups comprising several chemical compound that directly interact with the binding site or a homologue thereof.

The potential inhibitory or binding effect of a chemical compound on a pol-β APC binding site may be analyzed prior to its actual synthesis and testing by the use of computer modeling techniques. If the theoretical structure of the given compound suggests insufficient interaction and association between it and the target binding site, testing of the compound is obviated. However, if computer modeling indicates a strong interaction, the molecule is synthesized and tested for its ability to bind a pol-β sequence or to test its biological activity by assaying for example, cytotoxicity in a neoplastic cell, by assaying an increase in the efficacy of an alkylating agent in a neoplastic cell. Candidate compounds may be computationally evaluated by means of a series of steps in which chemical entities or fragments are screened and selected for their ability to associate with the APC binding site.

One skilled in the art may use one of several methods to screen chemical compounds, or fragments for their ability to associate with a APC binding site. This process may begin by visual inspection of, for example, a APC binding site on the computer screen based on the a pol-β structure coordinates described herein, or other coordinates which define a similar shape generated from the machine-readable storage medium. Selected fragments or chemical compounds are then positioned in a variety of orientations, or docked, within that binding site as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding site.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention (see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modem Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology 4, pp. 777-781 (1994)).

Once a compound has been designed or selected, the efficiency with which that entity may bind to a binding site may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein (see, e.g., Examples). Many thousands of compounds can be rapidly screened and the best virtual compounds can be selected for further screening (e.g., by synthesis and in vitro or in vivo testing). Small molecule databases can be screened for chemical entities or compounds that can bind, in whole or in part, to an APC binding site. In this screening, the quality of fit of such entities to the binding site may be judged either by shape complementarity or by estimated interaction energy.

A computer for producing a three-dimensional representation of a) a molecule or molecular complex, wherein said molecule or molecular complex comprises a binding site in the linker sequence of a pol-β polypeptide defined by structure coordinates of amino acid residues in the APC binding site; or b) a three-dimensional representation of a homologue of said molecule or molecular complex, wherein said homologue comprises a binding site that has a root mean square deviation from the backbone atoms of said amino acids of not more than about 2.0 (more preferably not more than 1.5) angstroms, wherein said computer comprises:

(i) a machine-readable data storage medium comprising a data storage material encoded with machine-readable data, wherein said data comprises the structure coordinates of structure coordinates of amino acid residues in the APC binding site of a pol-β polypeptide;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation. As described in the Examples, compounds identified using in silico methods may optionally be tested in vitro or in vivo, for example, using the "Additional Screening Methods" described below, or any other method known in the art.

Additional Screening Methods

As described above, the invention provides specific examples of chemical compounds that are cytotoxic to neoplastic cells when administered alone or in combination with an alkylating agent. However, the invention is not so limited. The invention further provides a simple means for identifying agents (including nucleic acids, peptides, small molecule inhibitors, and mimetics) that are capable of binding to a pol-β polypeptide, for example, binding to an APC binding site, and that are cytotoxic to a neoplastic cell, particularly when administered in combination with an alkylating agent or other chemotherapeutic. Such compounds are also expected to be useful for the treatment or prevention of a neoplasia (e.g., colon cancer, glioblastoma, lung cancer).

In particular, based in part on the discovery that agents that bind to pol-β at an APC binding site reduce the activity of a BER pathway, such agents are likely useful as therapeutics for the treatment or prevention of a neoplasia.

Virtually any agent that specifically binds to a pol-β polypeptide and that reduces BER activity may be employed in the methods of the invention. Methods of the invention are useful for the high-throughput low-cost screening of candidate agents that reduce, slow, or stabilize the growth or proliferation of a neoplasia. A candidate agent that specifically binds to pol-β is then isolated and tested for activity in an in vitro assay or in vivo assay for its ability to reduce neoplastic cell proliferation, increase the efficacy of an alkylating agent, and/or increase neoplastic cell death. One skilled in the art appreciates that the effects of a candidate agent on a cell is typically compared to a corresponding control cell not contacted with the candidate agent. Thus, the screening methods include comparing the proliferation of a neoplastic cell contacted by a candidate agent to the proliferation of an untreated control cell.

In other embodiments, the expression or activity of pol-β in a cell treated with a candidate agent is compared to untreated control samples to identify a candidate compound that decreases the expression or biological activity of a pol-β polypeptide in the contacted cell. Polypeptide expression or activity can be compared by procedures well known in the art, such as Western blotting, flow cytometry, immunocytochemistry, binding to magnetic and/or pol-β-specific antibody-coated beads, in situ hybridization, fluorescence in situ hybridization (FISH), ELISA, microarray analysis, RT-PCR, Northern blotting, or colorimetric assays, such as the Bradford Assay and Lowry Assay.

In one working example, one or more candidate agents are added at varying concentrations to the culture medium containing a neoplastic cell. An agent that binds in an APC binding site of pol-β or that reduces the expression or activity of a pol-β protein expressed in the cell is considered useful in the invention; such an agent may be used, for example, as a therapeutic to prevent, delay, ameliorate, stabilize, or treat a neoplasia. Once identified, agents of the invention (e.g., agents that specifically bind to and/or antagonize pol-β) may be used to treat a neoplasia. An agent identified according to a method of the invention is locally or systemically delivered to treat a neoplasia in situ.

If one embodiment, the effect of a candidate agent may, in the alternative, be measured at the level of pol-β polypeptide production using the same general approach and standard immunological techniques, such as Western blotting or immunoprecipitation with an antibody specific for pol-β. For example, immunoassays may be used to detect or monitor the expression of pol-β in a neoplastic cell. In one embodiment, the invention identifies a polyclonal or monoclonal antibody (produced as described herein) that is capable of binding to a pol-β APC binding site and reducing the biological activity of a pol-βpolypeptide. A compound that reduces the expression or activity of a pol-P polypeptide is considered particularly useful. Again, such an agent may be used, for example, as a therapeutic to prevent or treat a neoplasia.

Alternatively, or in addition, candidate compounds may be identified by first assaying those that specifically bind to and antagonize a pol-β polypeptide of the invention and subsequently testing their effect on neoplastic cells as described in the Examples. In one embodiment, the efficacy of a candidate agent is dependent upon its ability to interact with the pol-β polypeptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate neoplastic cell proliferation may be assayed by any standard assays (e.g., those described herein). In one embodiment, division of neoplastic cells is determined by assaying BrdU incorporation using flow cytometry analysis. In another embodiment, pol-β expression is monitored immunohistochemically.

Potential pol-β antagonists include organic molecules, peptides, peptide mimetics, polypeptides, nucleic acid ligands, aptamers, and antibodies that bind to a pol-β polypeptide and reduce its activity. In one particular example, a candidate compound that binds to a pol-β polypeptide may be identified using a chromatography-based technique. For example, a recombinant pol-P polypeptide of the invention may be purified by standard techniques from cells engineered to express the polypeptide, or may be chemically synthesized, once purified the peptide is immobilized on a column. A solution of candidate agents is then passed through the column, and an agent that specifically binds the pol-β polypeptide or a fragment thereof is identified on the basis of its ability to bind to pol-β polypeptide and to be immobilized on the column. To isolate the agent, the column is washed to remove non-specifically bound molecules, and the agent of interest is then released from the column and collected. Agents isolated by this method (or any other appropriate method) may, if desired, be further purified (e.g., by high performance liquid chromatography). In addition, these candidate agents may be tested for their ability to reduce neoplastic cell proliferation or viability. Agents isolated by this approach may also be used, for example, as therapeutics to treat or prevent a neoplasia. Compounds that are identified as binding to a pol-β polypeptide with an affinity constant less than or equal to 1 nM, 5 nM, 10 nM, 100 nM, 1 μM or 10 μM are considered particularly useful in the invention.

Test Compounds and Extracts

In general, pol-β antagonists (e.g., agents that specifically bind and reduce the activity of a pol-β polypeptide) are identified from large libraries of natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Agents used in screens may include known those known as therapeutics for the treatment of a neoplasia. Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, *Protective Groups in Organic Synthesis,* 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have pol-β binding activity further fractionation of the positive lead extract is necessary to isolate molecular constituents responsible for the observed effect. Thus, the goal of the extraction, fractionation, and purification process is the careful characterization and identification of a chemical entity within the crude extract that reduces neoplastic cell proliferation or viability. Methods of fractionation and purification of such heterogenous extracts are known in the art. If desired, compounds shown to be useful as therapeutics are chemically modified according to methods known in the art.

Pharmaceutical Therapeutics

In other embodiments, agents discovered to have medicinal value using the methods described herein are useful as a drug or as information for structural modification of existing compounds, e.g., by rational drug design. Such methods are useful for screening agents having an effect on a neoplasia.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound. A compound is administered at a dosage that is cytotoxic to a neoplastic cell, that reduces pol-β expression or biological activity, or that reduces the proliferation, survival, or invasiveness of a neoplastic cell as determined by a method known to one skilled in the art, or using any that assay that measures the expression or the biological activity of a pol-β polypeptide.

Formulation of Pharmaceutical Compositions

The administration of a compound for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active anti-neoplasia therapeutic substance). The coating may be applied on the solid dosage form in a similar manner as that described in Encyclopedia of Pharmaceutical Technology, supra.

At least two anti-neoplasia therapeutics may be mixed together in the tablet, or may be partitioned. In one example, the first active anti-neoplasia therapeutic is contained on the inside of the tablet, and the second active anti-neoplasia therapeutic is on the outside, such that a substantial portion of the second anti-neoplasia therapeutic is released prior to the release of the first anti-neoplasia therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil.

Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active anti-neoplasia therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

The present invention provides methods of treating neoplastic disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a neoplastic disease or disorder or symptom thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplastic disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which pol-β may be implicated.

In one embodiment, the invention provides a method of monitoring treatment progress. The method includes the step of determining a level of diagnostic marker (Marker) (e.g., any target delineated herein modulated by a compound herein, a protein or indicator thereof; etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

Optionally, an anti-neoplasia therapeutic, such as NSC-124584 and NSC-666715, may be administered in combination with any other standard anti-neoplasia therapy or conventional chemotherapeutic agent, such as an alkylating agent; such methods are known to the skilled artisan and described in Remington's Pharmaceutical Sciences by E. W. Martin. If desired, agents of the invention are administered in combination with any conventional anti-neoplastic therapy, including but not limited to, surgery, radiation therapy, or chemotherapy. Conventional chemotherapeutic agents include, but are not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine. In one preferred embodiment, an agent that binds to an APC binding site on pol-P (e.g., APC or an APC mimetic, such as NSC-124584 and NSC-666715) is administered in combination with temozolomide.

Kits or Pharmaceutical Systems

The present compositions may be assembled into kits or pharmaceutical systems for use in ameliorating a neoplasia. Kits or pharmaceutical systems according to this aspect of the invention comprise a carrier means, such as a box, carton, tube or the like, having in close confinement therein one or more container means, such as vials, tubes, ampoules, bottles and the like. The kits or pharmaceutical systems of the invention may also comprise associated instructions for using the agents of the invention. Kits of the invention include at least one or more agents that bind to an APC binding site on pol-β or that reduce pol-P or BER pathway activity (e.g., APC or an APC mimetic, such as NSC-124584 and NSC-666715). If desired, the kit also includes an alkylating agent, such as temozolomide. Optionally, the kit includes instructions for administering the alkylating agent in combination with one or more agents that bind to an APC binding site on pol-β or that reduce pol-β or BER pathway activity, thereby increasing the efficacy of the alkylating agent relative to the efficacy of the alkylating agent administered alone. Methods for measuring the efficacy of alkylating agents are known in the art and are described herein (e.g., measuring the $IC_{50}$).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Adenomatous polyposis coli (APC), a tumor suppressor, is known to play a diversified role in cell migration, cell-cell adhesion, β-catenin regulation, cellular proliferation and chromosomal segregation. Mutations in the APC gene are associated with an early onset of colorectal carcinogenesis.

Example 1

Role of APC in Base Excision Repair

Figure 3:
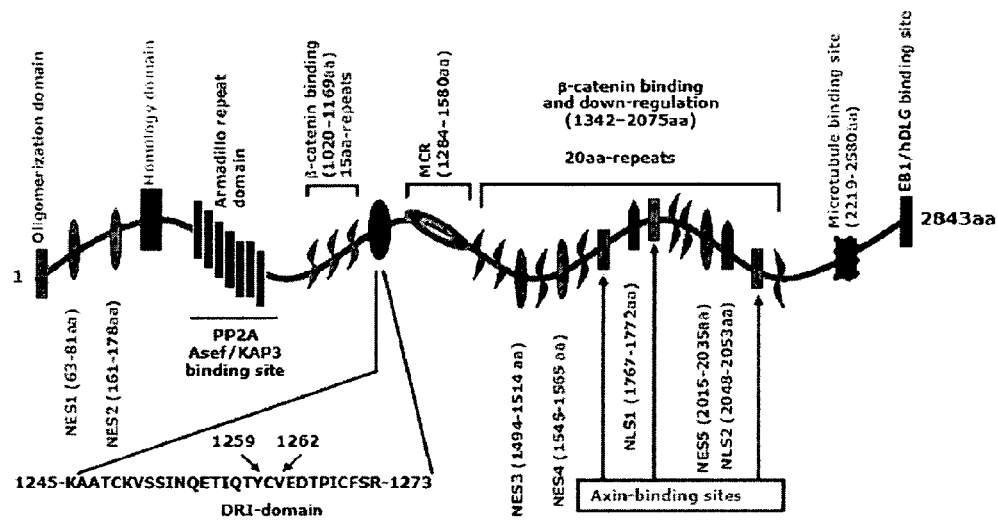
FIG. 3 is a schematic representation of the structure of APC. The 2843 amino acid sequence displays an armadillo domain near the N-terminus. There are two β-catenin binding domains. The first 15-amino acid repeat can bind β-catenin, but its functional significance is still obscure, while the 20-amino acid repeat can bind β-catenin with a high affinity upon phosphorylation. The DRI-domain (SEQ ID NO: 21) is just upstream of mutation cluster region (MCR), which is involved in the regulation of base excision repair pathway. Terms used in the figures are defined as follows: Asef, APC-stimulated guanine nucleotide exchange factor; DLG, *Drosophila* discs large; EB1, end-binding protein 1, KAP3A, kinesin superfamily-associated protein 3A; NES, nuclear export signal; NLS, nuclear localization signal; PP2-B56alpha, protein phosphates 2A B56α subunit.

A PCNA-interacting protein (PIP)-like box Qxx(h)xx(aa) in APC (amino acids 1256Q, 1259I and 1262Y) was identified in APC. Site-directed mutagenesis identified amino acid residues 1259I and 1262Y of APC as important for the interaction and functional activity of pol-β. This interacting domain of APC was thus identified as a DNA repair inhibitory (DRI)-domain. Most common mutations in the APC gene occur in the MCR region and produce a truncated protein, which has compromised function and contributes to chromosomal instability. The DRI-domain of APC is located in the N-terminal region and is spared by MCR (FIG. 3). Thus, the wild-type or mutant APC protein (with intact DRI-domain) contributes to base excision repair (FIGS. 2 and 3). To determine the mechanism by which APC blocks base excision repair activities, a series of in vitro and in vivo experiments was performed showing that APC blocks single nucleotide- and long patch-base excision repair by blocking dRP-lyase and strand-displacement activities of pol-β. The biological significance of APC-mediated blockage of alkylation damage-induced single nucleotide- and long patch-base excision repair activities was addressed. Cigarette smoke condensate (CSC), a surrogate of cigarette smoke, induced APC gene expression, blocked long patch-base excision repair and contributed to the transformation of spontaneously immortalized normal breast epithelial cells (Kundu et al., (2006) *Oncogene* (August 21; [Epub ahead of print] PMID: 16924228). The induced levels of APC in mouse embryonic fibroblast cells block long patch-base excision repair and increase apoptosis after MMS treatment. These studies suggested a role of APC in DNA damage-induced apoptosis.

Example 2

APC Binds with the Linker-Region of 8-kDa Domain of Pol-β

Abasic sites in DNA are induced by stressors, such as spontaneous oxidation/reduction, alkylation, and temperature changes. Abasic sites are repaired primarily by single-nucleotide (SN)- or long-patch (LP)-base excision repair pathways. In order to map the region of pol-β used to interact with APC, deletion constructs of pol-β were made through PCR amplification and cloned into the pGAD-C3 vector. These constructs were then used in a yeast two-hybrid analysis with APC wild-type (wt) and mutant APC (I-A,Y-A) expression plasmids (FIG. 5A). An interaction of APCwt, but not of APC(I-A,Y-A) with pol-βwt was observed (FIG. 5B, compare slice 1 with 2, respectively). The interaction of pol-βwt with proliferating cell nuclear antigen (PCNA)wt served as positive control (FIG. 5B, slice 11). Results with PCNAwt were consistent with previous findings. The pol-β wt alone was used in the assay to determine the background growth of the yeast cells (FIG. 5B, slice 12). A positive interaction of APCwt was observed with polβ (60-120) and polβ (80-170) constructs (FIG. 5B, slices 3 and 5, respectively). Other pol-β constructs such as polβ (140-200) and polβ (160-250) did not show interaction with APCwt. These results indicated that the interaction domain of pol-β with APC is located within the stretch of residues 80-120.

To further identify residues of pol-β that might be involved in the interaction with APC, the solvent surface accessibility of residues suspected from the yeast two-hybrid analysis to interact with APC was examined. Since the crystal structure of APC has not been solved, it was not feasible to identify probable interactions through possible docking modes. The crystal structure of a substrate complex of pol-β indicates that it is composed of two-domains with distinct enzymatic activities necessary for single nucleotide-base excision repair: an amino-terminal lyase domain and a carboxyl-terminal polymerase domain (FIG. 4A) (Beard, W. A., and Wilson, S. H. (2006) *Chem. Rev.* 106, 361-382). Residues suspected of interacting with APC are in a stretch of amino acids (80-120) that connect these domains. From the structure of the ternary substrate complex (Batra, V. K., Beard, W. A., Shock, D. D., Krahn, J. M., Pedersen, L. C., and Wilson, S. H. (2006) *Structure* 14, 757-766), two regions—Set-1 (amino acid Thr79, Lys81 and Arg83) and Set-2 (amino acid Arg89, Gln90 and Asp92) were identified that exhibited high solvent accessibility (FIGS. 4B and 4C, respectively). The protein backbone of this region was observed in several conformations depending on the liganded state of pol-β (Beard, W. A., and Wilson, S. H. (1998) *Chem. Biol.* 5, R7-13). Alteration of the backbone dynamics of this region was expected to affect pot-B-dependent substrate binding and/or catalysis. Alanine (A) mutations in Set-1 and Set-2 amino acids (FIGS. 4A and 4B) were introduced by site-directed mutagenesis and the role of these amino acids in the interaction with APC was defined in yeast two-hybrid analysis (FIGS. 6A and 6B). Appropriate positive and negative controls were run to validate the assay conditions. Results showed that the Set-1 mutant (pol-βMut-1) abolished the interaction of pol-β with APC (FIG. 6, slice 3). Mutations in Set-2 (pol-βMut-2) showed no effect (FIG. 6, slice 2). From these results it became clear that the amino acid residues Thr79, Lys81 and Arg83 of pol-β function in the interaction with APC, and likely play a role in the mechanism of APC-mediated blockage of pol-β activity.

Example 3

Pol-βMut-1 Mimics APC-Dependent Blockage of Strand-Displacement Synthesis of Long Patch-Base Excision Repair To determine the effect of APC on strand-displacement synthesis of long patch-base excision repair, $^{32}$P-F-DNA was used as a substrate in a reconstituted in vitro base excision repair assay system. In F-DNA, an AP-site analog is inserted at the $24^{th}$ position of the 63-mer oligonucleotide and does not serve as a substrate for the dRP-lyase reaction necessary for single nucleotide-base excision repair. Accordingly, the F-residue must be removed by long patch-base excision repair pathway (Jaiswal, A. S., Bloom, L. B., and Narayan, S. (2002) *Oncogene* 21, 5912-5922). Different concentrations of either APCwt or APC(I-A,Y-A) mutant peptides were incubated with pol-βwt and strand-displacement synthesis was assayed (FIG. 7A). A dose-dependent decrease in strand-displacement synthesis was observed in the presence of APCwt, but not with APC(I-A,Y-A) (FIG. 7B, compare lane 3 with 4-6 and 7-9, respectively). Interestingly, pol-β-mediated single-nucleotide incorporation was unaffected by either APCwt pr APC(I-A,Y-A) peptides. These results also indicated that strand-displacement synthesis was blocked by APCwt (Jaiswal, A. S., Balusu, R., Armas, M. L., Kundu, C. N., and Narayan, S. (2006) *Biochemistry* 45, 15903-15914; Narayan, S., Jaiswal, A. S., and Balusu, R. (2005) *J. Biol. Chem.* 280, 6942-6949).

Figure 8:
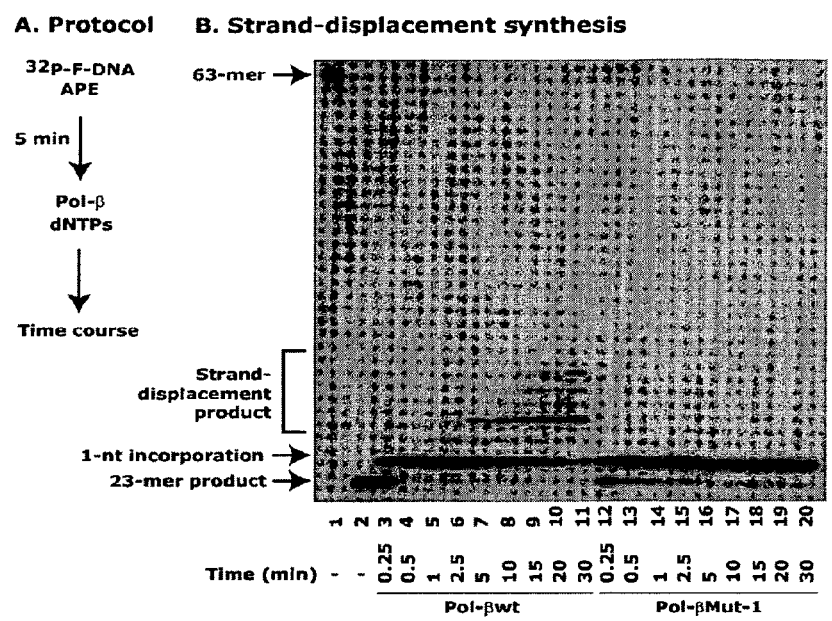
FIGS. 8A and 8B show that Pol-βMut-1 blocks strand-displacement synthesis in a time-dependent manner.

The determination that amino acid residues Thr79, Lys81 and Arg83 of pol-β (FIG. 9) were required for pol-β interaction with APC, suggested that these amino acid residues were likely to play a role in APC-mediated blockage of pol-β-directed strand-displacement synthesis. To test this hypothesis, His-tagged pol-βwt and polβMut-1 (T79A/K81A/R83A) proteins were overexpressed and purified. These wild-type and mutant pol-β proteins were then used in a strand-displacement assay where $^{32}$P-F-DNA was used as a substrate (FIG. 8A). The results of this assayed showed that strand-displacement synthesis with pol-βwt protein was carried out in a time-dependent (FIG. 8B, compare lane 2 with 3-11) and concentration-dependent manner (FIG. 9B, compare lane 2 with 3-5). In contrast, the pol-βMut-1 completely abolished the strand-displacement synthesis in both time- (FIG. 8B, compare lane 2 with 12-20) and concentration-dependent assay conditions (FIG. 8B, compare lane 2 with 6-8). Interestingly, the single-nucleotide incorporation activity of pol-β with a $^{32}$P-F-DNA substrate was unaffected and was similar to the effect of APC as shown in FIG. 7B (lane 4-6). Thus, these results indicated that the Set-1-amino acids of pol-β were required for both physical and functional interactions with APC.

Example 4

Crystal Structure of DNA Polymerase β Provides the Basis for Structure-Based Molecular Docking of Small Chemical Compounds at the APC-Binding Site Desirably, agents identified according to the methods of the invention should be highly active against neoplasms and have few or no side effects. Preferably, agents identified according to the methods described herein are small molecules that may be used to prevent or treat a neoplasm or to enhance the activity of other anti-chemotherapeutic agents, including alkylating agents. In order to achieve these goals, the small chemical compound is designed to structurally interact with a selected target site. Having identified the site where APC interacts with pol-β, the structure surrounding this site can be used to blocks the activity of pol-β. Thus, a High Performance Computing and Simulation Method was used to screen 420,000 small chemical compounds that may fit at the APC-binding site of pol-β and block its activity. The NCI/DTP maintains a repository of these compounds (Monga M, Sausville EA. Developmental therapeutics program at the NCI: molecular target and drug discovery process. Leukemia 16: 520-526, 2002; Irwin J J, Shoichet B K. ZINC-a free database of commercially available compounds for virtual screening. J. Chem. Inf. Model. 45: 177-182, 2005). The three-dimensional coordinates for the NCI/DTP plated compound set was obtained in the MDLSD format and converted to the mol2 format by the DOCK utility program SDF2MOL2 (UCSF). Partial atomic charges, solvation energies and van der Waals parameters for the ligands were calculated using SYBDB (Tripos, Inc.) and added to the plated compound set mol2 file. All docking calculations were performed with the DOCK6 development version of DOCK (Charifson P S, Corkery J J, Murcko M A, Walters W P. Consensus scoring: A method for obtaining improved hit rates from docking databases of three-dimensional structures into proteins. J. Med. Chem. 42: 5100-5109, 1999; Ewing T J, Makino S, Skillman A G, Kuntz I D. DOCK 4.0: search strategies for automated molecular docking of flexible molecule databases. J. Computer-Aided Mol. Design. 15: 411-428, 2001). The general features of DOCK include rigid orienting of ligands to receptor spheres, AMBER energy scoring, GB/SA solvation scoring, contact scoring, internal non-bonded energy scoring, ligand flexibility and both rigid and torsional simplex minimization (Good A C, Ewing T J, et al. New molecular shape descriptors: application in database screening. J. Computer-Aided Mol. Design. 9: 1-12, 1995; Gschwend D A, Good A C, Kuntz I D. Molecular docking towards drug discovery. J. Mol. Recognit. 9: 175-186, 1996).

The crystal structure of human pol-β (PDB code 1BPZ; FIGS. 22A-22BI) was utilized to provide the basis for molecular docking, which was previously used to identify a novel inhibitor of murine JAK2 in this manner (Sandberg E M, Ma X, He K, Frank S J, Ostrov D A, Sayeski P P. Identification of 1,2,3,4,5,6-hexabromocyclohexane as a small molecule inhibitor of jak2 tyrosine kinase autophosphorylation [correction of autophosphorylation]. J. Med. Chem. 48: 2526-233, 2005). To prepare the site for docking, all water molecules were removed. The atomic coordinates of this structure are provided at FIGS. 22A-22BI. Protonation of pol-β residues was performed with SYBYL (Tripos, St. Louis, Mo.). Intermolecular AMBER energy scoring (vdw+columbic), contact scoring and bump filtering were implemented in DOCK5.1.0 (Gschwend D A, Good A C, Kuntz I D. Molecular docking towards drug discovery. J. Mol. Recognit. 9: 175-186, 1996). SETOR (Evans S V. SETOR: hardware-lighted three-dimensional solid model representations of macromolecules. J. Mol. Graphics. 11: 134-348, 127-128, 1993) and GRASP (Petrey D, Honig B. GRASP2: visualization, surface properties, and electrostatics of macromolecular structures and sequences. Meth. Enzymol. 374: 492-509, 2003) were used to generate molecular graphic images. Each of the small molecules was positioned in the selected site in 100 different orientations, and the best orientations and their scores (contact and electrostatic) were calculated. The scored compounds were ranked and the 30 highest scoring compounds were requested for functional evaluation. The most two active compounds NSC-124584 and NSC-666715, are shown in the selected site of pol-β in FIGS. 15A and 15B.

Example 5

Small Chemical Compounds CN1 and CN2 Block DNA Polymerase β-Directed dRP-Lyase Activity To determine whether small chemical compounds, which mimic the APC-binding to pol-β will inhibit pol-β-directed dRP-lyase activity just as APC does (FIGS. 13A and 13B), the activity of four chemical compounds identified in Example 4 were tested.

CN1=NSC124854
CN2=NSC666715
CN3=NSC21371
CN4=NSC91855

The structure of each of these is shown in FIG. 21. A representative dRP-lyase activity is shown in FIGS. 16A and 16B (Lane 2 shows the position of the dRP-lyase substrate and the lane 3 shows the pol-β-directed cleaved dRP-lyase product). Although CN3 and CN4 did not inhibit dRP-lyase activity (FIG. 16, compare lane 3 with 4-8 and 9-13, respectively), NSC-124584 and NSC-666715 successfully blocked dRP-lyase activity in a dose-dependent manner (FIG. 16, compare lane 3 with 14-18 and 19-23, respectively). Since the dRP-lyase is a rate-limiting step in single nucleotide base extension repair, this suggests that NSC-124584 and NSC-666715 block single nucleotide base extension repair by blocking dRP-lyase activity.

Example 6

Figure 17:
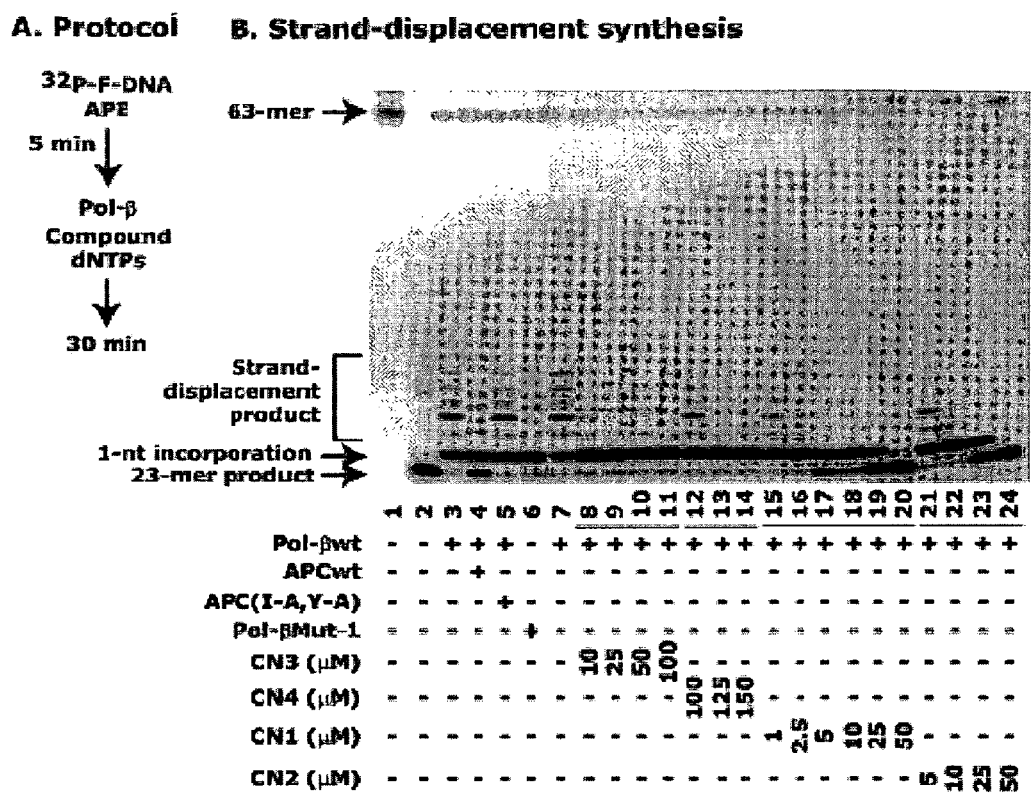
FIGS. 17A and 17B show that NSC-124584 and NSC-666715 block pol-β-directed strand-displacement synthesis.

Small Chemical Compounds NSC-124584 and NSC-666715 Block DNA Polymerase β-Directed Strand-Displacement Synthesis To determine the effect of small chemical compounds on strand-displacement synthesis, $^{32}$P-F-DNA was used as a substrate in a reconstituted in vitro base excision repair assay system (Jaiswal A S, Bloom L B, Narayan S. Long-patch base excision repair of apurinic/apyrimidinic site DNA is decreased in mouse embryonic fibroblast cell lines treated with plumbagin: involvement of cyclin-dependent kinase inhibitor p21Waf-1/Cip-1. Oncogene 21: 5912-5922, 2002). APCwt and APC(I-A,Y-A) mutant peptide or different concentrations of NSC-124584, NSC-666715, CN3 and CN4 were incubated with pol-β wt protein and the strand-displacement synthesis was assayed (FIG. 17A). A representative autoradiogram is shown in FIG. 17B. First, the effect of different controls on pol-β-directed strand-displacement synthesis was examined. Results in lane 1 and 2 show the $^{32}$P-labeled 63-mer F-DNA and APE cut 23-mer product, respectively. Results in lane 3 show the strand displacement synthesis, which is blocked by APCwt (lane 4), but not by APC(I-A,Y-A) mutant peptide (lane 5). The pol-β Mut-1 (T79A/K81A/R83A) also blocked the strand-displacement synthesis (compare lane 6 with 3). Next, the effect of small chemical compounds, which mimic the binding of APC on pol-β on the strand-displacement synthesis, was determined. The results showed a dose-dependent decrease in the strand-displacement synthesis in the presence of CN3 (compare lane 7 with 8-11), CN4 (compare lane 7 with 12-14), NSC-124584 (compare lane 7 with 15-20) and NSC-666715 (compare lane 7 with 8-11), respectively. Among the four compounds tested, CN1 and CN2 were most potent. These two compounds inhibited the strand-displacement synthesis at lower concentrations. Interestingly, pol-β-directed single-nucleotide incorporation was unaffected by both Compound CN3 and CN4 at all the concentrations tested; however, it was inhibited by and NSC-666715 at 50 μM concentration (see lane 20 and 24, respectively). These results suggest that NSC-124584 and NSC-666715 completely blocked the DNA synthesis (1-nt and strand-displacement) as well as dRP-lyase activity (FIGS. 16A and 16B) of pol-β. Thus, these are useful as APC function mimetics in vivo and are likely to be useful as chemotherapeutics.

The effect of NSC-124584 and NSC-666715 on single nucleotide- and long patch-base excision repair activities was determined using a reporter plasmid based in vivo excision repair assay. Multiple cytosine (C) residues of the p21(Waf1/Cip1)-luciferase promoter DNA were randomly modified into uracil (U) residues (U-p21P; a substrate for SP-BER). This plasmid DNA was further treated with uracil-DNA glycosylase (UDG) and then with sodium borohydride to create a reduced abasic p21P (R-p21P) substrate for LP-BER. Modification of DNA by this technique is described in (Jaiswal A S, Bloom L B, Narayan S. Long-patch base excision repair of apurinic/apyrimidinic site DNA is decreased in mouse embryonic fibroblast cell lines treated with plumbagin: involvement of cyclin-dependent kinase inhibitor p21 Waf-1/Cip-1. Oncogene 21: 5912-5922, 2002). The principle behind this assay is that the modified p21P plasmid when transfected into cells should show poor promoter activity as compared to the unmodified p21P plasmid. The promoter activity is restored if the modified DNA is allowed to go through DNA repair process(es) in the cell. The assay is quick, sensitive and quantitative. To determine the effect of residues Leu77, Gly80 and Lys81 on pol-β-mediated SN- and LP-BER activities in vivo, the wild-type or mutant pCMV-polβ$^{-/-}$ plasmids are transiently co-transfected with U-p21P (for SN- and LP-BER) or R-p21P (for LP-BER) and 0.5 μg pCMV-β-galactoside (β-gal) plasmids in MEF-polβ$^{-/-}$ cells. pCMV-β-gal serves as an internal control to correct for differences in transfection efficiency. After 5 hours of transfection, the cells are acclimatized, and one set of cells is harvested. The promoter activity is determined at this time point (the zero time point). The medium of the remaining dishes is aspirated and replaced with complete medium supplemented with 10% FBS. Cells are harvested at different time intervals and base excision repair activity is measured by determining the luciferase gene-reporter activity of cellular lysates using a Moonlight™ 3010 Illuminometer (Promega, San Diego, Calif.). The effect of NSC-124584 and NSC-666715 on the blockage of SN- and LP-BER activities is determined by transfecting U-p21P and R-p21P plasmids in MEFpol-β$^{+/+}$ and MEF-polβ$^{-/-}$ cells and treating them with NSC-124584 and NSC-666715 for 48 hour. The MEF-polβ$^{-/-}$ serves as a control for these experiments. (Jaiswal et al., Biochemistry 45: 15903-15914, 2006; Kundu et al., Oncogene 2006 Aug. 21; [Epub ahead of print], PMID: 16924228; see Jaiswal et al., Biochemistry 45: 15903-15914, 2006).

Example 7

Cytotoxicity of Temozolomide (TMZ) is Higher in HCT-116(APC$^{+/+}$) than in HCT-116(APC$^{-/-}$) Colon Cancer Cell Lines The cytotoxicity of the majority of chemotherapeutic drugs, as well as of ionizing radiation, is directly related to the drug's ability to cause DNA damage. There are several possible cellular responses to such potentially cytotoxic insults, such as induction of apoptosis, modulation of cell cycle progression, tolerance of damage and initiation of DNA repair. These responses ultimately determine whether the cell is fated to survive with a mutated genome or to die by apoptosis. Responses that promote cell survival have a negative impact on treatment efficacy and lead to resistance to therapies. Thus, agents that increase DNA damage and reduce DNA repair can be an appropriate strategy for cancer treatment. Temozolomide (TMZ) is an DNA-alkylating drug approved for the treatment of glioblastoma (Kim L, Curr. Treat. Options Oncol. 7: 467-478, 2006; Robins et al., Curr. Oncol. Rep. 9: 66-70, 2007). TMZ can cross the blood brain barrier. It is nonenzymatically hydrolyzed in solution to the active compound 3-methyl-(triazen-1-yl)imidazole-4-carboxamide (MTIC). Activated 3-MTIC methylates DNA primarily at the $N^7$ and $O^6$ positions of guanine and the $N^3$ of adenine (70%, 5%, and 9%, respectively). Both $N^7$mG and $N^3$ mA lesions of DNA are repaired by the base excision repair pathway. These lesions, if not repaired, can accumulate and cause strand breaks that can lead to apoptosis. Since APC blocks base excision repair, HCT-116(APC$^{+/+}$) cells will likely be more sensitive due to decreased base excision repair than the HCT-116(APC$^{-/-}$) cells in response to TMZ treatment.

Figure 18:
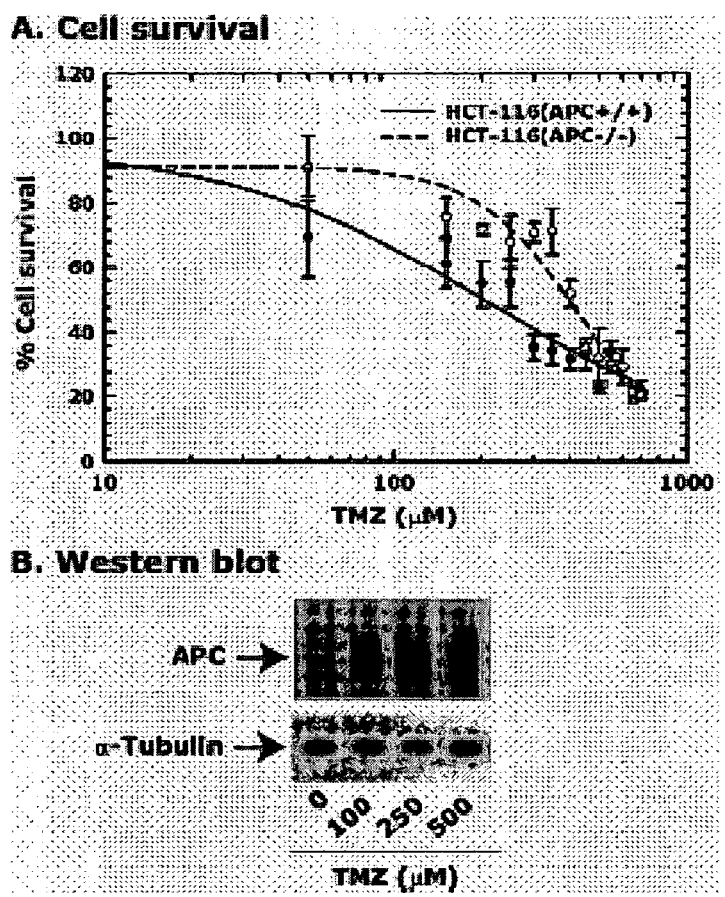
FIGS. 18A and 18B show a dose response analysis of TMZ cytotoxicity in HCT-116(APC$^{+/+}$) and HCT-116(APC$^{-/-}$) cell lines.

The IC$_{50}$ (the drug concentration needed to prevent cell proliferation by 50%) of TMZ was determined using a sulforhodamine B (SRB) colorimetric assay. This assay relies on the ability of SRB to bind the protein components of cells that have been fixed to tissue culture plates by trichloroacetic acid (TCA) (Vachai V, Kirtikara K. Sulforhodamine B colorimetric assay for cytotoxicity screening. Nat. Proto. 3: 1122-1116, 2006). Briefly, the HCT-116(APC$^{+/+}$) and HCT-116(APC$^{-/-}$) were seeded in 96-well plates at a density of 500 cells per well. After 24 hours, while the cells were in the log phase of cell growth, the cells were treated with different concentrations of TMZ for 48 hours. The cells were subsequently fixed with 10% (w/v) of tricholoroacetic acid, washed with double distilled water, and stained with 0.4% SRB. Cells were then repeatedly washed with 1% (v/v) of acetic acid to remove the unbound dye. The protein bound dye was dissolved in 10 mM Tris-base solution (pH 10.5). The developed color was measured at 564 nm. The percentage of cell survival as a function of drug concentration was then plotted to determine the IC$_{50}$ value. The IC$_{50}$ of TMZ in HCT-116(APC$^{+/+}$) and HCT-116 (APC$^{-/-}$) cells was 200 and 400 μM, respectively (FIG. 18A). Results of these studies indicated that HCT-116(APC$^{+/+}$) cells are 2-times more sensitive to TMZ treatment than HCT-116(APC$^{-/-}$) cells. This is consistent with the hypothesis that APC-mediated blockage of base excision repair increase d the sensitivity to TMZ in APC$^{+/+}$ cells. SRB assays were then used to determine whether TMZ-induced cytotoxicity was correlative to the increased level of APC in HCT-116 (APC$^{+/+}$) cells. Results of these studies showed that TMZ treatment caused an increase in the APC protein level in a dose-dependent manner (FIG. 18B). Thus, the increased level of APC likely blocked BER and increased cytotoxicity of TMZ treatment in these cells. These results are consistent with findings describing the role of DNA damage-induced levels of APC in base excision repair.

Example 8

Cytotoxicity of Temozolomide in Colon Cancer Cells is Increased with NSC-124584 and NSC-666715

Figure 19:
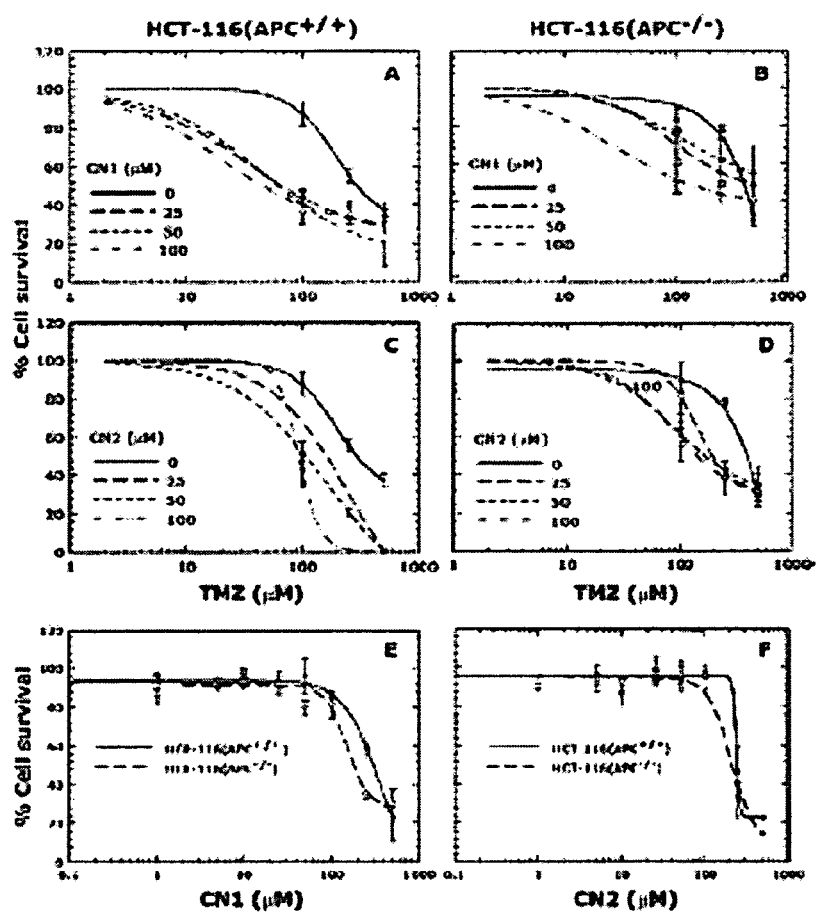
FIGS. 19A-19F show the efficacy of NSC-124584 and NSC-666715 to increase the cytotoxicity of TMZ against HCT-116(APC$^{+/+}$) and HCT-116(APC$^{-/-}$) colon cancer cell lines in culture.

APC blocked base excision repair and sensitized colon cancer cells after TMZ treatment. To determine whether the small chemical compounds NSC-124584 and NSC-666715 mimicked APC-binding to pol-β and sensitized colon cancer cells to TMZ treatment, HCT-116(APC$^{+/+}$) and HCT-116 (APC$^{-/-}$) cell lines were treated with different concentrations of TMZ alone or in combination with different concentrations of NSC-124584 and NSC-666715. The cellular toxicity was determined by sulforhodamine B (SRB) colorimetric assay as described above. The results of this assay showed that both NSC-124584 and NSC-666715 increased the cytotoxicity of TMZ in both HCT-116(APC$^{+/+}$) and HCT-116(APC$^{-/-}$) cell liens. The cytotoxicity of these compounds was greater in HCT-116(APC$^{+/+}$) cells than in HCT-116(APC$^{-/-}$) cells (FIG. 19, compare the results of Panel A with B and C with D, respectively). The cytotoxicity of NSC-124584 and NSC-666715 alone was very low up to 100 μM concentrations (FIGS. 19E and F, respectively). Therefore, 50 μM of NSC-124584 and NSC-666715 with 100 μM of TMZ is likely to be effective for chemotherapy. These results indicated that NSC-124584 and NSC-666715 are capable of mimicking the effect of APC on the blockage of base excision repair, which is evident from their cytotoxic effect on HCT-116(APC$^{-/-}$) cells. In these cells, NSC-124584 and NSC-666715 interact with pol-β at the APC-binding site and block the base excision repair.

Example 9

Figure 20:
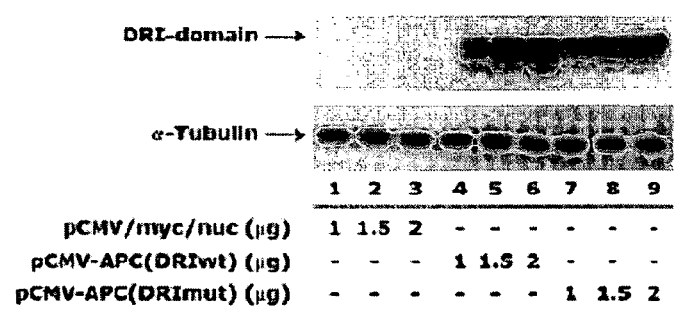
FIG. 20 is a Western blot showing that pCMV-APC (DRIwt) and pCMV-APC(DRImut) plasmid were expressed in the nuclear fraction of HCT-116(APC$^{-/-}$) cells.

Generation of his-Tagged Wild-Type and Mutant APC-DRI Domain Recombinant Plasmids To determine whether the overexpression of APC(DRI) domain increases the cytotoxicity of TMZ, wild-type [APC (DRIwt); 1259I, 1262Y] and DRI-domain mutant[APC (DRImut); 1259I/A, 1262Y/A] human APC cDNA (from 3649-3937 nucleotides/1216-1312 amino acids) were cloned into a pET23d vector (carboxyl-terminal hexahistidine tag) (SEQ ID NO: 2). The pCMV-APC plasmid was used as a template for PCR amplification of the APC fragment using Vent DNA polymerase and cloned into the pET23d vector sites between NcoI and Hind III. The sequence of the recombinant construct was then checked for in-frame alignment by sequencing. The plasmids were transfected into HCT-116 (APC$^{-/-}$) cells for thirty-six hours and the expression of APC (DRIwt) and APC(DRImut) proteins was determined by Western blot analysis. The β-tubulin expression level was used as a control. Results of these assays showed that APC (DRIwt) and APC(DRImut) proteins were robustly overexpressed in a plasmid concentration-dependent manner (FIG. 20).

In sum, the results described herein indicated the interaction of APC with pol-β and showed that this interaction blocked pol-β-directed dRP-lyase and strand-displacement activities. By screening the chemical library of 240,000 compounds, two small chemical compounds which mimic the binding of APC on pol-β at amino acid residues Thr79, Lys81 and Arg83 were successfully identified. These residues were mutated in pol-β. The pol-βMut-1 protein (T79A/K81A/R83A) lost its dRP-lyase and strand-displacement activities.

Example 10

Pol-βMut-1 does not Block the Repair of F-DNA

Figure 10:
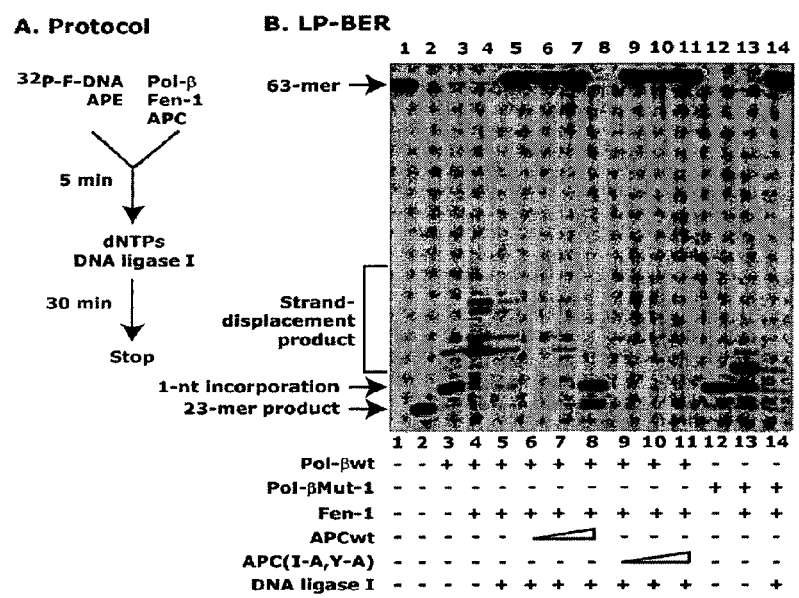
FIGS. 10A and 10B show a comparison of pol-βwt and pol-βMut-1 activity on the repair of F-DNA.

To determine whether the blockage in the strand-displacement synthesis by the pol-βMut-1 was sufficient to block long patch-base excision repair, a long patch-base excision repair assay was set up as outlined in FIG. 10A. Results with this assay system showed a Fen-1-dependent increase in the pol-β-directed strand-displacement synthesis (FIG. 10B, compare lane 3 with 4). Complete DNA repair was observed in the presence of DNA ligase I (FIG. 10B, lane 5; see the formation of the 63-mer ligated product). This DNA repair was blocked in the presence of 2 μM APCwt peptide, but not with APC(I-A,Y-A) peptide (FIG. 10B, compare lane 5 with 8 for APCwt and with 9-11 for APC(I-A,Y-A), respectively, for the formation of the 63-mer ligated product). When determined with pol-βMut-1 protein, complete DNA repair was observed in the presence of DNA ligase I (FIG. 10B, lane 14; see the formation of the 63-mer ligated product), which was similar to that with pol-βwt (FIG. 10B, lane 5). Interestingly, Fen-1 partially relieved the blockage of pol-βMut-1-directed strand-displacement synthesis and stimulated 2-nucleotide incorporation (FIG. 10B, compare lane 12 with 13) as compared to the 6-nucleotide incorporation with pol-βwt (FIG. 10B, compare lane 3 with 4). The 2-nucleotide strand-displacement synthesis by pol-βMut-1 protein was sufficient to carry out long patch-base excision repair in the presence of Fen-1. These results indicate that pol-βMut-1 can process F-DNA, but in a different manner than pol-βwt.

Example 11

APC-Dependent Blockage of Base Excision Repair Activity with F-DNA is Mediated Through Fen-1

Figure 11:
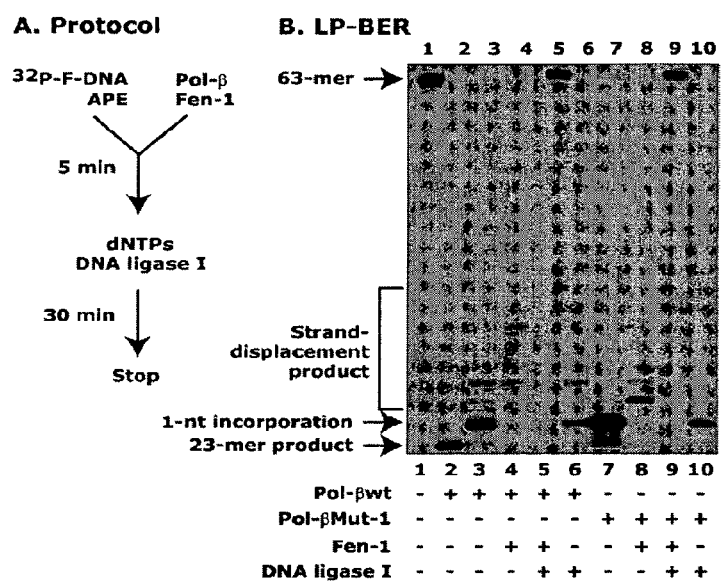
FIGS. 11A and 11B show that Fen-1 is necessary for pol-βMut-1-directed base excision repair activity with F-DNA.

From the above experiments, it is clear that pol-βMut-1 does not completely block strand-displacement synthesis and supports Fen-1-mediated long patch-base excision repair. Since APC does not interact with pol-βMut-1, the APC-mediated blockage of long patch-base excision repair may occur through Fen-1. APC interacted with Fen-1 and blocked its 5'-flap endonuclease and 3'-5' exonuclease activities in addition to strand-displacement synthesis. Since Fen-1 activity was important to the completion of long patch-base excision repair with F-DNA, it is possible that Fen-1 plays a role in APC-mediated blockage of long patch-base excision repair. To determine the role of Fen-1 in APC-mediated blockage of long patch-base excision repair by pol-βMut-1, the long patch-base excision repair assay was assembled as shown in FIG. 11A. A complete repair of $^{32}$P-F-DNA was observed when pol-βwt, Fen-1 and DNA ligase I were added together (FIG. 11B, lane 5). Complete repair was not observed in the absence of Fen-1 (FIG. 11B, lane 6). The long patch-base excision repair activity of pol-βMut-1 protein with $^{32}$P-F-DNA was assayed. The results with the pol-βMut-1 protein were similar to those obtained with pol-βwt protein, i.e., a complete repair of $^{32}$P-F-DNA was observed with pol-βMut-1, Fen-1 and DNA ligase I (FIG. 11B, lane 9). Again, complete repair was not observed in the absence of Fen-1 (FIG. 11B, lane 10). These results indicated that APC blocks long patch-base excision repair of $^{32}$P-F-DNA by blocking Fen-1 activity.

Example 12

APC Blocks pol-β-Mediated Single Nucleotide-Base Excision Repair

Figure 12:
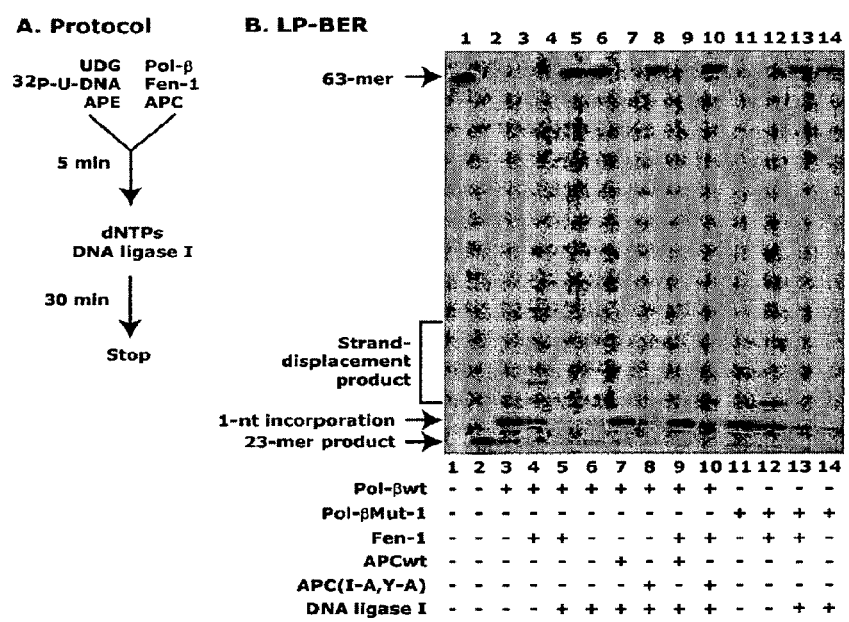
FIGS. 12A and 12B show a comparison of the role of APC on pol-βwt and pol-βMut-1-directed base excision repair with U-DNA.

Having established the role of APC in long patch-base excision repair, it was desirable to determine whether APC affects single nucleotide-base excision repair and whether Set-1 residues of pol-β are involved in this process. This question was addressed using a single nucleotide-base excision repair assay system with purified proteins and $^{32}$P-U-DNA. Prior to the reaction, the uracil was removed by uracil-DNA glycosylase (UDG) to generate an apurinic/apyrimidinic-site. Then the apurinic/apyrimidinic-site was 5'-incised by apurinic/apyrimidinic endonuclease (FIG. 12A). Next, the resulting 5'-phosphate/sugar was released either as the 5'-dRP (SN-BER) or as 5'-dRP moiety attached to a short oligonucleotide produced after strand-displacement and flap incision by Fen-1 (LP-BER) (FIG. 12A). Under assay conditions, there was single-nucleotide incorporation with pol-βwt, which was stimulated to strand-displacement products by Fen-1 (FIG. 12B, compare lane 2 with 3 and 4, respectively). Thus, $^{32}$P-U-DNA can be repaired by both long patch- and single nucleotide-base excision repair pathways, depending upon the presence or absence of Fen-1 (FIG. 12B, see lane 5 and 6, respectively, for the 63-mer repaired and DNA ligase I-ligated product). Both long patch—as well as single nucleotide-base excision repair pathways were blocked by APCwt (FIG. 12B, compare lane 5 with 9 and 6 with 7, respectively), but not by APC(I-A,Y-A) (FIG. 10B, compare lane 5 with 10 and 6 with 8, respectively). From these results, it appears that APC can block the repair of $^{32}$P-U-DNA by both long patch- and single nucleotide-base excision repair pathways.

Next, the mechanism by which APC might be involved in the blockage of the repair of $^{32}$P-U-DNA by long patch- and single nucleotide-base excision repair pathways was determined. Since APC interacts at Set-1 of pol-β (Thr79, Lys81 and Arg83), Set-1 mutant pol-β protein (pol-βMut-1) were used in these studies to mimic the effect of APC. The single-nucleotide incorporation activity of pol-βMut-1 protein with $^{32}$P-U-DNA was similar to that of pol-βwt protein (FIG. 12B, see lane 11 and 3, respectively). The pol-βMut-1 was less efficient for Fen-1 stimulated strand-displacement synthesis. pol-βMut-1 showed only single-nucleotide strand-displacement product as compared to the 3-5-nucleotide strand-displacement product by pol-βwt protein (FIG. 12B, see lane 12 and 4, respectively). Then, the effect of pol-βMut-1 was determined on the complete repair reaction in the presence of DNA ligase I. Results showed that pol-βMut-1 did not block the repair of $^{32}$P-U-DNA by both long patch- or single nucleotide-base excision repair pathways, i.e., in the presence (FIG. 12B, lane 13) or absence of Fen-1 (FIG. 12B, lane 14). These results indicated that pol-βMut-1 retains dRP-lyase activity and supports single nucleotide-base excision repair in the absence of Fen-1. Since Fen-1 cannot remove the 5'-dRP residue alone, but can remove them along with strand-displacement products, the result suggested that pol-βMut-1-directed long patch-base excision repair is accomplished in the presence of Fen-1.

Example 13

Figure 4:
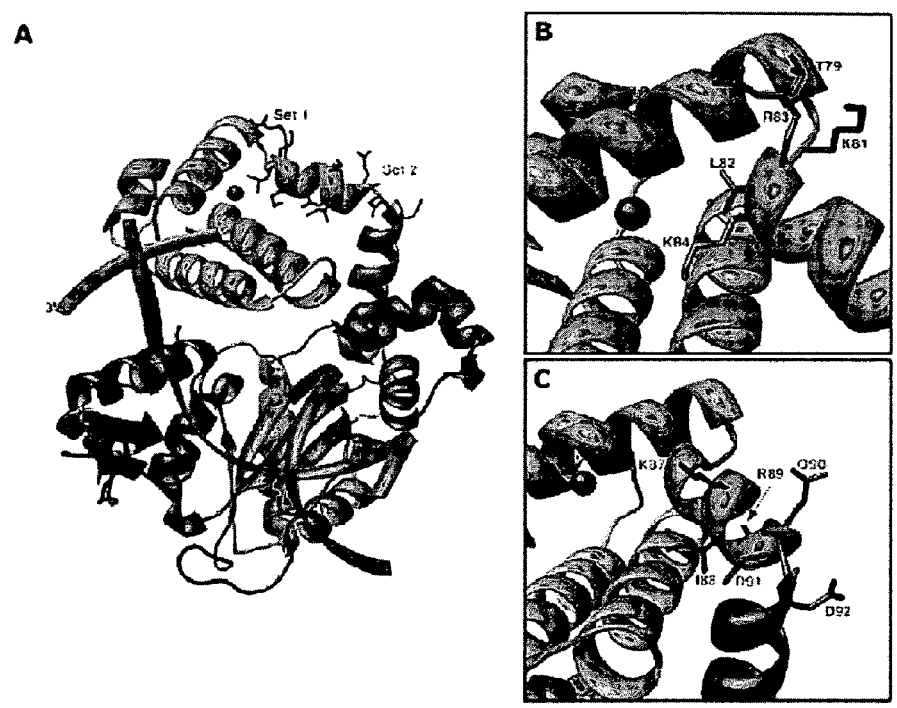
FIG. 4 shows a ribbon representation of pol-β highlighting the position of key mutant sets. Panel A, Set-1 (red) and 2 (magenta) residues are displayed on a ribbon representation of a ternary substrate complex of pol-β (pdb accession code 2FMS). The lyase and polymerase domains are colored gold and blue, respectively, and the DNA backbone is orange. Additionally, a light blue sphere (catalytic $Mg^{2+}$) identifies the polymerase active site and the red sphere (NZ of Lys72) identifies the dRP-lyase active site. The 3'-end of the downstream gapped DNA strand is also indicated. Panels B and C highlight Set-1 (residues 79-84) and Set-2 (residues 87-92) side chains, respectively. This figure was made with the UCSF chimera (50).
Figure 13:
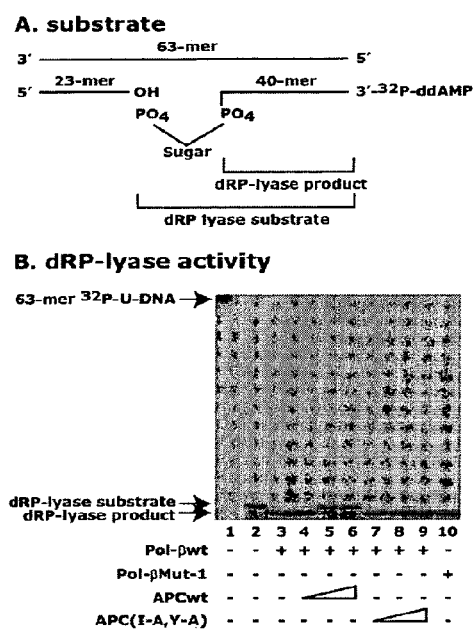
FIGS. 13A and 13B show that APC blocks pol-β-directed dRP-lyase activity.

APC Blocks Single Nucleotide-Base Excision Repair by Blocking dRP-Lyase Activity Since APC blocks Fen-1 activity, the blockage of long patch-base excision repair by APC can be explained by the blockage of Fen-1 activity. This effect does not explain how APC blocks single nucleotide-base excision repair activity. 2'-deoxyribose 5'-phosphate lyase activity is a rate-limiting step in single nucleotide-base excision repair. To determine whether APC affects 2'-deoxyribose 5'-phosphate lyase activity, a 3'-end labeled 63-mer U-DNA substrate was used as described below. Once the U-DNA is treated with uracil-DNA glycosylase and apurinic/apyrimidinic endonuclease, it generates a 2'-deoxyribose 5'-phosphate (dRP) lyase substrate (40-mer with 5'-dRP). This 5'-dRP moiety, is then cleaved by the 2'-deoxyribose 5'-phosphate lyase activity of pol-β to form the dRP-lyase product (40-mer with 5'-phosphate) (FIG. 13A). First, the effect of APCwt on dRP-lyase activity of pol-βwt was determined. Results showed a very efficient dRP-lyase activity of pol-βwt (FIG. 13B, compare lane2 with 3), which was blocked by APCwt peptide in a dose-dependent manner (FIG. 13B, compare lane 3 with 4-6). On the other hand, APC(I-A,Y-A) did not show any effect on the dRP-lyase activity of pol-βwt (FIG. 13B, compare lane 3 with lane 7-9). Second, the effect of pol-βMut-1 on its dRP-lyase activity was determined. The results showed that pol-βMut-1 has efficient dRP-lyase activity (FIG. 13B, compare lane 2 with 10). These results indicated that APC blocks single nucleotide-base excision repair by blocking dRP-lyase activity of pol-β protein. Note that APC interacts with pol-β near the lyase active site (FIG. 4).

Example 14

Figure 14:
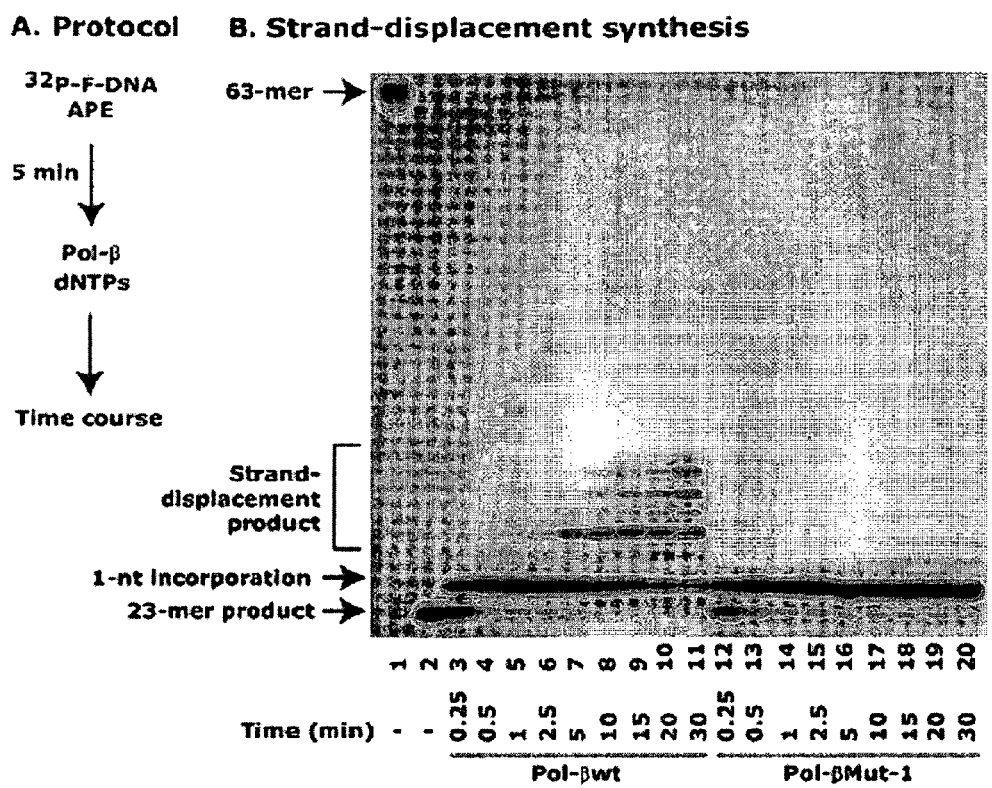
FIGS. 14A and 14B show that APC blocks pol-β-directed strand-displacement synthesis.

Pol-β Mut-1 Mimics APC-Dependent Blockage of DNA Polymerase β-Directed Strand-Displacement Synthesis Based on the analysis that determined the site of interaction of APC with amino acid residues Thr79, Lys81 and Arg83 of pol-β, it is likely that these amino acid residues play a role in APC-mediated blockage of pol-β-directed strand-displacement synthesis. To test this hypothesis, His-tagged pol-βwt and polβMut-1 (T79A/K81A/R83A) proteins were overexpressed and purified. A strand-displacement assay was performed by using $^{32}$P-F-DNA as a substrate for LP-BER (FIG. 14A). In this DNA, an AP site analog (3-hydroxy-2-hydroxymethyltetrahydrofuran, noted as F) was introduced at the 24$^{th}$ position as described earlier. The results showed a strand-displacement synthesis with pol-βwt protein in a time-dependent manner (FIG. 14B, compare lane 2 with 3-11). However, the pol-βMut-1 completely abolished the strand-displacement synthesis (FIG. 14B, compare lane 2 with 12-20). Thus, these results suggested that the Set-1-mutant of pol-β is important for both physical and functional interaction with APC.

Example 15

NSC-124854 and NSC-666715 Blocked DNA Polymerase β-directed SN- and LP-BER

Figure 23:
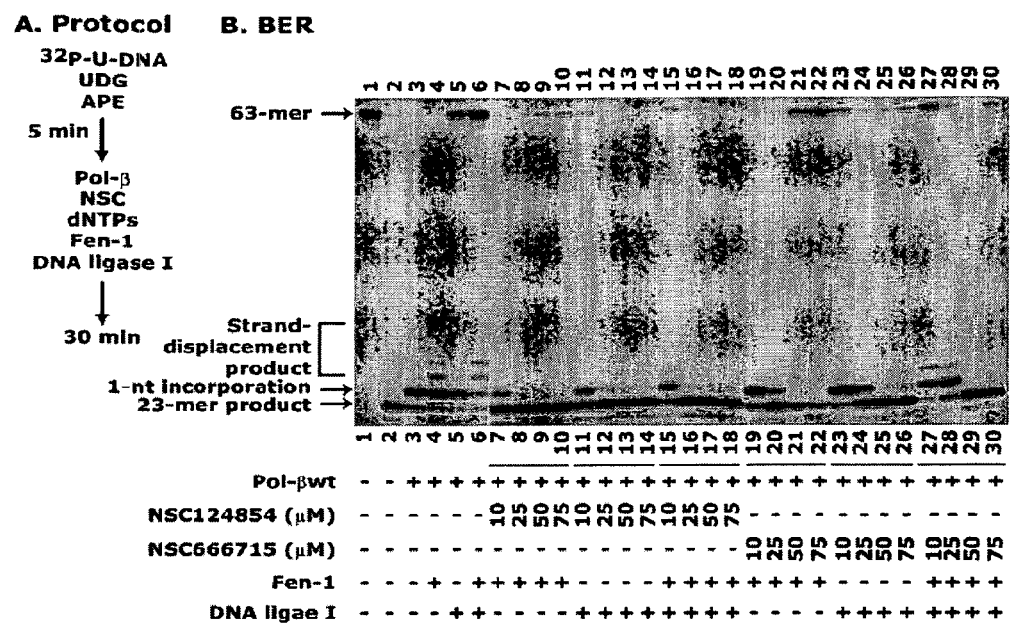
FIGS. 23A and 23B show that NSC-124854 and NSC-666715 blocked Pol-β-directed single nucleotide- and long patch-BER activities.

Having determined that the small molecule inhibitor-mediated block of dRP-lyase and strand-displacement activities inhibited Pol-β-directed single nucleotide- and long patch-BER activities, BER assays were performed. The experimental protocol is depicted in FIG. 23A. Using $^{32}$P-U-DNA as a substrate, the SN- and LP-BER pathways can be distinguished by the addition of Fen-1. In the presence of Fen-1, $^{32}$P-U-DNA shows strand-displacement synthesis and the repair takes place through LP-BER. Results of this analysis showed that Pol-β-mediated 1-nt incorporation (FIG. 23B, compare lane 2 with 3) as well strand-displacement synthesis in the presence of Fen-1 (FIG. 23B, compare lane 2 with 4). The complete repair of DNA by SN- and LP-BER pathways is mediated by DNA ligase I (FIG. 23B, lane 5 and 6, respectively). Both NSC-124854 and NSC-666715, blocked 1-nt incorporation as well as strand-displacement synthesis in a dose-dependent manner (NSC-124854, FIG. 23B, compare lane 4 with 7-10; NSC-666715, FIG. 23B, compare lane 4 with 19-22). Furthermore, the complete repair of $^{32}$P-U-DNA by the SN-BER pathway was blocked in a dose-dependent manner by NSC-124854 (FIG. 23B, compare lane 5 with 11-14) and NSC-666715 (FIG. 23B, compare lane 5 with 23-26). The complete repair of $^{32}$P-U-DNA by the LP-BER pathway was also blocked in a dose-dependent manner by NSC-124854 (FIG. 23B, compare lane 5 with 15-18) and NSC-666715 (FIG. 23B, compare lane 5 with 27-30). The blockade of SN- and LP-BER activities by NSC-124854 and NSC-666715 was due to the blockade of Pol-β activity that enabled Pol-β for DNA synthesis as can be seen by the blockage of 1-nt incorporation.

Example 16

Figure 24A:
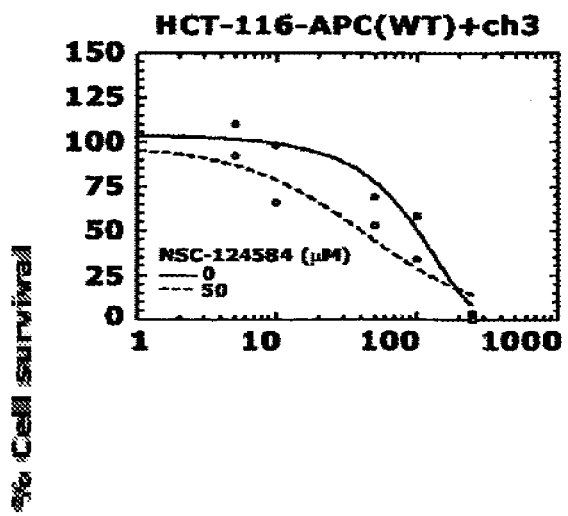
FIGS. 24A and 24D NSC-124854 enhanced the cytotoxicity of TMZ in both MMR-positive and MMR-negative colon cancer cell lines in culture. MMR-proficient [HCT-116-APC(WT)+ch3 and SW480 (Panel 24A and 25B)] and MMR-deficient [CACO-2 and LoVo (Panel 24C and 24D)] cells were pretreated for 2 hours with 50 µM of NSC-124854 followed by the treatment with different concentrations of TMZ. After 48 hours, cells were harvested and processed for cytotoxicity determination. Data presented are the mean±SE of three different estimations.
Figure 24B:
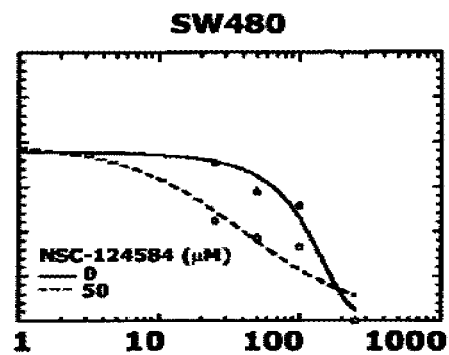

Small Molecular Weight Inhibitors, NSC-124584 and NSC-666715, Enhanced Cytotoxicity of TMZ in Both MMR-Proficient and MMR-Deficient Colon Cancer Cell Lines The $O^6$-MeG lesion is less frequently methylated than other positions, but is highly mutagenic. This lesion is repaired by the $O^6$-methylguanine DNA methyltransferase (MGMT) pathway. If unrepaired, then the $O^6$-MeG lesion tends to mispair during DNA replication resulting in GC to AT transitions. If the unrepaired $O^6$-MeG lesion is present in replicating DNA, the mismatch repair (MMR) system can be involved in abortive processing of this lesion. The MMR system recognizes the $O^6$-MeG lesion in a cyclic manner leading to cell death via abortive repair. Since DNA repair pathways in general act to promote cell survival, the involvement of MMR in cell death is paradoxical. In the absence of MGMT and MMR systems, the cytotoxicity of the $O^6$-MeG lesion can be avoided, but this is associated with increased mutagenicity. Several studies have shown that MMR-deficient cells are resistant to treatment with alkylating agents. APC blocks BER and increases cellular toxicity in response to DNA-alkylation damage. The blockage of BER may decrease the resistance and increase the cytotoxicity of DNA-alkylation damage in MMR-deficient cells. Since HCT-116-APC(WT) and HCT-1,6-APC(KD) are MMR-deficient due to lack of hMLH1 expression, the effect of APC on TMZ-induced cytotoxicity in MMR-proficient HCT-116-APC (WT)+ch3 and SW480 cell lines was analyzed. In HCT-116-APC(WT)+ch3 cells, a single copy of chromosome 3 harboring hMLH1 gene has been inserted (Taverna et al., Cancer Chemother. Pharmacol. 46: 507-516, 2000). The SW480 cells express truncated APC (1-1337 amino acids) with an intact DRI-domain. The HCT-116-APC(WT)+ch3 and SW480 cells showed a greater cytotoxicity of TMZ treatment ($IC_{50}$=100 and 120 mM, respectively) (FIGS. 24A and 24B). The combination of 50 mM of NSC-124584 further reduced the $IC_{50}$ of TMZ by 2.5-fold in both HCT-116-APC (WT)+ch3 and SW480 cell lines (FIGS. 24A and 24B).

Figure 24C:
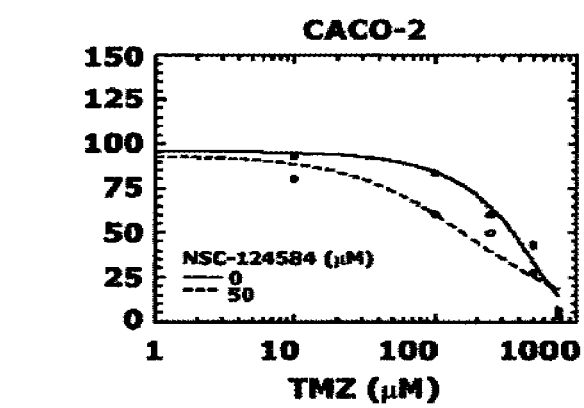
Figure 24D:
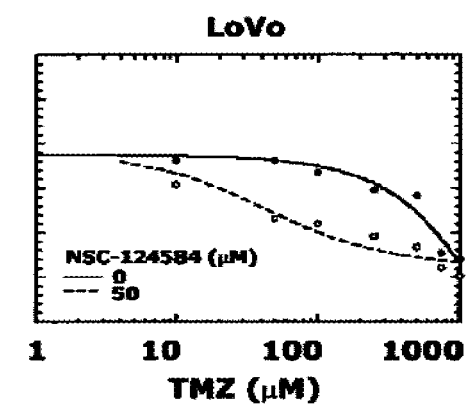

To determine whether MMR-deficient cells with truncated APC that lacks the DRI-domain exhibit sensitivity to the small molecule inhibitors and TMZ treatment, MMR-deficient colon cancer cell lines CACO-2 (truncated APC, 1-1367 amino acids, DRI-domain present) and LoVo (truncated APC, 1-1114 amino acids, DRI-domain absent) were used (Watanabe et al., Mol. Carcinog. 29: 37-49, 2000). Interestingly, CACO-2 and LoVo cells were less sensitive to TMZ treatment ($IC_{50}$=364 and 677 μM, respectively) (FIGS. 24C and 24D) than the MMR-proficient HCT-116-APC(WT)+ch3 and SW480 cells (FIGS. 24A and 24B). NSC-124584 was equally or more effective in reducing the $IC_{50}$ of TMZ in both CACO-2 and LoVo cell lines ($IC_{50}$=164 and 100 μM, respectively) (FIGS. 24C and 24D). These results suggest that NSC-124854 interacts with Pol-β at the APC-binding site and blocks BER and can be useful chemotherapeutic intervention of progression of both MMR-proficient and MMR-deficient colorectal tumors. Thus, the invention provides compositions and methods for treating patients that do not respond to conventional chemotherapeutic agents (e.g., MMR-deficient neoplasias).

Example 17

Figure 25:
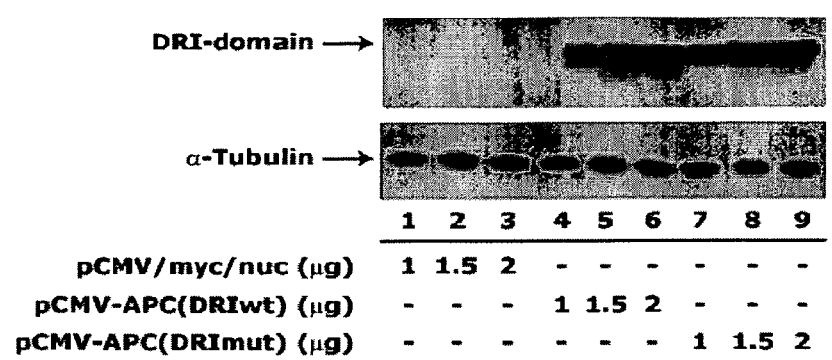
FIG. 25 shows nuclear expression of pCMV-APC(DRIwt) and pCMV-APC(DRImut) plasmid in HCT-116-APC(KD) cells.

Generation of his-Tagged Wild-Type and Mutant APC-DRI Domain Recombinant Plasmids To determine whether the overexpression of APC(DRI) domain can increase the cytotoxicity of TMZ, wild-type [APC(DRIwt); 1259I, 1262Y] and DRI-domain mutant [APC(DRImut); 1259I/A, 1262Y/A] human APC cDNA (from 3649-3937 nucleotides/1216-1312 amino acids) were cloned into pET23d vector (carboxyl-terminal hexahistidine tag) (SEQ ID NO: 2). The pCMV-APC plasmid was used as a template for PCR amplification of the APC fragment using Vent DNA polymerase and cloned into the pET23d vector sites between NcoI and HindIII. The sequences of the recombinant constructs were then checked for in-frame alignment by sequencing. The plasmids were transfected into HCT-116-APC(KD) cells, and the expression of APC(DRIwt) and APC (DRImut) proteins were determined by Western blot analysis. The α-tubulin expression level was used as a control. The results (FIG. 25) show a robust overexpression of both the APC(DRIwt) and APC(DRImut) proteins that were dependent on the concentration of the plasmid.

The above referenced experiments were carried out using the following materials and methods.

Chemicals

All oligonucleotides were purchased from Sigma-Genosys (The Woodlands, Tex.). Restriction enzymes, T4 polynucleotide kinase (PNK), terminal deoxynucleotidyltransferase (TdT) and Vent-DNA polymerase were from New England Biolabs (Ipswich, Mass.) and radionuclides [α-$^{32}$P]ATP and [α-$^{32}$P]ddATP were purchased from MP Biomedicals, Solon, Ohio and Amersham Biosciences, Piscataway, N.J., respectively.

APC Peptides

The wild-type (1250-KVSSINQETIQTYCVEDTPI-1269) (SEQ ID NO: 3) and the mutant (I-A,Y-A) (1250-KVSSINQETAQTACVEDTPI-1269) (SEQ ID NO: 4) APC peptides of 20-amino acids in length were synthesized at the Protein Chemistry and Biomarkers core facility at the ICBR, University of Florida. These peptides represent the DNA repair inhibitory (DRI)-domain of APCwt, in which amino acid residues Ile1259 and Tyr1262 were replaced with alanine (A) to generate mutant APC(I-A,Y-A). The mutant residues are shown in italics in FIG. 1A.

Generation of pol-β Deletion Constructs

Four deletion constructs (amino acids 60-120, 80-170, 140-200, and 160-250) of pol-β were designed to identify interacting amino acids of pol-β with the DRI-domain of APC. These deletion fragments were subcloned into the pGAD-C3 vector between PstI and BamHI restriction sites. The following primers were used to generate various pol-β deletion constructs: polβ(60-120) (sense primer, 5'-CGCG-GATCCAAGAAATTGCCTGGAGTA-3'(SEQ ID NO: 5) and antisense primer, 5'-CCAATGCATTGGTTCTG-CAGTTTAATTCCTTCATCTAC-3' (SEQ ID NO: 6)), polβ (80-170) (sense primer, 5'-CGCGGATCCGGAAAAT-TACGTAAACT CGCGGATCCGGAAAATTACGTAAACTG-3' (SEQ ID NO: 7) and antisense primer, 5'-CCAATGCATTGGTTCTG-CAGATCCACTTTTTTAACTT-3' (SEQ ID NO: 8)), polβ (140-200) (sense primer, 5'-CGCGGATCCCT-GAAATATTTTGGGGAC-3' (SEQ ID NO: 9) and antisense primer, 5'-CCAATGCATTGGTTCTGCAGGAAGCTGG-GATGGGTCAG-3' (SEQ ID NO: 10)), and polβ(160-250) (sense primer, 5'-CGCGGATCCGATATTGTTCTAAAT-GAA-3' (SEQ ID NO: 11) and antisense primer, 5'-CCAAT-GCATTGGTTCTGCAGATATTCTTTTTCATCATT-3' (SEQ ID NO: 12)).

Site-Directed Mutagenesis of pol-β

Two different sets of pol-β mutants, Set-1 mutant (T79A/K81A/R83A) and Set-2 mutant (R89A/Q90A/D92A) were generated using the Quick Change site-directed mutagenesis kit from Stratagene (La Jolla, Calif.). The following primer pairs were used for Set-1 and Set-2 mutants: Set-1, sense primer (5'-GAAAAGATTGATGAGTTTTTAGCAGCCG-GAGCGTTAGCTAAACTGGAAAAGATTCGGC AG-3' (SEQ ID NO: 13)) and antisense primer (5'-CTGC-CGAATCTTTTCCAGTTTAGCTAACGCTC-CGGCTGCTAAAAACTCATCAATCTTTTC-3' (SEQ ID NO: 14)); Set-2, sense primer (5'-GGAAAATTACG-TAAACTGGAAAAGATTGCCGCGGATGC-TACGAGTTCATCCATCAATT TCCTG-3' (SEQ ID NO: 15)) and antisense primer (5'-CAGGAAATTGATGGAT-GAACTCGTAGCATCCGCG-GCAATCTTTTCCAGTTTACGTAATT TTCC-3' (SEQ ID NO: 16)).

Yeast Two-Hybrid Interaction Assay

The yeast two-hybrid assay was employed to identify critical amino acids of pol-β to define the functional interaction with APC in vivo. The APC cDNA fragments containing the wild-type (residues 1190-1328) or the mutant DRI-domain (residues 1200-1324, in which amino acids Ile1259, and Tyr1262 were replaced with alanine) were fused to the yeast Gal4 DNA-binding domain (BD) in plasmid pGBDU-C3. The interacting pol-β protein fragments, such as full-length and deletion fragments (residues 60-120, 80-170, 140-200, and 160-250), were fused to the yeast Gal4 activation domain (AD) in plasmid pGAD-C3. Set-1 (T79A/K81A/R83A) and Set-2 (R89A/Q90A/D92A) Pol-β mutants were also cloned into plasmid pGAD-C3. Appropriate restriction enzyme sites were included in the inserts for the correct in-frame insertion into the plasmid vectors pGBDU-C3 or pGAD-C3. The yeast strain S. cerevisiae PJ69-4A was co-transformed with PGBDU-C3 and pGAD-C3 derived plasmids and spread on plates containing yeast synthetic dropout (SD)-UL medium. The SD-UL medium lacks only vector markers Ura for pGBDU-C3 derived plasmids and Leu for pGAD-C3 derived plasmids. Plasmids were introduced into yeast strain PJ69-4A by the standard lithium acetate transformation method. To test for potential protein-protein interactions, transformants were screened for growth on yeast SD-ULH medium which lacked Ura, Leu, and His but contained 5 mM His3 inhibitor, 3-amino-1,2,4-triazole, to prevent His3-reporter gene auto-activation.

Overexpression of Fen-1 and DNA Ligase I Proteins

Recombinant human Fen-1 (pET23d-Ct-his-hFen1) was overexpressed in Escherichia coli strain BL21(DE3)pLysS as a histidine-tagged protein and purified to homogeneity as described (44). The full-length human DNA ligase I (pET-his-hDNA Ligase I) was overexpressed and purified to homogeneity according to the published protocol (45).

Generation of his-Tagged pol-βwt and Mutant Recombinant Constructs

Human pol-β cDNA was cloned into pET23d vector (carboxyl-terminal hexahistidine tag (SEQ ID NO: 2)). pWL11-hpolβ was used as a template for PCR amplification of the pol-β gene using Vent DNA polymerase and cloned into the pET23d vector. The following pair of primers was used for making pol-β mutant (T79A/K81A/R83A) using the Quick Change II site-directed mutagenesis kit (Stratagene, La Jolla, Calif.): sense primer (5'-GAAAAGATTGATGAGTTTT-TAGCAGCCGGAGCGTTAGCTAAACTG-GAAAAGATTCGGC AG-3' (SEQ ID NO: 13)) and antisense primer (5'-CTGCCGAATCTTTTCCAGTTTAGC TAACGCTCCGGCTGCTAAAAACTCATCAATCTT TTC-3' (SEQ ID NO: 14)). The sequence of recombinant construct was then checked for in-frame alignment by sequencing.

Purification of His-Tagged Pol-βwt and Pol-βMut-1 (T79A/K81A/R83A) Proteins

The hexa-histidine (SEQ ID NO: 2) fusion proteins of the pol-βwt and pol-βMut-1 (T79A/K81A/R83A) were purified as described previously with some modifications (46). The pol-βwt and pol-βMut-1 overexpression constructs were transformed in Escherichia coli strain BL21(DE3)pLysS (Novagen Inc., Madison, Wis.). The transformed cells were grown at 37° C. until log phase ($A_{600}$ of 0.6). Subsequently cells were induced with 1.0 mM of isopropyl-beta-D-thiogalactopyranoside (IPTG). The cultures were grown for an additional 3 hours. The cells were pelleted and then resuspended in 1X-binding buffer (5.0 mM imidazole, 0.5 M NaCl, 20 mM Tris-HCl, pH 7.9). Cell lysates were prepared by disrupting the cells in a French-pressure-cell (Thermo Electron Corporation, Waltham, Mass.) at 16,000 lb/in$^2$ and then spun at 20,000×g for 20 min. Cell lysates were passed through syringe-top 0.4 μM filter. Pre-cleared cell lysates were loaded onto small disposable columns containing 2.5 ml of chelating chromatographic resin (e.g., SEPHAROSE-FAST-FLOW RESIN) (Pharmacia Biotech, Inc., Piscataway, N.J.). Before loading the lysate, the column was charged with 50 mM $NiSO_4$ and equilibrated with 1X binding buffer. Further steps in the purification were followed according to pET instruction manual. Finally proteins were eluted with 1X-elution buffer (500 mM imidazole, 0.4 M NaCl, 20 mM Tris-HCl, pH 7.9). The proteins were dialyzed against the storage buffer (50 mM Tris.Cl, pH 7.5; 1.0 mM EDTA, 200 mM NaCl, 20% Glycerol).

Synthesis and Labeling of Base Excision Repair Substrates

To study long patch- and single nucleotide-base excision repair activities, different types of DNA substrates were used. For long patch-base excision repair activity, an AP-site analog (3-hydroxy-2-hydroxymethyltetrahydrofuran, noted as F) was introduced at the 24$^{th}$ position of the 63-mer DNA (5'-CTAGATGCCTGCAGCTGATGCGCFG-TACGGATCCACGTGTACGGTACCGAGGGCGGGT CGACA-3' (SEQ ID NOS 17-18)), which was called F-DNA (27). For making U-DNA, uracil was introduced at the 24$^{th}$ position of 63-mer sense oligonucleotide (5'-TAGATGCCT-GCAGCTGATGCGCUGTACGGATCCACGT-GTACGGTACCGAGGGCGGGTC GACA-3' (SEQ ID NO: 19)). Sense strands of F-DNA and U-DNA were 5'-end labeled by [a-$^{32}$P]ATP and T4 polynucleotide kinase and purified with a nick-column (GE Healthcare, Piscataway, N.J.). Later they were annealed with the complementary 63-mer oligonucleotide (5'-TGTCGACCCGCCCTCGG-TACCGTACACGTGGATCCGTACCGCG-CATCAGCTGCAGGCAT CTAG-3' (SEQ ID NO: 20)) at a 1:1 molar ratio.

In Vitro Base Excision Repair Assays

For strand-displacement synthesis, the reaction was reconstituted using purified proteins under the following conditions. The reaction mixture contained 30 mM Hepes, pH 7.5; 30 mM KCl, 8.0 mM MgCl$_2$, 1.0 mM DTT, 100 µg/ml BSA, 0.01% (v/v) Nonidet P-40, 0.5 mM ATP, and 10 µM each of dATP, dCTP, dGTP, dTTP in a final volume of 20 µl. The base excision repair reaction mixture was assembled on ice by the addition of 1 nM apurinic/apyrimidinic endonuclease, 1 nM pol-β and 0.3 nM Fen-1. This mixture was pre-incubated with APCwt and APC(I-A,Y-A) peptides for 5 minutes at 22° C. The amounts of the APCwt and APC(I-A,Y-A) peptides used in each experiment are given in respective figure legends. The strand displacement synthesis was initiated by the addition of 2.5 nM $^{32}$P-labeled F-DNA or U-DNA to corresponding tubes and further incubated for 30 minutes at 37° C. For complete base excision repair, a 0.2 nM DNA ligase I was added to the above reaction mixture and incubated for 30 minutes at 37° C. Each reaction was terminated by the addition of 20 µl of stop solution (5.0 mM EDTA, 0.4% (w/v) SDS) with 1 µg of proteinase K and 5 µg carrier tRNA. After incubation for an additional 20 minutes at 37° C., the DNA was extracted with an equal volume of phenol/chloroform/isoamyl alcohol (25:24:1, v/v) followed by ethanol precipitation. The reaction products were resolved on a 15% polyacrylamide-7 M urea gel.

3'-End Labeling of U-DNA

A 63-mer oligonucleotide containing uracil at 24$^{th}$ position was labeled at the 3'-end by terminal deoxynucleotidyltransferase using [α-$^{32}$P]ddATP and annealed to the complementary oligonucleotide. To remove uracil, the 3'-end labeled double-stranded oligonucleotide (2.5 nM) was treated with UDG (40 nM) for 20 minutes at 37° C. in 20 µl buffer containing 30 mM Hepes, pH 7.5, 30 mM KCl, 8.0 mM MgCl$_2$, 1.0 mM DTT, 100 µg/ml bovine serum albumin, 0.01% (v/v) Nonidet P-40, and 0.5 mM ATP. After incubation, the mixture was supplemented with 1.0 nM apurinic/apyrimidinic endonuclease and further incubated for 10 minutes, thus generating the substrate for dRP-lyase activity.

dRP-Lyase Activity Assay

One nM of pol-βwt and pol-βMut-1 proteins were preincubated with variable amounts of APCwt or APC(I-A,Y-A) peptides for 5 minutes at 22° C. The reaction was initiated by adding these preincubated protein and peptide complexes with dRP-lyase substrate and incubated at 37° C. for 15 minutes. After incubation, NaBH$_4$ was added to a final concentration of 340 nM, and kept on ice for 30 minutes. The stabilized (reduced) DNA products were ethanol precipitated in the presence of 5.0 µg carrier tRNA, and resuspended in 10 µl of gel-loading buffer [95% (v/v) of formamide, 20 mM EDTA, 0.02% (w/v) bromophenol blue, and 0.02% (w/v) xylene cyanol]. After incubation at 75° C. for 2 minutes, the reaction products were resolved on 15% polyacrylamide-7 M urea gel.

1. Hoeijmakers, J. H. (2001) *Nature* 411, 366-374
2. Barnes, D. E., and Lindahl, T. (2004) *Annu. Rev. Genet.* 38, 445-476
3. Biade, S., Sobol, R. W., Wilson, S. H., and Matsumoto, Y. (1998) *J. Biol. Chem.* 273, 898-902
4. Klungland, A., and Lindahl, T. (1997) *EMBO J.* 16, 3341-3348
5. El-Andaloussi, N., Valovka, T., Toueille, M., Steinacher, R., Focke, F., Gehrig, P., Covic, M., Hassa, P. O., Schar, P., Hubscher, U., and Hottiger, M. O. (2006) *Mol. Cell.* 22, 51-62
6. Huffman, J. L., Sundheim, O., and Tainer, J. A. (2005) *Mutat. Res.* 577, 55-76
7. Matsumoto, Y., and Kim, K. (1995) *Science* 269, 699-702
8. Podlutsky, A. J., Dianova, II, Podust, V. N., Bohr, V. A., and Dianov, G. L. (2001) *EMBO J.* 20, 1477-1482
9. Bambara, R. A., Murante, R. S., and Henricksen, L. A. (1997) *J. Biol. Chem.* 272, 4647-4650
10. Lieber, M. R. (1997) *Bioessays* 19, 233-240
11. Memisoglu, A., and Samson, L. (2000) *Mutat. Res.* 451, 39-51
12. Norbury, C. J., and Hickson, I. D. (2001) *Annu. Rev. Pharmacol. Toxicol.* 41, 367-401
13. Moon, R. T., Kohn, A. D., De Ferrari, G. V., and Kaykas, A. (2004) *Nat. Rev. Genet.* 5, 691-701
14. Bodmer, W. F., Bailey, C. J., Bodmer, J., Bussey, H. J., Ellis, A., Gorman, P., Lucibello, F. C., Murday, V. A., Rider, S. H., Scambler, P., and et al. (1987) *Nature* 328, 614-616
15. Su, L. K., Kinzler, K. W., Vogelstein, B., Preisinger, A. C., Moser, A. R., Luongo, C., Gould, K. A., and Dove, W. F. (1992) *Science* 256, 668-670
16. Powell, S. M., Zilz, N., Beazer-Barclay, Y., Bryan, T. M., Hamilton, S. R., Thibodeau, S. N., Vogelstein, B., and Kinzler, K. W. (1992) *Nature* 359, 235-237
17. Fearnhead, N. S., Britton, M. P., and Bodmer, W. F. (2001) *Hum. Mol. Genet.* 10, 721-733
18. Fearon, E. R., and Vogelstein, B. (1990) *Cell* 61, 759-767
19. Thomas, H. J. (1991) *Curr. Opin. Oncol.* 3, 702-710
20. Fodde, R. (2003) *Nat. Cell Biol.* 5, 190-192
21. Kuraguchi, M., Wang, X. P., Bronson, R. T., Rothenberg, R., Ohene-Baah, N. Y., Lund, J. J., Kucherlapati, M., Maas, R. L., and Kucherlapati, R. (2006) *PLoS Genet.* 2, e146
22. Narayan, S., and Roy, D. (2003) *Mol. Cancer.* 2, 41
23. Nathke, I. S. (2004) *Annu. Rev. Cell. Dev. Biol.* 20, 337-366
24. Zhang, T., Otevrel, T., Gao, Z., Gao, Z., Ehrlich, S. M., Fields, J. Z., and Boman, B. M. (2001) *Cancer Res.* 61, 8664-8667
25. Jaiswal, A. S., Balusu, R., Armas, M. L., Kundu, C. N., and Narayan, S. (2006) *Biochemistry* 45, 15903-15914
26. Kundu, C. N., Balusu, R., Jaiswal, A. S., Gairola, C. G., and Narayan, S. (2006) *Oncogene* (August 21; [Epub ahead of print] PMID: 16924228)
27. Narayan, S., Jaiswal, A. S., and Balusu, R. (2005) *J. Biol. Chem.* 280, 6942-6949
28. Narayan, S., and Jaiswal, A. S. (1997) *J. Biol. Chem.* 272, 30619-30622
29. Jaiswal, A. S., and Narayan, S. (2001) *J. Biol. Chem.* 276, 18193-18199
30. Jaiswal, A. S., Balusu, R., and Narayan, S. (2006) *Carcinogenesis* 27, 252-261
31. Beard, W. A., and Wilson, S. H. (2006) *Chem. Rev.* 106, 361-382
32. Kumar, A., Abbotts, J., Karawya, E. M., and Wilson, S. H. (1990) *Biochemistry* 29, 7156-7159
33. Beard, W. A., and Wilson, S. H. (1995) *Methods Enzymol.* 262, 98-107

34. Singhal, R. K., and Wilson, S. H. (1993) *J. Biol. Chem.* 268, 15906-15911
35. Ollis, D. L., Brick, P., Hamlin, R., Xuong, N. G., and Steitz, T. A. (1985) *Nature* 313, 762-766
36. Pelletier, H., Sawaya, M. R., Kumar, A., Wilson, S. H., and Kraut, J. (1994) *Science* 264, 1891-1903
37. Liu, D., Prasad, R., Wilson, S. H., DeRose, E. F., and Mullen, G. P. (1996) *Biochemistry* 35, 6188-6200
38. Pelletier, H., and Sawaya, M. R. (1996) *Biochemistry* 35, 12778-12787
39. Piersen, C. E., Prasad, R., Wilson, S. H., and Lloyd, R. S. (1996) *J. Biol. Chem.* 271, 17811-17815
40. Prasad, R., Beard, W. A., Chyan, J. Y., Maciejewski, M. W., Mullen, G. P., and Wilson, S. H. (1998) *J. Biol. Chem.* 273, 11121-11126
41. Deterding, L. J., Prasad, R., Mullen, G. P., Wilson, S. H., and Tomer, K. B. (2000) *J. Biol. Chem.* 275, 10463-10471
42. Prasad R, Batra V K, Yang X P, Krahn J M, Pedersen L C, Beard W A, Wilson S H. (2005) *DNA Repair (Amst)* 4, 1347-1357
43. Mizushina, Y., Kamisuki, S., Kasai, N., Shimazaki, N., Takemura, M., Asahara, H., Linn, S., Yoshida, S., Matsukage, A., Koiwai, O., Sugawara, F., Yoshida, H., and Sakaguchi, K. (2002) *J. Biol. Chem.* 277, 630-638
44. Stucki, M., Jonsson, Z. O., and Hubscher, U. (2001) *J. Biol. Chem.* 276, 7843-7849
45. Mackenney, V. J., Barnes, D. E., and Lindahl, T. (1997) *J. Biol. Chem.* 272, 11550-11556
46. Opresko, P. L., Shiman, R., and Eckert, K. A. (2000) *Biochemistry* 39, 11399-11407
47. Kedar, P. S., Kim, S. J., Robertson, A., Hou, E., Prasad, R., Horton, J. K., and Wilson, S. H. (2002) *J. Biol. Chem.* 277, 31115-31123
48. Batra, V. K., Beard, W. A., Shock, D. D., Krahn, J. M., Pedersen, L. C., and Wilson, S. H. (2006) *Structure* 14, 757-766
49. Beard, W. A., and Wilson, S. H. (1998) *Chem. Biol.* 5, R7-13
50. Pettersen E F, Goddard T D, Huang C C, Couch G S, Greenblatt D M, Meng E C, Ferrin T E. (2004) *J. Comput. Chem.* 25, 1605-1612
51. Jaiswal, A. S., Bloom, L. B., and Narayan, S. (2002) *Oncogene* 21, 5912-5922
52. Gomez-Lazaro, M., Fernandez-Gomez, F. J., and Jordan, J. (2004) *J. Physiol. Biochem.* 60, 287-307
53. Narayan, S., Jaiswal, A. S., Kang, D., Srivastava, P., Das, G. M., and Gairola, C. G. (2004) *Oncogene* 23, 5880-5889
54. Dianov, G. L., Sleeth, K. M., Dianova, II, and Allinson, S. L. (2003) *Mutat. Res.* 531, 157-163
55. Petermann, E., Ziegler, M., and Oei, S. L. (2003) *DNA Repair (Amst)* 2, 1101-1114
56. Harrigan, J. A., Opresko, P. L., von Kobbe, C., Kedar, P. S., Prasad, R., Wilson, S. H., and Bohr, V. A. (2003) *J. Biol. Chem.* 278, 22686-22695
57. Harrigan, J. A., Wilson, D. M., 3rd, Prasad, R., Opresko, P. L., Beck, G., May, A., Wilson, S. H., and Bohr, V. A. (2006) *Nucleic Acids Res.* 34, 745-754
58. Dantzer, F., de La Rubia, G., Menissier-De Murcia, J., Hostomsky, Z., de Murcia, G., and Schreiber, V. (2000) *Biochemistry* 39, 7559-7569
59. Prasad, R., Lavrik, O. I., Kim, S. J., Kedar, P., Yang, X. P., Vande Berg, B. J., and Wilson, S. H. (2001) J. Biol. Chem. 276, 32411-32414
60. Fortini, P., Pascucci, B., Parlanti, E., Sobol, R. W., Wilson, S. H., and Dogliotti, E. (1998) *Biochemistry* 37, 3575-3580
61. Matsumoto, Y., Kim, K., and Bogenhagen, D. F. (1994) *Mol. Cell. Biol.* 14, 6187-6197
62. Zhou, J., Ahn, J., Wilson, S. H., and Prives, C. (2001) *EMBO J.* 20, 914-923
63. DeMott M S, Zigman S, Bambara R A. (1998) *J. Biol. Chem.* 273, 27492-27498
64. Thompson, L. H., and West, M. G. (2000) *Mutat Res.* 459, 1-18
65. Maitra, M., Gudzelak, A., Jr., Li, S. X., Matsumoto, Y., Eckert, K. A., Jager, J., and Sweasy, J. B. (2002) *J. Biol. Chem.* 277, 35550-35560
66. Srivastava, D. K., Berg, B. J., Prasad, R., Molina, J. T., Beard, W. A., Tomkinson, A. E., and Wilson, S. H. (1998) *J. Biol. Chem.* 273, 21203-21209
67. Piersen, C. E., Prasad, R., Wilson, S. H., and Lloyd, R. S. (1996) *J. Biol. Chem.* 271, 17811-17815

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for treating colon cancer in a subject, the method comprising administering to said subject an effective amount of temozolamide and NSC-124854 having the following structure:

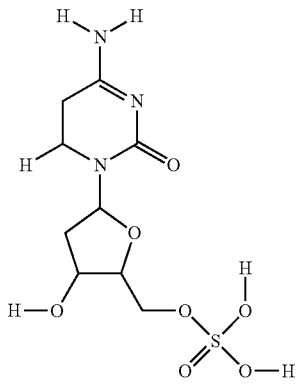

thereby treating the colon cancer.

2. The method of claim 1, wherein NSC-124854 binds polβ at an adenomatous polyposis coli (APC) binding site comprising amino acids Thr79, Lys81 and Arg83, and reduces pol-β-directed dRP-lyase activity or pol-β-directed strand-displacement synthesis, thereby treating the colon cancer.

3. The method of claim 1, wherein NSC-124854 binds polβ at an adenomatous polyposis coli (APC) binding site comprising polβ amino acids selected from the group consisting of amino acids 60-120, 60-170, and 80-170.

4. A method for treating colon cancer in a subject, the method comprising administering to said subject an effective amount of NSC-124854 having the following structure:

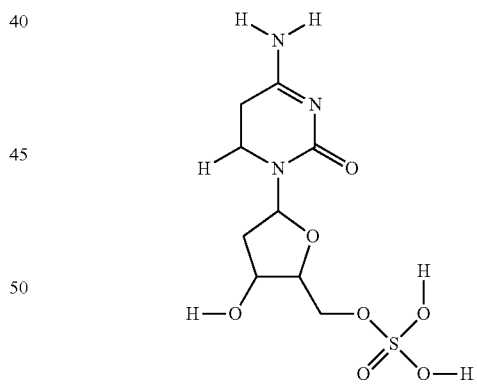

, and temozolamide, wherein the effective amount of NSC-424854 and temozolomide has reduced toxicity relative to the administration of an effective amount of temozolamide alone, thereby treating the colon cancer.

5. The method of claim 1, wherein the subject is identified as having a colon cancer that does not respond to a conventional chemotherapeutic or that is DNA mismatch repair deficient.

6. The method of claim 1, wherein the method further comprises the step of identifying the subject as having an MMR-deficient colon cancer or a colon cancer that does not respond to conventional chemotherapeutics.

7. The method of claim 6, wherein an effective amount of NSC-124854 and temozolomide has reduced toxicity relative to the administration of an effective amount of temozolamide alone.
8. A pharmaceutical composition for the treatment of colon cancer, the composition comprising an effective amount of NSC124854 having the following structure:
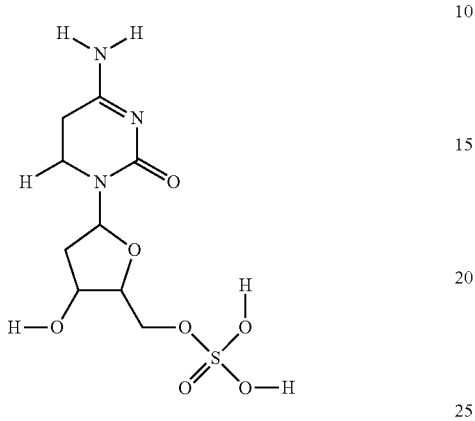
and temozolomide.
* * * * *

UNITED STATES PATENT AND TRADEMARK OFFICE
CERTIFICATE OF CORRECTION

| | | |
|---|---|---|
| PATENT NO. | : 9,144,596 B2 | Page 1 of 1 |
| APPLICATION NO. | : 12/527164 | |
| DATED | : September 29, 2015 | |
| INVENTOR(S) | : Satya Narayan et al. | |

It is certified that error appears in the above-identified patent and that said Letters Patent is hereby corrected as shown below:

In the specification

Column 1 lines 4-11 should read

THE STATEMENT OF RIGHTS TO INVENTIONS MADE UNDER FEDERALLY SPONSORED RESEARCH

This work was supported by the following grants from the National Institutes of Health, Grant Nos: RO1-CA097031 and RO1-CA100247. The government has certain rights in the invention.

Signed and Sealed this
Fifth Day of April, 2016

Michelle K. Lee
*Director of the United States Patent and Trademark Office*

SEQUENCE LISTING

<160> NUMBER OF SEQ ID NOS: 28

<210> SEQ ID NO 1
<211> LENGTH: 2843
<212> TYPE: PRT
<213> ORGANISM: Homo sapiens

<400> SEQUENCE: 1

```
Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30
```

```
His Leu Thr Lys Leu Glu Thr Glu Ala Ser Asn Met Lys Glu Val Leu
         35                  40                  45
Lys Gln Leu Gln Gly Ser Ile Glu Asp Glu Ala Met Ala Ser Ser Gly
 50                  55                  60
Gln Ile Asp Leu Leu Glu Arg Leu Lys Glu Leu Asn Leu Asp Ser Ser
 65                  70                  75                  80
Asn Phe Pro Gly Val Lys Leu Arg Ser Lys Met Ser Leu Arg Ser Tyr
                 85                  90                  95
Gly Ser Arg Glu Gly Ser Val Ser Arg Ser Gly Glu Cys Ser Pro
                100                 105                 110
Val Pro Met Gly Ser Phe Pro Arg Arg Gly Phe Val Asn Gly Ser Arg
                115                 120                 125
Glu Ser Thr Gly Tyr Leu Glu Glu Leu Glu Lys Glu Arg Ser Leu Leu
                130                 135                 140
Leu Ala Asp Leu Asp Lys Glu Glu Lys Glu Lys Asp Trp Tyr Tyr Ala
145                 150                 155                 160
Gln Leu Gln Asn Leu Thr Lys Arg Ile Asp Ser Leu Pro Leu Thr Glu
                165                 170                 175
Asn Phe Ser Leu Gln Thr Asp Met Thr Arg Arg Gln Leu Glu Tyr Glu
                180                 185                 190
Ala Arg Gln Ile Arg Val Ala Met Glu Glu Gln Leu Gly Thr Cys Gln
                195                 200                 205
Asp Met Glu Lys Arg Ala Gln Arg Arg Ile Ala Arg Ile Gln Gln Ile
                210                 215                 220
Glu Lys Asp Ile Leu Arg Ile Arg Gln Leu Leu Gln Ser Gln Ala Thr
225                 230                 235                 240
Glu Ala Glu Arg Ser Ser Gln Asn Lys His Glu Thr Gly Ser His Asp
                245                 250                 255
Ala Glu Arg Gln Asn Glu Gly Gln Gly Val Gly Glu Ile Asn Met Ala
                260                 265                 270
Thr Ser Gly Asn Gly Gln Gly Ser Thr Thr Arg Met Asp His Glu Thr
                275                 280                 285
Ala Ser Val Leu Ser Ser Ser Thr His Ser Ala Pro Arg Arg Leu
290                 295                 300
Thr Ser His Leu Gly Thr Lys Val Glu Met Val Tyr Ser Leu Leu Ser
305                 310                 315                 320
Met Leu Gly Thr His Asp Lys Asp Asp Met Ser Arg Thr Leu Leu Ala
                325                 330                 335
Met Ser Ser Ser Gln Asp Ser Cys Ile Ser Met Arg Gln Ser Gly Cys
                340                 345                 350
Leu Pro Leu Leu Ile Gln Leu Leu His Gly Asn Asp Lys Asp Ser Val
                355                 360                 365
Leu Leu Gly Asn Ser Arg Gly Ser Lys Glu Ala Arg Ala Arg Ala Ser
                370                 375                 380
Ala Ala Leu His Asn Ile Ile His Ser Gln Pro Asp Asp Lys Arg Gly
385                 390                 395                 400
Arg Arg Glu Ile Arg Val Leu His Leu Leu Glu Gln Ile Arg Ala Tyr
                405                 410                 415
Cys Glu Thr Cys Trp Glu Trp Gln Glu Ala His Glu Pro Gly Met Asp
                420                 425                 430
Gln Asp Lys Asn Pro Met Pro Ala Pro Val Glu His Gln Ile Cys Pro
                435                 440                 445
Ala Val Cys Val Leu Met Lys Leu Ser Phe Asp Glu Glu His Arg His
```

```
                450             455             460
Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                    485                 490                 495

Leu Arg Arg Tyr Ala Gly Met Ala Leu Thr Asn Leu Thr Phe Gly Asp
                500                 505                 510

Val Ala Asn Lys Ala Thr Leu Cys Ser Met Lys Gly Cys Met Arg Ala
            515                 520                 525

Leu Val Ala Gln Leu Lys Ser Glu Ser Glu Asp Leu Gln Gln Val Ile
        530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
                    565                 570                 575

Leu Glu Val Lys Lys Glu Ser Thr Leu Lys Ser Val Leu Ser Ala Leu
                580                 585                 590

Trp Asn Leu Ser Ala His Cys Thr Glu Asn Lys Ala Asp Ile Cys Ala
            595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
                    645                 650                 655

Arg Glu Asn Asn Cys Leu Gln Thr Leu Leu Gln His Leu Lys Ser His
                660                 665                 670

Ser Leu Thr Ile Val Ser Asn Ala Cys Gly Thr Leu Trp Asn Leu Ser
            675                 680                 685

Ala Arg Asn Pro Lys Asp Gln Glu Ala Leu Trp Asp Met Gly Ala Val
        690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                    725                 730                 735

Tyr Lys Asp Ala Asn Ile Met Ser Pro Gly Ser Ser Leu Pro Ser Leu
                740                 745                 750

His Val Arg Lys Gln Lys Ala Leu Glu Ala Glu Leu Asp Ala Gln His
            755                 760                 765

Leu Ser Glu Thr Phe Asp Asn Ile Asp Asn Leu Ser Pro Lys Ala Ser
        770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                    805                 810                 815

Gly Asn Met Thr Val Leu Ser Pro Tyr Leu Asn Thr Thr Val Leu Pro
                820                 825                 830

Ser Ser Ser Ser Arg Gly Ser Leu Asp Ser Arg Ser Glu Lys
            835                 840                 845

Asp Arg Ser Leu Glu Arg Glu Arg Gly Ile Gly Leu Gly Asn Tyr His
        850                 855                 860

Pro Ala Thr Glu Asn Pro Gly Thr Ser Ser Lys Arg Gly Leu Gln Ile
865                 870                 875                 880
```

```
Ser Thr Thr Ala Ala Gln Ile Ala Lys Val Met Glu Val Ser Ala
                885                 890                 895

Ile His Thr Ser Gln Glu Asp Arg Ser Ser Gly Ser Thr Thr Leu
                900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
    930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Glu Ser
                980                 985                 990

Lys Phe Cys Ser Tyr Gly Gln Tyr  Pro Ala Asp Leu Ala  His Lys Ile
            995                 1000                 1005

His Ser  Ala Asn His Met Asp  Asp Asp Gly Glu  Leu Asp Thr
    1010                 1015                 1020

Pro Ile  Asn Tyr Ser Leu Lys  Tyr Ser Asp Glu Gln  Leu Asn Ser
    1025                 1030                 1035

Gly Arg  Gln Ser Pro Ser Gln  Asn Glu Arg Trp Ala  Arg Pro Lys
    1040                 1045                 1050

His Ile  Ile Glu Asp Glu Ile  Lys Gln Ser Glu Gln  Arg Gln Ser
    1055                 1060                 1065

Arg Asn  Gln Ser Thr Thr Tyr  Pro Val Tyr Thr Glu  Ser Thr Asp
    1070                 1075                 1080

Asp Lys  His Leu Lys Phe Gln  Pro His Phe Gly Gln  Gln Glu Cys
    1085                 1090                 1095

Val Ser  Pro Tyr Arg Ser Arg  Gly Ala Asn Gly Ser  Glu Thr Asn
    1100                 1105                 1110

Arg Val  Gly Ser Asn His Gly  Ile Asn Gln Asn Val  Ser Gln Ser
    1115                 1120                 1125

Leu Cys  Gln Glu Asp Asp Tyr  Glu Asp Asp Lys Pro  Thr Asn Tyr
    1130                 1135                 1140

Ser Glu  Arg Tyr Ser Glu Glu  Glu Gln His Glu Glu  Glu Glu Arg
    1145                 1150                 1155

Pro Thr  Asn Tyr Ser Ile Lys  Tyr Asn Glu Glu Lys  Arg His Val
    1160                 1165                 1170

Asp Gln  Pro Ile Asp Tyr Ser  Leu Lys Tyr Ala Thr  Asp Ile Pro
    1175                 1180                 1185

Ser Ser  Gln Lys Gln Ser Phe  Ser Phe Ser Lys Ser  Ser Ser Gly
    1190                 1195                 1200

Gln Ser  Ser Lys Thr Glu His  Met Ser Ser Ser Ser  Glu Asn Thr
    1205                 1210                 1215

Ser Thr  Pro Ser Ser Asn Ala  Lys Arg Gln Asn Gln  Leu His Pro
    1220                 1225                 1230

Ser Ser  Ala Gln Ser Arg Ser  Gly Gln Pro Gln Lys  Ala Ala Thr
    1235                 1240                 1245

Cys Lys  Val Ser Ser Ile Asn  Gln Glu Thr Ile Gln  Thr Tyr Cys
    1250                 1255                 1260

Val Glu  Asp Thr Pro Ile Cys  Phe Ser Arg Cys Ser  Ser Leu Ser
    1265                 1270                 1275
```

-continued

Ser Leu Ser Ser Ala Glu Asp Glu Ile Gly Cys Asn Gln Thr Thr
    1280            1285            1290

Gln Glu Ala Asp Ser Ala Asn Thr Leu Gln Ile Ala Glu Ile Lys
    1295            1300            1305

Glu Lys Ile Gly Thr Arg Ser Ala Glu Asp Pro Val Ser Glu Val
    1310            1315            1320

Pro Ala Val Ser Gln His Pro Arg Thr Lys Ser Ser Arg Leu Gln
    1325            1330            1335

Gly Ser Ser Leu Ser Ser Glu Ser Ala Arg His Lys Ala Val Glu
    1340            1345            1350

Phe Ser Ser Gly Ala Lys Ser Pro Ser Lys Ser Gly Ala Gln Thr
    1355            1360            1365

Pro Lys Ser Pro Pro Glu His Tyr Val Gln Glu Thr Pro Leu Met
    1370            1375            1380

Phe Ser Arg Cys Thr Ser Val Ser Ser Leu Asp Ser Phe Glu Ser
    1385            1390            1395

Arg Ser Ile Ala Ser Ser Val Gln Ser Glu Pro Cys Ser Gly Met
    1400            1405            1410

Val Ser Gly Ile Ile Ser Pro Ser Asp Leu Pro Asp Ser Pro Gly
    1415            1420            1425

Gln Thr Met Pro Pro Ser Arg Ser Lys Thr Pro Pro Pro Pro Pro
    1430            1435            1440

Gln Thr Ala Gln Thr Lys Arg Glu Val Pro Lys Asn Lys Ala Pro
    1445            1450            1455

Thr Ala Glu Lys Arg Glu Ser Gly Pro Lys Gln Ala Ala Val Asn
    1460            1465            1470

Ala Ala Val Gln Arg Val Gln Val Leu Pro Asp Ala Asp Thr Leu
    1475            1480            1485

Leu His Phe Ala Thr Glu Ser Thr Pro Asp Gly Phe Ser Cys Ser
    1490            1495            1500

Ser Ser Leu Ser Ala Leu Ser Leu Asp Glu Pro Phe Ile Gln Lys
    1505            1510            1515

Asp Val Glu Leu Arg Ile Met Pro Pro Val Gln Glu Asn Asp Asn
    1520            1525            1530

Gly Asn Glu Thr Glu Ser Glu Gln Pro Lys Glu Ser Asn Glu Asn
    1535            1540            1545

Gln Glu Lys Glu Ala Glu Lys Thr Ile Asp Ser Glu Lys Asp Leu
    1550            1555            1560

Leu Asp Asp Ser Asp Asp Asp Asp Ile Glu Ile Leu Glu Glu Cys
    1565            1570            1575

Ile Ile Ser Ala Met Pro Thr Lys Ser Ser Arg Lys Ala Lys Lys
    1580            1585            1590

Pro Ala Gln Thr Ala Ser Lys Leu Pro Pro Pro Val Ala Arg Lys
    1595            1600            1605

Pro Ser Gln Leu Pro Val Tyr Lys Leu Leu Pro Ser Gln Asn Arg
    1610            1615            1620

Leu Gln Pro Gln Lys His Val Ser Phe Thr Pro Gly Asp Asp Met
    1625            1630            1635

Pro Arg Val Tyr Cys Val Glu Gly Thr Pro Ile Asn Phe Ser Thr
    1640            1645            1650

Ala Thr Ser Leu Ser Asp Leu Thr Ile Glu Ser Pro Pro Asn Glu
    1655            1660            1665

Leu Ala Ala Gly Glu Gly Val Arg Gly Gly Ala Gln Ser Gly Glu

-continued

```
              1670              1675              1680
Phe Glu Lys Arg Asp Thr Ile Pro Thr Glu Gly Arg Ser Thr Asp
              1685              1690              1695
Glu Ala Gln Gly Gly Lys Thr Ser Ser Val Thr Ile Pro Glu Leu
              1700              1705              1710
Asp Asp Asn Lys Ala Glu Glu Gly Asp Ile Leu Ala Glu Cys Ile
              1715              1720              1725
Asn Ser Ala Met Pro Lys Gly Lys Ser His Lys Pro Phe Arg Val
              1730              1735              1740
Lys Lys Ile Met Asp Gln Val Gln Gln Ala Ser Ala Ser Ser Ser
              1745              1750              1755
Ala Pro Asn Lys Asn Gln Leu Asp Gly Lys Lys Lys Lys Pro Thr
              1760              1765              1770
Ser Pro Val Lys Pro Ile Pro Gln Asn Thr Glu Tyr Arg Thr Arg
              1775              1780              1785
Val Arg Lys Asn Ala Asp Ser Lys Asn Asn Leu Asn Ala Glu Arg
              1790              1795              1800
Val Phe Ser Asp Asn Lys Asp Ser Lys Lys Gln Asn Leu Lys Asn
              1805              1810              1815
Asn Ser Lys Val Phe Asn Asp Lys Leu Pro Asn Asn Glu Asp Arg
              1820              1825              1830
Val Arg Gly Ser Phe Ala Phe Asp Ser Pro His His Tyr Thr Pro
              1835              1840              1845
Ile Glu Gly Thr Pro Tyr Cys Phe Ser Arg Asn Asp Ser Leu Ser
              1850              1855              1860
Ser Leu Asp Phe Asp Asp Asp Val Asp Leu Ser Arg Glu Lys
              1865              1870              1875
Ala Glu Leu Arg Lys Ala Lys Glu Asn Lys Glu Ser Glu Ala Lys
              1880              1885              1890
Val Thr Ser His Thr Glu Leu Thr Ser Asn Gln Gln Ser Ala Asn
              1895              1900              1905
Lys Thr Gln Ala Ile Ala Lys Gln Pro Ile Asn Arg Gly Gln Pro
              1910              1915              1920
Lys Pro Ile Leu Gln Lys Gln Ser Thr Phe Pro Gln Ser Ser Lys
              1925              1930              1935
Asp Ile Pro Asp Arg Gly Ala Ala Thr Asp Glu Lys Leu Gln Asn
              1940              1945              1950
Phe Ala Ile Glu Asn Thr Pro Val Cys Phe Ser His Asn Ser Ser
              1955              1960              1965
Leu Ser Ser Leu Ser Asp Ile Asp Gln Glu Asn Asn Asn Lys Glu
              1970              1975              1980
Asn Glu Pro Ile Lys Glu Thr Glu Pro Pro Asp Ser Gln Gly Glu
              1985              1990              1995
Pro Ser Lys Pro Gln Ala Ser Gly Tyr Ala Pro Lys Ser Phe His
              2000              2005              2010
Val Glu Asp Thr Pro Val Cys Phe Ser Arg Asn Ser Ser Leu Ser
              2015              2020              2025
Ser Leu Ser Ile Asp Ser Glu Asp Asp Leu Leu Gln Glu Cys Ile
              2030              2035              2040
Ser Ser Ala Met Pro Lys Lys Lys Lys Pro Ser Arg Leu Lys Gly
              2045              2050              2055
Asp Asn Glu Lys His Ser Pro Arg Asn Met Gly Gly Ile Leu Gly
              2060              2065              2070
```

```
Glu Asp Leu Thr Leu Asp Leu Lys Asp Ile Gln Arg Pro Asp Ser
    2075            2080                2085

Glu His Gly Leu Ser Pro Asp Ser Glu Asn Phe Asp Trp Lys Ala
    2090            2095                2100

Ile Gln Glu Gly Ala Asn Ser Ile Val Ser Ser Leu His Gln Ala
    2105            2110                2115

Ala Ala Ala Ala Cys Leu Ser Arg Gln Ala Ser Ser Asp Ser Asp
    2120            2125                2130

Ser Ile Leu Ser Leu Lys Ser Gly Ile Ser Leu Gly Ser Pro Phe
    2135            2140                2145

His Leu Thr Pro Asp Gln Glu Glu Lys Pro Phe Thr Ser Asn Lys
    2150            2155                2160

Gly Pro Arg Ile Leu Lys Pro Gly Glu Lys Ser Thr Leu Glu Thr
    2165            2170                2175

Lys Lys Ile Glu Ser Glu Ser Lys Gly Ile Lys Gly Gly Lys Lys
    2180            2185                2190

Val Tyr Lys Ser Leu Ile Thr Gly Lys Val Arg Ser Asn Ser Glu
    2195            2200                2205

Ile Ser Gly Gln Met Lys Gln Pro Leu Gln Ala Asn Met Pro Ser
    2210            2215                2220

Ile Ser Arg Gly Arg Thr Met Ile His Ile Pro Gly Val Arg Asn
    2225            2230                2235

Ser Ser Ser Ser Thr Ser Pro Val Ser Lys Lys Gly Pro Pro Leu
    2240            2245                2250

Lys Thr Pro Ala Ser Lys Ser Pro Ser Glu Gly Gln Thr Ala Thr
    2255            2260                2265

Thr Ser Pro Arg Gly Ala Lys Pro Ser Val Lys Ser Glu Leu Ser
    2270            2275                2280

Pro Val Ala Arg Gln Thr Ser Gln Ile Gly Gly Ser Ser Lys Ala
    2285            2290                2295

Pro Ser Arg Ser Gly Ser Arg Asp Ser Thr Pro Ser Arg Pro Ala
    2300            2305                2310

Gln Gln Pro Leu Ser Arg Pro Ile Gln Ser Pro Gly Arg Asn Ser
    2315            2320                2325

Ile Ser Pro Gly Arg Asn Gly Ile Ser Pro Pro Asn Lys Leu Ser
    2330            2335                2340

Gln Leu Pro Arg Thr Ser Ser Pro Ser Thr Ala Ser Thr Lys Ser
    2345            2350                2355

Ser Gly Ser Gly Lys Met Ser Tyr Thr Ser Pro Gly Arg Gln Met
    2360            2365                2370

Ser Gln Gln Asn Leu Thr Lys Gln Thr Gly Leu Ser Lys Asn Ala
    2375            2380                2385

Ser Ser Ile Pro Arg Ser Glu Ser Ala Ser Lys Gly Leu Asn Gln
    2390            2395                2400

Met Asn Asn Gly Asn Gly Ala Asn Lys Lys Val Glu Leu Ser Arg
    2405            2410                2415

Met Ser Ser Thr Lys Ser Ser Gly Ser Glu Ser Asp Arg Ser Glu
    2420            2425                2430

Arg Pro Val Leu Val Arg Gln Ser Thr Phe Ile Lys Glu Ala Pro
    2435            2440                2445

Ser Pro Thr Leu Arg Arg Lys Leu Glu Glu Ser Ala Ser Phe Glu
    2450            2455                2460
```

```
Ser Leu Ser Pro Ser Ser Arg Pro Ala Ser Pro Thr Arg Ser Gln
2465                2470                2475

Ala Gln Thr Pro Val Leu Ser Pro Ser Leu Pro Asp Met Ser Leu
2480                2485                2490

Ser Thr His Ser Ser Val Gln Ala Gly Gly Trp Arg Lys Leu Pro
2495                2500                2505

Pro Asn Leu Ser Pro Thr Ile Glu Tyr Asn Asp Gly Arg Pro Ala
2510                2515                2520

Lys Arg His Asp Ile Ala Arg Ser His Ser Glu Ser Pro Ser Arg
2525                2530                2535

Leu Pro Ile Asn Arg Ser Gly Thr Trp Lys Arg Glu His Ser Lys
2540                2545                2550

His Ser Ser Ser Leu Pro Arg Val Ser Thr Trp Arg Arg Thr Gly
2555                2560                2565

Ser Ser Ser Ser Ile Leu Ser Ala Ser Ser Glu Ser Ser Glu Lys
2570                2575                2580

Ala Lys Ser Glu Asp Glu Lys His Val Asn Ser Ile Ser Gly Thr
2585                2590                2595

Lys Gln Ser Lys Glu Asn Gln Val Ser Ala Lys Gly Thr Trp Arg
2600                2605                2610

Lys Ile Lys Glu Asn Glu Phe Ser Pro Thr Asn Ser Thr Ser Gln
2615                2620                2625

Thr Val Ser Ser Gly Ala Thr Asn Gly Ala Glu Ser Lys Thr Leu
2630                2635                2640

Ile Tyr Gln Met Ala Pro Ala Val Ser Lys Thr Glu Asp Val Trp
2645                2650                2655

Val Arg Ile Glu Asp Cys Pro Ile Asn Asn Pro Arg Ser Gly Arg
2660                2665                2670

Ser Pro Thr Gly Asn Thr Pro Pro Val Ile Asp Ser Val Ser Glu
2675                2680                2685

Lys Ala Asn Pro Asn Ile Lys Asp Ser Lys Asp Asn Gln Ala Lys
2690                2695                2700

Gln Asn Val Gly Asn Gly Ser Val Pro Met Arg Thr Val Gly Leu
2705                2710                2715

Glu Asn Arg Leu Asn Ser Phe Ile Gln Val Asp Ala Pro Asp Gln
2720                2725                2730

Lys Gly Thr Glu Ile Lys Pro Gly Gln Asn Asn Pro Val Pro Val
2735                2740                2745

Ser Glu Thr Asn Glu Ser Ser Ile Val Glu Arg Thr Pro Phe Ser
2750                2755                2760

Ser Ser Ser Ser Ser Lys His Ser Ser Pro Ser Gly Thr Val Ala
2765                2770                2775

Ala Arg Val Thr Pro Phe Asn Tyr Asn Pro Ser Pro Arg Lys Ser
2780                2785                2790

Ser Ala Asp Ser Thr Ser Ala Arg Pro Ser Gln Ile Pro Thr Pro
2795                2800                2805

Val Asn Asn Asn Thr Lys Lys Arg Asp Ser Lys Thr Asp Ser Thr
2810                2815                2820

Glu Ser Ser Gly Thr Gln Ser Pro Lys Arg His Ser Gly Ser Tyr
2825                2830                2835

Leu Val Thr Ser Val
2840
```

```
<210> SEQ ID NO 2
<211> LENGTH: 6
<212> TYPE: PRT
<213> ORGANISM: Artificial sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 20
<212> TYPE: PRT
<213> ORGANISM: Homo sapiens

<400> SEQUENCE: 3

Lys Val Ser Ser Ile Asn Gln Glu Thr Ile Gln Thr Tyr Cys Val Glu
1               5                   10                  15

Asp Thr Pro Ile
            20

<210> SEQ ID NO 4
<211> LENGTH: 20
<212> TYPE: PRT
<213> ORGANISM: Artificial sequence
<220> FEATURE:
<223> OTHER INFORMATION: Description of Artificial Sequence: Synthetic
      peptide

<400> SEQUENCE: 4

Lys Val Ser Ser Ile Asn Gln Glu Thr Ala Gln Thr Ala Cys Val Glu
1               5                   10                  15

Asp Thr Pro Ile
            20

<210> SEQ ID NO 5
<211> LENGTH: 27
<212> TYPE: DNA
<213> ORGANISM: Artificial sequence
<220> FEATURE:
<223> OTHER INFORMATION: Description of Artificial Sequence: Synthetic
      primer

<400> SEQUENCE: 5
cgcggatcca agaaattgcc tggagta                                              27

<210> SEQ ID NO 6
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 6
ccaatgcatt ggttctgcag tttaattcct tcatctac                                  38

<210> SEQ ID NO 7
<211> LENGTH: 53
<212> TYPE: DNA
<213> ORGANISM: Artificial sequence
<220> FEATURE:
<223> OTHER INFORMATION: Description of Artificial Sequence: Synthetic
      primer
```

```
<400> SEQUENCE: 7
cgcggatccg gaaaattacg taaactcgcg gatccggaaa attacgtaaa ctg        53

<210> SEQ ID NO 8
<211> LENGTH: 37
<212> TYPE: DNA
<213> ORGANISM: Artificial sequence
<220> FEATURE:
<223> OTHER INFORMATION: Description of Artificial Sequence: Synthetic
      primer

<400> SEQUENCE: 8
ccaatgcatt ggttctgcag atccactttt ttaactt                          37

<210> SEQ ID NO 9
<211> LENGTH: 27
<212> TYPE: DNA
<213> ORGANISM: Artificial sequence
<220> FEATURE:
<223> OTHER INFORMATION: Description of Artificial Sequence: Synthetic
      primer

<400> SEQUENCE: 9
cgcggatccc tgaaatattt tggggac                                     27

<210> SEQ ID NO 10
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 10
ccaatgcatt ggttctgcag gaagctggga tgggtcag                         38

<210> SEQ ID NO 11
<211> LENGTH: 27
<212> TYPE: DNA
<213> ORGANISM: Artificial sequence
<220> FEATURE:
<223> OTHER INFORMATION: Description of Artificial Sequence: Synthetic
      primer

<400> SEQUENCE: 11
cgcggatccg atattgttct aaatgaa                                     27

<210> SEQ ID NO 12
<211> LENGTH: 38
<212> TYPE: DNA
<213> ORGANISM: Artificial sequence
<220> FEATURE:
<223> OTHER INFORMATION: Description of Artificial Sequence: Synthetic
      primer

<400> SEQUENCE: 12
ccaatgcatt ggttctgcag atattctttt tcatcatt                         38

<210> SEQ ID NO 13
<211> LENGTH: 60
<212> TYPE: DNA
<213> ORGANISM: Artificial sequence
<220> FEATURE:
<223> OTHER INFORMATION: Description of Artificial Sequence: Synthetic
      primer

<400> SEQUENCE: 13
```

```
gaaaagattg atgagttttt agcagccgga gcgttagcta aactggaaaa gattcggcag    60
```

<210> SEQ ID NO 14
<211> LENGTH: 60
<212> TYPE: DNA
<213> ORGANISM: Artificial sequence
<220> FEATURE:
<223> OTHER INFORMATION: Description of Artificial Sequence: Synthetic
      primer

<400> SEQUENCE: 14

```
ctgccgaatc ttttccagtt tagctaacgc tccggctgct aaaaactcat caatcttttc    60
```

<210> SEQ ID NO 15
<211> LENGTH: 63
<212> TYPE: DNA
<213> ORGANISM: Artificial sequence
<220> FEATURE:
<223> OTHER INFORMATION: Description of Artificial Sequence: Synthetic
      primer

<400> SEQUENCE: 15

```
ggaaaattac gtaaactgga aaagattgcc gcggatgcta cgagttcatc catcaatttc    60
ctg                                                                  63
```

<210> SEQ ID NO 16
<211> LENGTH: 63
<212> TYPE: DNA
<213> ORGANISM: Artificial sequence
<220> FEATURE:
<223> OTHER INFORMATION: Description of Artificial Sequence: Synthetic
      primer

<400> SEQUENCE: 16

```
caggaaattg atggatgaac tcgtagcatc cgcggcaatc ttttccagtt tacgtaattt    60
tcc                                                                  63
```

<210> SEQ ID NO 17
<211> LENGTH: 23
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 17

```
ctagatgcct gcagctgatg cgc                                            23
```

<210> SEQ ID NO 18
<211> LENGTH: 39
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 18

```
gtacggatcc acgtgtacgg taccgagggc gggtcgaca                           39
```

<210> SEQ ID NO 19
<211> LENGTH: 62
<212> TYPE: DNA
<213> ORGANISM: Artificial sequence
<220> FEATURE:
<223> OTHER INFORMATION: Description of Combined DNA/RNA Molecule:

-continued

Synthetic oligonucleotide
<220> FEATURE:
<223> OTHER INFORMATION: Description of Artificial Sequence: Synthetic
      oligonucleotide

<400> SEQUENCE: 19
tagatgcctg cagctgatgc gcugtacgga tccacgtgta cggtaccgag ggcgggtcga    60
ca                                                                  62

<210> SEQ ID NO 20
<211> LENGTH: 63
<212> TYPE: DNA
<213> ORGANISM: Artificial sequence
<220> FEATURE:
<223> OTHER INFORMATION: Description of Artificial Sequence: Synthetic
      oligonucleotide

<400> SEQUENCE: 20
tgtcgacccg ccctcggtac cgtacacgtg gatccgtacc gcgcatcagc tgcaggcatc    60
tag                                                                 63

<210> SEQ ID NO 21
<211> LENGTH: 29
<212> TYPE: PRT
<213> ORGANISM: Homo sapiens

<400> SEQUENCE: 21

Lys Ala Ala Thr Cys Lys Val Ser Ser Ile Asn Gln Glu Thr Ile Gln
1               5                   10                  15

Thr Tyr Cys Val Glu Asp Thr Pro Ile Cys Phe Ser Arg
            20                  25

<210> SEQ ID NO 22
<211> LENGTH: 25
<212> TYPE: PRT
<213> ORGANISM: Homo sapiens

<400> SEQUENCE: 22

Lys Ala Ala Thr Cys Lys Val Ser Ser Ile Asn Gln Glu Thr Ile Gln
1               5                   10                  15

Thr Tyr Cys Val Glu Asp Thr Pro Ile
            20                  25

<210> SEQ ID NO 23
<211> LENGTH: 27
<212> TYPE: PRT
<213> ORGANISM: Artificial sequence
<220> FEATURE:
<223> OTHER INFORMATION: Description of Artificial Sequence: Synthetic
      peptide

<400> SEQUENCE: 23

Ala Glu Lys Ile Asp Glu Phe Leu Ala Thr Gly Lys Leu Arg Lys Leu
1               5                   10                  15

Glu Lys Ile Arg Gln Asp Asp Thr Ser Ser Ser
            20                  25

<210> SEQ ID NO 24
<211> LENGTH: 27
<212> TYPE: PRT
<213> ORGANISM: Artificial sequence
<220> FEATURE:
<223> OTHER INFORMATION: Description of Artificial Sequence: Synthetic
      peptide

```
<400> SEQUENCE: 24

Ala Glu Lys Ile Asp Glu Phe Leu Ala Ala Gly Ala Leu Ala Lys Leu
1               5                   10                  15

Glu Lys Ile Arg Gln Asp Asp Thr Ser Ser Ser
            20                  25

<210> SEQ ID NO 25
<211> LENGTH: 27
<212> TYPE: PRT
<213> ORGANISM: Artificial sequence
<220> FEATURE:
<223> OTHER INFORMATION: Description of Artificial Sequence: Synthetic
      peptide

<400> SEQUENCE: 25

Ala Glu Lys Ile Asp Glu Phe Leu Ala Thr Gly Lys Leu Arg Lys Leu
1               5                   10                  15

Glu Lys Ile Ala Ala Asp Ala Thr Ser Ser Ser
            20                  25

<210> SEQ ID NO 26
<211> LENGTH: 335
<212> TYPE: PRT
<213> ORGANISM: Homo sapiens

<400> SEQUENCE: 26

Met Ser Lys Arg Lys Ala Pro Gln Glu Thr Leu Asn Gly Gly Ile Thr
1               5                   10                  15

Asp Met Leu Thr Glu Leu Ala Asn Phe Glu Lys Asn Val Ser Gln Ala
            20                  25                  30

Ile His Lys Tyr Asn Ala Tyr Arg Lys Ala Ala Ser Val Ile Ala Lys
        35                  40                  45

Tyr Pro His Lys Ile Lys Ser Gly Ala Glu Ala Lys Lys Leu Pro Gly
    50                  55                  60

Val Gly Thr Lys Ile Ala Glu Lys Ile Asp Glu Phe Leu Ala Thr Gly
65                  70                  75                  80

Lys Leu Arg Lys Leu Glu Lys Ile Arg Gln Asp Asp Thr Ser Ser Ser
                85                  90                  95

Ile Asn Phe Leu Thr Arg Val Ser Gly Ile Gly Pro Ser Ala Ala Arg
            100                 105                 110

Lys Phe Val Asp Glu Gly Ile Lys Thr Leu Glu Asp Leu Arg Lys Asn
        115                 120                 125

Glu Asp Lys Leu Asn His His Gln Arg Ile Gly Leu Lys Tyr Phe Gly
    130                 135                 140

Asp Phe Glu Lys Arg Ile Pro Arg Glu Glu Met Leu Gln Met Gln Asp
145                 150                 155                 160

Ile Val Leu Asn Glu Val Lys Lys Val Asp Ser Glu Tyr Ile Ala Thr
                165                 170                 175

Val Cys Gly Ser Phe Arg Arg Gly Ala Glu Ser Ser Gly Asp Met Asp
            180                 185                 190

Val Leu Leu Thr His Pro Ser Phe Thr Ser Glu Ser Thr Lys Gln Pro
        195                 200                 205

Lys Leu Leu His Gln Val Val Glu Gln Leu Gln Lys Val His Phe Ile
    210                 215                 220

Thr Asp Thr Leu Ser Lys Gly Glu Thr Lys Phe Met Gly Val Cys Gln
225                 230                 235                 240
```

```
Leu Pro Ser Lys Asn Asp Glu Lys Glu Tyr Pro His Arg Arg Ile Asp
                245                 250                 255

Ile Arg Leu Ile Pro Lys Asp Gln Tyr Tyr Cys Gly Val Leu Tyr Phe
                260                 265                 270

Thr Gly Ser Asp Ile Phe Asn Lys Asn Met Arg Ala His Ala Leu Glu
            275                 280                 285

Lys Gly Phe Thr Ile Asn Glu Tyr Thr Ile Arg Pro Leu Gly Val Thr
        290                 295                 300

Gly Val Ala Gly Glu Pro Leu Pro Val Asp Ser Glu Lys Asp Ile Phe
305                 310                 315                 320

Asp Tyr Ile Gln Trp Lys Tyr Arg Glu Pro Lys Asp Arg Ser Glu
                325                 330                 335

<210> SEQ ID NO 27
<211> LENGTH: 16
<212> TYPE: DNA
<213> ORGANISM: Homo sapiens

<400> SEQUENCE: 27
ccgaccacgc atcagc                                                            16

<210> SEQ ID NO 28
<211> LENGTH: 11
<212> TYPE: DNA
<213> ORGANISM: Homo sapiens

<400> SEQUENCE: 28
gctgatgcgt g                                                                 11
```